United States Patent
Foote et al.

(10) Patent No.: US 7,132,442 B2
(45) Date of Patent: *Nov. 7, 2006

(54) 6H-THIENO[2, 3-B]PYRROLE DERIVATIVES AS ANTAGONISTS OF GONADOTROPIN RELEASING HORMONE (GNRH)

(75) Inventors: Kevin Michael Foote, Cheshire (GB); Zbigniew Matusiak, Cheshire (GB); Alexander Graham Dossetter, Cheshire (GB); Jean Claude Arnould, Reims Cedex 2 (FR); Maryannick Andree Lamorlette, Reims Cedex 2 (FR); Benedicte Delouvrie, Reims Cedex 2 (FR); Annie Hamon, Reims Cedex 2 (FR)

(73) Assignee: AstraZeneca AB, Sodertalje (SE)

( * ) Notice: Subject to any disclaimer, the term of this patent is extended or adjusted under 35 U.S.C. 154(b) by 36 days.

This patent is subject to a terminal disclaimer.

(21) Appl. No.: 10/524,978

(22) PCT Filed: Aug. 19, 2003

(86) PCT No.: PCT/GB03/03631

§ 371 (c)(1),
(2), (4) Date: Feb. 18, 2005

(87) PCT Pub. No.: WO2004/018480

PCT Pub. Date: Apr. 3, 2004

(65) Prior Publication Data

US 2006/0004082 A1   Jan. 5, 2006

(30) Foreign Application Priority Data

Aug. 21, 2002 (EP) .................................. 02292074

(51) Int. Cl.
*A61K 31/40* (2006.01)
*A61K 31/407* (2006.01)
*A61K 31/381* (2006.01)
*C07D 401/00* (2006.01)
*C07D 495/02* (2006.01)
*C07D 207/06* (2006.01)

(52) U.S. Cl. ...................... 514/414; 514/338; 514/422; 514/423; 514/443; 546/276.7; 548/453; 548/530; 549/50

(58) Field of Classification Search ................ 514/338, 514/414, 422, 423, 443; 546/276.7; 548/453; 548/530; 549/50
See application file for complete search history.

(56) References Cited

U.S. PATENT DOCUMENTS

2006/0004053 A1* 1/2006 Arnould ..................... 514/323

FOREIGN PATENT DOCUMENTS

| JP | 4179949(A) | 6/1992 |
|---|---|---|
| JP | 4179949 A2 * | 6/1992 |
| JP | 4356029(A) | 12/1992 |
| WO | WO 97/21435 A1 | 6/1997 |
| WO | WO 97/21703 A1 | 6/1997 |
| WO | WO 97/21704 A1 | 6/1997 |
| WO | WO 97/21707 A1 | 6/1997 |
| WO | WO 98/55116 A1 | 12/1998 |
| WO | WO 98/55119 A1 | 12/1998 |
| WO | WO 98/55123 A1 | 12/1998 |
| WO | WO 98/55470 A1 | 12/1998 |
| WO | WO 98/55479 A1 | 12/1998 |
| WO | WO 99/21553 A1 | 5/1999 |
| WO | WO 99/21557 A1 | 5/1999 |
| WO | WO 99/41251 A1 | 8/1999 |
| WO | WO 99/41252 A1 | 8/1999 |
| WO | WO 99/51231 A1 | 10/1999 |
| WO | WO 99/51232 A1 | 10/1999 |
| WO | WO 99/51233 A1 | 10/1999 |
| WO | WO 99/51234 A1 | 10/1999 |
| WO | WO 99/51595 A1 | 10/1999 |
| WO | WO 99/51596 A1 | 10/1999 |
| WO | WO 00/04013 A1 | 1/2000 |
| WO | WO 00/53178 A1 | 8/2000 |
| WO | WO 00/53179 A1 | 8/2000 |
| WO | WO 00/53180 A1 | 8/2000 |
| WO | WO 00/53181 A1 | 8/2000 |
| WO | WO 00/53185 A1 | 8/2000 |
| WO | WO 00/53602 A1 | 8/2000 |
| WO | 00/53602 | 9/2000 |
| WO | WO 00/69433 A1 | 11/2000 |
| WO | 02/24703 | 3/2002 |
| WO | WO 02/24703 A1 | 3/2002 |
| WO | WO 02/66459 A1 | 8/2002 |
| WO | WO 02/92565 A2 | 11/2002 |

OTHER PUBLICATIONS

Simeone, et al. "Synthesis of chiral B-methyl tryptamine-derived GnRH antagonists" Tetrahedron Letters 2001, pp. 6459-6461.*
Ashton et al. 'Substituted Indole-5-carboxamides and -acetamides as Potent Nonpeptide GnRH Receptor Antagonist.' Bioorganic & Medicinal Chemistry Letters 2001, vol. 11, pp. 1723-1726.

(Continued)

*Primary Examiner*—Golam M. M. Shameem
*Assistant Examiner*—Joseph R. Kosack
(74) *Attorney, Agent, or Firm*—Lucy Padget

(57) ABSTRACT

The invention relates to a group of novel thieno-pyrrole compounds of Formula (I): wherein: $R^1$, $R^2$, $R^3$, $R^4$ and $R^5$ are as defined in the specification, which are useful as gonadotrophin releasing hormone antagonists. The invention also relates to pharmaceutical formulations of said compounds, methods of treatment using said compounds and to processes for the preparation of said compounds.

18 Claims, No Drawings

OTHER PUBLICATIONS

Ashton et al. 'Potent Nonpeptide GnHR Receptor Antagonists Derived from Substituted Indole-5-carboxamides and -acetamides Bearing a Pyridine Side-Chain Terminus.' Bioorganic & Medicinal Chemistry Letters 2001, vol. 11, pp. 1727-1731.

Ashton et al. 'Orally Bioavailable, Indole-Based Nonpeptide GnHR Receptor Antagonists with High Potancy and Functional Activity.' Bioorganic and medicinal Chemistry Letters 2001, vol. 11, pp. 2597-2602.

Chu et al. 'Initial Structure-Activity Relationship of a Novel Class of Nonpeptidyl GnHR Receptor Antagonists: 2-Arylindoles.' Bioorganic and Medicinal Chemistry Letters 2001, vol. 11, pp. 509-513.

Chu et al. 'SAR Studies of novel 5-Substituted 2-Arylindoles as Nonpeptidyl GnHR Receptor Antagonists.' Bioorganic and Medicinal Chemistry Letters 2001, vol. 11, pp. 515-517.

Freidinger, R. M. 'Nonpeptide ligands for peptide and protein receptors.' Current Opinion in Chemical Biology 1999, vol. 3, pp. 395-406.

Goulet, M. T. 'Gonadotropin Releasing Hormone Antagonists.' Annual Reports in Medicinal Chemistry 1995, vol. 30, pp. 169-178.

Lin et al. '2-(3,5-Dimethylphenyl)tryptamine Derivatives That Bind to the GnHR Receptor.' Bioorganic & Medicinal Chemistry Letters 2001, vol. 11, pp. 1073-1076.

Lin et al. 'Heterocyclic Derivatives of 2-(3,5-Dimethylphenyl)tryptamine as GnHR Receptor Antagonists.' Bioorganic & Medicinal Chemistry Letters 2001, vol. 11, pp. 1077-1080.

Simoene, J. P. 'Synthesis of chiral β-methyl tryptamine-derived GnHR antagonists.' Tetrahedron Letters 2001, vol. 42, pp. 6459-6461.

Walsh et al. 'A convergent synthesis of (S)-β-methyl-2-aryltryptamine based gonadotropin releasing hormone antagonists.' Tetrahedron, 2001, vol. 57, pp. 5233-5241.

Young et al. '2-Arylindoles as Gonadotropin Releasing Hormone (GnHR) Antagonists: Optimization of the Tryptamine Side Chain.' Bioorganic & Medicinal Chemistry Letters 2002, vol. 12, pp. 827-832.

Ujjainwalla, F. 'Total synthesis of 6- and 7-azaindole derived GnHR antagonists.' Tetrahedron Letters, 2001, vol. 42, pp. 6441-6445.

Simeone et al. 'Modification of the Pyridine Moiety of Non-peptidyl Indole GnHR Receptor Antagonists.' Bioorganic & Medicinal Chemistry Letters, 2002, vol. 12, pp. 3329-3332.

Gibbs, J. B. 'Pharmaceutical Research in Molecular Oncology.' Cell, 1994, vol. 792, pp. 193-198.

Wensbo, D. 'Indoel-3-pyruvic acid Oxime ethers and Thieno analogues by Heck Cyclisation. Application to the Synthesis of Thia Tyrptophans' Tetrahedron, 1996, vol. 52(47), pp. 14975-14988.

Blair et al 'Thieno[3,2-b] and Thieno[2,3-b]pyrrole Bioisosteric Analogues of Hallucinogen and Serotonin Agonist N.N-Dimethyltryptamine' J. Med. Chem 1999, vol. 42, pp. 1106-1111.

Colburn et al 'Condensed Thiophen Ring Systems. Part 20. Synthesis of 5-Arylthieno-[3,2-b]pyrroles and 5-Arylthieno[3,2-c]pyrazoles' Journal of the Chemical Society Perkins I 1977, pp. 2436-2441.

Humphries et al 'The Synthesis of 6-substituted Thieno[3,2-b]pyrroles. Analogs of Tryptophan, Tryptamine and Indoleacetic acid' The Journal of Organic Chemistry 1972, vol. 37, pp. 3626-3629.

Keener et al 'The Synthesis of 6-Substituted Thieno[3,2-b]pyrroles' The Journal of Organic Chemistry 1968, vol. 33(4), pp. 1355-1359.

Srinivasan et al 'A New Synthesis of 5-Arylthieno[2,3-b]pyrroles and 5-Arylthieno[3,2-b]pyrroles' Synthesis 1973, 313-315.

Synder et al 'Synthesis of the Thieno[3,2-b]pyrrole System' Journal of the American Chemical Society 1957, vol. 79, pp. 2556-2559.

Gale et al 'Preparation and Reactions of 5-Carbethoxythieno[3,2-b]pyrrole and Some of Its Derivatives' The Journal of Organic Chemistry 1964, vol. 29, pp. 2160-2165.

Aoyama, T. Chemical & Pharmaceutical Bulletin 1981 vol. 11, pp. 3249-3255.

Geetha et al Indian Journal of Chemistry Section B 1979, vol. 17B(2), pp. 163-164.

Kumar et al Indian Journal of Chemistry Section B 1979, vol. 18B(2), pp. 541-543.

Kvitko et al Zhurnal Organicheskoi Khimii 1976, vol. 12(7), pp. 1574-1585 (+ Abstract).

Kvitko et al 'Enamines of formyl derivatives of thio- and selenopyrrolone and synthesis of thieno- an selenopheno[2,3-b]pyrroles' Khim Geterotsikl Soedin 1973, vol. (4), pp. 565-566 (+ Abstract).

* cited by examiner

6H-THIENO[2, 3-B]PYRROLE DERIVATIVES AS ANTAGONISTS OF GONADOTROPIN RELEASING HORMONE (GNRH)

CROSS-REFERENCE TO RELATED APPLICATIONS

This application is a US National Stage under 35 U.S.C § 371 of International Application No. PCT/GB2003/003631, filed Aug. 19, 2003, which claims priority under 35 U.S.C. § 119(a)–(d) to European Patent Application No. 02292074.8 filed on Aug. 21, 2002, the specification of which is incorporated by reference herein.

The present invention relates to compounds which are antagonists of gonadotropin releasing hormone (GnRH) activity. The invention also relates to pharmaceutical formulations, the use of a compound of the present invention in the manufacture of a medicament, a method of therapeutic treatment using such a compound and processes for producing the compounds.

Gonadotropin releasing hormone (GnRH) is a decapeptide that is secreted by the hypothalamus into the hypophyseal portal circulation in response to neural and/or chemical stimuli, causing the biosynthesis and release of luteinizing hormone (LH) and follicle-stimulating hormone (FSH) by the pituitary. GnRH is also known by other names, including gonadoliberin, LH releasing hormone (LHRH), FSH releasing hormone (FSH RH) and LH/FSH releasing factor (LH/FSH RF).

GnRH plays an important role in regulating the action of LH and FSH (by regulation of their levels), and thus has a role in regulating the levels of gonadal steroids in both sexes, including the sex hormones progesterone, oestrogens and androgens. More discussion of GnRH can be found in WO 98/5519 and WO 97/14697, the disclosures of which are incorporated herein by reference.

It is believed that several diseases would benefit from the regulation of GnRH activity, in particular by antagonising such activity. These include sex hormone related conditions such as sex hormone dependent cancer, benign prostatic hypertrophy and myoma of the uterus. Examples of sex hormone dependent cancers are prostatic cancer, uterine cancer, breast cancer and pituitary gonadotrophe adenoma.

The following disclose compounds purported to act as GnRH antagonists: WO 97/21435, WO 97/21703, WO 97/21704, WO 97/21707, WO 55116, WO 98/55119, WO 98/55123, WO 98/55470, WO 98/55479, WO 99/21553, WO 99/21557, WO 99/41251, WO 99/41252, WO 00/04013, WO 00/69433, WO 99/51231, WO 99/51232, WO 99/51233, WO 99/51234, WO 99/51595, WO 99/51596, WO 00/53178, WO 00/53180, WO 00/53179, WO 00/53181, WO 00/53185, WO 00/53602, WO 02/066477, WO 02/066478, WO 02/06645 and WO 02/092565.

It would be desirable to provide further compounds, such compounds being GnRH antagonists. Thus, according to the first aspect of the invention there is provided a compound of Formula (I),

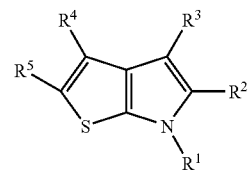

Formula (I)

wherein:
$R^1$ is selected from: hydrogen, optionally-substituted $C_{1-6}$alkyl, optionally substituted $C_{1-6}$alkanoyl, optionally substituted aryl or optionally-substituted aryl$C_{1-6}$alkyl;
$R^2$ is an optionally-substituted mono or bi-cyclic aromatic ring;
$R^3$ is selected from a group of Formula (IIa) to Formula (IIf):

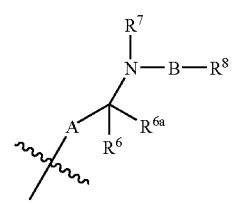

Formula (IIa)

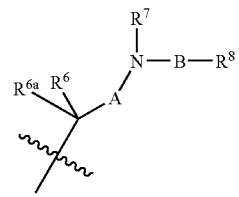

Formula (IIb)

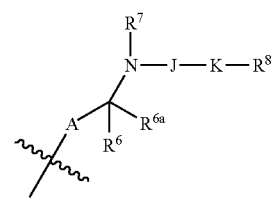

Formula (IIc)

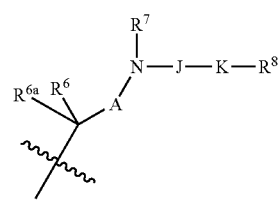

Formula (IId)

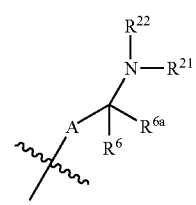

Formula (IIe)

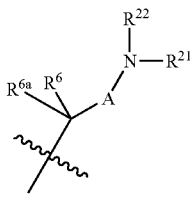

Formula (IIf)

$R^4$ is selected from: hydrogen, optionally substituted $C_{1-6}$alkyl, optionally substituted aryl, $C_{1-3}$perfluoroalkyl, cyano, nitro, halo, $R^9O(CH_2)_m$—, $R^9C(O)N(R^{10})(CH_2)_m$—, $R^9R^{10}NC(O)N(R^{10})(CH_2)_m$—, $R^9S(O_n)(CH_2)_m$— or $R^9R^{10}NC(O)$—$(CR^9R^{10})_t(CH_2)_m$—;

$R^5$ is a group of Formula (m):

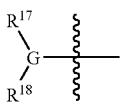

Formula (III)

$R^6$ and $R^{6a}$ are independently selected from hydrogen, fluoro, optionally substituted $C_{1-6}$alkyl, optionally-substituted aryl or optionally substituted aryl$C_{1-6}$alkyl, or $R^6$ and $R^{6a}$ taken together and the carbon atom to which they are attached form a carbocyclic ring of 3–7 atoms, or $R^6$ and $R^{6a}$ taken together and the carbon atom to which they are attached form a carbonyl group;

or when A is not a direct bond the group

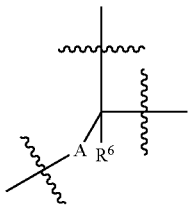

forms a carbocyclic ring of 3–7 carbon atoms or a heterocyclic ring containing one or more heteroatoms;
  or the group

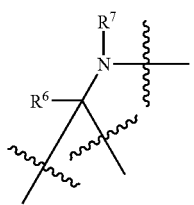

forms a heterocyclic ring containing 3–7 carbon atoms and one or more heteroatoms;

$R^7$ is selected from: hydrogen, optionally-substituted $C_{1-6}$alkyl, optionally-substituted aryl$C_{1-6}$alkyl, optionally-substituted aryl, optionally substituted heterocyclyl, optionally substituted heterocyclyl$C_{1-6}$alkyl, $R^9OC_{1-6}$alkyl-, $R^9R^{10}NC_{1-6}$alkyl-, $R^9R^{10}NC(O)C_{1-6}$alkyl, —$C(NR^9R^{10})$=NH;

or when $R^3$ is a group of Formula (IIc) or (IId) $R^7$ can also be of the formula —J—K—$R^8$;

$R^8$ is selected from:
(i) hydrogen, $C_{1-6}$alkyl, $C_{2-6}$alkenyl, $C_{2-6}$alkynyl, halo$C_{1-6}$alkyl, $C_{1-4}$alkoxy$C_{1-4}$alkyl, hydroxy, hydroxy$C_{1-6}$alkyl, cyano, N—$C_{1-4}$alkylamino, N,N-di-$C_{1-4}$alkylamino, $C_{1-6}$alkyl-$S(O_n)$—, —O—$R^b$, —$NR^bR^c$, —C(O)—$R^b$, —C(O)O—$R^b$, —$CONR^bR^c$, NH—C(O)—$R^b$ or —$S(O_n)NR^bR^c$,
where $R^b$ and $R^c$ are independently selected from hydrogen and $C_{1-4}$alkyl optionally substituted with hydroxy, amino, N—$C_{1-4}$alkylamino, N,N-di-$C_{1-4}$alkylamino, HO—$C_{2-4}$alkyl-NH— or HO—$C_{2-4}$alkyl-N($C_{1-4}$alkyl)-;
(ii) nitro when B is a group of Formula (IV) and X is CH and p is 0;
(iii) $C_{3-7}$cycloalkyl, aryl or aryl$C_{1-6}$alkyl each of which is optionally substituted by $R^{12}$, $R^{13}$ and $R^{14}$;
(iv) —(Q)-aryl, —(Q)-heterocyclyl, -aryl-(Q)-aryl, each of which is optionally substituted by $R^{12}$, $R^{13}$ and $R^{14}$
wherein —(Q)— is selected from E, F or a direct bond;
(v) heterocyclyl or heterocyclyl$C_{1-6}$alkyl each of which is optionally substituted by up to 4 substituents independently selected from $R^{12}$, $R^{13}$ and $R^{14}$;
(vi) a group selected from $R^{12}$, $R^{13}$ and $R^{14}$;

$R^9$ and $R^{10}$ are independently selected from: hydrogen, hydroxy, optionally substituted $C_{1-6}$alkyl, optionally substituted aryl, optionally substituted aryl$C_{1-6}$alkyl, an optionally substituted carbocyclic ring of 3–7 atoms, optionally substituted heterocyclyl, optionally substituted heterocyclyl$C_{1-6}$alkyl or $R^9$ and $R^{10}$ taken together can form an optionally substituted ring of 3–9 atoms or $R^9$ and $R^{10}$ taken together with the carbon atom to which they are attached form a carbonyl group;

$R^{11}$ is selected from: hydrogen, optionally substituted $C_{1-6}$alkyl, or $N(R^9R^{10})$;

$R^{12}$ is selected from: hydrogen, hydroxy, $R^{17}R^{18}N(CH_2)_{cc}$—, $R^{17}R^{18}NC(O)(CH_2)_{cc}$—, optionally substituted $C_{1-6}$alkyl-$C(O)N(R^9)(CH_2)_{cc}$—, $R^{17}R^{18}NC(O)N(R^9)(CH_2)_{cc}$—, $R^{17}R^{18}NC(O)O(CH_2)_{cc}$—, optionally substituted $C_{1-6}$alkyl-$OC(O)N(R^9)(CH_2)_{cc}$—, optionally substituted $C_{1-6}$alkyl-$SO_2N(R^9)$—, optionally substituted aryl-$SO_2N(R^9)$—, $C_{1-3}$perfluoroalkyl-$SO_2N(^9)$—; optionally substituted $C_{1-6}$alkyl-$N(R^9)SO_2$—, optionally substituted aryl-$N(R^9)SO_2$—, $C_{1-3}$perfluoroalkyl-$N(R^9)SO_2$— optionally substituted $C_{1-6}$alkanoyl-$N(R^9)SO_2$—; optionally substituted aryl-$C(O)N(R^9)SO_2$—, optionally substituted $C_{1-6}$alkyl-$S(O_n)$—, optionally substituted aryl-$S(O_n)$—, $C_{1-3}$perfluoroalkyl-, $C_{1-3}$perfluoroalkoxy, optionally substituted $C_{1-6}$alkoxy, carboxy, halo, nitro or cyano;

$R^{13}$ and $R^{14}$ are independently selected from: hydrogen, hydroxy, oxo, optionally substituted $C_{1-6}$alkyl, optionally substituted $C_{1-6}$alkanoyl, optionally substituted $C_{2-6}$alkenyl, cyano, nitro, $C_{1-3}$perfluoroalkyl-, $C_{1-3}$perfluoroalkoxy, optionally substituted aryl, optionally substituted aryl$C_{1-6}$alkyl, $R^9O(CH_2)_s$—, $R^9(O)O(CH_2)_s$—, $R^9OC(O)(CH_2)_s$—, $R^{16}S(O_n)(CH_2)_s$—, $R^9R^{10}NC(O)(CH_2)_s$— or halo;

$R^{15}$ is selected from: hydrogen, optionally substituted $C_{1-6}$alkyl, $R^{19}OC(O)$—, $R^9R^{10}NC(O)$—, $R^9C(O)$—, $R^9S(O_n)$—;

$R^{16}$ is selected from: hydrogen, $C_{1-6}$alkyl, $C_{1-3}$perfluoroalkyl or optionally-substituted aryl;

$R^{17}$ is independently selected from: hydrogen, hydroxy, cyano or optionally substituted $C_{1-6}$alkyl;

$R^{18}$ is a group of formula $R^{18a}$—$C(R^9R_{10})_{0-1}$— wherein $R^{18a}$ is selected from: $R^{19}OC(O)$—, $R^9R^{10}NC(O)$—, $R^9R^{10}N$—, $R^9C(O)$—, $R^9C(O)N(R^{10})$—, $R^9R^{10}NC(O)$—, $R^9R^{10}NC(O)N(R^{10})$—, $R^9SO_2N(R^{10})$—, $R^9R^{10}NSO_2N(R^{10})$—, $R^9C(O)O$—, $R^9OC(O)$—, $R^9R^{10}NC(O)O$—, $R^9O$—, $R^9S(O_n)$—, $R^9R^{10}NS(O_n)$—, hydrogen, optionally substituted $C_{1-6}$alkyl, optionally substituted heterocyclyl;

or $R^{17}$ and $R^{18}$ when taken together form an optionally substituted carbocyclic ring of 3–7 atoms or optionally substituted heterocyclyl;

$R^{19}$ is selected from: hydrogen, optionally substituted $C_{1-6}$alky, optionally substituted aryl, optionally substituted aryl$C_{1-6}$alkyl, optionally substituted $C_{3-7}$cycloalkyl, optionally substituted heterocyclyl or optionally substituted heterocyclyl$C_{1-6}$alkyl;

$R^{20}$ is selected from $R^{12}$ or $R^{13}$;

$R^{21}$ and $R^{22}$ are independently selected from hydrogen, optionally substituted $C_{1-6}$alkyl, optionally substituted $C_{3-7}$cycloalkyl, optionally substituted heterocyclyl, optionally substituted heterocyclyl$C_{1-6}$alkyl, optionally substituted $C_{3-6}$alkenyl, optionally substituted $C_{3-6}$alkynyl, —$(C_{1-5}$alkyl$)_{aa}$-S$(O_n)$—$(C_{1-5}$alkyl$)_{bb}$-; $R_9R^{10}NC_{2-6}$alkyl, $R^9OC_{2-6}$alkyl or $R^9R^{10}NC(O)C_{2-6}$alkyl, with the proviso that $R^9$ and $R^{10}$ independently or taken together are not optionally substituted aryl or optionally substituted aryl$C_{1-6}$alkyl; or $R^{21}$ and $R^{22}$ taken together form an optionally substituted non-aromatic heterocyclic ring;

A is selected from:
(i) a direct bond;
(ii) optionally-substituted $C_{1-5}$alkylene wherein the optional substituents are independently selected from: optionally-substituted $C_{1-6}$alkyl optionally-substituted aryl or optionally substituted aryl$C_{1-6}$alkyl;
(iii) a carbocyclic ring of 3–7 atoms;
(iv) a carbonyl group or —C(O)—C$(R^dR^d)$—, wherein $R^d$ is independently selected from hydrogen and $C_{1-2}$alkyl;

or when $R^3$ is a group of Formula (IIa) or (IIb), the group

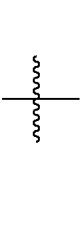

forms a heterocyclic ring containing 3–7 carbon atoms and one or more heteroatoms;

or when $R^3$ is a group of Formula (IIa), (IIb), (IIc) or (IId), the group

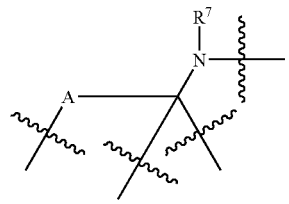

forms a heterocyclic ring containing 3–7 carbon atoms and one or more heteroatoms;

B is selected from:
(i) a direct bond;
(ii) a group of Formula (IV)

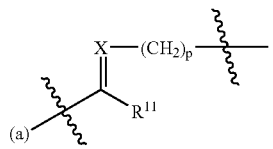

Formula (IV)

wherein:
X is selected from N, CH or a saturated heterocyclic ring;
wherein at position (a) Formula (IV) is attached to the nitrogen atom and the (CH$_2$)p group is attached to $R^8$; and (iii) a group independently selected from: optionally substituted $C_{1-6}$alkylene, optionally substituted $C_{3-7}$cycloalkyl, optionally substituted $C_{3-6}$alkenylene, optionally substituted $C_{3-6}$alkynyl, $C_{1-6}$alkoxy, $(C_{1-5}$alkyl$)_{aa}$-S$(O_n)$—$(C_{1-5}$alkyl$)_{bb}$-, $(C_{1-5}$alkyl$)_{aa}$-O—$(C_{1-5}$alkyl$)_{bb}$- or $(C_{1-5}$alkyl$)_{aa}$-N$(R^{15})$—$(C_{1-5}$alkyl$)_{bb}$, wherein $R^{15}$ and the $(C_{1-5}$alkyl$)_{aa}$ or $(C_{1-5}$alkyl$)_{bb}$ chain can be joined to form a ring;

or the group —B—$R^8$ represents a group of Formula (V)

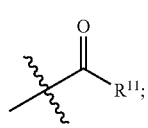

Formula (V)

or the group

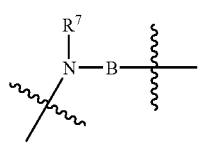

together forms an optionally substituted heterocyclic ring containing 4–7 carbons atoms;

or the group

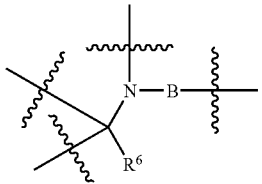

forms a heterocyclic ring containing 3–7 carbon atoms and one or more heteroatoms;

E is —O—, —S($O_n$), —C(O)—, —$NR^{15}$— or —C($^9R^{10}$)$_q$;

F is —E($CH_2$)$_r$— or —($CH_2$)$_r$E—;

G is selected from: hydrogen, halo, CN, $NO_2$, N, O, S($O_n$), C(O), C($R^9R^{10}$)$_t$, optionally substituted $C_{2-6}$alkenylene, optionally substituted $C_{2-6}$alkynylene, optionally substituted heterocyclyl or a direct bond to $R^{18}$, J is a group of the formula: —($CH_2$)$_s$—L—($CH_2$)$_s$— wherein when s is greater than 0, the alkylene group is optionally substituted, or the group

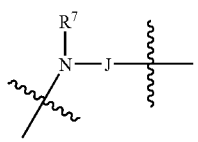

together forms an optionally substituted heterocyclic ring containing 4–7 carbons atoms;

K is selected from: a direct bond, —($CH_2$)$_{s1}$—, —($CH_2$)$_{s1}$—O—($CH_2$)$_{s2}$—, —($CH_2$)$_{s1}$—C(O)—($CH_2$)$_{s2}$—, —($CH_2$)$_{s1}$—S($O_n$)—($CH_2$)$_{s2}$—, —($CH_2$)$_{s1}$—N($R^{18}$)—($CH_2$)$_{s2}$—, —($CH_2$)$_{s1}$—C(O)N($R^9$)—($CH_2$)$_{s2}$—, —($CH_2$)$_{s1}$—N($R^9$)C(O)—($CH_2$)$_{s2}$—, —($CH_2$)$_{s1}$—N($R^9$)C(O)N($R^9$)—($CH_2$)$_{s2}$—, —($CH_2$)$_{s1}$—OC(O)—($CH_2$)$_{s2}$—, —($CH_2$)$_{s1}$—C(O)O—($CH_2$)$_{s2}$—, —($CH_2$)$_{s1}$—N($R^9$)C(O)O—($CH_2$)$_{s2}$—, —($CH_2$)$_{s1}$—OC(O)N($R^9$)—($CH_2$)$_{s2}$—, —($CH_2$)$_{s1}$—OS($O_n$)—($CH_2$)$_{s2}$—, or —($CH_2$)$_{s1}$—S($O_n$)—O—($CH_2$)$_{s2}$—, —($CH_2$)$_{s1}$—S(O)$_2$ N($R^9$)—($CH_2$)$_{s2}$—, —($CH_2$)$_{s1}$—N($R^9$)S(O)$_2$—($CH_2$)$_{s2}$—; wherein the —($CH_2$)$_{s1}$— and —($CH_2$)$_{s2}$— groups are independently optionally substituted by hydroxy or $C_{1-4}$alkyl;

L is selected from optionally substituted aryl or optionally substituted heterocyclyl;

m is an integer from 0 to 4;
n is an integer from 0 to 2;
p is an integer from 0 to 4;
q is an integer from 0 to 4;
r is an integer from 0 to 4;
s is an integer from 0 to 4;
s1 and s2 are independently selected from an integer from 0 to 4, and s1+s2 is less than or equal to 4; and
t is an integer from 0 to 4;
aa and bb are independently selected from 0 or 1;
cc is an integer from 0 to 2;
with the proviso that
(i) when G is hydrogen, halo, CN or $NO_2$, then $R^{17}$ and $R^{18}$ are both absent;

(ii) when G is O, S($O_n$), C(O) or C($R^{11}R^{12}$)$_t$ then G is substituted by a single group independently selected from the definition of $R^{17}$ or $R^{18}$ and when G is a direct bond to $R^{18}$ then G is substituted by a single group selected from $R^{18}$; and (iii) when $R^3$ is a group of Formula (IIb), B is a group of Formula (IV), $R^8$ is selected from group (i) or (ii) above, $R^{11}$ is a group of the formula N($R^{10}R^{11}$) and $R^1$, $R^2$ and $R^5$ are as defined above then $R^4$ cannot be hydrogen;

or a salt, pro-drug or solvate thereof.

According to a further feature of the first aspect of the invention there is provided a compound of Formula (Ia),

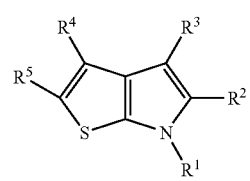

Formula (Ia)

wherein:
$R^1$ is selected from: hydrogen, optionally-substituted $C_{1-6}$alkyl, optionally substituted $C_{1-6}$alkanoyl, optionally substituted aryl or optionally-substituted aryl$C_{1-6}$alkyl;

$R^2$ is an optionally-substituted mono or bi-cyclic aromatic ring;

$R^3$ is selected from a group of Formula (IIa) to Formula (IIf):

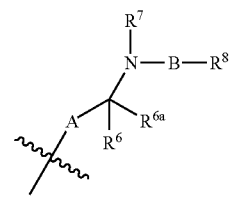

Formula (IIa)

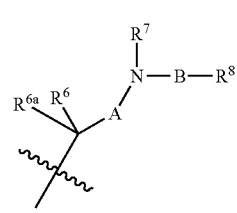

Formula (IIb)

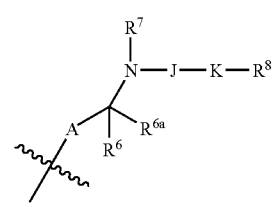

Formula (IIc)

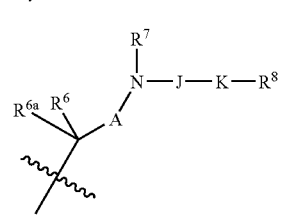

Formula (IId)

-continued

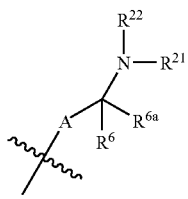

Formula (IIe)

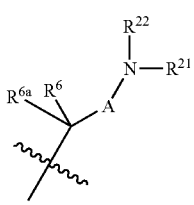

Formula (IIf)

$R^4$ is selected from: hydrogen, optionally substituted $C_{1-6}$alkyl, optionally substituted aryl, $C_{1-3}$perfluoroalkyl, cyano, nitro, halo, $R^9O(CH_2)_m$—, $R^9C(O)N(R^{10})$—, $R^9R^{10}NC(O)N(R^{10})$—, $R^9S(O_n)$— or or $R^9R^{10}NC(O)$—$(CR^9R^{10})_r$—;

$R^5$ is a group of Formula (III):

Formula (III)

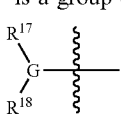

$R^6$ and $R^{6a}$ are independently selected from hydrogen, optionally substituted $C_{1-6}$alkyl, optionally-substituted aryl or optionally substituted aryl$C_{1-6}$alkyl, or $R^6$ and $R^{6a}$ taken together and the carbon atom to which they are attached form a carbocyclic ring of 3–7 atoms, or $R^6$ and $R^{6a}$ taken together and the carbon atom to which they are attached form a carbonyl group;

or when A is not a direct bond the group

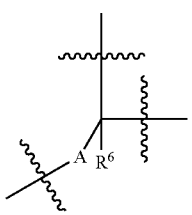

forms a carbocyclic ring of 3–7 carbon atoms or a heterocyclic ring containing one or more heteroatoms;

or the group

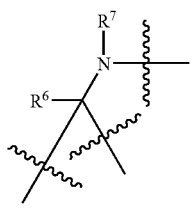

forms a heterocyclic ring containing 3–7 carbon atoms and one or more heteroatoms;

$R^7$ is selected from: hydrogen, optionally-substituted $C_{1-6}$alkyl, optionally-substituted aryl$C_{1-6}$alkyl, optionally-substituted aryl, optionally substituted heterocyclyl, optionally substituted heterocyclyl$C_{1-6}$alkyl, $R^9OC_{1-6}$alkyl-, $R^9R^{10}NC_{1-6}$alkyl-, $R^9R^{10}NC(O)C_{1-6}$alkyl, —$C(NR^9R^{10})$=NH;

or when $R^3$ is a group of Formula (IIc) or (IId) $R^7$ is of the formula —J—K—$R^8$;

$R^8$ is selected from:

(i) hydrogen, $C_{1-6}$alkyl, $C_{2-6}$alkenyl, $C_{2-6}$alkynyl, halo$C_{1-6}$alkyl, $C_{1-4}$alkoxy$C_{1-4}$alkyl, hydroxy, hydroxy$C_{1-6}$alkyl, cyano, N—$C_{1-4}$alkylamino, N,N-di-$C_{1-4}$alkylamino, $C_{1-4}$alkyl-$S(O_n)$—, —O—$R^b$, —$NR^bR^c$, —$C(O)$—$R^b$, —$C(O)O$—$R^b$, —$CONR^bR^c$ or NH—$C(O)$—$R^b$, where $R^b$ and $R^c$ are independently selected from hydrogen and $C_{1-4}$alkyl optionally substituted with hydroxy, amino, N—$C_{1-4}$alkylamino, N,N-di-$C_{1-4}$alkylamino, HO—$C_{2-4}$alkyl-NH— or HO—$C_{2-4}$alkyl-N($C_{1-4}$alkyl)-;

(ii) nitro when B is a group of Formula (IV) and X is CH and p is 0;

(iii) $C_{3-7}$cycloalkyl, aryl or aryl$C_{1-6}$alkyl each of which is optionally substituted by $R^{12}$, $R^{13}$ and $R^{14}$;

(iv) —(Q)-aryl, —(Q)-heterocyclyl, -aryl-(Q)-aryl, each of which is optionally substituted by $R^{12}$, $R^{13}$ and $R^{14}$ wherein —(Q)— is selected from E, F or a direct bond;

(v) heterocyclyl or heterocyclyl$C_{1-6}$alkyl each of which is optionally substituted by $R^{12}$, $R^{13}$ and $R^{14}$;

(vi) a group selected from $R^{12}$, $R^{13}$ and $R^{14}$;

$R^9$ and $R^{10}$ are independently selected from: hydrogen, hydroxy, optionally substituted $C_{1-6}$alkyl, optionally substituted aryl, optionally substituted aryl$C_{1-6}$alkyl, an optionally substituted carbocyclic ring of 3–7 atoms, optionally substituted heterocyclyl, optionally substituted heterocyclyl$C_{1-6}$alkyl or $R^9$ and $R^{10}$ taken together can form an optionally substituted ring of 3–9 atoms or $R^9$ and $R^{10}$ taken together with the carbon atom to which they are attached form a carbonyl group;

$R^{11}$ is selected from: hydrogen, optionally substituted $C_{1-6}$alkyl, or $N(R^9R^{10})$;

$R^{12}$ is selected from: hydrogen, hydroxy, $R^{17}R^{18}N$—, optionally substituted $C_{1-6}$alkyl-$SO_2N(R^9)$—, optionally substituted aryl-$SO_2N(F^9)$—, $C_{1-3}$perfluoroalkyl-$SO_2N(R^9)$—; optionally substituted $C_{1-6}$alkyl-$N(R^9)SO_2$—, optionally substituted aryl-$N(R^9)SO_2$—, $C_{1-3}$perfluoroalkyl-$N(R^9)SO_2$— optionally substituted $C_{1-6}$alkanoyl-$N(R^9)SO_2$—; optionally substituted aryl-$C(O)N(R^9)SO_2$—, optionally substituted $C_{1-6}$alkyl-$S(O_n)$—, optionally substituted aryl-$S(O_n)$—, $C_{1-3}$perfluoroalkyl-, $C_{1-3}$perfluoroalkoxy, optionally substituted $C_{1-6}$alkoxy, carboxy, halo, nitro or cyano;

$R^{13}$ and $R^{14}$ are independently selected from: hydrogen, optionally substituted $C_{1-6}$alkyl, optionally substituted $C_{2-6}$alkenyl, cyano, nitro, $C_{1-3}$perfluoroalkyl-, $C_{1-3}$perfluoroalkoxy, optionally substituted aryl, optionally substituted aryl$C_{1-6}$alkyl, $R^9O(CH_2)_s$—, $R^9(O)O(CH_2)_s$—, $R^9OC(O)(CH_2)_s$—, $R^{16}S(O_n)(CH_2)_s$—, $R^9R^{10}NC(O)(CH_2)_s$— or halo;

$R^{15}$ is selected from: hydrogen, optionally substituted $C_{1-6}$alkyl, $R^{19}OC(O)$—, $R^9R^{10}NC(O)$—, $R^9C(O)$—, $R^9S(O_n)$—;

$R^{16}$ is selected from: hydrogen, $C_{1-6}$alkyl, $C_{1-3}$perfluoroalkyl or optionally-substituted aryl;

$R^{17}$ is independently selected from: hydrogen, hydroxy, cyano or optionally substituted $C_{1-6}$alkyl;

$R^{18}$ is a group of formula $R^{18a}$—C($R^9R^{10}$)$_{0-1}$— wherein $R_{18a}$ is selected from: $R^{19}OC(O)$—, $R^9R^{10}NC(O)$—, $R^9R^{10}N$—, $R^9C(O)$—, $R^9C(O)N(R^{10})$—, $R^9R^{10}NC(O)$—, $R^9R^{10}NC(O)N(R^{10})$—, $R^9SO_2N(R^{10})$—, $R^9R^{10}NSO_2N(R^{10})$—, $R^9C(O)O$—, $R^9OC(O)$—, $R^9R^{10}NC(O)O$—, $R^9O$—, $R^9S(O_n)$—, $R^9R^{10}NS(O_n)$—, optionally substituted $C_{1-6}$alkyl, optionally substituted heterocyclyl;

or $R^{17}$ and $R^{18}$ when taken together form an optionally substituted carbocyclic ring of 3–7 atoms or optionally substituted heterocyclyl;

$R^{19}$ is selected from: hydrogen, optionally substituted $C_{1-6}$alky, optionally substituted aryl, optionally substituted aryl$C_{1-6}$alkyl, optionally substituted $C_{3-7}$cycloalkyl, optionally substituted heterocyclyl or optionally substituted heterocyclyl$C_{1-6}$alkyl;

$R^{20}$ is selected from $R^{12}$ or $R^{13}$;

$R^{21}$ and $R^{22}$ are independently selected from hydrogen, optionally substituted $C_{1-6}$alkyl, optionally substituted $C_{3-7}$cycloalkyl, optionally substituted heterocyclyl, optionally substituted heterocyclyl$C_{1-6}$alkyl, optionally substituted $C_{3-6}$alkenyl, optionally substituted $C_{3-6}$alkyl, —($C_{1-5}$alkyl)$_{aa}$-S(O$_n$)—($C_{1-5}$alkyl)$_{bb}$-; $R^9R^{10}NC_{2-6}$alkyl, $R^9OC_{2-6}$alkyl or $R^9R^{10}NC(O)C_{2-6}$alkyl, with the proviso that $R^9$ and $R^{10}$ independently or taken together are not optionally substituted aryl or optionally substituted aryl$C_{1-6}$alkyl; or $R^{21}$ and $R^{22}$ taken together form an optionally substituted non-aromatic heterocyclic ring;

A is selected from:
(i) a direct bond;
(ii) optionally-substituted $C_{1-5}$alkylene wherein the optional substituents are independently selected from: optionally-substituted $C_{1-6}$alkyl optionally-substituted aryl, optionally substituted aryl$C_{1-6}$alkyl or substituted aryl$C_{1-6}$alkyl;
(iii) a carbocyclic ring of 3–7 atoms;
(iv) a carbonyl group;

or when $R^3$ is a group of Formula (IIa) or (IIb), the group

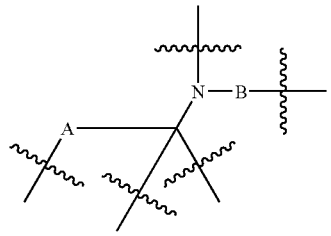

forms a heterocyclic ring containing 3–7 carbon atoms and one or more heteroatoms;

or when $R^3$ is a group of Formula (IIa), (IIb), (IIc) or (IId), the group

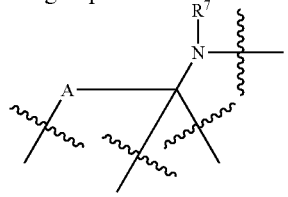

forms a heterocyclic ring containing 3–7 carbon atoms and one or more heteroatoms;

B is selected from:
(i) a direct bond;

(ii) a group of Formula (IV)

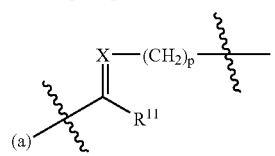

Formula (IV)

wherein:
X is selected from N, CH or a saturated heterocyclic ring;
wherein at position (a) Formula (IV) is attached to the nitrogen atom and the (CH$_2$)p group is attached to $R^8$; and (iii) a group independently selected from: optionally substituted $C_{1-6}$alkylene, optionally substituted $C_{3-7}$cycloalkyl, optionally substituted $C_{3-6}$alkenylene, optionally substituted $C_{3-6}$alkynyl, $C_{1-6}$alkoxy, ($C_{1-5}$alkyl)$_{aa}$-S(O$_n$)—($C_{1-5}$alkyl)$_{bb}$-, ($C_{1-5}$alkyl)$_{aa}$-O—($C_{1-5}$alkyl)$_{bb}$- or ($C_{1-5}$alkyl)$_{aa}$-N($R^{15}$)—($C_{1-5}$alkyl)$_{bb}$,
wherein $R^{15}$ and the ($C_{1-5}$alkyl)$_{aa}$ or ($C_{1-5}$alkyl)$_{bb}$ chain can be joined to form a ring;

or the group —B—$R^8$ represents a group of Formula (V)

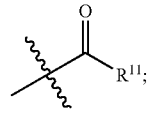

Formula (V)

or the group

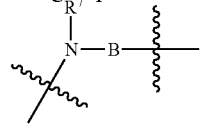

together forms a heterocyclic ring containing 5–7 carbons atoms;

or the group

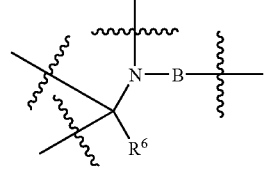

forms a heterocyclic ring containing 3–7 carbon atoms and one or more heteroatoms;

E is —O—, —S(O$_n$), —C(O)—, —NR$^{15}$— or —C($R^9R^{10}$)$_q$;

F is —E(CH$_2$)$_r$— or —(CH$_2$)$_r$E—;

G is selected from: hydrogen, halo, CN, NO$_2$, N, O, S(O$_n$), C(O), C($R^9R^{10}$)$_t$, optionally substituted $C_{2-6}$alkenylene, optionally substituted $C_{2-6}$alkynylene, optionally substituted heterocyclyl or a direct bond to $R^{18}$, J is a group of the formula: —(CH$_2$)$_s$—L—(CH$_2$)$_s$— wherein when s is greater than 0, the alkylene group is optionally substituted K is selected from: a direct bond, —O—(CH$_2$)$_s$—, —C(O)—(CH$_2$)$_s$—, —S(O$_n$)—(CH$_2$)$_s$—, —N($R^{18}$)—(CH$_2$)$_s$—, —OC(O)—(CH$_2$)$_s$—, —C(O)O—(CH$_2$)$_s$—, —OS(O$_n$)—(CH$_2$)$_s$—, or —S(O$_n$)—O—(CH$_2$)$_s$—;

L is selected from optionally substituted aryl or optionally substituted heterocyclyl;
n is an integer between 0 and 2;
p is an integer between 0 and 4;
q is an integer between 0 and 4;
r is an integer between 0 and 4;
s is an integer between 0 and 4; and
t is an integer between 0 and 4;
aa and bb are independently selected from 0 or 1
with the proviso that
  (i) when G is hydrogen, halo, CN or $NO_2$, then $R^{17}$ and $R^{18}$ are both absent;
  (ii) when G is O, $S(O_n)$, C(O) or $C(R^{11}R^{12})_r$ then G is substituted by a single group independently selected from the definition of $R^{17}$ or $R^{18}$ and when G is a direct bond to $R^{18}$ then G is substituted by a single group selected from $R^{18}$; and
or a salt, pro-drug or solvate thereof.

According to a further feature of the first aspect of the invention there is provided a pharmaceutical formulation comprising a compound of Formula (I) or Formula (Ia), or salt, pro-drug or solvate thereof, and a pharmaceutically acceptable diluent or carrier.

According to a further feature of the first aspect of the invention there is provided the following uses of a compound of Formula (I) or Formula (Ia), or salt, pro-drug or solvate thereof:
(a) the use in the manufacture of a medicament for antagonising gonadotropin releasing hormone activity;
(b) the use in the manufacture of a medicament for administration to a patient, for reducing the secretion of luteinizing hormone by the pituitary gland of the patient; and
(c) the use in the manufacture of a medicament for administration to a patient, for therapeutically treating and/or preventing a sex hormone related condition in the patient, preferably a sex hormone related condition selected from prostate cancer and pre-menopausal breast cancer.

According to a further aspect of the invention there is provided a method of antagonising gonadotropin releasing hormone activity in a patient, comprising administering a compound of Formula (I) or Formula (Ia), or salt, pro-drug or solvate thereof, to a patient.

Whilst pharmaceutically-acceptable salts of compounds of the invention are preferred, other non-pharmaceutically-acceptable salts of compounds of the invention may also be useful, for example in the preparation of pharmaceutically-acceptable salts of compounds of the invention.

Whilst the invention comprises compounds of the invention, and salts, pro-drugs or solvates thereof, in a further embodiment of the invention, the invention comprises compounds of the invention and salts thereof.

In the present specification, unless otherwise indicated, an alkyl, alkylene, alkenyl or alkynyl moiety may be linear or branched. The term "alkylene" refers to the group —$CH_2$—. Thus, $C_8$ alkylene for example is —$(CH_2)_8$—.

The term 'propylene' refers to trimethylene and the branched alkyl chains —CH($CH_3$)$CH_2$— and $CH_2$—CH($CH_3$)—. The straight chain propylene di-radcial is preferred, i.e. —$CH_2CH_2CH_2$—. Specific propylene radicals refer to the particular structure, thus the term, propyl-2-ene refers to the group —$CH_2$—CH($CH_3$)—. Similar notation is used for other divalent alkyl chains such as butylene.

The term '2-propenyl' refers to the group —$CH_2$—CH=CH—.

The term "aryl" refers to phenyl or naphthyl.
The term "carbamoyl" refers to the group —C(O)$NH_2$.
The term "halo" refers to fluoro, chloro, bromo or iodo.

The term "heterocyclyl" or "heterocyclic ring" refers to a 4–12 membered, preferably 5–10 membered, aromatic mono or bicyclic ring or a 4–12 membered, preferably 5–10 membered, saturated or partially saturated mono or bicyclic ring, said aromatic, saturated or partially unsaturated rings containing up to 5 heteroatoms independently selected from nitrogen, oxygen or sulphur, linked via ring carbon atoms or ring nitrogen atoms where a bond from a nitrogen is allowed, for example no bond is possible to the nitrogen of a pyridine ring, but a bond is possible through the 1-nitrogen of a pyrazole ring. Examples of 5- or 6-membered aromatic heterocyclic rings include pyrrolyl, furanyl, imidazolyl, triazolyl, pyrazinyl, pyrimidinyl, pyridazinyl, pyridinyl, isoxazolyl, oxazolyl, 1,2,4 oxadiazolyl, isothiazolyl, thiazolyl and thienyl. A 9 or 10 membered bicyclic aromatic heterocyclic ring is an aromatic bicyclic ring system comprising a 6-membered ring fused to either a 5 membered ring or another 6 membered ring. Examples of 5/6 and 6/6 bicyclic ring systems include benzofuranyl, benzimidazolyl, benzthiophenyl, benzthiazolyl, benzisothiazolyl, benzoxazolyl, benzisoxazolyl, indolyl, pyridoimidazolyl, pyrimidoimidazolyl, quinolinyl, isoquinolinyl, quinoxalinyl, quinazolinyl, phthalazinyl, cinnolinyl and naphthyridinyl. Examples of saturated or partially saturated heterocyclic rings include pyrrolinyl, pyrrolidinyl, morpholinyl, piperidinyl, piperazinyl, dihydropyridinyl and dihydropyrimidinyl. This definition further comprises sulphur-containing rings wherein the sulphur atom has been oxidised to an S(O) or S(O2) group.

The term "aromatic ring" refers to a 5–10 membered aromatic mono or bicyclic ring 30 optionally containing up to 5 heteroatoms independently selected from nitrogen, oxygen or sulphur. Examples of such "aromatic rings" include: phenyl, pyrrolyl, furanyl, imidazolyl, triazolyl, pyrazinyl, pyrimidinyl, pyridazinyl, pyridinyl, isoxazolyl, oxazolyl, 1,2,4 oxadiazolyl, isothiazolyl, thiazolyl and thienyl. Preferred aromatic rings include phenyl, thienyl and pyridyl.

The symbol

denotes where the respective group is linked to the remainder of the molecule.

For the avoidance of doubt where two groups or integers appear within the same definition, for example, —$(CH_2)_s$—L—$(CH_2)_s$— or $R^9R^{10}NSO_2N(R^{10})$—, then these can be the same of different.

For the avoidance of doubt, where several groups together form a ring, for example:

'the group

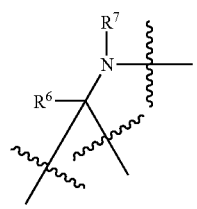

forms a heterocyclic ring containing 3–7 carbon atoms and one or more heteroatoms', then the groups shown cyclises to form a ring, i.e

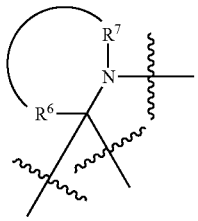

the component of which are defined by the definitions of the groups which form the ring, thus in the above example the ring would include a nitrogen atom. For example in Example 2 this group forms a piperazine ring.

The term $C_{1-3}$perfluoroalkyl refers to a $C_{1-3}$alkyl chain in which all hydrogens have been replaced with a fluorine atom. Examples of $C_{1-3}$perfluoroalkyl include trifluoromethyl, pentafluoroethyl and 1-trifluoromethyl-1,2,2,2-tetrafluoroethyl-. Preferably $C_{1-3}$perfluoroalkyl is trifluromethyl.

Examples of $C_{1-8}$alkyl include: methyl, ethyl, propyl, isopropyl, butyl, iso-butyl, tert-butyl and 2-methyl-pentyl; example of $C_{1-8}$alkylene include: methylene, ethylene and 2-methyl-propylene; examples of $C_{1-6}$alkenyl include alkyl (2-propenyl) and 2-butenyl, examples of $C_{1-6}$alkynyl 2-propynyl and 3-butynyl, examples of halo$C_{1-6}$alkyl include fluoroethyl, chloropropyl and bromobutyl, examples of hydroxy$C_{1-6}$alkyl include hydroxymethyl, hydroxyethyl and hydroxybutyl, examples of $C_{1-8}$alkoxy include methoxy, ethoxy and butyloxy; examples of $C_{1-4}$alkoxy$C_{1-4}$alkyl include methoxyethyl, propoxybutyl and propoxymethyl, examples of $C_{1-6}$alkanoyl incude formyl, ethanoyl, propanoyl or pentanoyl, examples of N—$C_{1-4}$alkylamino include N-methylamino and N-ethylamino; examples of N,N-di-$C_{1-4}$alkylamino include N,N-dimethylaminoethyl, N,N-di-methylaminopropyl and N,N-dipropylaminoethyl, examples of HO-$C_{2-4}$alkyl-NH include hydroxymethylamino hydroxyethylamino and hydroxypropyamino, examples of HO-$C_{2-4}$alkyl-N($C_{1-4}$alkyl) include N-methyl-hydroxymethylamino, N-ethyl-hydroxyethylamino, and N-propyl-hydroxypropyamino, examples of $C_{1-6}$alkyl-S$(O_n)$—methylthio, methylsulphinyl, ethylsulphinyl, ethylsulphonyl and propylsulphonyl, include examples of aryl$C_{1-6}$alkyl include benzyl, phenethyl and phenylbutyl, examples of heterocyclyl$C_{1-6}$alkyl include pyrrolidin-1-yl ethyl, imidazolylethyl, pyridylmethyl and pyrimidinylethyl.

It is to be understood that, insofar as certain of the compounds of the invention may exist in optically active or racemic forms by virtue of one or more asymmetric carbon atoms, the invention includes in its definition any such optically active or racemic form which possesses the property of antagonizing gonadotropin releasing hormone (GnRH) activity. The synthesis of optically active forms may be carried out by standard techniques of organic chemistry well known in the art, for example by synthesis from optically active starting materials or by resolution of a racemic form. Similarly, activity of these compounds may be evaluated using the standard laboratory techniques referred to hereinafter.

The invention also relates to any and all tautomeric forms of the compounds of the different features of the invention that possess the property of antagonizing gonadotropin releasing hormone (GnRH) activity.

It will also be understood that certain compounds of the present invention may exist in solvated, for example hydrated, as well as unsolvated forms. It is to be understood that the present invention encompasses all such solvated forms which possess the property of antagonizing gonadotropin releasing hormone (GnRH) activity.

Preferred compounds of Formula (I) are those wherein any one of the following or any combination of the following apply.

Preferably $R^1$ is selected from hydrogen or optionally substituted $C_{1-6}$alkyl. More preferably $R^1$ represents hydrogen or unsubstituted $C_{1-6}$alkyl. Yet more preferably $R^1$ represents hydrogen, methyl, ethyl or tert-butyl. Most preferably $R^1$ represents hydrogen.

Preferably optional substituents on $R^1$ are independently selected from: optionally-substituted $C_{1-6}$alkyl, optionally-substituted $C_{2-6}$alkenyl, cyano, nitro, $C_{1-3}$perfluoroalkyl, $C_{1-3}$perfluoroalkoxy, optionally-substituted aryl, optionally-substituted aryl$C_{1-6}$alkyl, $R^9O(CH_2)_v$—; $R^9C(O)O(CH_2)_v$—, $R^9OC(O)(CH_2)_v$—, $R^{16}S(O_n)(CH_2)_v$—, $R^9R^{10}NC(O)(CH_2)_v$—, or halo wherein v is an integer between 0 and 4, and where 2 optional substituents are present together they can optionally form a $C_{3-7}$carbocyclic ring or a heterocyclic ring.

Preferably $R^2$ is an optionally substituted monocyclic aromatic ring structure. Most preferably $R^2$ represents optionally substituted phenyl.

Preferably optional substituents on $R^2$ are independently selected from: optionally substituted $C_{1-6}$alkyl, optionally substituted $C_{2-6}$alkenyl, cyano, nitro, $C_{1-3}$perfluoroalkyl, $C_{1-3}$perfluoroalkoxy, optionally substituted aryl, optionally substituted aryl$C_{1-6}$alkyl, $R^9O(CH_2)_p$—, $R^9C(O)O(CH_2)_w$—, $R^9OC(O)(CH_2)_w$—, $R^{16}S(O_n)(CH_2)_w$—, $R^9R^{10}NC(O)(CH_2)_w$—, $R^9R^{10}N$— or halo; wherein w is an integer between 0 and 4 and $R^9$ and $R^{10}$ are as defined above. Further preferably the optional substituents on $R^2$ are independently selected from cyano, $R^eR^fN$—, optionally substituted $C_{1-6}$alkyl (preferably, $C_{1-4}$alkyl, eg, methyl or ethyl), optionally substituted $C_{1-6}$alkoxy (preferably, $C_{1-4}$alkoxy, eg, methoxy, ethoxy or tert-butoxy) or halo (eg, F, Br or Cl) wherein $R^e$ and $R^f$ are independently selected from hydrogen, $C_{1-6}$alkyl or aryl. Yet further preferably optional substituents on $R^2$ are independently selected from methyl, ethyl, methoxy, ethoxy, tert-butoxy, F or Cl. Most preferably optional substituents on $R^2$ are independently selected from methyl, F or Cl. Preferably $R^2$ bears 1, 2 or 3 substituents.

Most preferably $R^2$ represents

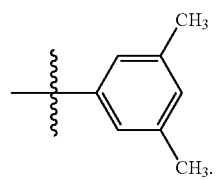

Preferably $R^3$ is selected from a group of Formula (IIa), Formula (IIb), Formula (IIc) or Formula (IId). Most preferably $R^3$ is a group of Formula (IIc) or Formula (IId).

Preferably $R^4$ is selected from hydrogen or $C_{1-4}$alkyl. Most preferably $R^4$ is hydrogen. Preferably the group of Formula (III):

Formula (III)

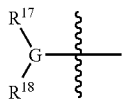

is selected from one of a group of Formula III-a to III-l;

III-a
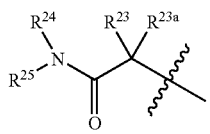

III-b
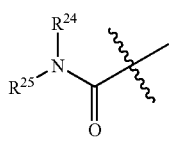

III-c
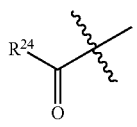

III-d
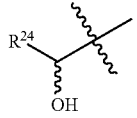

III-e
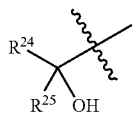

III-f
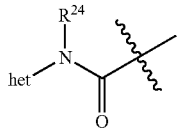

III-g
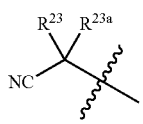

III-h
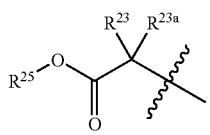

III-i
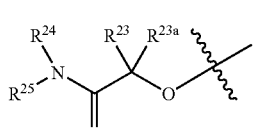

III-j
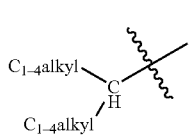

-continued

III-k
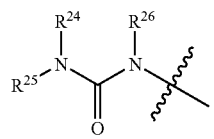

III-l
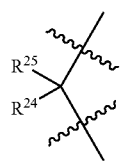

wherein:

het represents an optionally substituted 3- to 8-membered heterocyclic ring containing from 1 to 4 heteroatoms independently selected from O, N and S;

$R^{23}$ and $R^{23a}$ are independently selected from:
(i) hydrogen, fluoro or optionally substituted $C_{1-8}$alkyl; or
(ii) $R^{23}$ and $R^{23a}$ together with the carbon to which they are attached form an optionally substituted 3 to 7-membered cycloalkyl ring;

$R^{24}$ and $R^{25}$ are selected from:
(i) $R^{24}$ selected from hydrogen; optionally substituted $C_{1-8}$alkyl; optionally substituted aryl; —$R^d$—Ar, where $R^d$ represents $C_{1-8}$alkylene and Ar represents optionally substituted aryl; and optionally substituted 3- to 8-membered heterocyclic ring optionally containing from 1 to 3 further heteroatoms independently selected from O, N and S; and $R^{25}$ is selected from hydrogen; optionally substituted $C_{1-8}$alkyl and optionally substituted aryl;
(ii) wherein the group of Formula (III) represents a group of Formula III-a, III-b or III-i, then the group $NR^{24}$(—$R^{25}$) represents an optionally substituted 3- to 8-membered heterocyclic ring optionally containing from 1 to 3 further heteroatoms independently selected from O, N and S; or
(iii) wherein the group of Formula (I) represents structure III-e, represents an optionally substituted 3- to 8-membered heterocyclic ring optionally containing from 1 to 4 heteroatoms independently selected from O, N and S; $R^{26}$ is selected from hydrogen or $C_{1-4}$alkyl. Preferably $R^{26}$ is selected from hydrogen, methyl or ethyl. Most preferably $R^{26}$ is hydrogen.

Preferably the group of Formula (III) is selected from a group of Formula III-a, III-g, III-h, or III-i:

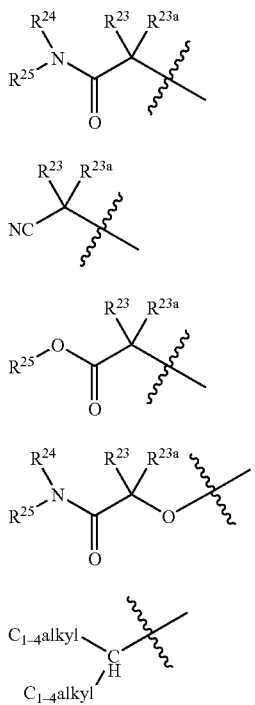

wherein $R^{23}$, $R^{23a}$, $R^{24}$ and $R^{25}$ are as defined above.

Further preferably the group of Formula (III) is selected from one of the following groups:

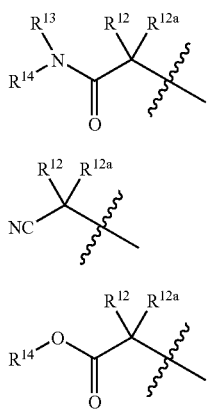

wherein $R^{23}$, $R^{23a}$, $R^{24}$ and $R^{25}$ are as defined above.

Yet further preferably the group of Formula (III) is selected from one of the following groups:

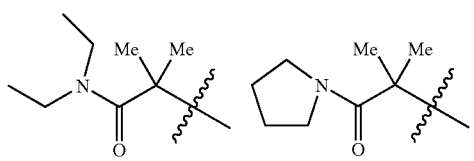

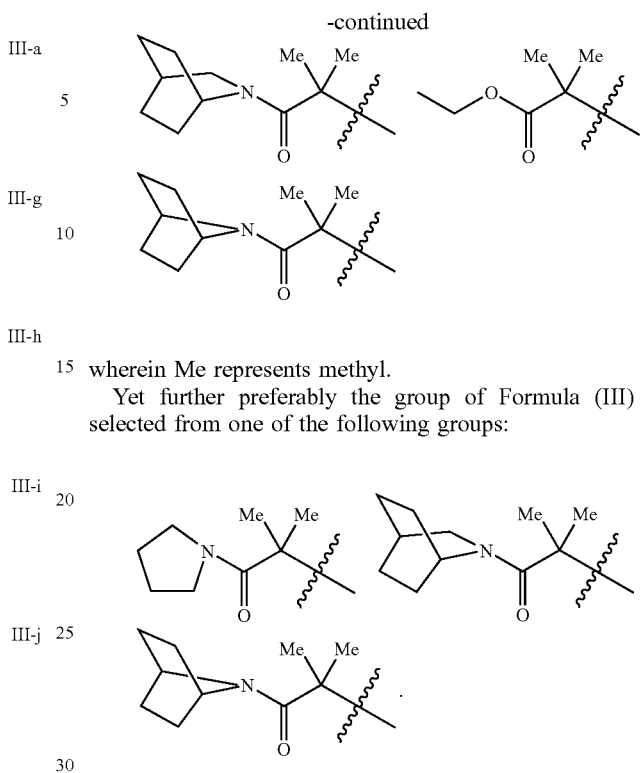

wherein Me represents methyl.

Yet further preferably the group of Formula (III) is selected from one of the following groups:

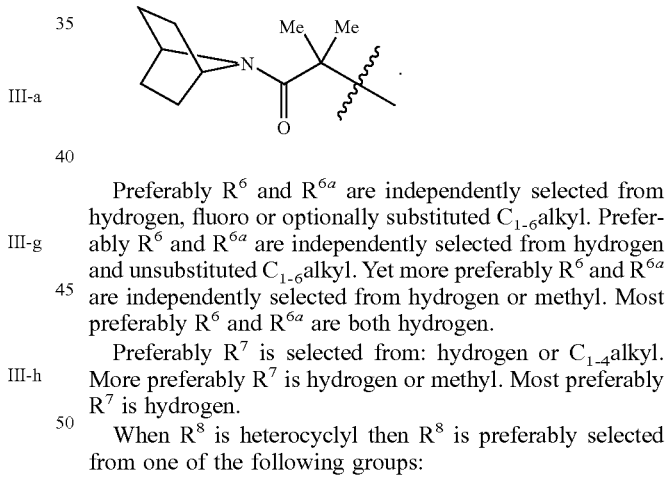

Most preferably the group of Formula (III) is:

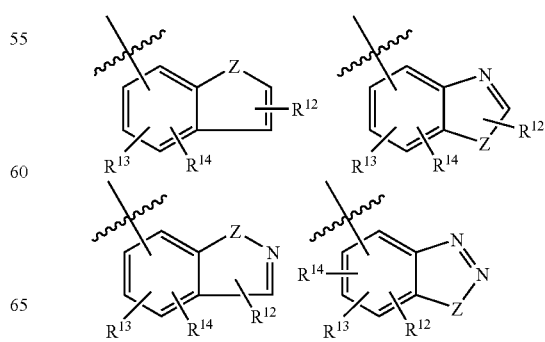

Preferably $R^6$ and $R^{6a}$ are independently selected from hydrogen, fluoro or optionally substituted $C_{1-6}$alkyl. Preferably $R^6$ and $R^{6a}$ are independently selected from hydrogen and unsubstituted $C_{1-6}$alkyl. Yet more preferably $R^6$ and $R^{6a}$ are independently selected from hydrogen or methyl. Most preferably $R^6$ and $R^{6a}$ are both hydrogen.

Preferably $R^7$ is selected from: hydrogen or $C_{1-4}$alkyl. More preferably $R^7$ is hydrogen or methyl. Most preferably $R^7$ is hydrogen.

When $R^8$ is heterocyclyl then $R^8$ is preferably selected from one of the following groups:

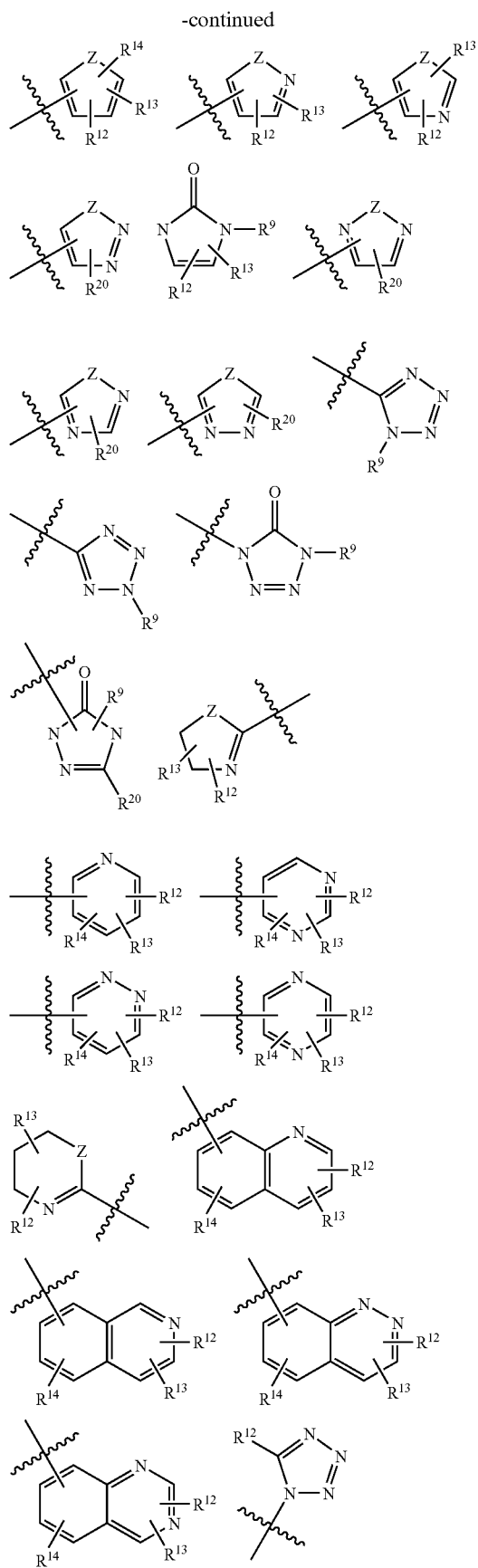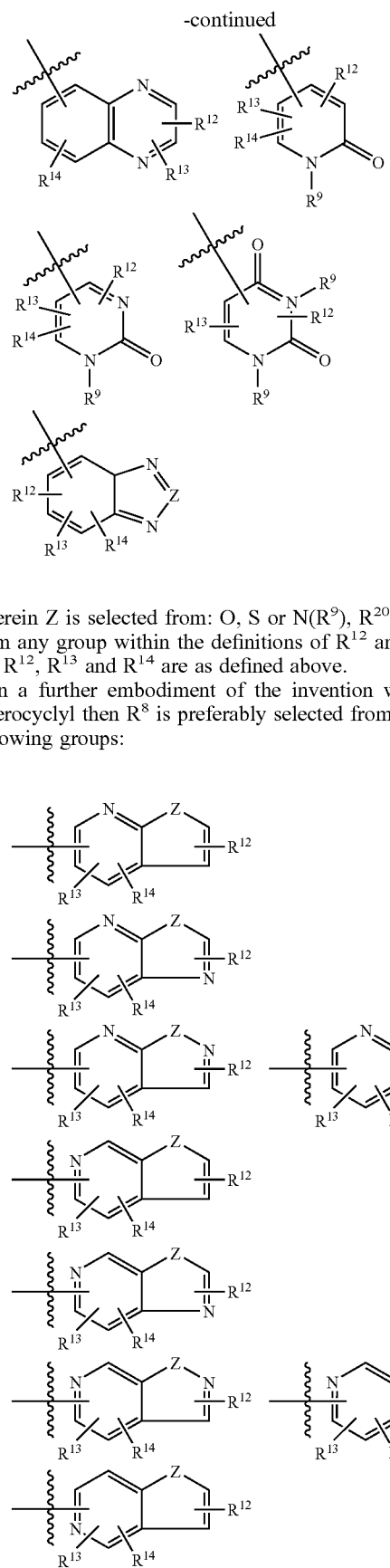
wherein Z is selected from: O, S or N(R$^9$), R$^{20}$ is selected form any group within the definitions of R$^{12}$ and R$^{13}$, and R$^9$, R$^{12}$, R$^{13}$ and R$^{14}$ are as defined above.
In a further embodiment of the invention when R$^8$ is heterocyclyl then R$^8$ is preferably selected from one of the following groups:

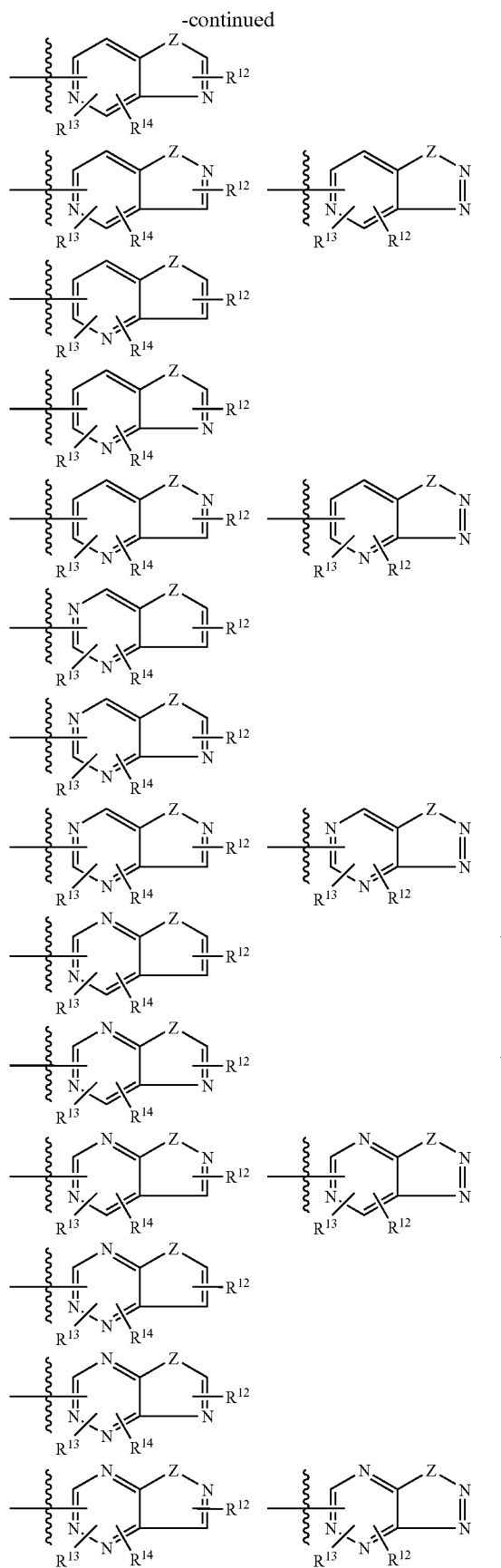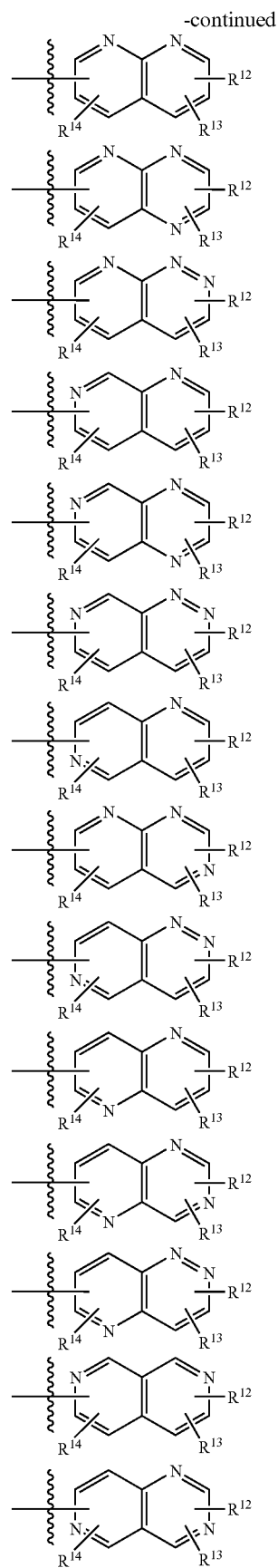

-continued

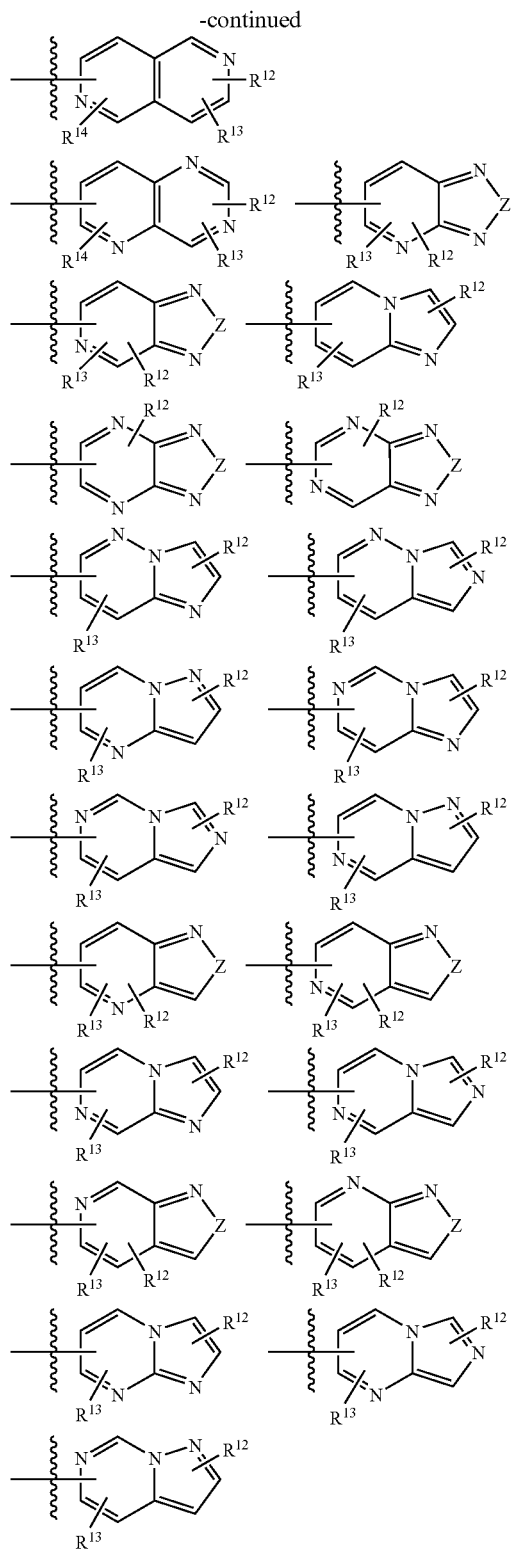

wherein Z is selected from: O, S or N(R⁹) and R⁹, R¹² and R¹³ are as defined above.

When R⁸ is aryl or aryl-(Q)-aryl optionally substituted by R¹², R¹³ and R¹⁴, R⁸ is preferably selected one of the following groups:

wherein D is selected from group E, group F or a direct bond;

Preferably R⁸ is selected from
(i) hydrogen, $C_{1-6}$alkyl, $C_{2-6}$alkenyl, halo$C_{1-6}$alkyl, hydroxy, cyano, $C_{1-6}$alkylS(O$_n$)—, —O—R$^b$, $C_{1-4}$alkoxy$C_{1-4}$alkyl, —C(O)—R$^b$, C(O)O—R$^b$, —NH—C(O)—R$^b$, N,N-di-$C_{1-4}$alkylamino, —S(O$_n$)NR$^b$R$^c$
where R$^b$ and R$^c$ are independently selected from hydrogen and $C_{1-6}$alkyl, and n is 0, 1 or 2;
(ii) —(Q)-aryl, wherein aryl is optionally substituted;
(iii) optionally substituted $C_{4-7}$heterocyclyl,
more preferably optionally substituted $C_{4-7}$heterocyclyl selected from: azirinyl, azetidinyl, pyrrolidinyl, pyrazolinyl, pyrazolidinyl, imidazolinyl, imidazolidinyl, piperidinyl, piperazinyl, hexahydropyrimidinyl, hexahydropyridazinyl, hexahydrotriazinyl, tetraydrotriazinyl, dihydrotriazinyl, tetrahydrofuranyl, dioxolanyl, tetrahydropyranyl, dioxanyl, trioxanyl, tetrahydrothienyl, 1-oxotetrahydrothienyl, 1,1-dioxotetrahydrothienyl tetrahydrothiopyran, 1-oxotetrahydrothiopyran, 1,1-dioxotetrahydrothiopyran, dithianyl, trithianyl, morpholinyl, oxathiolanyl, oxathianyl, thiomorpholinyl, thiazinanyl, 1-oxothiomorpholinyl, 1,1-dioxo-thiomorpholinyl, thiazolidinyl, pyrrolyl, imidazolyl, triazolyl, pyridyl, pyrimidinyl, pyrazinyl, pyridazinyl, triazinyl, thiazolyl, thiadiazolyl, thiadiazinyl, oxazolyl, isoxazolyl, oxadiazolyl, furazanyl, octahydropyrrolopyrrolyl, octahydropyrrolopyrrolyl, benzotriazolyl, dihydrobenzotriazolyl, indolyl, indolinyl, benzimidazolyl, 2,3-dihydrobenzimidazoly, benzotriazolyl 2,3-dihydro benzotriazolyl quinolinyl, isoquinolinyl, cinnolinyl, phthalazinyl, quinazolinyl, quinozalinyl, naphthyridinyl, pteridinyl, benzodioxolyl, tetrahydrodioxolopyrrolyl, 1,5-dioxa-9-azaspiro[5.5]undecanyl and 8-oxa-3-azabicyclooctanyl; or
(iv) optionally substituted $C_{3-7}$carbocyclyl;

Further preferably R⁸ is selected from
(i) hydrogen, $C_{1-6}$alkyl, $C_{2-6}$alkenyl, halo$C_{1-6}$alkyl, hydroxy, cyano, $C_{1-6}$alkylS(O$_n$)—, —O—R$^b$, $C_{1-4}$alkoxy$C_{1-4}$alkyl, —C(O)—R$^b$, C(O)O—R$^b$, —NH—C(O)—R$^b$, N,N-di-$C_{1-4}$alkylamino, —S(O$_n$)NR$^b$R$^c$
where R$^b$ and R$^c$ are independently selected from hydrogen and $C_{1-6}$alkyl, and n is 0, 1 or 2;
(ii) —(Q)-aryl, wherein aryl is optionally substituted;
(iii) optionally substituted $C_{4-7}$heterocyclyl selected from: azetidinyl, tetrahydrofuranyl, tetrahydropyranyl, pyrrolidinyl, piperidinyl, piperazinyl, hexahydropyrimidinyl, morpholinyl, tetrahydrothienyl, 1,1-dioxotetrahydrothienyl, thiomorpholinyl, 1-oxo-thiomorpholinyl, 1,1-dioxo-thiomorpholinyl, imidazolyl, thiazolyl, isoxazolyl, pyridyl, pyrimidinyl, tetrahydro-3aH-[1,3]dioxolo[4,5-c]pyrrolyl, 1,5-dioxa-9-azaspiro[5.5]undecanyl, 8-oxa-3-azabicyclo[3.2.1]octanyl, benzodioxolyl, 2,3-dihydrobenzotriazolyl and octahydropyrrolo[3,4-c]pyrrolyl; or (iv) optionally substituted $C_{3-7}$carbocyclyl;

Yet further preferably $R^8$ is selected from (i) hydrogen, methyl, isopropyl, t-butyl, 1-methylethyl, alkyl, fluoroethyl, hydroxy, cyano, ethylsulphonyl, methoxy, 1-methyl-2-methoxyethyl, acetyl, t-butoxycarbonyl, acetylamino, dimethylamino, diethylamino, (1-methylethyl)amino, isopropylamino or aminosulphonyl;

(ii) optionally substituted phenyl;

(iii) optionally substituted $C_{4-7}$heterocyclyl selected from: azetidinyl, tetrahydrofuranyl, tetrahydropyranyl, pyrrolidinyl, piperidinyl, piperazinyl, hexahydropyrimidinyl, morpholinyl, tetrahydrothienyl, 1,1-dioxotetrahydrothienyl, thiomorpholinyl, 1-oxo-thiomorpholinyl, 1,1-dioxo-thiomorpholinyl, imidazolyl, thiazolyl, isoxazolyl, pyridyl, pyrimidinyl, tetrahydro-3aH-[1,3]dioxolo[4,5-c]pyrrolyl, 1,5-dioxa-9-azaspiro[5.5]undecanyl, 8-oxa-3-azabicyclo[3.2.1]octanyl, benzodioxolyl, 2,3-dihydrobenzotriazolyl or octahydropyrrolo[3,4-c]pyrrolyl; or (iv) optionally substituted $C_{3-7}$carbocyclyl selected from: cyclopropyl, cyclobutyl, cyclopentyl or cyclohexyl Yet further preferably $R^8$ is selected from optionally substituted $C_{4-7}$heterocyclyl selected from: piperidinyl or piperazinyl, azetidinyl, imidazolyl and thiazolyl.

Most preferably $R^8$ is optionally substituted $C_{4-7}$heterocyclyl selected from: piperidinyl or piperazinyl.

In another embodiment of the invention $R^8$ is selected from hydrogen, cyano, $C_{1-4}$alkyl (more preferably methyl), $C_{2-6}$alkynyl (more prefeably 2-propynyl), hydroxy$C_{1-6}$alkyl (more preferably hydroxyethyl), $C_{1-4}$alkoxy$C_{1-4}$alkyl (more preferably methoxyethyl), halo$C_{1-6}$alkyl (more preferably fluoroethyl), $C_{1-4}$alkanoyl (more preferably formyl), $C_{1-4}$alkoxycarbonyl (more preferably butyloxycarbonyl), N,N-di-$C_{1-4}$alkylamino (more preferably N,N-dimethylaminoethyl and N,N-dimethylaminopropyl), $C_{1-6}$alkyl-$S(O_n)$— (more preferably ethylsulphonyl), cyclopentyl, phenyl, benzyl, cyanophenyl, pyrrolidinyl, pyrrolidinylethyl, imidazolyl, imidazoly$C_{1-6}$alkyl (more preferably imidazolylethyl), thiazolyl, pyridyl, pyridyl$C_{1-6}$alkyl (more preferably pyridylmethyl) or pyrimidyl wherein a phenyl or heterocyclyl ring is optionally substituted by $C_{1-4}$alkyl.

When $R^9$ and/or $R^{10}$ is a component of group G, $R^9$ and $R^{10}$ are preferably independently selected from hydrogen, optionally substituted $C_{1-6}$alkyl, optionally substituted aryl, optionally substituted aryl$C_{1-6}$alkyl or $R^9$ and $R^{10}$ forms $C_{3-7}$cycloalkyl or heterocyclyl. Further preferably hydrogen or $C_{1-4}$alkyl. Most preferably hydrogen or methyl. Most preferably both $R^9$ and $R^{10}$ are methyl.

When $R^9$ and/or $R^{10}$ is a component of group $R^{18}$, $R^9$ and $R^{10}$ are preferably independently selected from hydrogen, optionally substituted $C_{1-6}$alkyl, optionally substituted aryl, optionally substituted aryl$C_{1-6}$alkyl or $R^9$ and $R^{10}$ forms $C_{3-7}$cycloalkyl or heterocyclyl. Further preferably when $R^9$ is a component of group $R^{18}$, $R^9$ is preferably heterocyclyl. Most preferably pyrrolidinyl, 7-azabicyclo[2.2.1]hept-7-yl or. 3-azabicyclo[3.2.2]nonyl.

Preferably $R^{17}$ is hydrogen, hydroxy, cyano or is absent. Most preferably $R^{17}$ is absent.

Preferably $R^{18}$ is selected from hydrogen, $R^9N(R^{10})C(O)$—, $R^9C(O)$—, $R^9OC(O)$— or $R^{18a}$—$C(^9R^{10})$— wherein $R^{18a}$ is $R^9N(R^{10})C(O)$—. Further preferably $R^9C(O)$—. Most preferably $R^9C(O)$— wherein $R^9$ is heterocyclyl.

Preferably A is selected from a direct bond, optionally substituted $C_{1-5}$alkylene, carbonyl or —C(O)—C($R^dR^d$)—, wherein $R^d$ is independently selected from hydrogen and $C_{1-2}$alkyl. Further preferably A is a direct bond, $C_{1-5}$alkylene optionally substituted with $C_{1-4}$alkyl, carbonyl or carbonylmethyl. Yet further preferably A is a direct bond, unsubstituted $C_{1-2}$alkylene or carbonyl. Most preferably A is methylene.

Preferably B is selected from optionally substituted $C_{1-6}$alkylene or the group

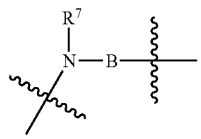

forms an optionally substituted $C_{4-7}$heterocyclic ring.

More preferably B is $C_{1-6}$alkylene or the group

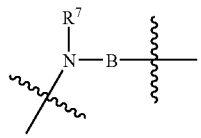

forms an optionally substituted saturated $C_{4-7}$heterocyclic ring.

Further preferably B is unsubstituted $C_{1-6}$alkylene or the group

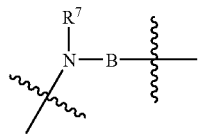

forms an optionally substituted saturated $C_{4-7}$heterocyclic ring selected from: azetidinyl, pyrrolidinyl, pyrazolinyl, pyrazolidinyl, imidazolinyl, imidazolidinyl, piperidinyl, piperazinyl, hexahydropyrimidinyl, hexahydropyridazinyl, hexahydrotriazinyl, tetrahydrotriazinyl, dihydrotriazinyl, morpholinyl, thiomorpholinyl, thiazinanyl, thiazolidinyl, 1,5-dioxa-9-azaspiro[5.5]undecanyl or octahydropyrrolopyrrolyl, wherein the optional substituents are selected from cyano, hydroxy, oxo, $C_{1-4}$alkyl, $C_{1-4}$alkoxy, $C_{1-4}$alkanoyl, $R^9OC(O)(CH_2)_w$—, $R^9R^{10}NC(O)(CH_2)_w$— or halo, wherein w is an integer between 0 and 4 and $R^9$ and $R^{10}$ are as defined above. Further preferably the optional substituents are selected from: cyano, hydroxy, oxo, $C_{1-4}$alkyl, $C_{1-4}$alkoxy and $C_{1-4}$alkanoyl.

Yet further preferably B is selected from: ethylene, propylene or butylene or the group

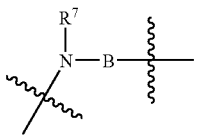

forms an optionally substituted saturated C$_{4-7}$heterocyclic ring selected from: azetidinyl, pyrrolidinyl, piperidinyl, piperazinyl, 1,5-dioxa-9-azaspiro[5.5]undecanyl or octahydropyrrolopyrrolyl, wherein the optional substituents are selected from oxo.

Most preferably the group

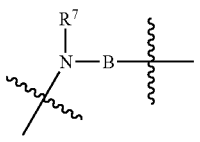

forms an optionally substituted saturated C$_{4-7}$heterocyclic ring selected from: piperidinyl or piperazinyl, wherein the optional substituents are selected from oxo.

In another embodiment of the invention B is selected from optionally substituted C$_{1-6}$alkylene or the group

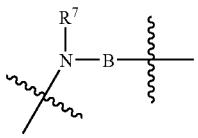

forms a C$_{5-7}$heterocyclic ring. Preferably unsubstituted C$_6$alkylene or a C$_{5-7}$heterocyclic saturated ring. Most preferably methylene, ethylene, propylene, butylene or piperazinyl.

Preferably G is a direct bond, —O— or —C(R$^9$R$^{10}$)—. More preferably —C(R$^9$R$^{10}$)—. Most preferably —C(CH$_3$)$_2$—.

When R$^3$ is selected from a group of Formula (IIc) or Formula (IId) then the group

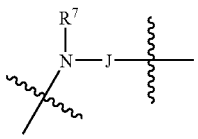

preferably forms an optionally substituted heterocyclic ring containing 4–7 carbons atoms.

More preferably the group

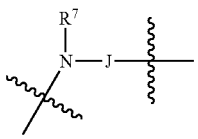

forms an optionally substituted saturated C$_{4-7}$heteocyclic ring.

Further preferably the group

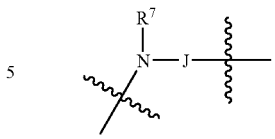

forms an optionally substituted saturated C$_{4-7}$heteocyclic ring selected from: azetidinyl, pyrrolidinyl, pyrazolinyl, pyrazolidinyl, imidazolinyl, imidazolidinyl, piperidinyl, piperazinyl, hexahydropyrimidinyl, hexahydropyridazinyl, hexahydrotriazinyl, tetraydrotriazinyl, dihydrotriazinyl, morpholinyl, thiomorpholinyl, thiazinanyl, thiazolidinyl or octahydropyrrolopyrrolyl, wherein the optional substituents are selected from oxo.

Further preferably the group

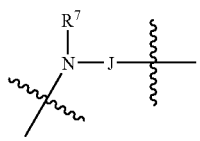

forms an optionally substituted saturated C$_{4-7}$heteocyclic ring selected from: pyrrolidinyl, piperidinyl or piperazinyl, wherein the optional substituents are selected from oxo.

Most preferably the group

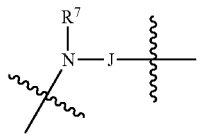

forms an optionally substituted saturated C$_{4-7}$heteocyclic ring selected from: piperidinyl or piperazinyl, wherein the optional substituents are selected from oxo.

Preferably K is selected from: —(CH$_2$)$_s$—, —(CH$_2$)$_s$—O—(CH$_2$)$_s$—, —(CH$_2$)$_s$—C(O)—(CH$_2$)$_s$—, —(CH$_2$)$_s$—N(R$^{18}$)—(CH$_2$)$_s$—, —(CH$_2$)$_s$—C(O)N(R$^{18}$)—(CH$_2$)$_s$—, —(CH$_2$)$_s$—N(R$^{18}$)C(O)—(CH$_2$)$_s$—, —(CH$_2$)$_s$—S(O)$_2$N(R$^{18}$)—(CH$_2$)$_s$—, or —(CH$_2$)$_s$—NHS(O)$_2$—(CH$_2$)s—, wherein s is independently selected from 0,1,2,3 or 4, R$^{18}$ is selected from hydrogen or C$_{1-4}$alkyl (preferably hydrogen) and the —(CH$_2$)$_s$— group is optionally substituted by hydroxy or C$_{1-4}$alkyl.

More preferably K is selected from: —(CH$_2$)$_{s1}$—, —(CH$_2$)$_{s1}$—O—(CH$_2$)$_{s2}$—, —(CH$_2$)$_{s1}$—C(O)—, —C(O)—(CH$_2$)$_{s2}$, —(CH$_2$)$_s$—N(R$^{18}$)—, —(CH$_2$)$_{s1}$—C(O)N(R$^{18}$)—, —(CH$_2$)$_{s1}$—N(R$^{18}$)C(O)—(CH$_2$)$_{s2}$—, —(CH$_2$)$_{s1}$—S(O)$_2$N(R$^{18}$)— or —(CH$_2$)$_{s1}$—NHS(O)$_2$—, wherein s1 and s2 are independently selected from 0, 1, 2, 3 or 4 and s1+s2 is less than or equal to 4, R$^{18}$ is selected from hydrogen or C$_{1-4}$alkyl (preferably hydrogen) and the —(CH$_2$)$_s$— group is optionally substituted by hydroxy or C$_{1-4}$alkyl.

More preferably K is selected from: methylene, ethylene, propylene, oxy, 2-hydroxypropylene, carbonyl, methylcarbonyl, ethylcarbonyl, (methyl)methylcarbonyl, (ethyl)methylcarbonyl, carbonylmethylene, carbonylethylene, ethoxyethylene, amino, 2-hydroxypropylamino, carbonylamino, methylcarbonylamino, aminocarbonyl, methylaminocarbonyl, methylaminocarbonylmethyl, propylsulphonylamino or methylaminosulphonyl.

Further preferabley K is selected from: methylene, carbonyl, carbonylaminio, methylcarbonylamino, aminocarbonyl, methylaminocarbonyl or methylaminosulphonyl.

Most preferably K is selected from: methylene, carbonyl or methylcarbonylamino;

Preferably optional substituents on heterocyclyl groups in $R^8$, $R^9$, $R^{10}$, $R^{18}$ and $R^{19}$ or on heterocyclyl groups formed when $R^{17}$ and $R^{18}$ together form a heterocyclic ring are selected from: optionally substituted $C_{1-6}$alkyl, $C_{1-6}$alkoxy, $C_{1-6}$alkanoyl, optionally substituted $C_{2-6}$alkenyl, cyano, nitro, $C_{1-3}$perfluoroalkyl, $C_{1-3}$perfluoroalkoxy, optionally substituted aryl, optionally substituted aryl$C_{1-6}$alkyl, $R^9O(CH_2)_p$—, $R^9C(O)O(CH_2)_w$—, $R^9OC(O)(CH_2)_w$—, $R^{16}S(O_n)(CH_2)_w$—, $R^9R^{10}NC(O)(CH_2)_w$— or halo; wherein w is an integer between 0 and 4 and p, $R^9$, $R^{10}$ and $R^{16}$ are as defined above.

More preferably optional substituents on $R^8$ are selected from: cyano, hydroxy, oxo, $C_{1-4}$alkyl, $C_{1-4}$alkoxy, $C_{1-4}$alkanoyl, $R^9OC(O)(CH_2)_w$—, $R^9R^{10}NC(O)(CH_2)_w$— or halo, wherein w is an integer between 0 and 4 and $R^9$ and $R^{10}$ are as defined above.

Further preferably optional substituents on $R^8$ are selected from: cyano, hydroxy, oxo, $C_{1-4}$alkyl, $C_{1-4}$alkoxy and $C_{1-4}$alkanoyl.

Most preferably optional substituents on $R^8$ are selected from: cyano, oxo, methyl, methoxy and acetyl.

Preferably the optional substituents on alkyl, alkenyl, alkynyl, cycloalkyl and aryl groups are independently selected from $C_{1-6}$alkyl, $C_{1-6}$alkoxy, $C_{3-7}$cycloalkyl, optionally substituted aryl, optionally substituted aryl$C_{1-6}$alkyl, hydroxy, oxo, cyano, $C_{1-6}$alkoxy, halo (preferably fluoro), $R^{16}S(O_n)(CH_2)_w$—, $R^9OC(O)$—, optionally substituted aryl$C_{1-3}$alkoxy wherein $R^9$ is as defined above.

Preferably the optional substituents on optionally substituted aryl and aryl$C_{1-6}$alkyl groups are selected from: optionally substituted $C_{1-6}$alkyl, optionally substituted $C_{2-6}$alkenyl, cyano, nitro, halo (preferably fluoro), $C_{1-3}$perfluoroalkyl, $C_{1-3}$perfluoroalkoxy, optionally substituted aryl, optionally substituted aryl$C_{1-6}$alkyl, $R^9O(CH_2)_p$—, $R^9C(O)O(CH_2)_w$—, $R^9OC(O)(CH_2)_w$—, $R^{16}S(O_n)(CH_2)_w$—, $R^9R_{10}NC(O)(CH_2)_w$— or halo; wherein w is an integer between 0 and 4 and n, $R^9$ and $R^{10}$ are as defined above.

In preferences for heterocyclyl in $R^8$ the nitrogen atoms contained in $R^8$ heteroaromatic rings exist either as drawn or, where chemically allowed, in their oxidised (N→O, N—OH) state.

Where optional substitution is mentioned at various places the optional substituents also comprise the following definition which refers to one, two, three or more optional substituents. Unless otherwise indicated above (i.e., where a list of optional substituents is specifically listed within a definition), each substituent can be independently selected from $C_{1-8}$alkyl (eg, $C_{2-6}$alkyl, and most preferably methyl, ethyl or tert-butyl); $C_{3-8}$cycloalkoxy, preferably cyclopropoxy, cyclobutoxy or cyclopentoxy; $C_{1-6}$alkoxy, preferably methoxy or $C_{2-4}$alkoxy; halo, preferably Cl or F; $Hal_3C$—, $Hal_2CH$—, $HalCH_2$—, $Hal_3CO$—, $Hal_2CHO$ or $Hal\ CH_2O$, wherein Hal represents halo (preferably F); $R^gCH2O$—, $R^hC(O)N(R)$—, $R^hSO_2N(R)$— or $R^g$—$R^hN$—, wherein $R^g$ and $R^h$ independently represent hydrogen or $C_{1-8}$alkyl (preferably methyl or $C_{2-6}$alkyl or $C_{2-4}$alkyl), or $R^g$—$R^hN$— represents an optionally substituted $C_{3-8}$, preferably $C_{3-6}$, heterocyclic ring optionally containing from 1 to 3 further heteroatoms independently selected from O, N and S; hydrogen; or $R^kC(O)O$— or $R^kC(O)$—, $R^k$ representing hydrogen, optionally substituted phenyl or $C_{1-6}$alkyl (preferably methyl, ethyl, iso-propyl or tert-butyl). For optional substitution of the heterocyclic ring represented by $R^g$—$R^hN$—, at least one (eg, one, two or three) substituents may be provided independently selected from $C_{1-6}$alkyl (eg, $C_{2-4}$alkyl, more preferably methyl); phenyl; $CF_3O$—; $F_2CHO$—; $C_{1-8}$alkoxy, preferably methoxy, ethoxy or $C_{3-6}$alkoxy; $C_{1-8}$alkoxyC(O), preferably methoxycarbonyl, ethoxycarbonyl, tert-butoxycarbonyl or $C_{3-6}$alkoxyC(O)—; phenoxycarbonyl; phenoxy; $C_{1-8}$alkanoyl, preferably acetyl, ethanoyl or $C_{3-6}$alkyanoyl; carboxy; $C_{1-8}$alkylS($O_{nn}$) wherein nn is an integer between 0 and 2, preferably methylthio, ethylthio, $C_{3-6}$alkylthio, methylsulphinyl, ethylsulphinyl, $C_{3-6}$alkylsulphinyl, methylsulphonyl, ethylsulphonyl or $C_{3-6}$alkylsulphonyl; hydroxy; halo (eg, F, Cl or Br); $R'''R''N$— where $R'''$ and $R''$ are independently hydrogen or $C_{1-6}$alkyl (preferably $C_{2-4}$alkyl, more preferably methyl, most preferably $R'''=R''$=methyl); and nitro.

According to a further aspect of the invention there is provided a compound of Formula (Ib)

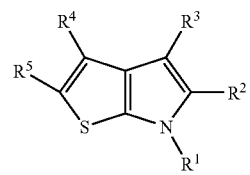

Formula (Ib)

wherein:

$R^1$ represents hydrogen or unsubstituted $C_{1-6}$alkyl;

$R^2$ represents optionally substituted phenyl;

$R^3$ is selected from a group of Formula (IIa) to Formula (IId):

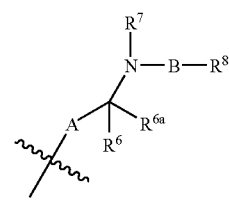

Formula (IIa)

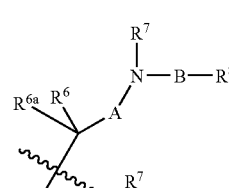

Formula (IIb)

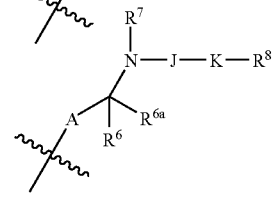

Formula (IIc)

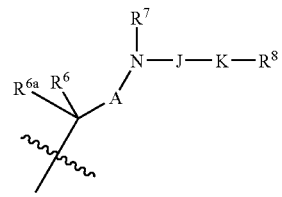

Formula (IId)

$R^4$ is selected from hydrogen or $C_{1-4}$alkyl;

$R^5$ is selected from a one of a group of Formula III-a to III-j:

III-a 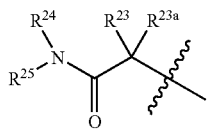

III-b 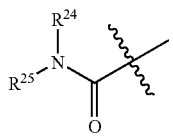

III-c 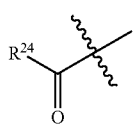

III-d 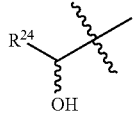

III-e 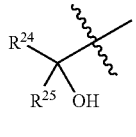

III-f 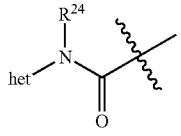

III-g 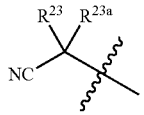

III-h 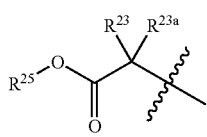

III-i 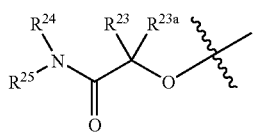

III-j 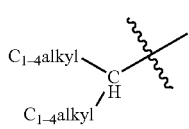

III-k 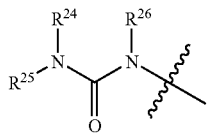

-continued

III-l 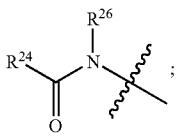

wherein:
het represents an optionally substituted 3- to 8-membered heterocyclic ring containing from 1 to 4 heteroatoms independently selected from O, N and S;

$R^{23}$ and $R^{23a}$ are independently selected from:
(i) hydrogen, fluoro or optionally substituted $C_{1-8}$alkyl; or
(ii) $R^{23}$ and $R^{23a}$ together with the carbon to which they are attached form an optionally substituted 3 to 7-membered cycloalkyl ring;

$R^{24}$ and $R^{25}$ are selected from:
(i) $R^{24}$ selected from hydrogen; optionally substituted $C_{1-8}$alkyl; optionally substituted aryl; —$R^d$—Ar, where $R^d$ represents $C_{1-8}$alkylene and Ar represents optionally substituted aryl; and optionally substituted 3- to 8-membered heterocyclic ring optionally containing from 1 to 3 further heteroatoms independently selected from O, N and S; and $R^{25}$ is selected from hydrogen; optionally substituted $C_{1-8}$alkyl and optionally substituted aryl;
(ii) wherein the group of Formula (III) represents a group of Formula III-a, III-b or III-i, then the group $NR^{24}(—R^{25})$ represents an optionally substituted 3- to 8-membered heterocyclic ring optionally containing from 1 to 3 further heteroatoms independently selected from O, N and S; or
(iii) wherein the group of Formula (E) represents structure III-e, represents an optionally substituted 3- to 8-membered heterocyclic ring optionally containing from 1 to 4 heteroatoms independently selected from O, N and S;

$R^{26}$ is selected from hydrogen or $C_{1-4}$alkyl.

$R^6$ and $R^{6a}$ are independently selected from hydrogen, fluoro or optionally substituted $C_{1-6}$alkyl.

$R^7$ is selected from: hydrogen or $C_{1-4}$alkyl;

$R^8$ is selected from
(i) hydrogen, $C_{1-6}$alkyl, $C_{2-6}$alkenyl, halo$C_{1-6}$alkyl, hydroxy, cyano, $C_{1-6}$alkylS(O$_n$)—, —O—$R^b$, $C_{1-4}$alkoxy$C_{1-4}$alkyl, —C(O)—$R^b$, C(O)O—$R^b$, —NH—C(O)—$R^b$, N,N-di-$C_{1-4}$alkylamino or —S(O$_n$)NR$^b$R$^c$
where $R^b$ and $R^c$ are independently selected from hydrogen and $C_{1-6}$alkyl, and n is 0, 1 or 2;
(ii) -aryl, optionally substituted by up to 4 substituents selected from $R^{12}$, $R^{13}$ and $R^{14}$;
(iii) $C_{4-7}$heterocyclyl, optionally substituted by up to 4 substituents selected from $R^{12}$, $R^{13}$ and $R^{14}$; or (iv) $C_{3-7}$carbocyclyl, optionally substituted by up to 4 substituents selected from $R^{12}$, $R^{13}$ and $R^{14}$; p1 $R^9$ and $R^{10}$ are independently selected from: hydrogen, hydroxy, optionally substituted $C_{1-6}$alkyl, optionally substituted aryl, optionally substituted aryl$C_{1-6}$alkyl, an optionally substituted carbocyclic ring of 3-7 atoms, optionally substituted heterocyclyl, optionally substituted heterocyclyl$C_{1-6}$alkyl or $R^9$ and $R^{10}$ taken together can form an optionally substituted ring of 3–9 atoms or $R^9$ and $R^{10}$ taken together with the carbon atom to which they are attached form a carbonyl group;

$R^{12}$ is selected from: hydrogen, hydroxy, $R^{17}R^{18}N(CH_2)_{cc}$—, $R^{17}R^{18}NC(O)(CH_2)_{cc}$—, optionally substituted $C_{1-6}$alkyl-C(O)N($R^9$)$(CH_2)_{cc}$—, optionally substituted $C_{1-6}$alkyl-SO$_2$N($R^9$)—, optionally substituted aryl-SO$_2$N($R^9$)—, $C_{1-3}$perfluoroalkyl-SO$_2$N($R^9$)—; optionally substituted $C_{1-6}$alkyl-N(R)SO$_2$—, optionally substituted aryl-N($R^9$)SO$_2$—, $C_{1-3}$perfluoroalkyl-N($R^9$)SO$_2$— optionally substituted $C_{1-6}$alkanoyl-N($R^9$)SO$_2$—; optionally substituted aryl-C(O)N($R^9$)SO$_2$—, optionally substituted $C_{1-6}$alkyl-S(O$_n$)—, optionally substituted aryl-S(O$_n$)—, $C_{1-3}$perfluoroalkyl-, $C_{1-3}$perfluoroalkoxy, optionally substituted $C_{1-6}$alkoxy, carboxy, halo, nitro or cyano;

$R^{13}$ and $R^{14}$ are independently selected from: hydrogen, hydroxy, oxo, optionally substituted $C_{1-6}$alkyl, optionally substituted $C_{1-6}$alkanoyl, optionally substituted $C_{2-6}$alkenyl, cyano, nitro, $C_{1-3}$perfluoroalkyl-, $C_{1-3}$perfluoroalkoxy, optionally substituted aryl, optionally substituted aryl$C_{1-6}$alkyl, $R^9O(CH_2)_s$—, $R^9(O)O(CH_2)_s$—, $R^9OC(O)(CH_2)_s$—, $R^{16}S(O_n)(CH_2)_s$—, $R^9R^{10}NC(O)(CH_2)_s$— or halo; A is selected from optionally substituted $C_{1-5}$alkylene, carbonyl or —C(O)—C($R^dR^d$)—, wherein $R^d$ is independently selected from hydrogen and $C_{1-2}$alkyl.;

$R^{17}$ is independently selected from: hydrogen, hydroxy, cyano or optionally substituted $C_{1-6}$alkyl;

$R^{18}$ is a group of formula $R^{18a}$—C($R^9R^{10}$)$_{0-1}$— wherein $R^{18a}$ is selected from: $R^{19}OC(O)$—, $R^9R^{10}NC(O)$—, $R^9R^{10}N$—, $R^9C(O)$—, $R^9C(O)N(R^{10})$—, $R^9R^{10}NC(O)$—, $R^9R^{10}NC(O)N(R^{10})$—, $R^9SO_2N(R^{10})$—, $R^9R^{10}NSO_2N(R^{10})$—, $R^9C(O)O$—, $R^9OC(O)$—, $R^9R^{10}NC(O)O$—, $R^9O$—, $R^9S(O_n)$—, $R^9R^{10}NS(O_n)$—, hydrogen, optionally substituted $C_{1-6}$alkyl, optionally substituted heterocyclyl;

or $R^{17}$ and $R^{18}$ when taken together form an optionally substituted carbocyclic ring of 3–7 atoms or optionally substituted heterocyclyl;

$R^{19}$ is selected from: hydrogen, optionally substituted $C_{1-6}$alky, optionally substituted aryl, optionally substituted aryl$C_{1-6}$alkyl, optionally substituted $C_{3-7}$cycloalkyl, optionally substituted heterocyclyl or optionally substituted heterocyclyl$C_{1-6}$alkyl;

B is selected from optionally substituted $C_{1-6}$alkylene or the group

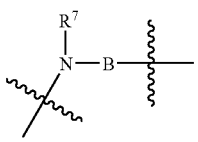

forms an optionally substituted $C_{4-7}$heterocyclic ring, wherein the optional substituents are selected from $R^{12}$, $R^{13}$ and $R^{14}$;

the group

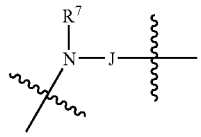

preferably forms an optionally substituted heterocyclic ring containing 4–7 carbons atoms, wherein the optional substituents are selected from $R^{12}$, $R^{13}$ and $R^{14}$;

K is selected from: a direct bond, —(CH$_2$)$_{s1}$—, —(CH$_2$)$_{s2}$—O—(CH$_2$)$_s$—, —(CH$_2$)$_{s1}$—C(O)—(CH$_2$)$_{s2}$—, —(CH$_2$)$_{s1}$—S(O$_n$)—(CH$_2$)$_{s2}$—, —(CH$_2$)$_{s1}$—N($R^{18}$)—(CH$_2$)$_{s2}$—, —(CH$_2$)$_{s1}$—C(O)N($R^9$)—(CH$_2$)$_{s2}$—, —(CH$_2$)$_{s1}$—N($R^9$)C(O)—(CH$_2$)$_{s2}$—, —(CH$_2$)$_{s1}$—N($R^9$)C(O)N($R^9$)—(CH$_2$)$_{s2}$—, —(CH$_2$)$_{s1}$—OC(O)—(CH$_2$)$_{s2}$—, —(CH$_2$)$_{s1}$—C(O)O—(CH$_2$)$_{s2}$—, —(CH$_2$)$_{s1}$—N($R^9$)C(O)O—(CH$_2$)$_{s2}$—, —(CH$_2$)$_{s1}$—OC(O)N($R^9$)—(CH$_2$)$_{s2}$—, —(CH$_2$)$_{s1}$—OS(O$_n$)—(CH$_2$)$_{s2}$—, or —(CH$_2$)$_{s1}$—S(O$_n$)—O—(CH$_2$)$_{s2}$—, —(CH$_2$)$_{s1}$—S(O)$_2$N($R^9$)—(CH$_2$)$_{s2}$—, —(CH$_2$)$_{s1}$—N($R^9$)S(O)$_2$—(CH$_2$)$_{s2}$—; wherein the —(CH$_2$)$_{s1}$— and —(CH$_2$)$_{s2}$— groups are independently optionally substituted by hydroxy, fluoro, cyano, carbamoyl, $C_{1-4}$alkyl and $C_{1-4}$alkoxy, n is an integer from 0 to 2;

s is an integer from 0 to 4;

s1 and s2 are independently selected from an integer from 0 to 4, and s1+s2 is less than or equal to 4;

cc is an integer between 0 to 2 or a salt, pro-drug or solvate thereof.

According to a further aspect of the invention there is provided a compound of Formula (Ic)

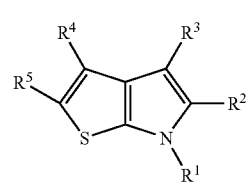

Formula (Ic)

wherein $R^3$ is selected from a group of Formula (IIa) or Formula (IIb):

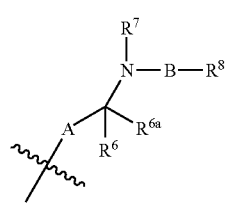

Formula (IIa)

-continued

Formula (IIb)

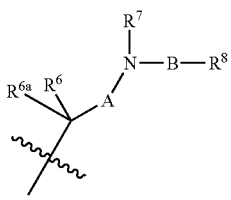

and $R^1$, $R^2$, $R^4$, $R^5$, $R^6$, $R^{6a}$, $R^7$, $R^8$, A and B are as defined above;

or salt, solvate or pro-drug thereof.

A further preferred group of compounds of the invention comprises a compound of formula (Ic), wherein:

A is optionally substituted $C_{1-5}$alkylene;

B is selected from optionally substituted $C_{1-6}$alkylene or the group

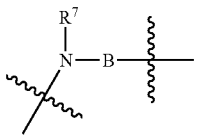

forms a ring containing $C_{5-7}$heterocyclic ring;

$R^1$ is hydrogen or $C_{1-4}$alkyl;

$R^6$ and $R^{6a}$, are independently selected from hydrogen and optionally substituted $C_{1-6}$alkyl;

$R^7$ is selected from: hydrogen or $C_{1-4}$alkyl;

$R^8$ is selected from hydrogen, cyano, $C_{1-6}$alkyl, halo$C_{1-6}$alkyl, $C_{2-6}$alkynyl, $C_{1-6}$alkanoyl, $C_{1-4}$alkoxy$C_{1-4}$alkyl, $C_{1-6}$alkoxycarbonyl, N,N-di-$C_{1-4}$alkylamino, aryl, aryl$C_{1-6}$alkyl, $C_{3-7}$cycloalkyl, $C_{3-7}$cycloalkyl$C_{1-6}$alkyl, heterocyclyl, heterocyclyl$C_{1-6}$alkyl, or heterocyclylcarbonyl$C_{1-4}$alkyl wherein aryl and heterocyclyl rings are optionally substituted by cyano and $C_{1-4}$alkyl; and $R^2$, $R^4$, and $R^5$; are as defined above or salt, solvate or pro-drug thereof.

A further preferred group of compounds of the invention comprises a compound of Formula (Ic), wherein:

A is optionally substituted $C_{1-5}$alkylene;

B is selected from optionally substituted $C_{1-6}$alkylene or the group

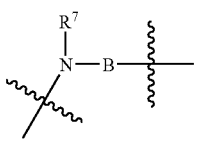

forms a ring containing $C_{5-7}$heterocyclic ring;

$R^1$ is hydrogen or $C_{1-4}$alkyl, preferably hydrogen;

$R^2$ is an optionally substituted monocyclic aromatic ring structure, preferably optionally substituted phenyl, most preferably 3,5-dimethylphen-1-yl;

$R^4$ is hydrogen or $C_{1-4}$alkyl, preferably hydrogen;

$R^5$ is a group of Formula (III) wherein the group of Formula (III) is selected from a group of Formula III-a; III-b; III-c; III-d; III-e; III-f, III-g, III-h, III-i,: III-j, III-k or III-l

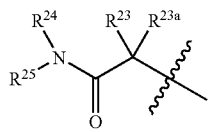
III-a

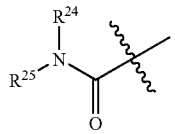
III-b

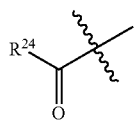
III-c

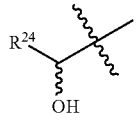
III-d

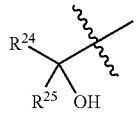
III-e

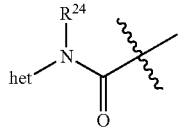
III-f

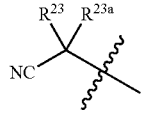
III-g

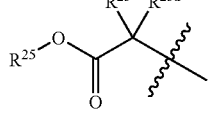
III-h

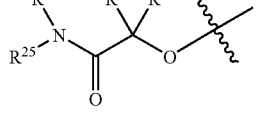
III-i

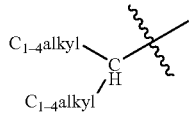
III-j

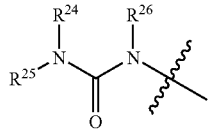
III-k

-continued

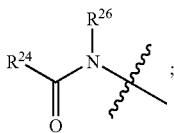

III-I wherein R²³, R²³ᵃ, R²⁴, R²⁵ and R²⁶ are as defined above, preferably the group of Formula (III) is selected from (III-a), (III-g) and (III-h);

R⁶ and R⁶ᵃ, are independently selected from hydrogen and optionally substituted $C_{1-6}$alkyl;

R⁷ is selected from: hydrogen or $C_{1-4}$alkyl;

R⁸ is selected from hydrogen, cyano, $C_{1-6}$alkyl, halo$C_{1-6}$alkyl, $C_{2-6}$alkynyl, $C_{1-6}$alkanoyl, $C_{1-4}$alkoxy$C_{1-4}$alkyl, $C_{1-6}$alkoxycarbonyl, N,N-di-$C_{1-4}$alkylamino, aryl, aryl$C_{1-6}$alkyl, $C_{3-7}$cycloalkyl, $C_{3-7}$cycloalkyl$C_{1-6}$alkyl, heterocyclyl, heterocyclyl$C_{1-6}$alkyl, or heterocyclylcarbonyl$C_{1-4}$alkyl wherein aryl and heterocyclyl rings are optionally substituted by cyano and $C_{1-4}$alkyl; and R², R⁴, and R⁵; are as defined above or salt, solvate or pro-drug thereof.

A further preferred group of compounds of the invention comprises a compound of formula (Id):

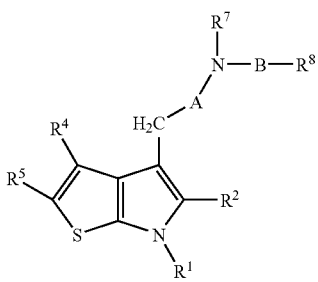

Formula (Id)

Wherein R¹, R², R⁴, R⁵; R⁷, R⁸, A and B are as defined above or salt, solvate or pro-drug thereof.

A yet further preferred group of compounds of the invention comprises a compound of Formula (I), (Ia), (Ib), (Ic) or (Id) wherein:

R⁵ is a group of Formula (III) wherein the group of Formula (III) is a group of formula IIIa:

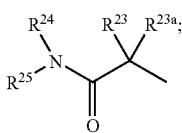

IIIa wherein R²³, R²³ᵃ, R²⁴ and R²⁵ are as defined above;

or a salt, pro-drug or solvate thereof.

According to a further aspect of the invention there is provided a compound of Formula (I) or (Ia), or salt, solvate or pro-drug thereof, wherein R³ is selected from a group of Formula (IIc) or Formula (IId) and R¹, R², R⁴ and R⁵ are as defined above.

According to a further aspect of the invention there is provided a compound of Formula (I) or (Ia), or salt, solvate or pro-drug thereof, wherein R³ is selected from a group of Formula (IIe) or Formula (IIf) and R¹, R², R⁴ and R⁵ are as defined above.

According to a further aspect of the invention there is provided a compound of Formula (I) or (Ia), or salt, solvate or pro-drug thereof, wherein R³ is selected from a group of Formula (Ia), Formula (IIc) or Formula (IIe) and R¹, R², R⁴ and R⁵ are as defined above.

According to a further aspect of the invention there is provided a compound of Formula (I) or (Ia), or salt, solvate or pro-drug thereof, wherein R³ is selected from a group of Formula (IIb), Formula (IId) or Formula (IIf) and R¹, R², R⁴ and R⁵ are as defined above.

A preferred group of compounds according to the present invention are wherein the compound is selected from:

{(2S)-2-[2-[2-(7-azabicyclo[2.2.1]hept-7-yl)-1,1-dimethyl-2-oxoethyl]-5-(3,5-dimethylphenyl)-6H-thieno[2,3-b]pyrrol-4-yl]propyl}(2-pyridin-4-ylethyl)amine;

2-[2-(7-azabicyclo[2.2.1]hept-7-yl)-1,1-dimethyl-2-oxoethyl]-5-(3,5-dimethylphenyl)-4-{2-[4-(2-morpholin-4-yl-2-oxoethyl)piperazin-1-yl]ethyl}-6H-thieno[2,3-b]pyrrole;

2-[1,1-dimethyl-2-oxo-2-(azabicyclo[2.2.1]heptan-7-yl)ethyl]-4-[4-(2-hydroxy-3-{4-acetylpiperazin-1-yl}prop-1-yl)piperazin-1-yl]ethyl-5-(3,5-dimethylphenyl)-6H-thieno[2,3-b]pyrrole;

2-[1,1-dimethyl-2-oxo-2-(azabicyclo[2.2.1]heptan-7-yl)ethyl]-4-[(2-{4-{2-hydroxy-3-piperiazin-1-ylprop-1-yl}piperazin-1-yl)ethyl]-5-(3,5-dimethylphenyl)-6H-thieno[2,3-b]pyrrole;

2-[2-(7-azabicyclo[2.2.1]hept-7-yl)-1,1-dimethyl-2-oxoethyl]-5-(3,5-dimethylphenyl)-4-[2-(3-pyridin-4-ylpyrrolidin-1-yl)ethyl]-6H-thieno[2,3-b]pyrrole;

2-[2-(7-azabicyclo[2.2.1]hept-7-yl)-1,1-dimethyl-2-oxoethyl]-5-(3,5-dimethylphenyl)-4-[2-(3-pyridin-2-ylpyrrolidin-1-yl)ethyl]-6H-thieno[2,3-b]pyrrole;

2-[1,1-Dimethyl-2-oxo-2-(azabicyclo[2.2.1]heptan-7-yl)ethyl]-4-[2-(4-{morpholinocarbonyl}piperidin-1-yl)ethyl]-5-(3,5-dimethylphenyl)-6H-thieno[2,3-b]pyrrole;

2-[2-(7-azabicyclo[2.2.1]hept-7-yl)-1,1-dimethyl-2-oxoethyl]-5-(3,5-dimethylphenyl)-4-[2-(4-{2,6-dimethylmorpholinocarbonyl}piperidin-1-yl)ethyl]-6H-thieno[2,3-b]pyrrole;

2-[1,1-Dimethyl-2-oxo-2-(azabicyclo[2.2.1]heptan-7-yl)ethyl]-4-[1-oxo-2-{4-(1,1-dioxidotetrahydrothien-3-yl)piperazin-1-yl}ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[1-oxo-2-{4-(pyrrolidin-1-ylcarbonylmethyl)piperazin-1-yl}ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[1-oxo-2-{4-(morpholinocarbonyl)piperazin-1-yl }ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[1-oxo-2-{3-methyl-4-(pyrrolidin-1-ylcarbonylmethyl)piperazin-1-yl}ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[1-oxo-2-methyl-2-{4-(1,1-dioxidotetrahydro-3-thienyl)piperazin-1-yl}ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[1-oxo-3-{4-(1,1-dioxidotetrahydro-3-thienyl)piperazin-1-yl }propyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[2-{4-(pyrrolidin-1-ylcarbonylmethyl)piperazin-1-yl}ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[2-{4-(2,4-dioxo-1,2,3,4-tetrahydropyrimidin-6-ylmethyl)piperazin-1-yl}ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]4-[2-{4-(6-hydroxypyrid-3-ylmethyl)piperazin-1-yl }ethyl]-5-(3,5-dimethylphenyl)-6H-thieno[2,3-b]pyrrole;

2-[1,1-dimethyl-2-oxo-2-(azabicyclo[2.2.1]heptan-7-yl)ethyl]-4-[2-(4-{(3aR,6aS)-tetrahydro-5H-[1,3]dioxolo[4,5-c]pyrrol-5-ylcarbonylmethyl}piperazin-1-yl)ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]4-[2-{4-(morpholinocarbonyl)piperazin-1-yl}ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[2-(4-{N,N-dimethylaminocarbonylmethyl}piperazin-1-yl)ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[N-isopropylamninocarbonylmethyl)piperazin-1-yl }ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[2-4-{tetrahydrofuran-2-ylcarbonyl}piperazin-1-yl)ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[2-{4-(1,3-dimethyl-2,4-dioxo-1,2,3,4-tetrahydropyrimidin-6-ylmethyl)piperazin-1-yl}ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[2-(4-{piperidin-1ylcarbonylmethyl}piperazin-1-yl)ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl-4-[2-(4-{azetidin-1ylcarbonylmethyl}piperazin-1-yl)ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[2-(4-pyrid-4-ylpiperidin-1-yl)ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[2-{4-(1,1-dioxidotetrahydro-3-thienyl)piperazin-1-yl}ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]4-[2-{4-(4-acetylpiperazin-1-yl)carbonylpiperidin-1-yl}ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[2-{4-((3aR,6aS)-tetrahydro-3aH-[1,3]dioxolo[4,5-c]pyrrol-5-ylcarbonyl)piperidin-1-yl}ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[2-(4-{morpholinocarbonylmethyl}piperidin-1-yl)ethyl]-5-(3,5-dimethylphenyl)-6H-thieno[2,3-b]pyrrole;

2-[1,1-Dimethyl-2oxo-2-(azabicyclo[2.2.1]heptan-7-yl)ethyl]-4-[(2-(4-{tetrahydro-2H-pyran-4-ylcarbonylamino}piperidin-1-yl)ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[2-(4-{morpholinocarbonylamino}piperidin-1-yl)ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[2-(4-{3-oxo-3-morpholinoprop-1-yl}piperidin-1-yl)ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[2-(4-{isopropylsulphonylaminomethyl}piperidin-1-yl)ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[2-(4-{3-hydroxypyrrolidin-1-ylcarbonyl}piperidin-1-yl)ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[2-(3-oxo-4{pyrrolidin-1-ylcarbonylmethyl}piperazin-1-yl)ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[2-(4-{4-oxo-4-pyrrolidin-1-ylbut-3-yl}piperazin-1-yl)ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[2-(4-{3-oxo-3-pyrrolidin-1-ylprop-2-yl }piperazin-1-yl)ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[2-(4-{pyrrolidin-1-ylcarbonylmethyl}piperazin-1-yl)ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[2-(4-methoxy-4-{N,N-diethylaminomethyl}piperidin-1-yl)ethyl]-5-(3,5-dimethylphenyl)-6H-thieno[2,3-b]pyrrole;

2-[1,1-Dimethyl-2-oxo-2-(azabicyclo[2.2.1]heptan-7-yl)ethyl]-4-[4-(pyrrolidin-1-ylcarbonylmethyl)piperazin-1-ylmethyl]-5-(3,5-dimethylphenyl)-6H-thieno[2,3-b]pyrrole; and 2-[1,1-Dimethyl-2-oxo-2-(azabicyclo[2.2.1]heptan-7-yl)ethyl]-4-[4-(morpholinocarbonyl)piperidin-1-ylmethyl]-5-(3,5-dimethylphenyl)-6H-thieno[2,3-b]pyrrole;

or a salt, pro-drug or solvate thereof.

A further preferred group of compounds according to the present invention are wherein the compound is selected from:

{(2S)-2-[2-[2-(7-azabicyclo[2.2.1]hept-7-yl)-1,1-dimethyl-2-oxoethyl]-5-(3,5-dimethylphenyl)-6H-thieno[2,3-b]pyrrol-4-yl]propyl}(2-pyridin-4-ylethyl)amine;

2-[2-(7-azabicyclo[2.2.1]hept-7-yl)-1,1-dimethyl-2-oxoethyl]-5-(3,5-dimethylphenyl)-4-{2-[4-(2-morpholin-4-yl-2-oxoethyl)piperazin-1-yl]ethyl}-6H-thieno[2,3-b]pyrrole;

2-[1,1-Dimethyl-2-oxo-2-(azabicyclo[2.2.1]heptan-7-yl)
  ethyl]-4-[2-(4-{morpholinocarbonyl}piperidin-1-yl)
  ethyl]-5-(3,5-dimethylphenyl)-6H-thieno[2,3-b]pyr-
  role;
2-[2-(7-azabicyclo[2.2.1]hept-7-yl)-1,1-dimethyl-2-oxo-
  ethyl]-5-(3,5-dimethylphenyl)-4-[2-(4-{2,6-
  dimethylmorpholinocarbonyl}piperidin-1-yl)ethyl]-
  6H-thieno[2,3-b]pyrrole;
2-[1,1-Dimethyl-2-oxo-2-(azabicyclo[2.2.1]heptan-7-yl)
  ethyl]-4-[1-oxo-2-{4-(1,1-dioxidotetrahydrothien-3-yl)
  piperazin-1-yl}ethyl]-5-(3,5-dimethylphenyl-6H-
  thieno[2,3-b]pyrrole;
2-[1,1-Dimethyl-2-oxo-2-(azabicyclo[2.2.1]heptan-7-yl)
  ethyl]4-[1-oxo-2-methyl-2-{4-(1,1-dioxidotetrahydro-
  3-thienyl)piperazin-1-yl}ethyl]-5-(3,5-dimethylphe-
  nyl)-6H-thieno[2,3-b]pyrrole;
2-[1,1-Dimethyl-2-oxo-2-(azabicyclo[2.2.1]heptan-7-yl)
  ethyl]4-[2-{4-(pyrrolidin-1-ylcarbonylmethyl)piper-
  azin-1-yl}ethyl]-5-(3,5-dimethylphenyl)-6H-thieno[2,
  3-b]pyrrole;
2-[1,1-Dimethyl-2-oxo-2-(azabicyclo[2.2.1]heptan-7-yl)
  ethyl]-4-[2-{4-(2,4-dioxo-1,2,3,4-tetrahydropyrimidin-
  6-ylmethyl)piperazin-1-yl}ethyl]-5-(3,5-dimethylphe-
  nyl)-6H-thieno[2,3-b]pyrrole;
2-[1,1-Dimethyl-2-oxo-2-(azabicyclo[2.2.1]heptan-7-yl)
  ethyl]-4-[2-{4-(morpholinocarbonyl)piperazin-1-
  yl}ethyl]-5-(3,5-dimethylphenyl)-6H-thieno[2,3-b]
  pyrrole;
2-[1,1-Dimethyl-2-oxo-2-(azabicyclo[2.2.1]heptan-7-yl)
  ethyl]-4-[2-(4-{N,N-
  dimethylaminocarbonylmethyl}piperazin-1-yl)ethyl]-
  5-(3,5-dimethylphenyl)-6H-thieno[2,3-b]pyrrole;
2-[1,1-Dimethyl-2-oxo-2-(azabicyclo[2.2.1]heptan-7-yl)
  ethyl]-4-[N-isopropylaminocarbonylmethyl)piperazin-
  1-yl}ethyl]-5-(3,5-dimethylphenyl)-6H-thieno[2,3-b]
  pyrrole;
2-[1,1-Dimethyl-2-oxo-2-(azabicyclo[2.2.1]heptan-7-yl)
  ethyl]4-[2-{4-(1,3-dimethyl-2,4-dioxo-1,2,3,4-tetrahy-
  dropyrimidin-6-ylmethyl)piperazin-1-yl}ethyl]-5-(3,5-
  dimethylphenyl)-6H-thieno[2,3-b]pyrrole;
2-[1,1-Dimethyl-2-oxo-2-(azabicyclo[2.2.1]heptan-7-yl)
  ethyl]-4-[2-(4-{azetidin-1ylcarbonylmethyl}piperazin-
  1-yl)ethyl]-5-(3,5-dimethylphenyl)-6H-thieno[2,3-b]
  pyrrole;
2-[1,1-Dimethyl-2-oxo-2-(azabicyclo[2.2.1]heptan-7-yl)
  ethyl]-4-[2-(4-pyrid4-ylpiperidin-1-yl)ethyl]-5-(3,5-
  dimethylphenyl)-6H-thieno[2,3-b]pyrrole;
2-[2-(1,1-Dimethyl-2-oxo-2-azabicyclo[2.2.1]heptan-7-
  ylethyl)]4-[2-{4-((3aR,6aS)-tetrahydro-3aH-[1,3]di-
  oxolo[4,5-c]pyrrol-5-ylcarbonyl)piperidin-1-yl}ethyl]-
  5-(3,5-dimethylphenyl)-6H-thieno[2,3-b]pyrrole;
2-[1,1-Dimethyl-2-oxo-2-(azabicyclo[2.2.1]heptan-7-yl)
  ethyl]-4-[2-(4-{3-hydroxypyrrolidin-1-
  ylcarbonyl}piperidin-1-yl)ethyl]-5-(3,5-dimethylphe-
  nyl)-6H-thieno[2,3-b]pyrrole;
2-[1,1-Dimethyl-2-oxo-2-(azabicyclo[2.2.1]heptan-7-yl)
  ethyl]-4-[2-(4-{3-oxo-3-pyrrolidin-1-ylprop-2-
  yl}piperazin-1-yl)ethyl]-5-(3,5-dimethylphenyl)-6H-
  thieno[2,3-b]pyrrole; and
2-[1,1-Dimethyl-2-oxo-2-(azabicyclo[2.2.1]heptan-7-yl)
  ethyl]-4-[2-(4-{pyrrolidin-1-
  ylcarbonylmethyl}piperazin-1-yl)ethyl]-5-(3,5-dim-
  ethylphenyl)-6H-thieno[2,3-b]pyrrole; and or a salt, pro-drug or solvate thereof.

A most preferred group of compounds according to the
present invention are wherein the compound is selected
from:

2-[1,1-Dimethyl-2-oxo-2-(azabicyclo[2.2.1]heptan-7-yl)
  ethyl)]-4-[2-(4-{morpholinocarbonyl}piperidin-1yl)
  ethyl]-5-(3,5-dimethylphenyl)-6H-thieno[2,3-b]pyr-
  role;
2-[1,1-Dimethyl-2-oxo-2-(azabicyclo[2.2.1]heptan-7-yl)
  ethyl]-4-[1-oxo-2-methyl-2-{4-(1,1-dioxidotetrahydro-
  3-thienyl)piperazin-1-yl}ethyl]-5-(3,5-dimethylphe-
  nyl)-6H-thieno[2,3-b]pyrrole;
2-[1,1-Dimethyl-2-oxo-2-(azabicyclo[2.2.1]heptan-7-yl)
  ethyl]-4-[2-{4-(pyrrolidin-1-ylcarbonylmethyl)piper-
  azin-1-yl }ethyl]-5-(3,5-dimethylphenyl)-6H-thieno[2,
  3-b]pyrrole;
2-[1,1-Dimethyl-2-oxo-2-(azabicyclo[2.2.1]heptan-7-yl-
  ethyl]-4-[2-{4-(2,4-dioxo-1,2,3,4-tetrahydropyrimidin-
  6-ylmethyl)piperazin-1-yl}ethyl]-5-(3,5-dimethylphe-
  nyl)-6H-thieno[2,3-b]pyrrole;
2-[1,1-Dimethyl-2-oxo-2-(azabicyclo[2.2.1]heptan-7-yl)
  ethyl]-4-[2-(4-{3-hydroxypyrrolidin-1-
  ylcarbonyl}piperidin-1-yl)ethyl]-5-(3,5-dimethylphe-
  nyl)-6H-thieno[2,3-b]pyrrole; and
2-[1,1-Dimethyl-2-oxo-2-(azabicyclo[2.2.1]heptan-7-yl)
  ethyl]-4-[2-(4-{3-oxo-3-pyrrolidin-1-ylprop-2-yl }pip-
  erazin-1-yl)ethyl]-5-(3,5-dimethylphenyl)-6H-thieno
  [2,3-b]pyrrole;

or a salt, pro-drug or solvate thereof.

In another embodiment of the invention a particularly
preferred group of compounds according to the present
invention are wherein the compound is selected from:

N-{2-[2-(1,1-dimethyl-2-oxo-2-pyrrolidin-1-ylethyl)-5-
  (3,5-dimethylphenyl)-6H-thieno[2,3-b]pyrrol4-yl]
  ethyl}4-pyridinylbutan-1-amine;
N-{2-[2-[2-(7-azabicyclo[2.2.1]hept-7-yl)-1,1-dimethyl-
  2-oxoethyl]-5-(3,5-dimethylphenyl)-6H-thieno[2,3-b]
  pyrrol-4-yl]ethyl}-4-pyridin-4-ylbutan-1-amine;
N-{2-[2-[2-(7-azabicyclo[2.2.1]hept-7-yl)-1,1-dimethyl-
  2-oxoethyl]-5-(3,5-dimethylphenyl)-6H-thieno[2,3-b]
  pyrrol-4-yl]ethyl}-4pyridin-4-ylethyl-1-amine;
{(2S)-2-[2-[2-(7-azabicyclo[2.2.1]hept-7-yl)-1,1-dim-
  ethyl-2-oxoethyl]-5-(3,5-dimethylphenyl)-6H-thieno
  [2,3-b]pyrrol-4-yl]propyl}(2-pyridin-4-ylethyl)amine;
N-{2-[2-[2-(2-azabicyclo[2.2.2]oct-2-yl)-1,1-dimethyl-2-
  oxoethyl]-5-(3,5-dimethylphenyl)-6H-thieno[2,3-b]
  pyrrol-4-yl]ethyl}-4-pyridin-4-ylbutan-1-amine;
N-{2-[2-[2-(2-azabicyclo[2.2.2]oct-2-yl)-1,1-dimethyl-2-
  oxoethyl]-5-(3,5-dimethylphenyl)-6H-thieno[2,3-b]
  pyrrol-4-yl]ethyl}-4-pyridin-4-ylethyl-1-amine;
{(2S)-2-[2-[2-(2-azabicyclo[2.2.2]oct-2-yl)-1,1-dim-
  ethyl-2-oxoethyl]-5-(3,5-dimethylphenyl)-6H-thieno
  [2,3-b]pyrrol-4-yl]propyl}(2-pyridin-4-ylethyl)amine;
2-(1,1-dimethyl-2-oxo-2-pyrrolidin-1-ylethyl)-5-(3,5-
  dimethylphenyl)-4-{2-[4-(pyridin-4-ylmethyl)piper-
  azin-1-yl]ethyl}-6H-thieno[2,3-b]pyrrole;
2-(1,1-dimethyl-2-oxo-2-pyrrolidin-1-ylethyl)-5-(3,5-
  dimethylphenyl)-4-{2-[4-(pyridin-2-ylmethyl)piper-
  azin-1-yl]ethyl}-6H-thieno[2,3-b]pyrrole;
2-(1,1-dimethyl-2-oxo-2-pyrrolidin-1-ylethyl)-5-(3,5-
  dimethylphenyl)-4-{2-[4-methylpiperazin-1-yl]ethyl}-
  6H-thieno[2,3-b]pyrrole;
2-(1,1-dimethyl-2-oxo-2-pyrrolidin-1-ylethyl)-5-(3,5-
  dimethylphenyl)-4-{2-[4-(pyridin-4-yl)piperazin-1-yl]
  ethyl}-6H-thieno[2,3-b]pyrrole;
2-[2-(2-azabicyclo[2.2.2]oct-2-yl)-1,1-dimethyl-2-oxoet-
  hyl]-5-(3,5-dimethylphenyl)-4-[2-(4-methylpiperazin-
  1-yl)ethyl]-6H-thieno[2,3-b]pyrrole;
4-[2-(4-allylpiperazin-1-yl)ethyl]-2-[2-(7-azabicyclo
  [2.2.1]hept-7-yl)-1,1-dimethyl-2-oxoethyl]-5-(3,5-
  dimethylphenyl)-6H-thieno[2,3-b]pyrrole;

2-[2-(7-azabicyclo[2.2.1]hept-7-yl)-1,1-dimethyl-2-oxo-ethyl]-5-(3,5-dimethylphenyl)-4-{2-[4-(2-morpholin-4-yl-2-oxoethyl)piperazin-1-yl]ethyl}-6H-thieno[2,3-b]pyrrole; and 2-[2-(7-azabicyclo[2.2.1]hept-7-yl)-1,1-dimethyl-2-oxo-ethyl]-5-(3,5-dimethylphenyl)-4-{2-[4-(pyridin4-ylm-ethyl)piperazin-1-yl]ethyl}-6H-thieno[2,3-b]pyrrole;

or a salt, pro-drug or solvate thereof.

The compounds of Formula (I) may be administered in the form of a pro-drug which is broken down in the human or animal body to give a compound of the Formula (I). Examples of pro-drugs include in-vivo hydrolysable esters of a compound of the Formula (1). Various forms of pro-drugs are known in the art. For examples of such pro-drug derivatives, see:

a) Design of Prodrugs, edited by H. Bundgaard, (Elsevier, 1985) and Methods in Enzymology, Vol. 42, p. 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113–191 (1991);

c) H. Bundgaard, Advanced Drug Delivery Reviews, 8, 1–38 (1992);

d) H. Bundgaard, et al., Journal of Pharmaceutical Sciences, 77, 285 (1988); and e) N. Kakeya, et al., Chem Pharm Bull, 32, 692 (1984).

An in-vivo hydrolysable ester of a compound of the Formula (1) containing a carboxy or a hydroxy group is, for example, a pharmaceutically-acceptable ester which is hydrolysed in the human or animal body to produce the parent acid or alcohol. Suitable pharmaceutically-acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cy-cloalkoxycarbonyloxy$C_{1-6}$alkyl esters for example 1-cyclohexylcarbonyloxyethyl; 1,3-dioxolen-2-onylmethyl esters, for example 5-methyl-1,3-dioxolen-2-onylmethyl; and $C_{1-6}$alkoxycarbonyloxyethyl esters.

An in-vivo hydrolysable ester of a compound of the Formula (I) containing a hydroxy group includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxy-methoxy. A selection of in-vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxy-ethyl)amine.

The compounds of Formula (I) can be prepared by a process comprising a step selected from (a) to (i) as follows, these processes are provided as a further feature of the invention:

(a) Reaction of a compound of formula XXXII with a compound of formula H—$R^{5'}$ to form a compound of Formula (I),

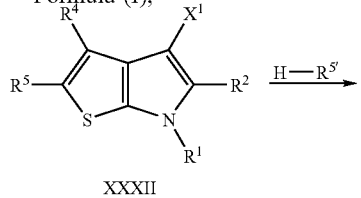

XXXII

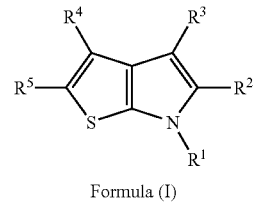

Formula (I)

wherein $X^1$ is selected from:

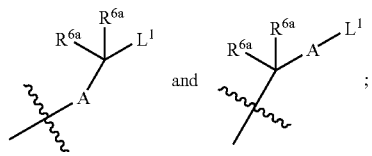

$L^1$ is a displaceable group;

H—$R^{5'}$ is selected from:

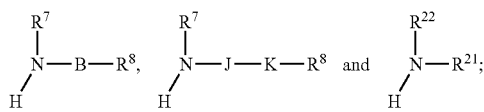

(b) Reaction of a compound of formula XXXIII with a compound of formula $L^2$—$R^{5''}$ to form a compound of Formula (I),

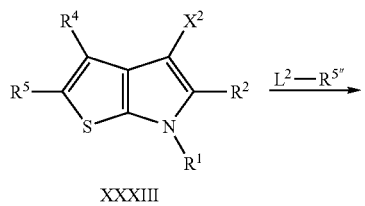

XXXIII

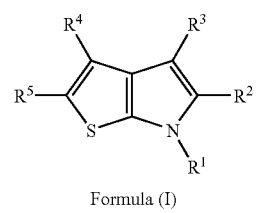

Formula (I)

wherein $X^2$ is selected from:

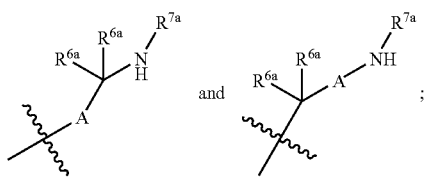

$L^2$ is a displaceable group and $R^{7a}$ is selected from the definition of $R^7$ or $R^{22}$ above, and $L^2$—$R^{5''}$ is selected from: $L^2$—B—$R^8$, L—J—K—$R^8$ and $L^2$—$R^{21}$;

(c) For compounds of Formula (I) wherein $R^3$ is a group of Formula (IIa), (IIb), (IIc) or (IId) and $R^7$ is other than part of a heterocyclic ring or hydrogen, reaction of a compound of Formula (I) wherein $R^3$ is a group of Formula (IIa), (IIb), (IIc) or (IId) and $R^7$ is hydrogen with a group of formula $L^3$—$R^{7a}$, wherein $R^{7a}$ is as defined above for $R^7$ with the exclusion of hydrogen and $L^3$ is a displaceable group;

(d) For compounds of Formula (I) wherein $R^3$ is a group of Formula (IIe) or (IIf) and $R^{21}$ is other than hydrogen, reaction of a compound of Formula (I) wherein $R^3$ is a group of Formula (IIe) or (IIf) and $R^{21}$ is hydrogen with a group of formula $L^4$-$R^{21a}$, wherein $R^{21a}$ is as defined above for $R^{21}$ with the exclusion of hydrogen and $L^4$ is a displaceable group;

(e) For compounds of Formula (I) wherein $R^3$ is a group of Formula (IIe) or (IIf) and $R^{22}$ is other than hydrogen, reaction of a compound of Formula (1) wherein $R^3$ is a group of Formula (IIe) or (IIf) and $R^{22}$ is hydrogen with a group of formula $L^5$—$R^{22a}$, wherein $R^{22a}$ is as defined above for $R^{22}$ with the exclusion of hydrogen and $L^5$ is a displaceable group;

(f) For compounds of Formula (I) wherein $R^3$ is a group of Formula (IIc) or (IId) and the group

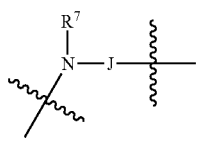

together forms an optionally substituted nitrogen-containing heterocyclic ring containing 4–7 carbons atoms, reaction of a compound of Formula XXXIVa or XXXIb, with a compound of Formula $L^6$—K—$R^8$, wherein $L^6$ is a displaceable group XXXIVa

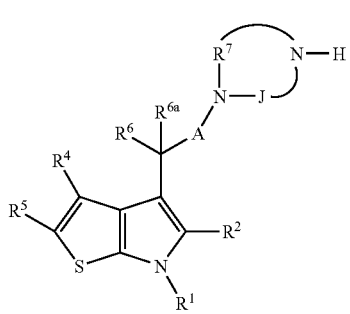

XXXIVb

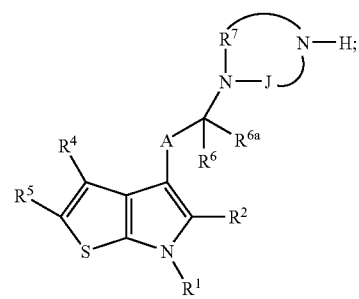

(g) For compounds of Formula (I) wherein $R^3$ is a group of Formula (IIc) or (IId), reaction of a compound of Formula XXXVa or XXXVb, with a compound of Formula $L^7$—K"—$R^8$, wherein $L^7$ is a displaceable group, and wherein the groups K' and K" comprise groups which when reacted together form K, XXXVa

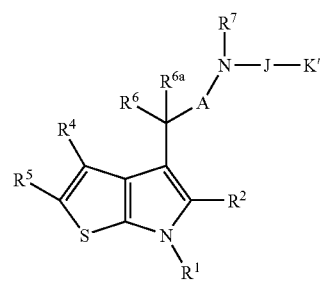

XXXVb

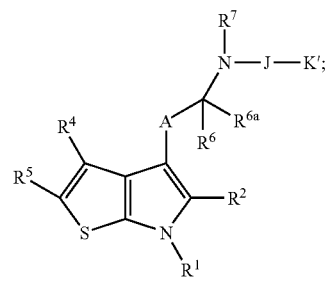

(h) reaction of a compound of Formula XXXVI with an electrophilic compound of the formula $L^8$—$R^5$, wherein $L^8$ is a displaceable group

XXXVI

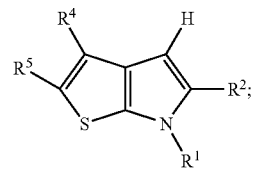

(i) reaction of a compound of Formula XXXVII with a compound of the formula $L^{10}$—$R^2$, wherein $L^9$ is a leaving group and $L^{10}$ is an activating group or $L^9$ is an activating group and $L^{10}$ is a leaving group

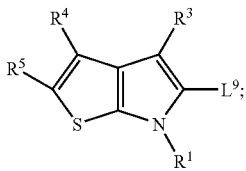

XXXVII and thereafter if necessary:
i) converting a compound of the Formula (I) into another compound of the Formula (I);
ii) removing any protecting groups;
iii) forming a salt, pro-drug or solvate.

Specific reaction conditions for the above reations are as follows:

Process a) Compounds of formula XXXII and H—R$^{5'}$ can be coupled together in the presence of an organic base (such as DIPEA [di-isopropylethylamine]) or an inorganic base (such as potassium carbonate) base, in a suitable solvent such as DMA or DMF, at a temperature from room temperature and 120° C. Suitable displaceable groups include: a halide, such as chloro, or a methane sulphonate or toluene sulphonate;

Process b) Compounds of XXXIII and L$^2$—R$^{5''}$ can be coupled together in the presence of an organic base(such as DIPEA) or an inorganic base (such as potassium carbonate), in a suitable solvent such as DMA or DMF, at a temperature from room temperature to 120° C. Suitable displaceable groups include: a halide, such as chloro, or a methane sulphonate or toluene sulphonate, alternatively if L$^2$ is a hydroxy group then the L$^2$—R$^{5''}$; can be reacted with a compound of formula XXXIII under Mitsunobu reaction conditions;

Process c, d, e and f) Reaction conditions to facilitate these reactions can be using (i) alkylation reaction conditions or (ii) acylation reaction conditions: Examples of said conditions include:
  (i) alkylation reaction conditions—the presence of an organic base(such as DIPEA) or an inorganic base (such as potassium carbonate), in a suitable solvent such as DMF, DMA, DCM, at a temperature from room temperature to 120° C. Suitable displaceable groups include: a halide, such as chloro, methane sulphonate or toluene sulphonate;
  (ii) acylation reaction conditions—presence of organic base, such as triethylamine, temperature 0° C. to 50–60° C. in a suitable solvent such as DCM. Suitable displaceable groups include an acylchloride or an acid anhydride, Process g) The skilled man would be familiar with a variety of reaction conditions and values for K' and K'', which when reacted together would form the group K, examples of said conditions and values for K' and K'' include:
  (i) For compounds of Formula (I) where K is —(CH$_2$)$_{s1}$—N(R$^9$)C(O)—(CH$_2$)$_{s2}$— these can be prepared by reacting a compound where K' is —(CH$_2$)$_{s1}$—N(R$^9$)H with a carboxylic acid for formula HOOC—(CH$_2$)$_{s2}$—R$^8$ to form the amide. Coupling of amino groups with carboxylic acids are well known in the art and can be facilitated by a number of chemical reactions using an appropriate coupling reagent. For example a carbodiimide coupling reaction can be performed with EDCl in the presence of DMAP in a suitable solvent such as DCM, chloroform or DMF at room temperature;
  (ii) For compounds of Formula (I) where K is —(CH$_2$)$_{s1}$—C(O)N(R$^9$)—(CH$_2$)$_{s2}$— these can be prepared by reacting a compound where K'$_9$ is —(CH$_2$)$_{s1}$—COOH with an amine of the HN(R$^9$)—(CH$_2$)$_{s2}$—R$^8$ to form the amide. Methodology is identical to processes described in (i) above in this section;
  (iii) For compounds of Formula (I) where K is —(CH$_2$)$_{s1}$—N(R$^9$)C(O)O—(CH$_2$)$_{s2}$— these can be prepared by reacting a compound where K' is —(CH$_2$)$_{s1}$—N(R$^9$)H with a chloroformate of formula ClC(O)O—(CH$^2$)$_{s2}$—R$^8$ in a suitable solvent, such as DCM or chloroform, in the presence of a base, such as N-methylmorpholine, pyridine or triethylamine, at a temperature between –10° C. and 0° C.;
  (iv) For compounds of Formula (I) where K is —(CH$_2$)$_{s1}$—OC(O)N(R$^9$—(CH$_2$)$_{s2}$— these can be prepared by reacting a compound where K' is —(CH$_2$)$_{s1}$—OC(O)Cl with a compound of formula HN(R$^9$)—(CH$_2$)$_{s2}$—R$^8$. Methodology is identical to processes described in (iii) above in this section;
  (v) For compounds of Formula (I) where K is —(CH$_2$)$_{s1}$—N(R$^9$)S(O$_2$)—(CH$_2$)$_{s2}$— these can be prepared by reacting a compound where K' is —(CH$_2$)$_{s1}$—N(R$^9$)H with a sulphonyl chloride of formula ClS(O$_2$)—(CH$_2$)$_{s2}$—R$^8$ in the presence of a base, such as triethylamine or pyridine, in a suitable solvent such as chloroform or DCM at a temperature between 0° C. and room temperature;
  (vi) For compounds of Formula (I) where K is —(CH$_2$)$_{s1}$—S(O$_2$)N(R$^9$)—(CH$_2$)$_{s2}$— these can be prepared by reacting a compound where K' is —(CH$_2$)$_{s1}$—S(O2)Cl with a compound of HN(R$^9$)—(CH$_2$)$_{s2}$—R$^8$. Methodology is identical to processes described in (v) above in this section
  (vii) For compounds of Formula (I) where K is —(CH$_2$)$_{s1}$—N(R$^9$)—(CH$_2$)$_{s2}$— these can be prepared by reacting a compound where K' is —(CH$_2$)$_{s1}$—L$^{11}$ with a compound of formula HN(R$^9$)—(CH$_2$)$_{s2}$—R$^8$, wherein L$^{11}$ is a displaceable group. This reaction can be performed in the presence of an organic base(such as DIPEA) or an inorganic base (such as potassium carbonate), in a suitable solvent such as DMA or DMF, at a temperature from room temperature to 120° C. Suitable displaceable groups include: a halide, such as chloro, or a methane sulphonate or toluene sulphonate. Compounds can also be prepared by reacting a compound wherein K' is —(CH$_2$)$_{s1}$—N(R$^9$)H with a compound of formula L$^{11}$—(CH$_2$)$_{s2}$—R$^8$, under identical conditions.
  (viii) For compounds of Formula (I) where K is —(CH$_2$)$_{s1}$—O—(CH$_2$)$_{s2}$— these can be prepared by reacting a compound where K' is —(CH$_2$)$_{s1}$—OH with a compound of formula L$^{12}$—(CH$_2$)$_{s2}$—R$^8$, wherein L$^{12}$ is a displaceable group. This reaction can be performed in the presence of an organic base (such as potassium t-butoxide) or an inorganic base (such as sodium hydride), in a suitable solvent such as DMA or DMF, at a temperature from room temperature to 120° C. Suitable displaceable groups include: a halide, such as bromo, or a methane sulphonate or toluene sulphonate. Compounds can also be prepared by reacting a compound wherein K' is —(CH$_2$)$_{s1}$—L$^{12}$ with a compound of formula HO—(CH$_2$)$_{s2}$—R$^8$, under identical conditions.

(ix) For compounds of Formula (I) where K is —(CH$_2$)$_{s1}$—C(O)—(CH$_2$)$_{s2}$— these can be prepared by reacting a compound where K' is —(CH$^2$)$_{s1}$—C(O)—L$^{13}$ with a Grignard reagent of formula BrMg(CH$_2$)$_{s2}$—R$^8$, wherein L$^{13}$ is a displaceable group. This reaction can be performed in a non-polar solvent such as THF or diethylether at a temperature between room temperature and the boilling point of the solvent. Suitable displaceable groups include: a halide, such as chloro, or an alkoxide. Compounds can also be prepared by reacting a compound wherein K' is —(CH$_2$)$_{s1}$—MgBr with a compound of formula L$^{13}$—C(O)—(CH$_2$)$_{s2}$—R$^8$, under identical conditions.

Process h) reaction of a compound of Formula XXXVI with a compound of the formula L$^8$—R$^5$, can be performed under Friedel Craft conditions, for example in the presence of diethylaluminium chloride in a suitable solvent, such as DCM, in an inert atmosphere such as nitrogen, at a temperature between room temperature and the boiling point of the solvent or under Mannich conditions, for example, formaldehyde and a primary or secondary amine in acetic acid, in an inert atmosphere such as nitrogen at a temperature between room temperature and 100° C.

Process i) reaction of a compound of Formula XXXVII with a compound of the formula L$^{10}$-R$^2$, wherein L$^9$ is a leaving group and L$^{10}$ is an activating group or L$^9$ is an activating group and L$^{10}$ is a leaving group, can be performed in an aprotic, polar solvent such as THF, using palladium chemistry under Suzuki or Stille conditions, at a temperature between 0 to 70° C.

It will be appreciated by those skilled in the art that in the processes of the present invention certain functional groups such as hydroxyl or amino groups in the starting reagents or intermediate compounds may need to be protected by protecting groups. Thus, the preparation of the compounds of Formula (I) may involve, at an appropriate stage, the addition and subsequent removal of one or more protecting groups.

The protection and de-protection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The de-protection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The de-protection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

Experimental

General Reaction Schemes

In the following schemes wherein Ri, Rii and Riii represent optional substituents on the phenyl ring which are optionally protected as necessary and R represents a protecting group, group C has been depicted as substituted phenyl for illustration purposes only. Other definitions of C are also appropriate.

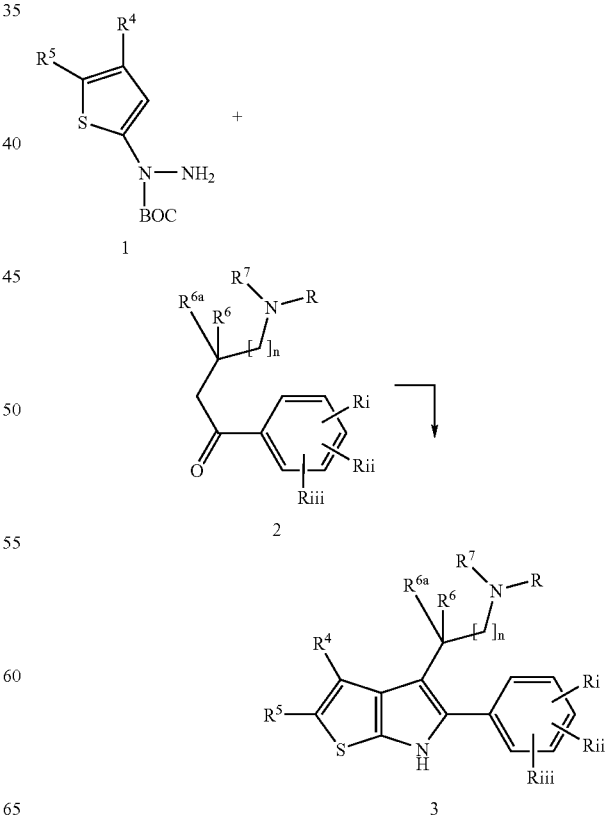

Scheme a

Thienopyrroles, such as 3 can be synthesised by the classic Fisher thienopyrrole synthesis reaction by the condensation of a hydrazine-HCl 1 and a ketone 2, bearing hydrogen atoms α to the carbonyl (Scheme a). Treatment of these reactants in a suitable solvent, such as acetic acid, ethanol, sec-butanol, toluene, in the presence of an acid, such as sulphuric, hydrochloric, polyphosphoric and/or a Lewis acid, for example, boron trifluoride, zinc chloride, magnesium bromide, at elevated temperatures (for example 100° C.), gives the desired product. R represents a protecting group, eg tert-butylcarbamate or phthalimide.

Scheme b

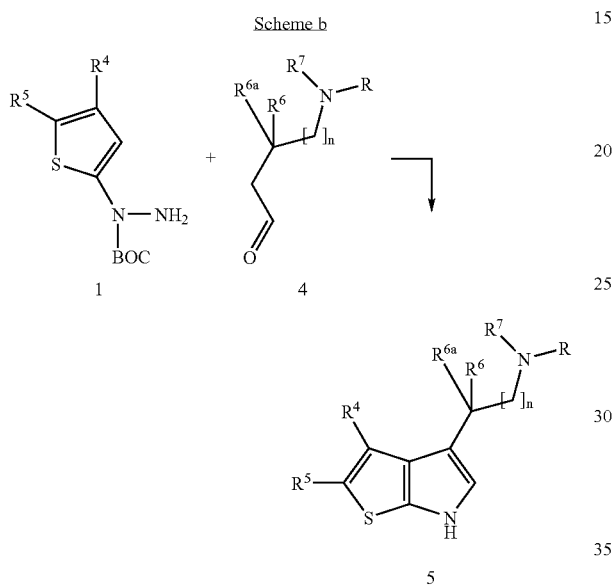

Thienopyrroles, such as represented in structure 5, can also be made using aldehydes 4, bearing hydrogen atoms α to the carbonyl, by cyclization using the conditions above. In this case the substituent at the 2-position must be added later (see scheme d).

Scheme c

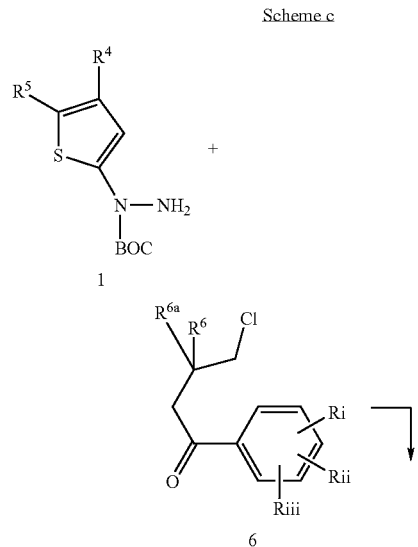

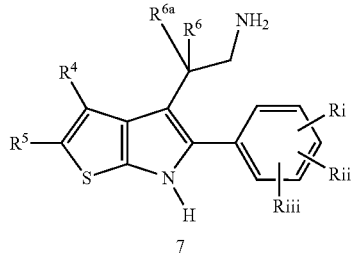

Thienopyrrole may also be synthesised utilising the Granburg reaction, wherein a hydrazine 1 is mixed with ketone 6, bearing a chlorine atom γ to the carbonyl, and heated in a suitable solvent such as ethanol, sec-butanol, toluene at a temperature between 50° C. and 120° C. (Scheme c).

Scheme d

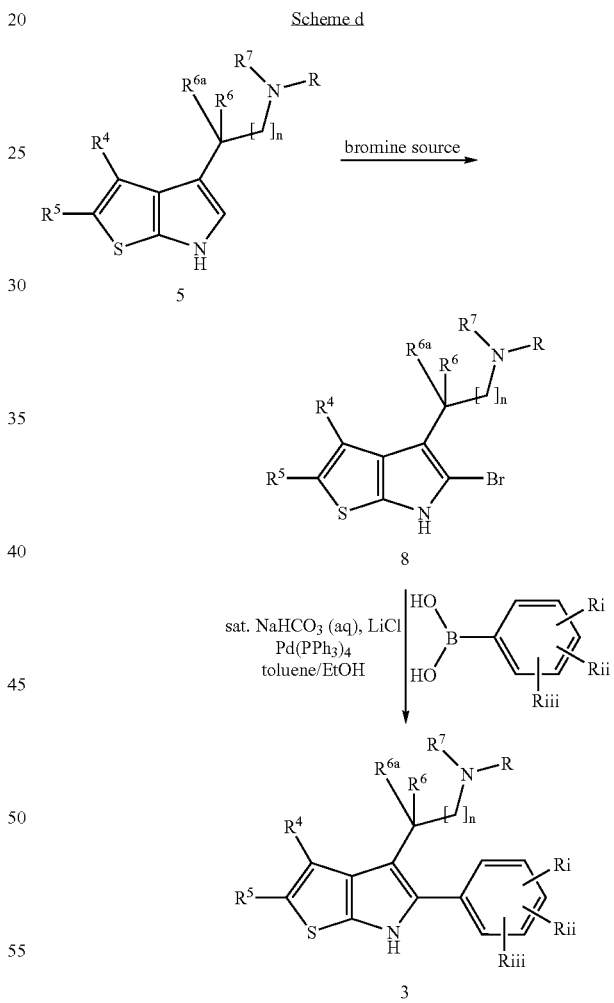

The thienopyrrole 5 can be treated with a 'bromine source', such as molecular bromide, pyridinium tribromide, pyrrolidone hydrobromide or polymer supported reagent equivalents, in an inert solvent such as chloroform, methylene chloride at −10° C. to 25° C. to yield the 2-bromo compound 8 (Scheme d). Reaction under Suzuki conditions with a palladium(0) catalyst, a weak base such as aqueous sodium carbonate or saturated sodium hydrogen carbonate and the like, and a substituted aryl boronic acid from commercial sources or prepared (as described in: Gronowitz, S.; Hornfeldt, A.-B.; Yang, Y.,-H *Chem. Sci.* 1986, 26, 311–314), in an inert solvent such as toluene, benzene, dioxane, THF, DMF and the like, with heating between 25° C. and 100° C., preferably 80° C., for a period of 1–12 hours, to give the desired compound 3.

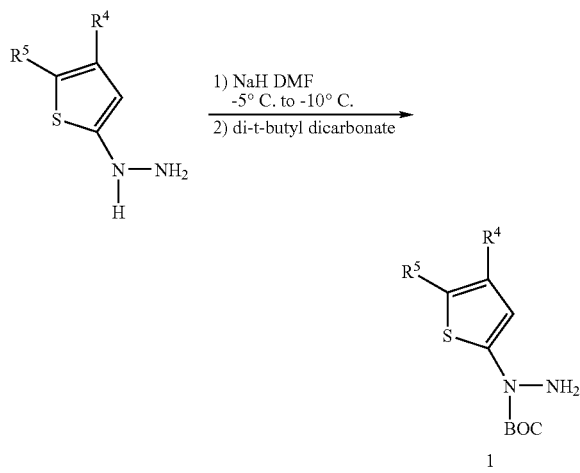

The thiophene 1 can be synthesised by reaction of a hydrazine under the preferred conditions of sodium hydride in DMF at a temperature between −10° C. and −5° C., followed by reaction with di-tert-butyldicarbonate in THF under reflux.

Scheme e.

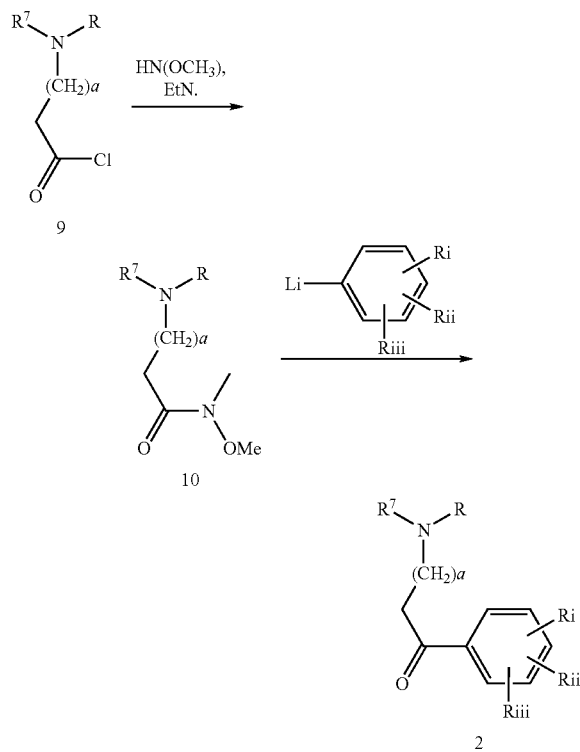

Substituted ketones 2 can be prepared, as outlined in Scheme e starting from appropriate acid chlorides such as 9. Treatment of the acid chloride with N,N-dimethylhydroxylamine hydrochloride in the presence of an amine base such as triethylamine, and a suitable solvent such as methylene chloride at a temperature of −10° C. to 25° C., yields the amide 10. Further reaction with a substituted aryl organolithium (prepared essentially as described in Wakefield B, J.; *Organolithium Methods* Academic Press Limited, 1988, pp. 27–29 and references therein) in an inert solvent such as tetrahydrofuran, diethyl ether, benzene, toluene or mixture thereof and the like, at a temperature between −100° C. and 0° C. then quenching of the reaction mixture with a mineral acid such as hydrochloric acid, yields the aryl ketone 2.

Scheme f.

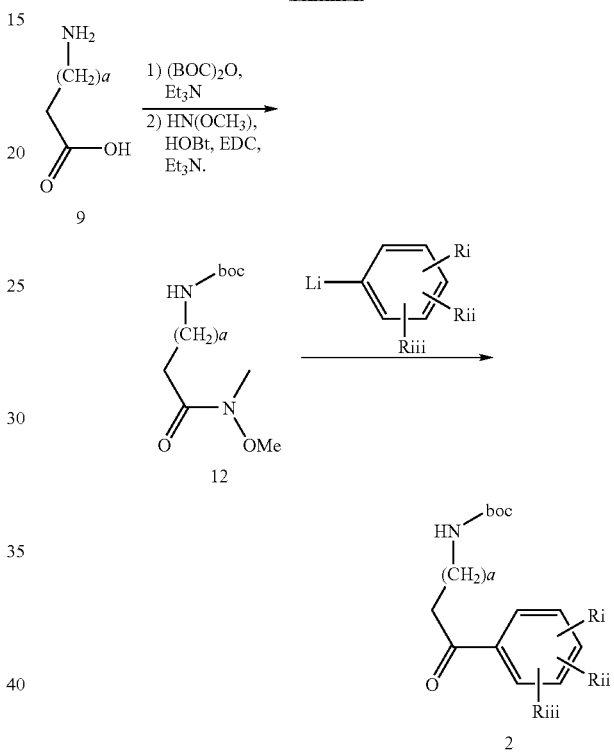

Commencing with a readily available amino acid with a suitable chain length [a] 11, the nitrogen atom can be brought in at the beginning of the synthesis by the route shown in Scheme f. Protection of the amine group of 11 with a tert-butylcarbamate group is achieved by condensation with di-tert-butyl di-carbonate in the presence of an amine base, for example triethylamine, in an inert solvent such as methylene chloride, chloroform, benzene, toluene, tetrahydrofuran and mixtures thereof and the like, at a temperature of −10° C. to 25° C. Coupling of the acid product with N,N-dimethylhydroxylamine in the presence of a coupling reagent 1-(3-dimethylaminopropyl)-3-ethylcarbodiimide hydrochloride (EDC) or 1,3-dicyclohexylcarbodiimide (DCC) or the like, with or without 1-hydroxybenzotriazole (HOBt), and suitable amine base, such as triethylamine and the like, in an inert solvent such as methylene chloride, chloroform, dimethylformamide, or mixture thereof, at or near room temperature for a period of 3 to 24 hours provided the corresponding coupled product 12. Following the same route described above for scheme e, the aryl group can then be installed.

Scheme g.

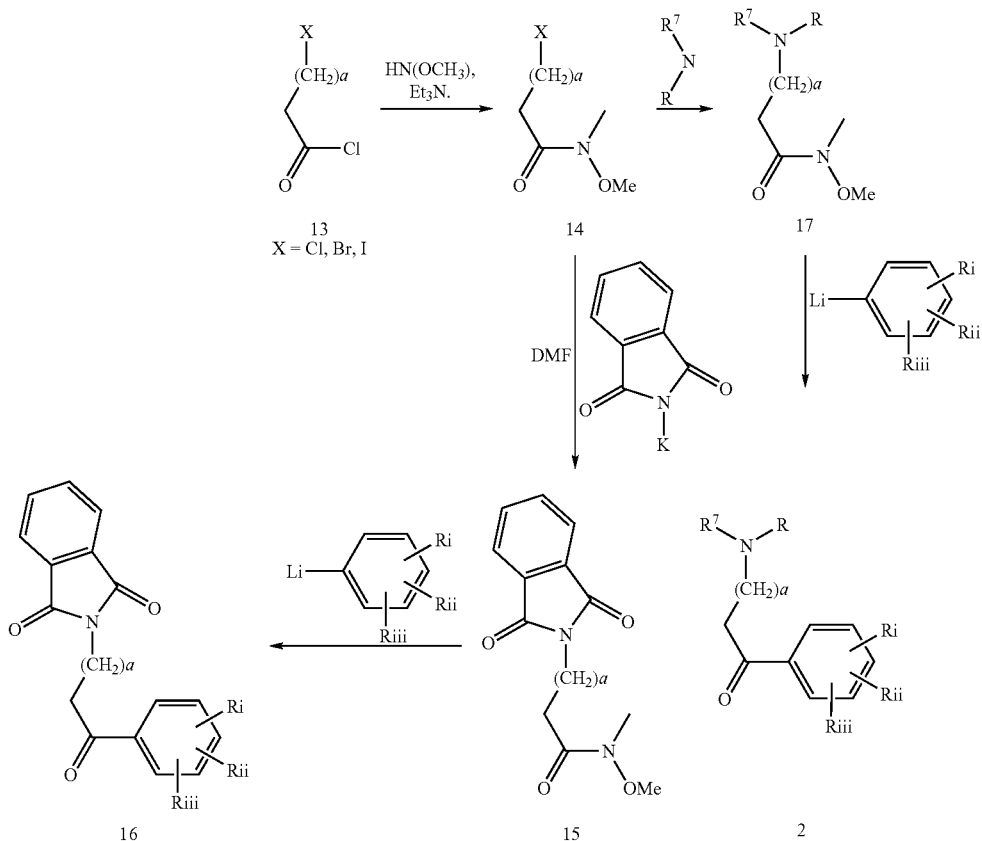

Scheme g illustrates another method for the synthesis of ketone such as 2 and 16, where the nitrogen group is introduced at a latter stage. As above a Weinreb amide 14 can be synthesised from an acid chloride. Treatment with the required amine, in an inert solvent such as THF, toluene, water and the such like can displace the group X to give 17. As above the aryl group can be introduced by displacement of the Weinreb amide with a suitable aryl lithium nucleophile. Alternatively the nitrogen atom can be introduced already protected as a phthalimide by displacement of the group X by potassium phthalimide, or similar salt thereof, by heating in an inert polar solvent such as DMF, DMSO, THF, toluene with or without the presence of a catalyst such as tetrabutylammonium iodide and the such like, to yield the compound 15. Again displacement of the Weinreb amide with an organolithium species completes the synthesis of ketone 16 suitable for cyclization under the Fischer condition described above for thienopyrrole synthesis.

Scheme h.

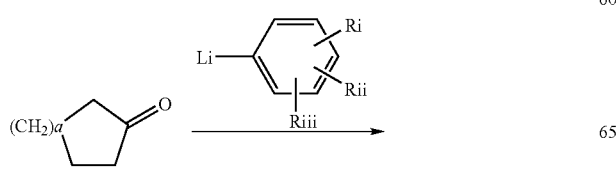

-continued

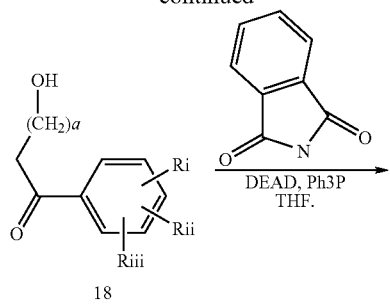

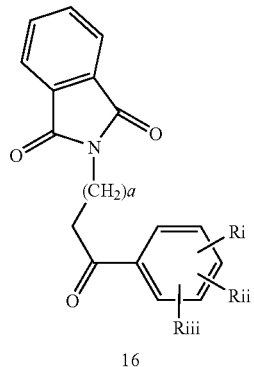

An alternative approach to a phthalimide protected nitrogen ketone, such as 16, can be taken by firstly treating a lactone, with an organolithium species as in the above schemes in a suitable solvent such as THF or ether at a low temperature of between −100° C. and −50° C. to yield a primary alcohol 18 (Scheme h). The hydroxyl function of 18 is replaced with a phthalimide group by a Mitsunobu reaction with an activating agent such as diethyldiazocarboxylate (DEAD), diisopropyldiazocarboxylate or the like with triphenylphosphine, tri-butylphosphine and the like, in an inert solvent such as benzene, toluene, tetrahydrofuran or mixtures thereof to give the desired ketone 16.

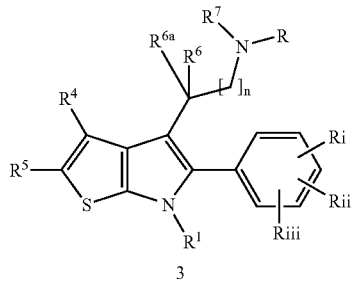

3

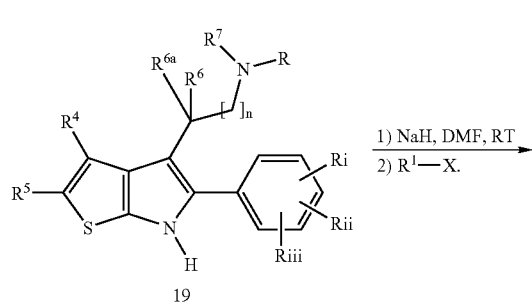

19

If the group $R^1$ was not present on the starting hydrazine before cyclization to form a thienopyrrole it may be added post cyclization by an alkylation reaction (19→3). The thienopyrrole is de-protonated by a strong base, such as sodium hydride, n-butyl lithium, lithium diisopropylamine, sodium hydroxide, potassium tert-butoxide in a suitable inert solvent such as THF, DMF, DMSO and the such like, and an alkyl halide added and the mixture stirred at room temperature.

Scheme i

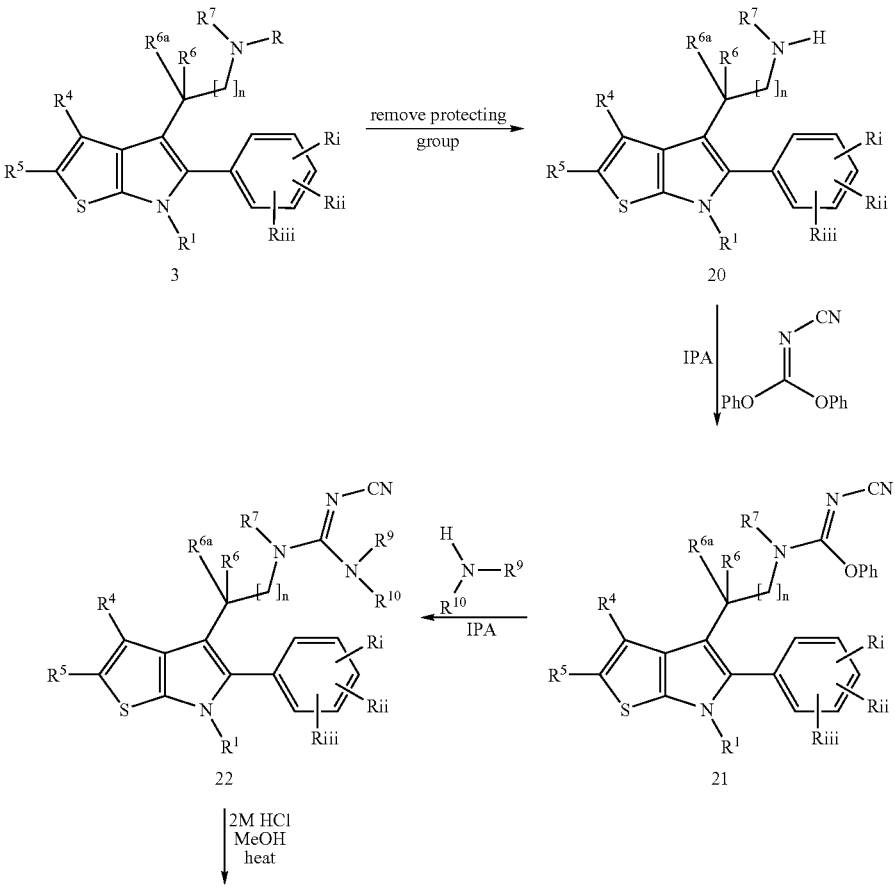

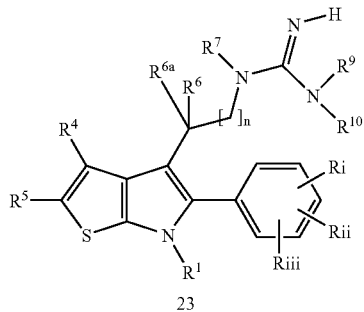

23

Depending on the route used above a thienopyrrole 20 suitable for conversion to a cyano-guanidine can be formed by removal of the protecting group, for example if a tert-butylcarbamate group was used then removal is accomplished using a strong acid, for example trifluoroacetic acid or hydrochloric acid in an inert solvent such as methylene chloride, chloroform, THF or dioxane at a temperature between −20° C. and 25° C. A phthalimide group, for example, can be removed by hydrazine in a suitable solvent for example methanol, ethanol, methylene chloride, chloroform, THF dioxane at a temperature between −20° C. and 25° C. The primary amine 20 can be converted to a cyano-guanidine 22 by the two step process of reaction with diphenyl cyanocarbonimidate in an inert organic solvent such as iso-propyl alcohol, methylene chloride, chloroform, benzene, tetrahydrofuran and the like, at a temperature between −20° C. and 50° C., followed by condensation with an appropriately substituted amine in an inert organic from the list above, with heating at a temperature between −20° C. and 100° C. (Scheme i 20→21→22). Further treatment of 22 with 2 molar Hydrochloric acid in methanol at elevated temperature yields guanidine compounds 23.

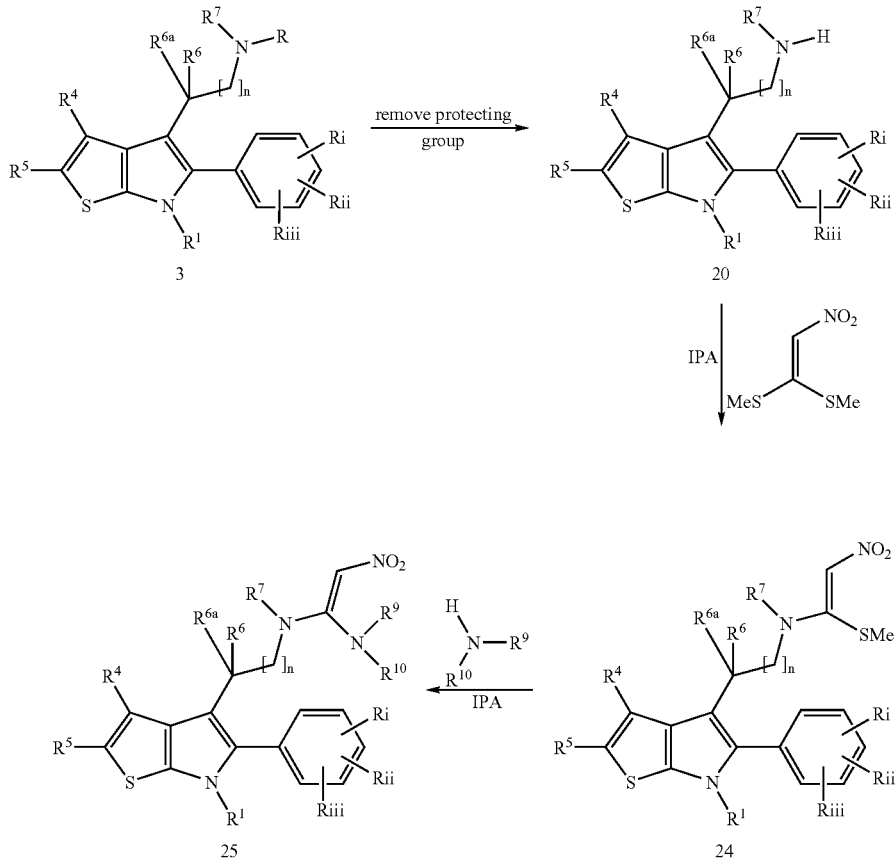

Scheme j.

Similarly, reaction with 1,1'-bis(methylthio)-2-nitroethylene in an inert solvent such methylene chloride, chloroform, benzene, tetrahydrofuran and the like, followed by condensation with an appropriately substituted amine in an inert organic solvent from the list above yields the nitroethylene-imidazo[1,2-α]pyridine 25 (Scheme j, 20→24→25).

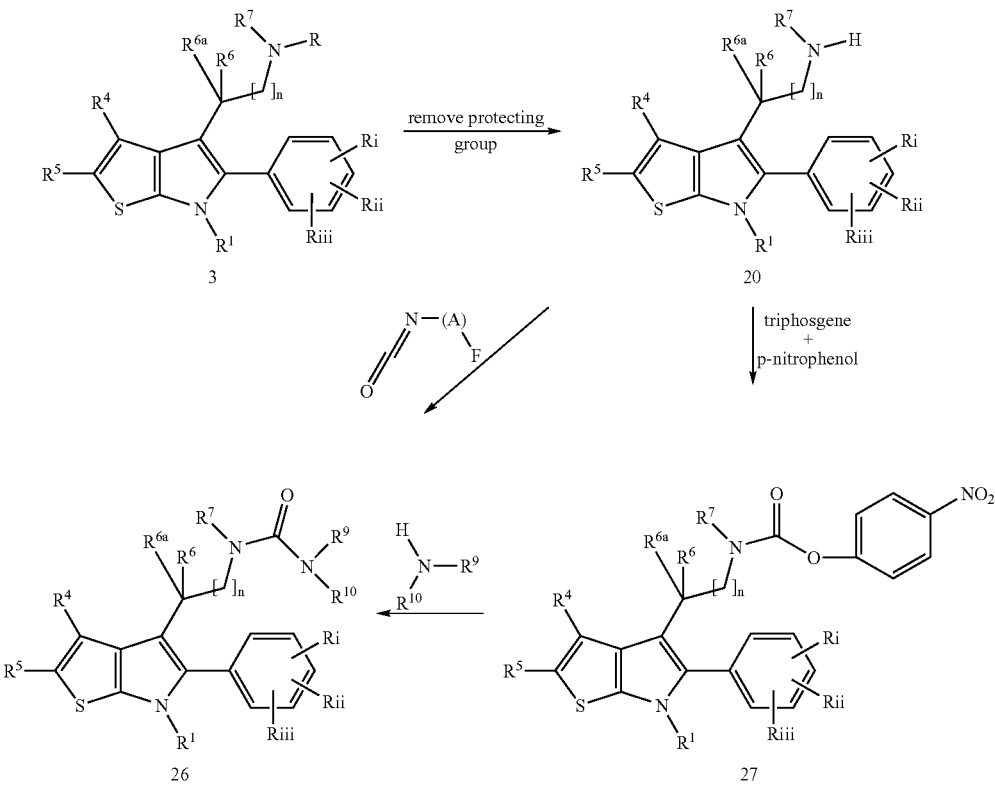

Again in a similar fashion the suitable thienopyrrole 20, derived from de-protection, can be converted to a urea by either direct treatment with an iso-cyanate in an inert solvent such as a methylene chloride, chloroform or THF and the such like, or by a two step procedure of reaction with triphosgene (20→27) followed by addition of an amine (27→26), bearing the required substitution to yield 26.

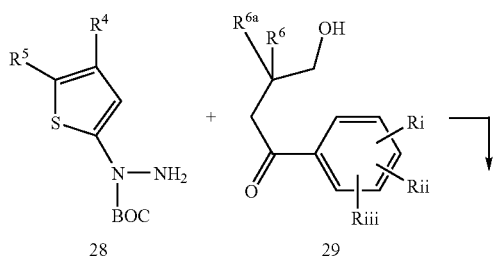

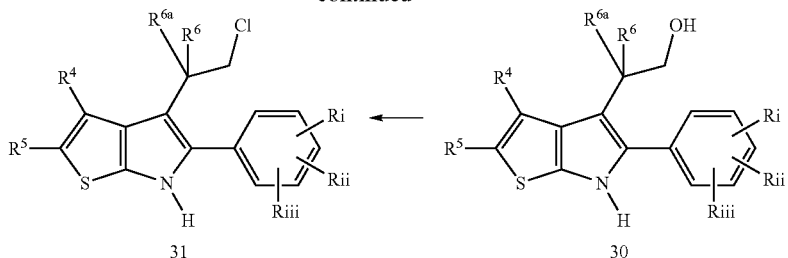

Chloro thieno-pyrrole intermediates, such as 31, can be made as shown in Scheme 1. 30 can synthesized by the classic Fisher thieno-pyrrole synthesis reaction by the condensation of a hydrazine-HCl 28 and a ketone 29, bearing hydrogen atoms α to the carbonyl. Treatment of these reactants in a suitable solvent, such as acetic acid, ethanol, sec-butanol, toluene, in the presence of an acid, such as sulphuric, hydrochloric, polyphosphoric and/or a Lewis acid, for example, boron trifluoride, zinc chloride, magnesium bromide, at elevated temperatures (for example 100° C.), gives the desired product. The chloro intermediate 31 can then be synthesized from 30 using, for example, either (i) sulphonyl chloride in methylene chloride at a temperature of about 0° C., or (ii) CCl$_4$ followed by triphenylphosphine in a solvent such as acetonitrile at a temperature of about 0° C. Thienopyrroles of the invention can then be prepared by displacement of chlorine atom using an appropriate side chain intermediate such as a substituted heterocyclic ring.

Scheme m.

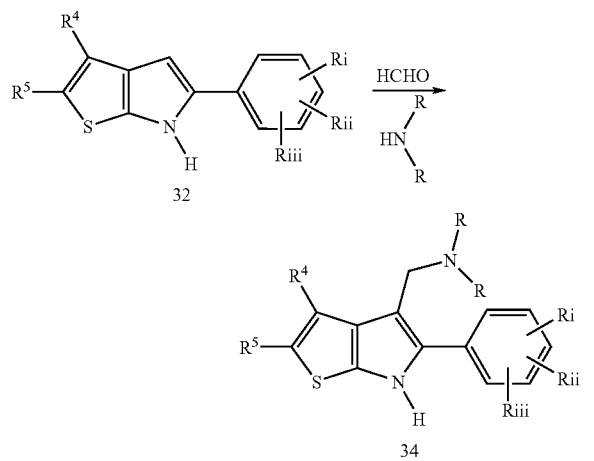

Thienopyrroles of Formula (I) wherein A is a direct bond and $R^6$ and $R^{6a}$ are both hydrogen can be prepared as shown in Scheme m. A thieno-pyrrole 32 can be reacted with formaldehyde and an amine, in a suitable solvent such as acetic acid/dioxan at a temperature of about 0° C. to 25° C. for between about 1 to 8 hours, form the thieno-pyrrole 34.

EXAMPLES

The invention will now be illustrated with the following non-limiting examples in which, unless otherwise stated:
(i) evaporations were carried out by rotary evaporation in vacuo and work-up procedures were carried out after removal of residual solids such as drying agents by filtration;
(ii) operations were carried out at room temperature, that is in the range 18–25° C. and under an atmosphere of an inert gas such as argon or nitrogen;
(iii) yields are given for illustration only and are not necessarily the maximum attainable;
(iv) the structures of the end-products of the Formula (I) were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;
(v) intermediates were not generally fully characterised and purity was assessed by thin layer chromatography (TLC), high-performance liquid chromatography (HPLC), infra-red (IR) or NMR analysis;
(vi) chromatography was performed on silica (Merck Keiselgel: Art.9385);
(vii) isolute™ refers to silica (SiO$_2$) based columns with irregular particles with an average size of 50 μm with nominal 60 Å porosity [Source: Jones Chromatography, Ltd., Glamorgan, Wales, United Kingdom].

| Abbreviations | |
|---|---|
| DCC | 1,3-dicyclohexylcarbodiimide |
| DCM | dichloromethane |
| DEAD | diethylazodicarboxylate |
| DIPEA | di-isopropylethylamine |
| DMA | dimethylacetamide |
| DMSO | dimethyl sulphoxide |
| DMAP | 4-dimethylaminopyridine |
| DMF | dimethylformamide |
| EDCI | 1-(3-dimethylaminopropyl)-3-ethylcarbodiimide hydrochloride |
| HOBt | 1-hydroxybenzotriazole |
| THF | tetrahydrofuran |

Example 1

2-(1,1-dimethyl-2-oxo-2-pyrrolidin-1-ylethyl)-4-N-(2-pyridin-4-ylethyl)aminoethyl-5-(3,5-dimethylphenyl)-6H-thieno[2,3-b]pyrrole

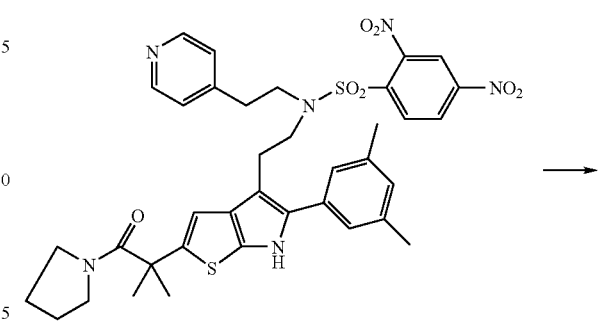

14

-continued

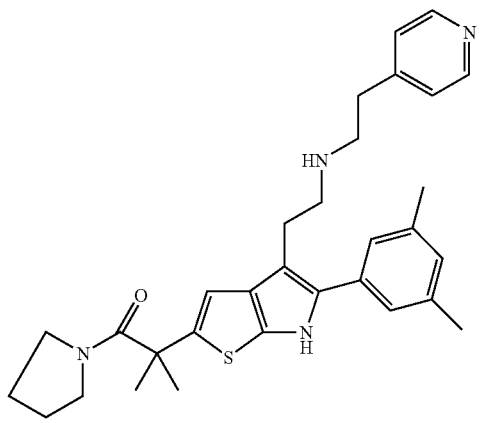

Example 1

A solution of 14 (0.486 g; 0.649 mmol) in $CH_2Cl_2$ (6 ml) was treated with n-propylamine (0.5 ml). The mixture was stirred at ambient temperature for 1 hour. After evaporation to dryness, the residue was taken up in AcOEt and treated at 0° C. with an HCl/ether mixture to give a precipitate which was washed with AcOEt and ether.

Yield: 81% MS-ESI: 515 $[M+H]^{+1}$H NMR (DMSOd6): 1.55 (s, 6H); 1.64 (m, 4H); 2.33 (s, 6H); 3–3.35 (m, 12H); 9.89 (s, 1H); 6.95 (s, 1H); 7.08 (s, 2H); 7.6–7.9 (br m, 1H); 8.04 (d, 2H); 8.93 (d, 2H).

The starting material was prepared as follows:

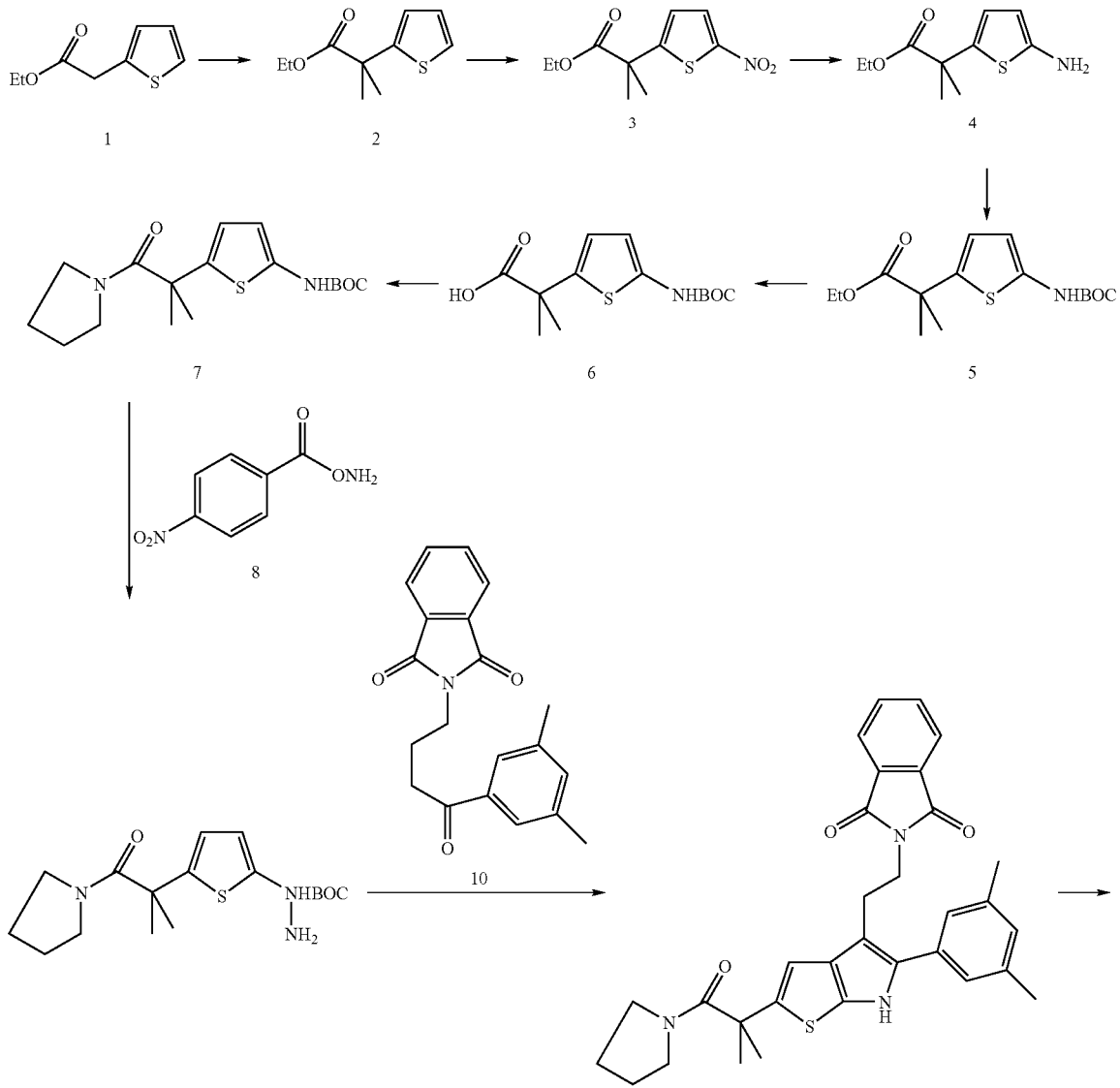

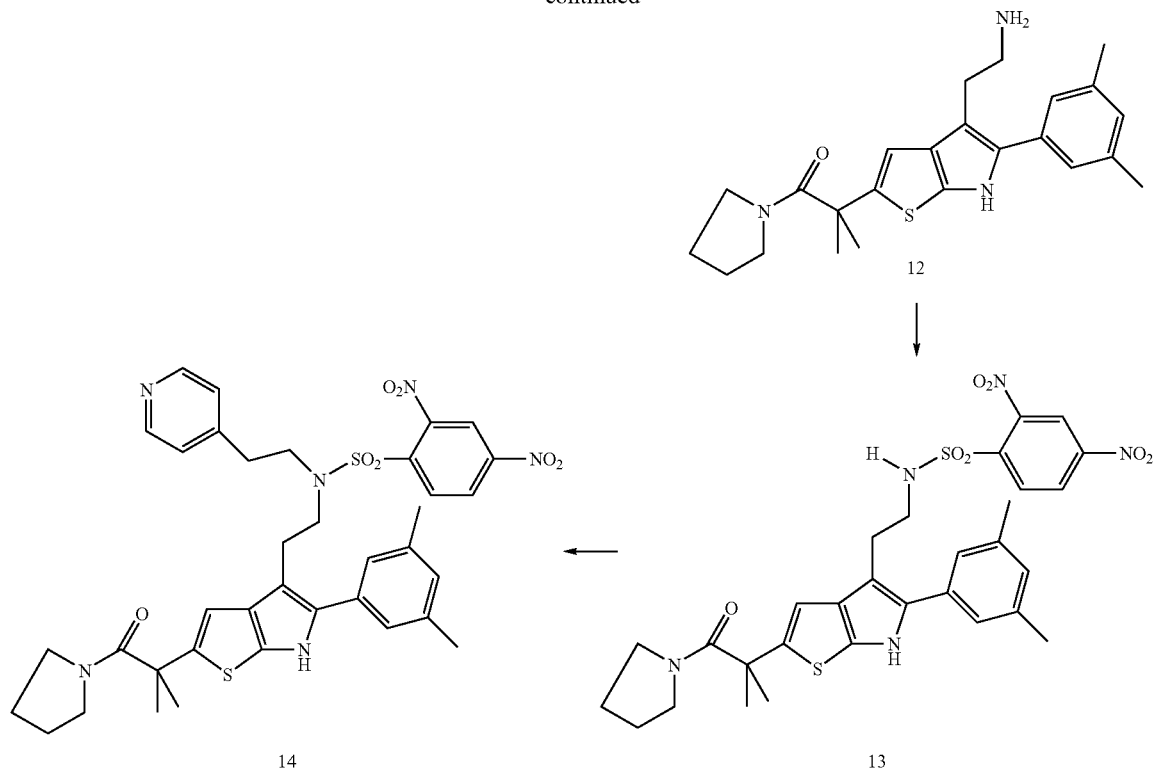

To a suspension of NaH (54 g; 1.35 mol), and 18-crown-6 in THF (2 l) stirred at ambient temperature under argon atmosphere, 1 (100 g; 0.588 mol) was added over a period of 30 minutes. After stirring overnight, the mixture was cooled at 0° C. and methyl iodide was added dropwise. The mixture was stirred at 18° C. for 3 hours, poured into a saturated solution of NH$_4$Cl and extracted with AcOEt. The organic phase was evaporated and purified by flash chromatography eluting with petroleum ether/ethyl acetate 95/5 to give 2 as an oil.

Yield: 90% $^1$H NMR (CDCl$_3$): 1.20 (t, 3H); 1.63 (s, 6H); 4.10 (q, 2H); 6.92 (m, 2H); 7.17 (m, 1H).

Nitronium tetrafluoroborate (77.9 g; 0.586 mol) was added at −55° C. to a solution of 2 (105.6 g; 0.583 mol) in DME (1.5 l). The mixture was allowed to warm up at −10° C. over 4 hours. After extraction with ethyl acetate, the organic phase was purified by flash chromatography, eluting with petroleum ether/AcOEt 95/5 to give 3.

Yield: 86% $^1$H NMR (CDCl$_3$): 1.23 (t, 3H); 1.65 (s, 6H); 4.14 (q, 2H); 6.90 (d, 1H); 7.75 (d, 1H).

A suspension of 3 (101.7 g; 0.41 mol) and 10% Pd/C (15 g) in a mixture of ethanol (700 ml) and ethyl acetate (300 ml) was hydrogenated under hydrogen atmosphere (5 bars) for 5 hours. After filtration of the catalyst on celite, the residue was evaporated and redissolved in THB (900 ml); di-tert-butyl dicarbonate (100 g; 0.46 mol) was added and the mixture was refluxed for 16 hours. After evaporation of the solvents, the resulting solid was taken up in petroleum ether and filtered to give 5.

Yield: 68% $^1$H NMR (CDCl$_3$): 1.20 (t, 3H); 1.48 (s, 9H); 1.58 (s, 6H); 4.10 (q, 2H); 6.30 (m, 1H); 6.60 (m, 1H).

A solution of 5 (50 g; 0.16 mol) and 2N NaOH (160 ml) in ethanol (300 ml) was refluxed for 1 h 30. After evaporation to dryness, the residue was partitioned between water and ether. The aqueous layer was acidified with saturated citric acid and extraction with ethyl acetate to give after evaporation a solid, which was triturated in pentane and filtered to give 6 as a solid.

Yield: 100% $^1$H NMR (DMSOd$_6$): 1.48 (m, 15H); 6.30 (d, 1H); 6.59 (d, 1H).

A solution of 6 (20.1 g; 0.07 mol), EDCI (20.1 g; 0.105 mol) and DMAP (2.56 g; 0.021 mol) in dichloromethane (200 ml) was stirred under argon atmosphere for 10 minutes. Pyrrolidine (11.69 ml; 0.14 mol) was then added and the mixture was stirred overnight at ambient temperature. After evaporation to dryness, the residue was purified by flash chromatography eluting with AcOEt/petroleum ether 40/60 to give after trituration in ether/pentane 7 as a solid.

Yield 73% $^1$H NMR (CDCl$_3$): 1.51 and 1.57 (s, 15 H); 1.7 (m, 4H); 3.03 (br, 2H); 3.50 (br, 2H); 6.35 (d, 1H); 6.48 (d, 1H); 7.26 (br, 1H).

7 (17 g; 0.05 mol) was added under argon atmosphere to a suspension of NaH 60% (2.42 g; 0.06 mol) in dioxan (240 ml). The mixture was stirred at 100° C. for 3 hours. After cooling to 10° C., 8 (10.1 g; 0.055 mol) was added. The reaction mixture was stirred at ambient temperature overnight. After filtration of the insoluble, the filtrate was evaporated and purified by flash chromatography, eluting with AcOEt/petroleum ether 45/55 to give 9 as a white solid.

Yield: 90% $^1$H NMR (CDCl$_3$): 1.55 and 1.57 (s, 15 H); 1.71 (s, 4H); 3.04 (s, 2H); 3.50 (s, 2H); 6.53 (d, 2H); 6.70 (s, 2H).

A solution of 9 hydrochloride salt (4 g; 0.0102 mol) and 10 (6.6 g; 0.0205 mol) in AcOH (20 ml) was heated at 120° C. under argon atmosphere for 3 hours. The reaction mixture was diluted with saturated NH$_4$Cl and extracted with AcOEt.

After evaporation, the crude was purified by flash chromatography eluting with AcOEt/petroleum ether 50/50 to give 11 as a foam.

Yield: 53% $^1$H NMR (CDCl$_3$): 1.53 and 1.58 (s, 6H); 1.69 (s, 4H); 2.29 (s, 6H); 3.12 (m, 4H); 3.52 (s, 2H); 3.91 (m, 2H); 6.80 (m, 2H); 7.02 (s, 2H); 7.6–7.8 (m, 4H); 8.10 (s, 1H). MS-ESI: 540 [M+H]$^+$ A solution of 11 (0.534 g; 0.99 mmol) and hydrazine (1 ml) in a mixture of EtOH (2 ml) and CH$_2$Cl$_2$ (2 ml) was stirred under argon atmosphere at ambient temperature overnight. After evaporation, the crude was extracted in a mixture of CH$_2$Cl$_2$ and saturated NaHCO$_3$. The organic layer was evaporated to give 12 as a foam.

Yield: 90% $^1$H NMR (CDCl$_3$): 1.52 and 1.62 (s, 6H); 1.69 (s, 4H); 2.33 (s, 6H); 2.80–3.2 (m, 6H); 3.52 (m, 2H); 6.74 (s, 1H); 6.93 (s, 1H); 7.05 (s, 2H); 8.15 (s, 1H). MS-ESI: 410 [M+H]$^+$ 2,4 dinitrobenzylsulfonyl chloride (0.238 g; 0.892 mmol) was added at 0° C., under argon atmosphere to a solution of 12 (0.365 g; 0.892 mmol) and collidine (0.118 ml; 0.892 mmol) in CH$_2$Cl$_2$ (5 ml). The mixture was stirred at 20° C. for 1 hour. After evaporation, the crude was purified by flash chromatography eluting with CH$_2$Cl$_2$/EtOH 96/4 to give 13.

Yield: 90% MS-ESI: 640 [M+H]$^+$

DEAD (0.295 ml; 1.5 mmol) was added at 0° C. under argon atmosphere to a solution of 13 (0.48 g; 0.75 mmol), PPh$_3$ (0.393 g; 1.5 mmol) and 2-hydroxyethyl-4-pyridine (0.185 g; 1.5 mmol) in THF (12 ml). The mixture was stirred at ambient temperature for 2 hours and purified by flash chromatography eluting with AcOEt/petroleum ether 80/20 to give 14.

Yield: 86% $^1$H NMR (CDCl$_3$): 1.55 (s, 6H); 1.55–1.8 (m, 4H); 2.3 (s, 6H); 2.75 (t, 2H); 3–3.2 (m, 4H); 3.4–3.7 (m, 6H); 6.71 (s, 1H); 6.88 (d, 2H); 6.93 (s, 1H); 6.94 (s, 2H); 7.86 (d, 1H); 8.20–8.25 (m, 2H); 8.31 (s, 1H); 8.43 (d, 2H).

Examples 1.1–1.12

Following a procedure similar to that described in Example 1, the compounds of Table 1 were prepared and purified by flash chromatography eluting with a gradient of 0–5% 3.5N NH$_3$-MeOH/CH$_2$Cl$_2$

TABLE 1

| Example | | MS-ESI |
|---|---|---|
| 1.1 | 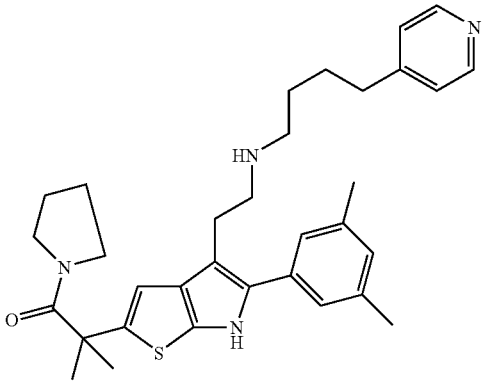 | 543 [M + H]$^+$ |
| 1.2 | 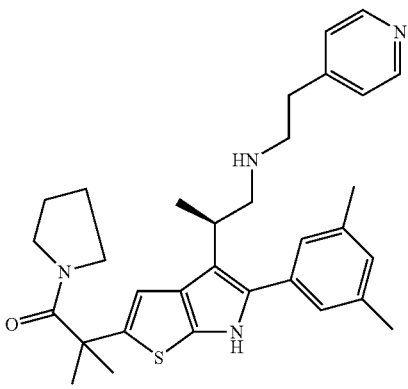 | 529 [M + H]$^+$ |

TABLE 1-continued
| Example | | MS-ESI |
|---|---|---|
| 1.3 | 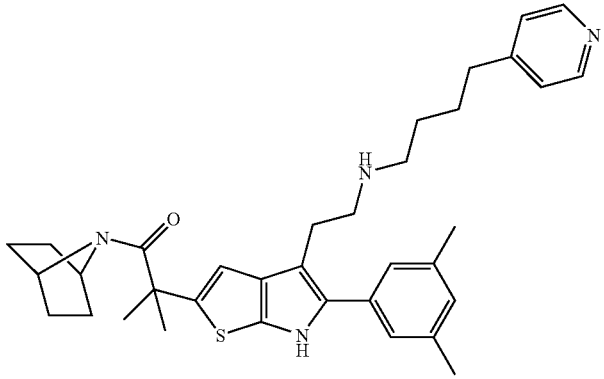 | 569 [M + H]+ |
| 1.4 | 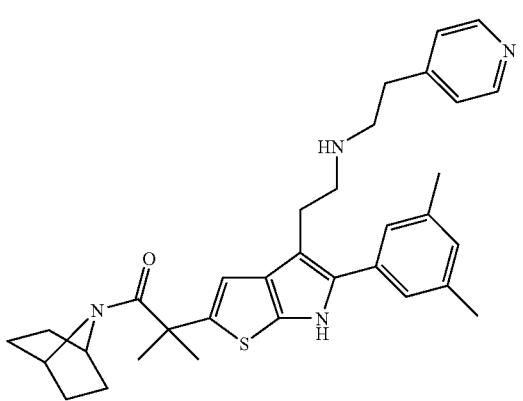 | 541 [M + H]+ |
| 1.5 | 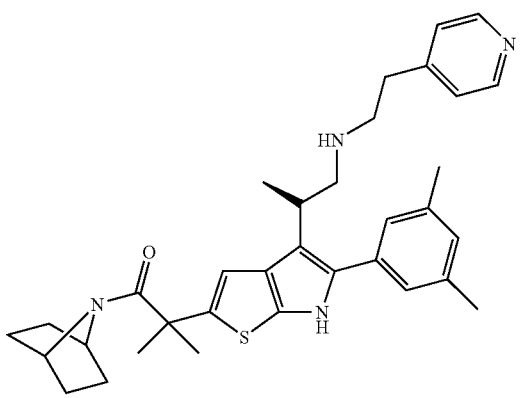 | 555 [M + H]+ |
| 1.6 | 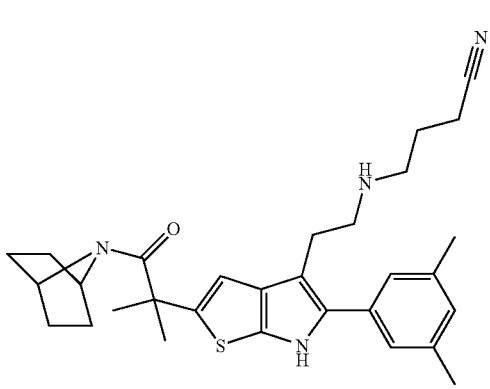 | 503 [M + H]+ |

TABLE 1-continued
| Example | | MS-ESI |
|---|---|---|
| 1.7 | 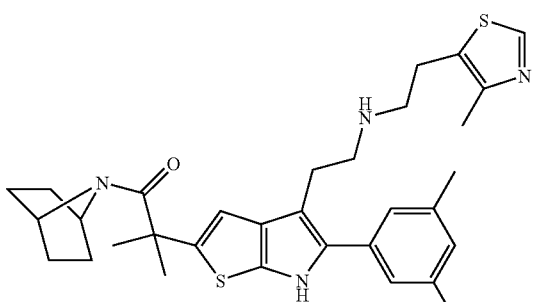 | 561 [M + H]+ |
| 1.8 | 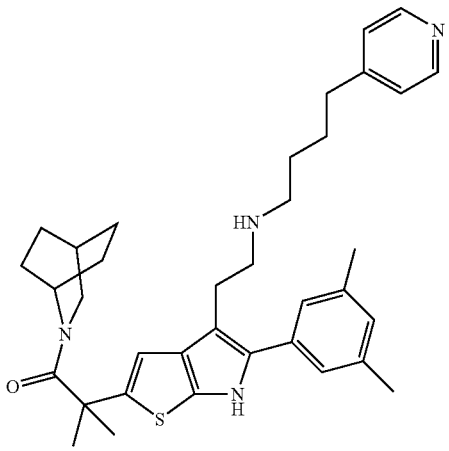 | 583 [M + H]+ |
| 1.9 | 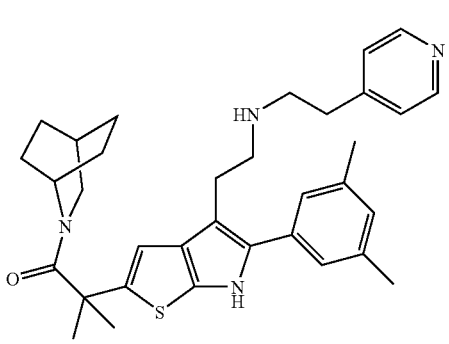 | 555 [M + H]+ |
| 1.10 | 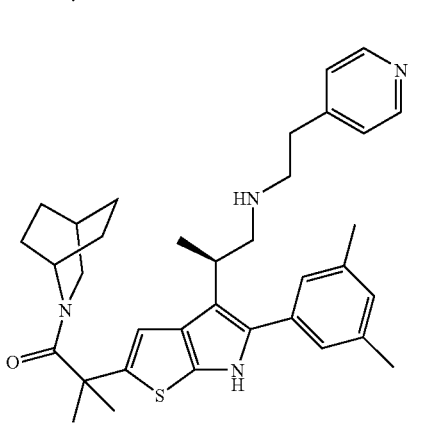 | 569 [M + H]+ |

TABLE 1-continued

| Example | | MS-ESI |
|---|---|---|
| 1.11 |  | 534 [M + H]+ |
| 1.12 | | 609 [M + H]+ |

Example 2

2-(1,1-dimethyl-2-oxo-2-pyrrolidin-1-ylethyl)-4-{2-[1-(pyridin-3-ylmethyl)piperazin-4-yl]ethyl}-5-(3,5-dimethylphenyl)-6H-thieno[2,3-b]pyrrole

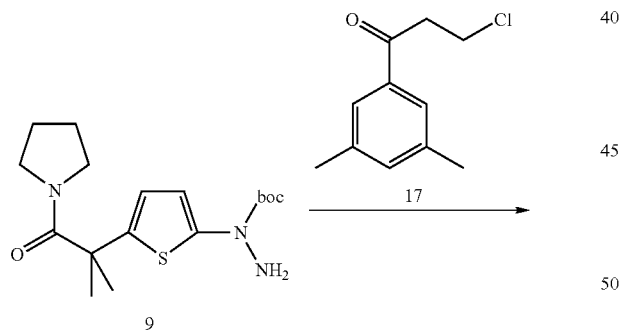

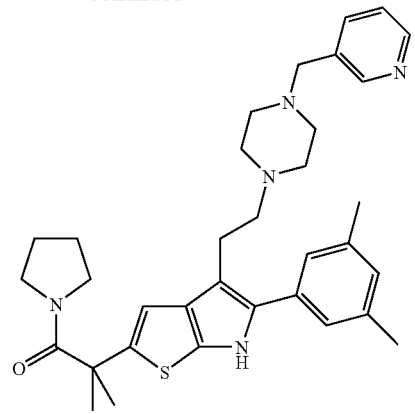

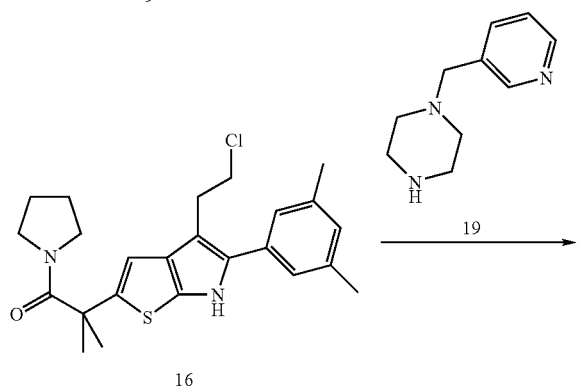

A mixture of 16 (0.362 g; 0.844 mmol), 17 (0.3 g; 1.68 mmol), K$_2$CO$_3$ (0.233 g; 1.68 mmol) in acetonitrile (6 ml) was heated at 85° C. under argon atmosphere for 5 hours. The mixture was extracted with AcOEt and the organic layer was evaporated and purified by flash chromatography, eluting with CH$_2$Cl$_2$ 3.5N NH$_3$ in MeOH 95/5 to give after trituration with ether-pentane Example 2 as a solid.

Yield: 62% MS-ESI: 570 [M+H]+ $^1$H NMR (CDCl$_3$): 1.64 (s, 6H); 1.6–1.7 (br m, 4H); 2.34 (s, 6H); 2.4–2.8 (m, 10H); 2.9–3 (m, 2H); 3.1–3.2 (m, 2H); 3.45–3.65 (m, 4H); 6.74 (s, 1H); 6.94 (s, 1H); 7.05 (s, 2H); 7.67 (d, 2H); 8.2 (s, 1H); 8.5 (d, 2H).

The starting material was prepared as follows:

A solution of 9 hydrochloride salt (2 g; 0.005 mol), 15 (2.16 g; 0.01 mol) in sec-butanol (5 ml) was heated at 105°

C. under argon atmosphere for 2 hours and at 60° C. overnight. The solvent was evaporated and the residue purified by flash chromatography eluting with petroleum ether/AcOEt 60/40 to give 16.

MS-ESI: 429 [M+H]$^+$ $^1$H NMR (DMSO d6): 1.53 (s, 6H); 1.64 (br m, 4H); 2–2.15 (m, 1H); 2.3 (s, 6H); 2.4–2.5 (br m, 1H); 3–3.10 (m, 4H); 3.35–3.5 (m, 7H); 3.8 (br m, 2H); 6.83 (s, 1H); 6.91 (s, 1H); 7.09 (s, 2H).

Examples 2.1–2.41

Following a procedure similar to that described in Example 2, the compounds of table 2 were prepared.

TABLE 2

| Example | | MS-ESI |
|---|---|---|
| 2.1 | | 570 [M + H]$^+$ |
| 2.2 | | 570 [M + H]$^+$ |
| 2.3 | | 521 [M + H]$^+$ |

TABLE 2-continued

| Example | | MS-ESI |
|---|---|---|
| 2.4 | (structure) | 493 [M + H]+ |
| 2.5 | (structure) | 556 [M + H]+ |
| 2.6 | (structure) | 576 [M + H]+ |

TABLE 2-continued

| Example | MS-ESI |
|---|---|
| 2.7 | 561 [M + H]+ |
| 2.8 | 619 [M + H]+ |
| 2.9 | 519 [M + H]+ |
| 2.10 | 533 [M + H]+ |

TABLE 2-continued
| Example | | MS-ESI |
|---|---|---|
| 2.11 | 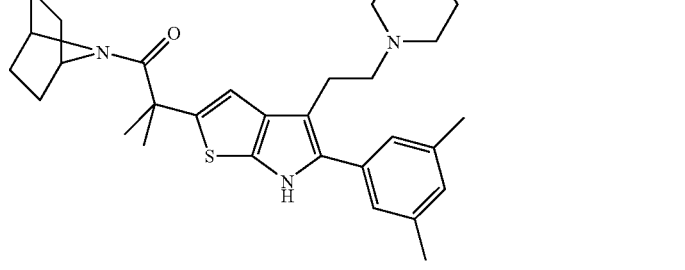 | 595 [M + H]+ |
| 2.12 | 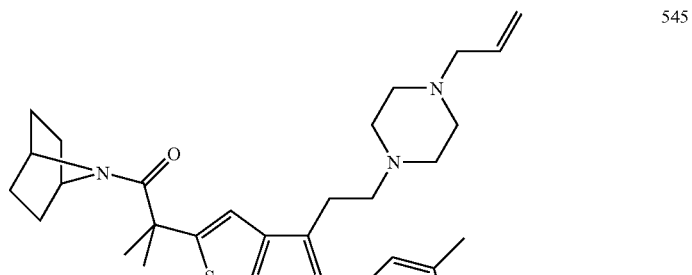 | 545 [M + H]+ |
| 2.13 | 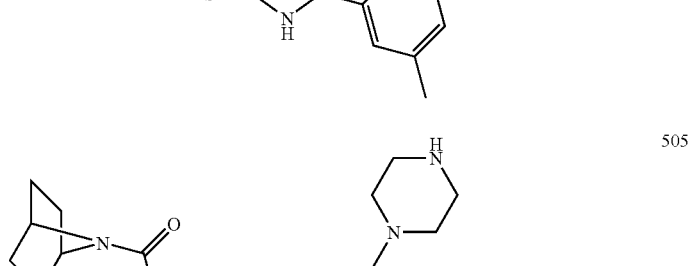 | 505 [M + H]+ |
| 2.14 | 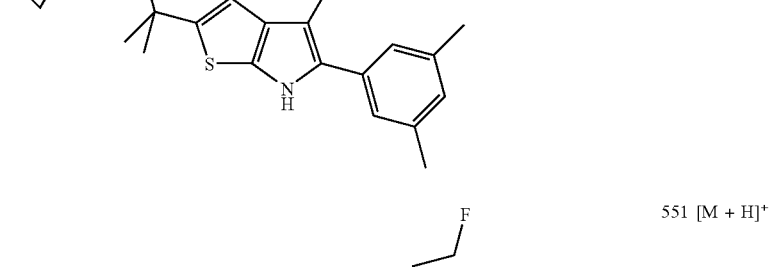 | 551 [M + H]+ |

TABLE 2-continued

| Example | MS-ESI |
|---|---|
| 2.15 | 543 [M + H]⁺ |
| 2.16 | 519 [M + H]⁺ |
| 2.17 | 576 [M + H]⁺ |
| 2.18 | 632 [M + H]⁺ |

TABLE 2-continued
| Example | | MS-ESI |
|---|---|---|
| 2.19 | 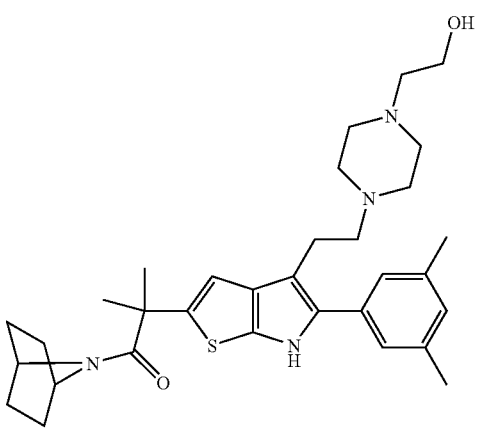 | 549 [M + H]+ |
| 2.20 | 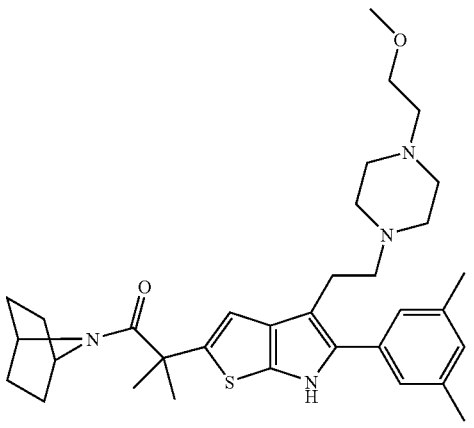 | 563 [M + H]+ |
| 2.21 | 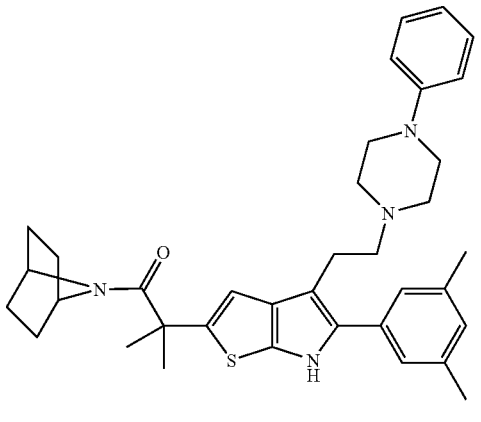 | 582 [M + H]+ |

TABLE 2-continued
| Example | | MS-ESI |
|---|---|---|
| 2.22 | 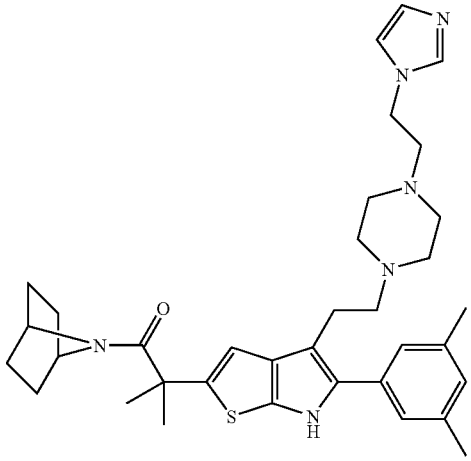 | 599 [M + H]+ |
| 2.23 | 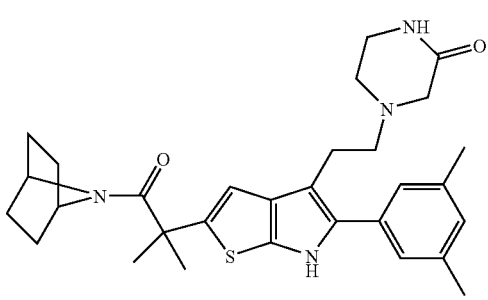 | 519 [M + H]+ |
| 2.24 | 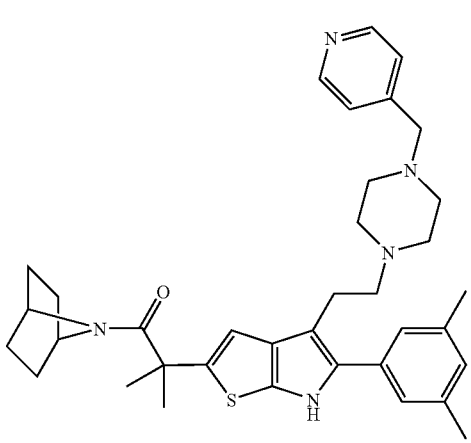 | 596 [M + H]+ |

TABLE 2-continued
| Example | | MS-ESI |
|---|---|---|
| 2.25 | 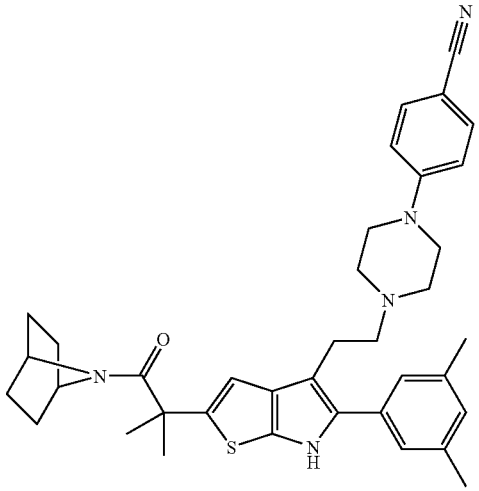 | 606 [M + H]+ |
| 2.26 | 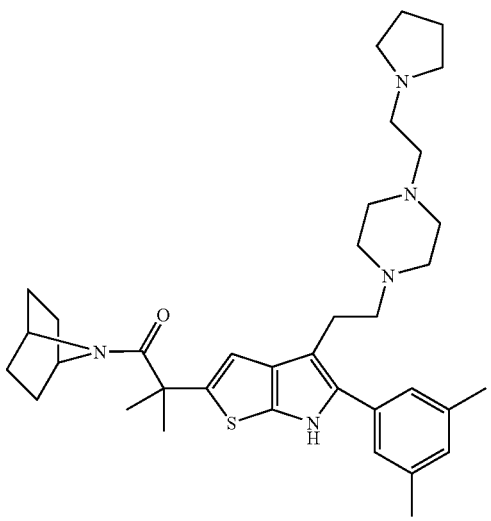 | 602 [M + H]+ |
| 2.27 | 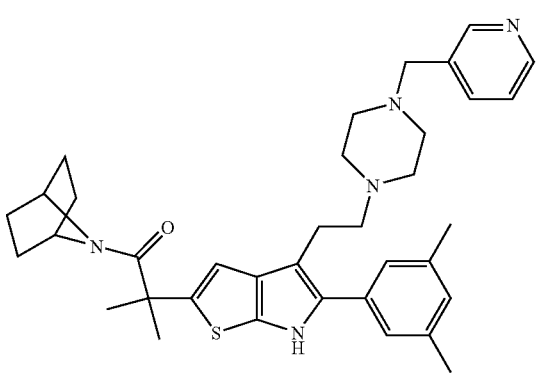 | 596 [M + H]+ |

TABLE 2-continued
| Example | | MS-ESI |
|---|---|---|
| 2.28 | 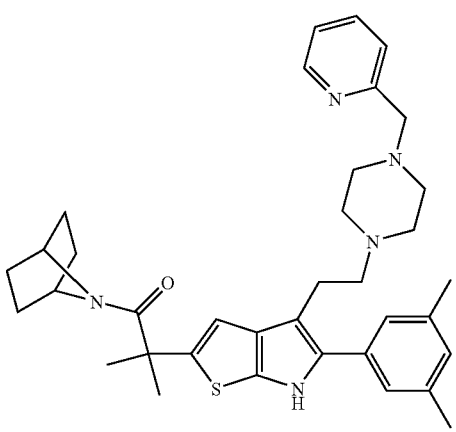 | 596 [M + H]⁺ |
| 2.29 | | 590 [M + H]⁺ |
| 2.30 | | 597 [M + H]⁺ |

TABLE 2-continued

| Example | MS-ESI |
|---|---|
| 2.31 | 583 [M + H]+ |
| 2.32 | 596 [M + H]+ |
| 2.33 | 573 [M + H]+ |
| 2.34 | 602 [M + H]+ |

TABLE 2-continued
| Example | | MS-ESI |
|---|---|---|
| 2.35 | 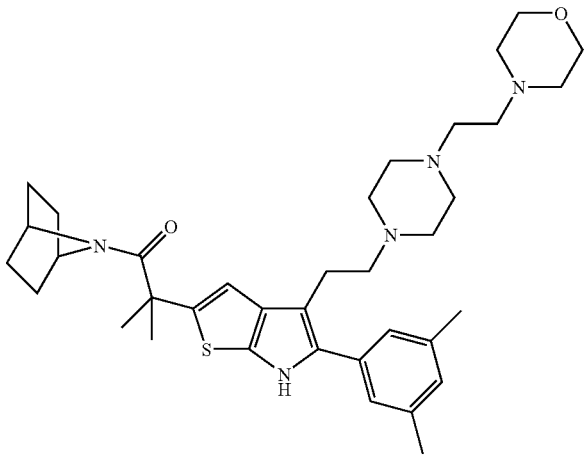 | 618 [M + H]+ |
| 2.36 | 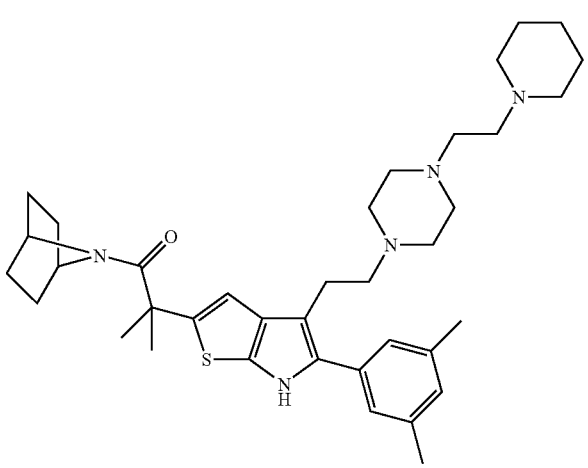 | 616 [M + H]+ |
| 2.37 | 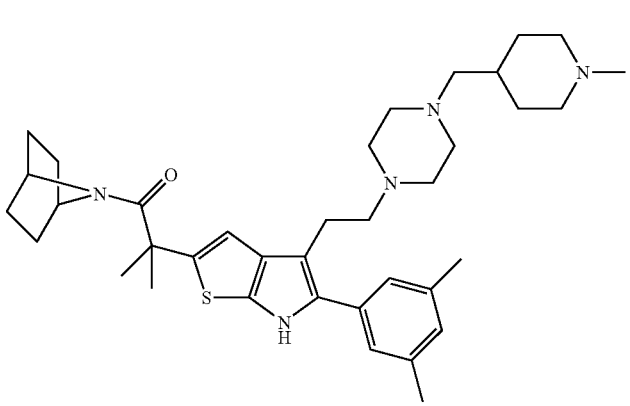 | 616 [M + H]+ |

TABLE 2-continued
| Example | | MS-ESI |
|---|---|---|
| 2.38 | 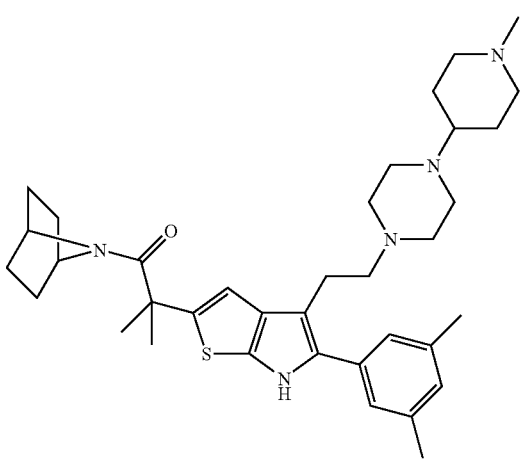 | 602 [M + H]+ |
| 2.39 | 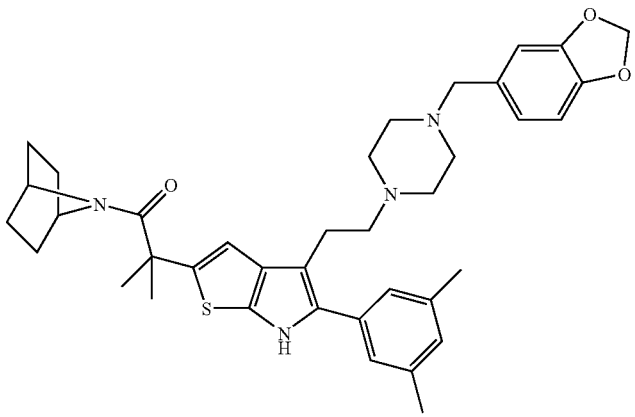 | 639 [M + H]+ |
| 2.40 | 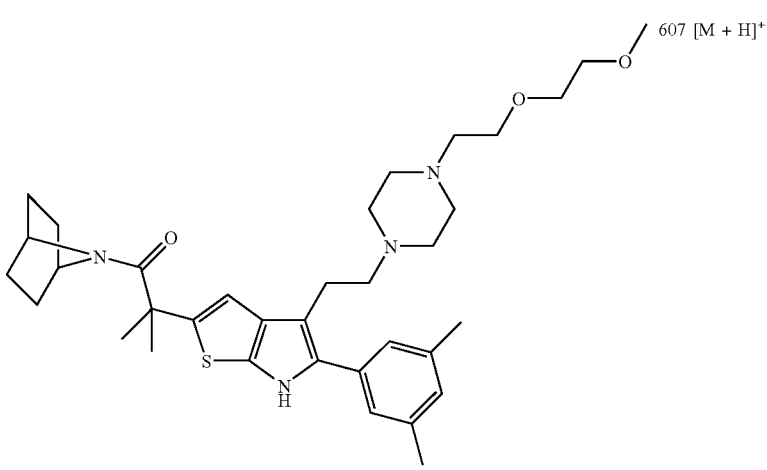 | 607 [M + H]+ |

TABLE 2-continued
| Example | | MS-ESI |
|---|---|---|
| 2.41 | 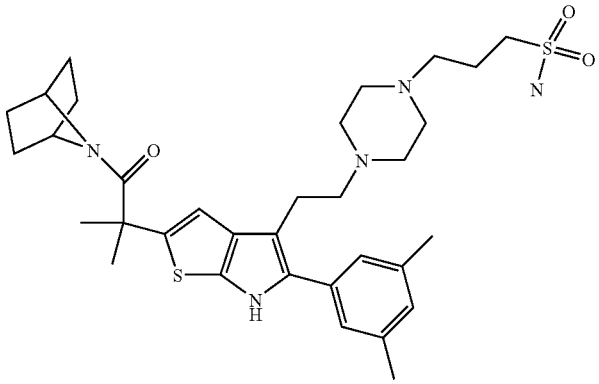 | 626 [M + H]+ |
Example 2.9 was obtained by deprotection of example 2.8 in the presence of TFA in methylene chloride
Example 3
2-[1,1-dimethyl-2-oxo-2-azabicyclo[2.2.1]heptan-7-ylethyl]-4-[2-{4-(2-hydroxy-3-{(3aR,6aS)-tetrahydro-5H-[1,3]dioxolo[4,5-c]pyrrol-5-yl}-prop-1-yl)piperazin-1-}ethyl]-5-(3,5-dimethylphenyl)-6H-thieno[2,3-b]pyrrole
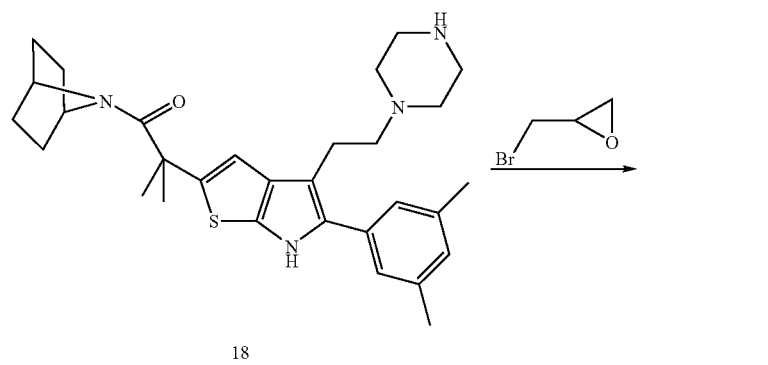
18
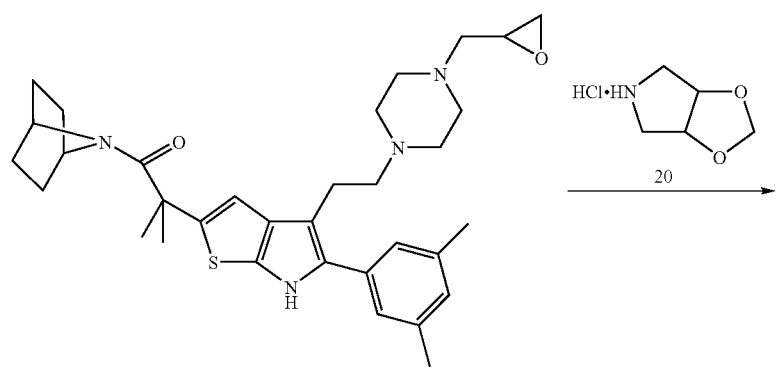
19

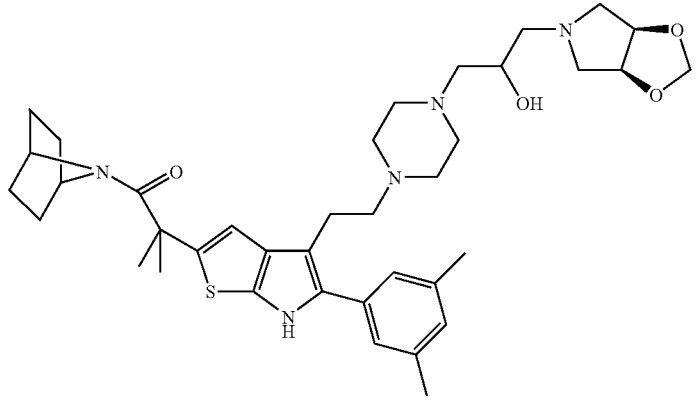

Example 3

A mixture of 19 (0.187 g; 0.33 mmol), amino hydrochloride salt 20 (0.152 g; 1.00 mmol) and triethylamine (0.140 ml; 1.00 mmol) in ethanol (2 ml) was heated at reflux for 2 hours. The mixture was concentrated and purified by flash chromatography, eluting with $CH_2Cl_2$ 3.5N $NH_3$ in MeOH 100/0 to 90/10 to give after trituration with ether-pentane Example 3 as a white solid.

Yield: 40% MS-ESI: 676 $[M+H]^{+1}H$ NMR ($CDCl_3$): 1.25–1.31 (m, 4H); 1.50–1.71 (m, 4H); 1.62 (s, 6H); 2.24 (d, 1H); 2.32 (m, 1H); 2.35 (s, 6H); 2.38–2.63 (m, 12H); 2.68 (m, 2H); 2.93 (m, 2H); 3.18 (d, 2H); 3.84 (m, 1H); 4.11 (br s, 1H); 4.58 (s, 2H); 4.72 (br s, 1H); 4.92 (s, 1H); 5.09 (s, 1H); 6.74 (s, 1H); 6.94 (s, 1H); 7.06 (s, 2H); 8.13 (s, 1H).

19 was prepared as follows:

To a mixture of 18 (1.75 g ; 3.4 mmol) and $K_2CO_3$ (0.55 g ; 4.0 mmol) in dimethylacetamide (15 ml) was added epibromhydrine (0.35 ml ; 4.0 mmol). The mixture was heated at 85° C. under argon atmosphere for 6 hours. After cooling, water was added and the mixture was extracted with AcOEt. The organic layer was washed with brine, dried with $MgSO_4$, evaporated and purified by flash chromatography, eluting with $CH_2Cl_2$.MeOH 95/5 to 93/7 to give 19 as a orange foam.

Yield: 78% MS-ESI: 561 $[M+H]^{+1}H$ NMR ($CDCl_3$): 1.31–2.17 (m, 14H); 2.35 (s, 6H); 2.17–2.33 (m, 2H); 2.49–2.79 (m, 12H); 2.94–3.11 (m, 2H); 3.11 (m, 1H); 4.23 (br m, 1H); 4.51 (br m, 1H); 6.75 (s, 1H); 6.94 (s, 1H); 7.07 (s, 2H); 8.14 (br m, NH).

The synthesis of 18 is described in example 11.

Examples 3.1–3.11

Following a procedure similar to that described in Example 3, the compounds of table 3 were prepared.

TABLE 3

| Example | | MS-ESI |
|---|---|---|
| 3.1 | (structure, Chiral) | 676 [M + H]+ |

TABLE 3-continued
| Example | | MS-ESI |
|---|---|---|
| 3.2 | 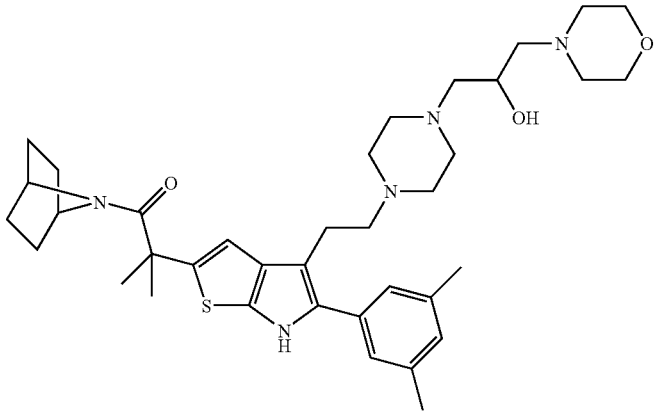 | 648 [M + H]+ |
| 3.3 | 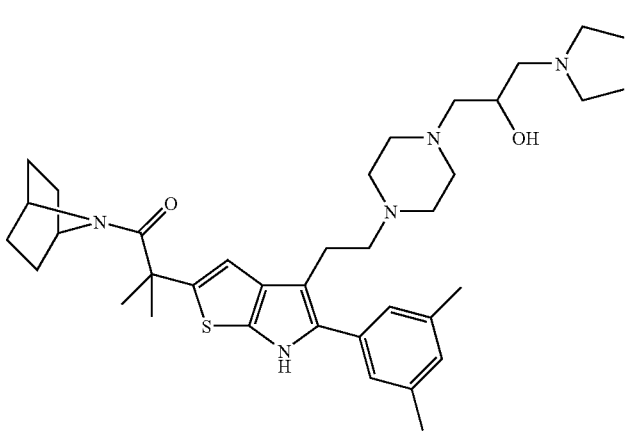 | 634 [M + H]+ |
| 3.4 | 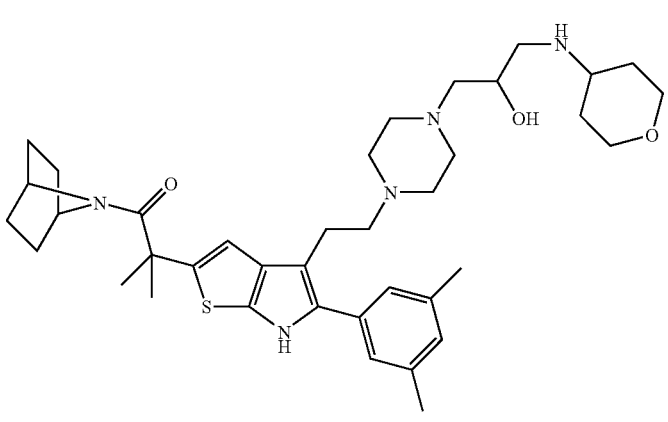 | 662 [M + H]+ |

TABLE 3-continued
| Example | | MS-ESI |
|---|---|---|
| 3.5 | 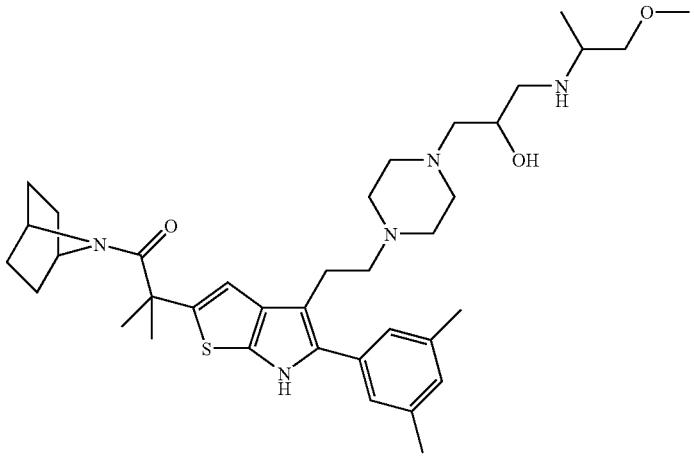 | 650 [M + H]+ |
| 3.6 | | 689 [M + H]+ |
| 3.7 | | 632 [M + H]+ |

TABLE 3-continued
| Example | | MS-ESI |
|---|---|---|
| 3.8 | 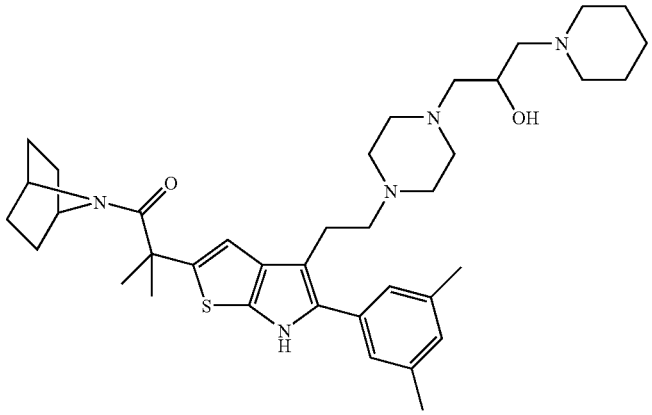 | 646 [M + H]+ |
| 3.9 | 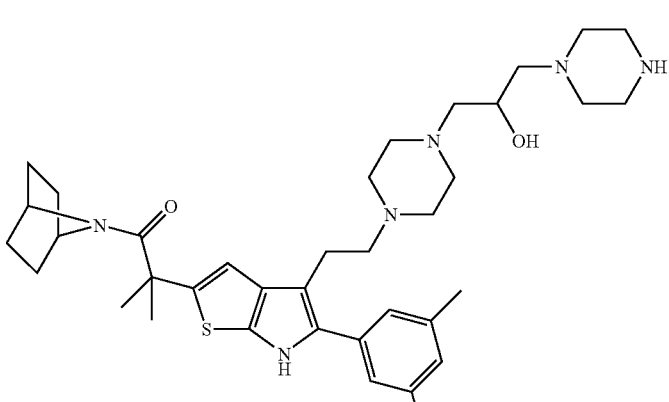 | 647 [M + H]+ |

TABLE 3-continued
| Example | | MS-ESI |
|---|---|---|
| 3.10 | 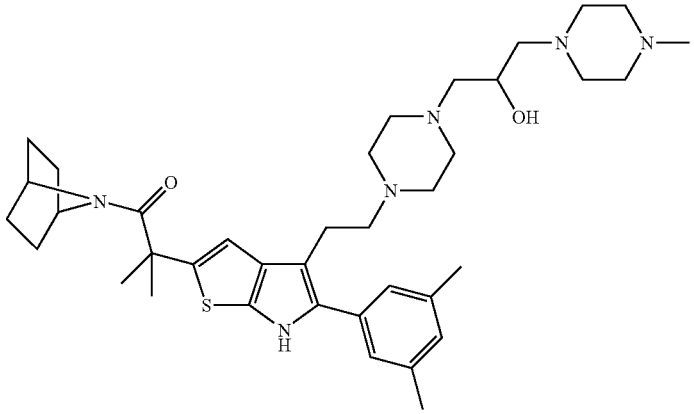 | 661 [M + H]⁺ |
| 3.11 | 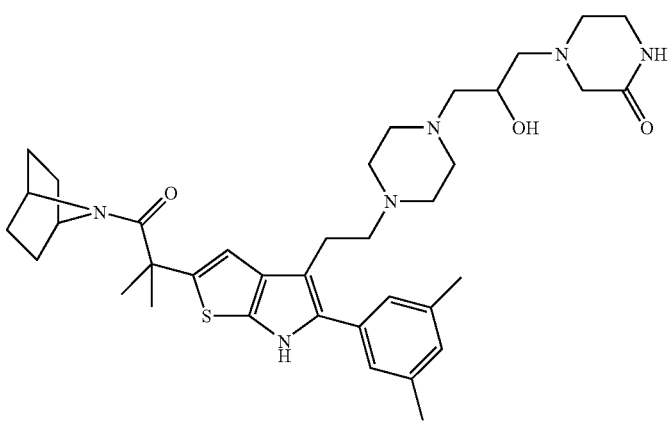 | 661 [M + H]⁺ |
Example 4
2-(1,1-dimethyl-2-oxo-2-pyrrolidin-1-ylethyl)-5-(3,5-dimethylphenyl)-4-[2-(3-pyridin-4-ylpyrrolidin-1-yl)ethyl]-6H-thieno[2,3-b]pyrrole
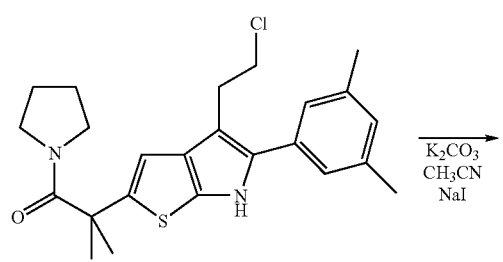
16
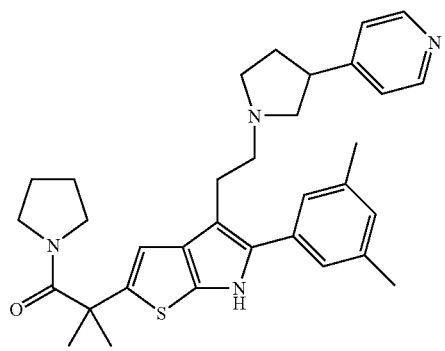
Example 4

A mixture of 16 (0.3 g; 0.7 mmol), 4-pyrrolidin-3-yl pyridine (0.31 g, 2.1 mmol), $K_2CO_3$ (0.29 g; 2.1 mmol) and NaI (0.314 g; 2.1 mmol) in acetonitrile (10 ml) was heated at 70° C. under argon atmosphere for 20 hours. The mixture was extracted with $CH_2Cl_2$ and the organic layer was evaporated and purified by flash chromatography eluting with a gradient 5–10% $MeOH/CH_2Cl_2$ to give Example 4 as a solid.

Yield: 40% MS-ESI: 541 [+H]$^{+1}$H NMR (CDCl$_3$): 1.63 (s, 6H); 1.6–1.75 (br m, 4H); 1.75–1.95 (m br, 1H); 2.31 (s, 6H); 2.3–2.35 (br m, 1H); 2.58 (m, 1H); 2.7–3.2 (m, 9H); 3.25–3.35 (m, 1H); 3.4–3.6 (m, 2H); 6.74 (s, 1H); 6.91 (s, 1H); 7.05 (s, 2H); 7.15 (d, 2H); 8.46 (d, 2H); 8.53 (s, 1H).

Examples 4.1

Following a procedure similar to that described in Example 4, example 4.1 were prepared.

TABLE 4

| Example | | MS-ESI |
|---|---|---|
| 4.1 | 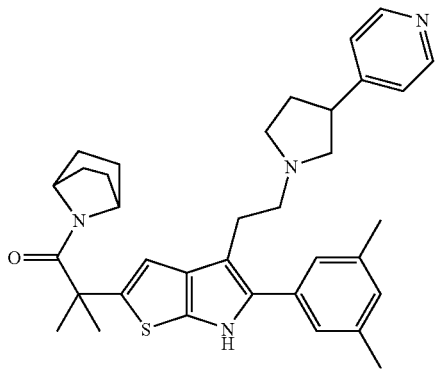 | 567 [M + H]$^+$ |

Example 5

2-[1,1-dimethyl-2-oxo-2-azabicyclo[2.2.1]heptan-7-ylethyl]-4-[2-(4-{morpholinocarbonyl}piperidin-1-yl)ethyl]-5-(3,5-dimethylphenyl)-6H-thieno[2,3-b]pyrrole A mixture of 29 (0.137 g; 0.3 mmol), 30 (0.150 g, 0.6 mmol), $K_2CO_3$ (0.125 g; 0.9 mmol) and NaI (0.045 g; 0.3 mmol) in dimethylacetamide (3 ml) was heated at 85° C. under argon atmosphere for 6 hours. The crude mixture was purified on preparative LC-MS (column Symetry $C_{18}$, AcOH buffer, $H_2O$—$CH_3CN$ gradient) and the residue was evaporated and cristallized in a pentane-Et2O mixture to give Example 5 as a white solid.

Yield: 55% MS-ESI: 617 [M+H]$^{+1}$H NMR (CDCl$_3$) 1.28 (m, 4H); 1.62 (s, 6H); 1.50–1.75 (m, 6H); 1.93 (m, 2H); 2.08 (m, 2H); 2.35 (s, 6H); 2.48 (m, 1H); 2.68 (m, 2H); 2.97 (br s, 2H); 3.09 (m, 2H); 3.50 (s, 2H); 3.62 (s, 2H); 3.68 (s, 4H); 4.12 (br s, 1H); 4.75 (br s, 1H); 6.75 (s, 1H); 6.94 (s, 1H); 7.06 (s, 2H); 8.13 (s, 1H).

The intermediate 29 was prepared as follows:

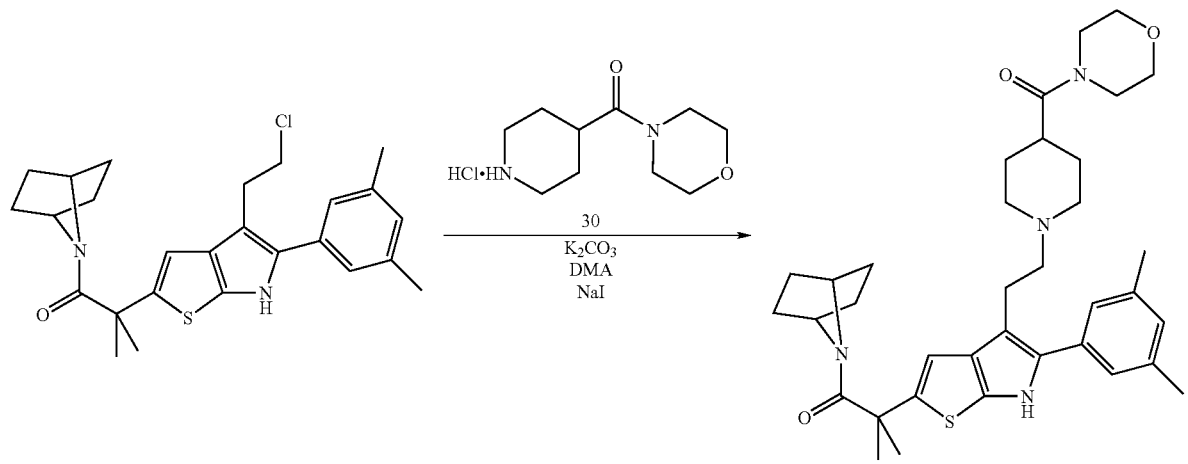

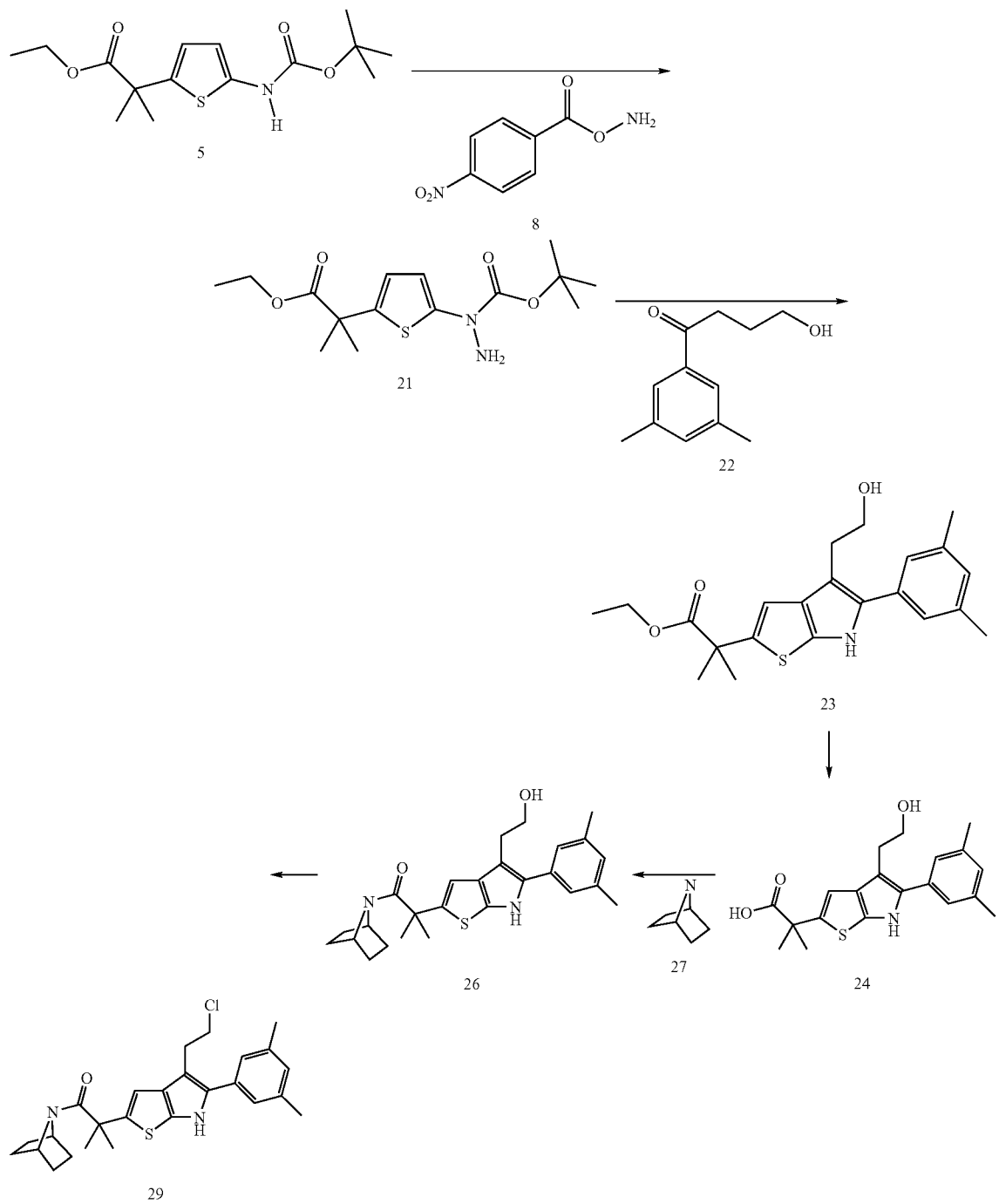

To a suspension of sodium hydride (44.6 g; 1.12 mol) in DMF (700 ml) at 10° C., was added a solution of 5 (290 g; 930 mmol) in DMF (1 l) over a period of 5 minutes. The resulting orange suspension was allowed to warm to room temperature and stirred for 2 hours. The resulting solution was cooled to −5° C. in an acetone/ice bath and a solution of 8 (201 g; 1.02 mol) in DMF (1.4 l) was added over a period of 1 hour. During this period additional DMF (1 l) was added to mobilize the thick precipitate which formed. The resulting suspension was allowed to warm to room temperature and stirred over night after which HPLC showed no remaining starting material. The suspension was poured into water (6 l) and extracted with diethyl ether (3×2 l). The organic extracts were combined and concentrated to approximately 3 l and washed with water (4×1.5 l), a saturated solution of brine (1 l), dried over magnesium sulfate and evaporated to dryness to afford the free base as an off-white solid in quantitative yield. To a stirred solution of the free base (150 g; 457 mmol) in diethyl ether (1.2 l) and heptane (600 ml) at 0° C., was added a 4.0M solution of HCl in 1,4-dioxane (145 ml; 570 mmol) over a period of 1 hour. The resulting thick, white precipitate was collected by filtration, washed with a mixture of diethyl ether-heptane (1:1, 500 ml) and dried to a constant weight to afford the 21.HCl (160.3 g) as a white solid.

Yield: 96% MS-ESI: 328 [M+H]+

To a stirred solution of 21 (141 g; 380 mmol) in 2-butanol (1.3 l) was added 22 (104 g; 540 mmol) and zinc chloride (106 g; 770 mmol). The resulting suspension was heated at 100° C. for 8 hours after which HPLC showed no remaining starting material. The resulting dark brown solution was evaporated to dryness on a rotary evaporator. The resulting dark brown residue was dissolved in DCM (100 ml), filtered and the filtrate was purified by flash chromatography eluting with DCM, ethyl acetate (9:1) to afford 23 (98 g) as a brown solid.

Yield: 67% MS-ESI: 386 [M+H]+

To a stirred solution of 23 (98 g; 254 mmol) in ethanol (1.8 l) was added 1N NaOH (1.27 l, 1270 mmol). The resulting solution was heated at 60° C. for 4 hours after which HPLC showed no remaining starting material. The reaction mixture was cooled to room temperature and the ethanol was removed on a rotary evaporator. The resulting brown solution was cooled to 5° C. and concentrated HCl was added dropwise with rapid agitation decreasing the pH to 1. The resulting precipitate was collected by filtration, washed to a neutral pH with water (3×1 l) and dried to a constant weight in a vacuum oven at 50° C. to afford 24 as a beige solid (68.3 g).

Yield: 75% MS-ESI: 358 [M+H]+

To a stirred solution of 24 (35.7 g; 100 mmol) and 27 (57 g; 150 mmol) in DCM (1 l) at 0° C., was added DIPEA (70 ml; 400 mmol) and solid HATU (57 g; 150 mmol) over a period of 15 minutes. The reaction mixture was allowed to warm to room temperature and stirred for 2 hours after which HPLC showed no remaining starting material. The reaction mixture was washed with a saturated aqueous solution of citric acid (350 ml), a saturated solution of sodium bicarbonate (350 ml) and water (3×350 ml). The organic layer was dried over anhydrous magnesium sulfate, filtered, and evaporated to dryness on a rotary evaporator. The resulting oily residue was triturated with ethyl acetate (100 ml) and the resulting precipitate collected by filtration and dried to a constant weight in a vacuum oven at 40° C. to afford 28 (31.4 g) as a beige solid.

Yield: 69% MS-ESI: 437 [M+H]+

To a stirred solution of 28 (29.7 g; 68.1 mmol) in DCM (700 ml) at 0° C. was added dropwise neat thionyl chloride (6 ml; 81.7 mmol) The mixture was allowed to warm to room temperature and stirred for a period of 2 h after which HPLC showed no remaining starting material. The reaction mixture was evaporated and purified by flash chromatography, eluting with methylene chloride, AcOEt (9:1) to give 29 as beige foam. The foam was triturated with diethyl ether (100 ml) and the resulting solid collected by filtration, washed with diethyl ether (2×50 ml) and dried to a constant weight in a vacuum oven at 40° C. to afford 29 as a white solid (26.5 g).

Yield: 85% MS-ESI: 454 [M+H]+ 1H NMR (DMSO-d6) 1.19–1.41 (m, 4H); 1.45–1.59 (m, 10H); 2.32 (s, 6H); 3.14 (t, 2H); 3.83 (t, 4H); 4.13 (br s, 1H); 4.43 (br s, 1H); 6.89–6.93 (two overlapping s, 2H); 7.08 (s, 2H).

The intermediate amine 27 was synthesised as follows:

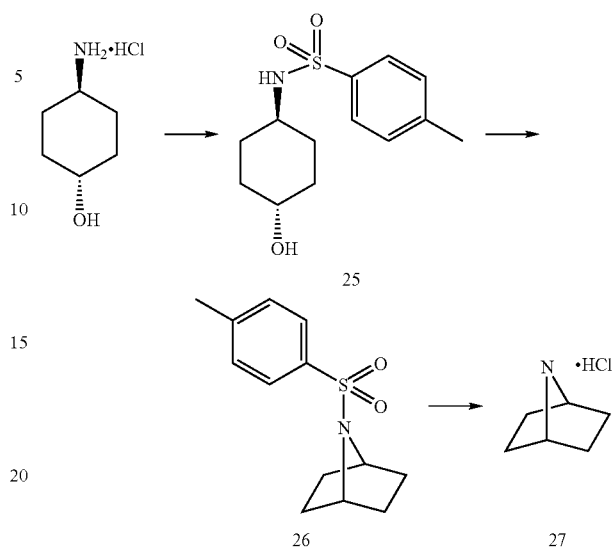

To a stirred suspension of trans-4-aminocyclohexanol (300 g; 1.98 mol) in isopropanol (3.5 l) at 0° C. was added triethylamine (1,1 l; 7.92 mol) followed by solid p-toluenesulfonyl chloride (377 g; 1.98 mmol) over a period of 30 minutes. The reaction mixture was heated at 60° C. for 2 hours after which HPLC showed no remaining starting material. The resulting suspension was cooled to room temperature and the precipitate of triethylamine hydrochloride removed by filtration. The filtrate was evaporated to dryness on a rotary evaporator to afford a colourless oil which was dissolved in ethyl acetate (3 l), washed with 0.5N HCl (800 ml), water (1.5 l) and dried over MgSO4. The solvent was evaporated on a rotary evaporator to afford 25 (456.5 g) as a white crystalline solid.

Yield: 86% MS-ESI: 270 [M+H]+

To a stirred solution of 25 (600 g; 2.23 mol) in THF (2 l) at −10° C. in an ice/acetone bath, was added triphenylphosphine (700 g; 2.67 mol) followed by di-tert-butylazadicarboxylate (DTBAD) (564 g; 2.45 mol) in THF (1.5 l) over a period of 1.5 hours maintaining the internal temperature below 10° C. The ice/acetone bath was removed and reaction mixture was allowed to warm to room temperature over a period of 1.5 hours after which HPLC showed no remaining starting material. The reaction mixture was evaporated to dryness and the residue was crystallised from hot MeOH (2.8 l). The resulting crystalline suspension was cooled to 0° C. and the crystals collected by filtration, washed with cold MeOH (2×200 ml) and dried to a constant weight in a vacuum oven to afford 26 (378.2 g) as a white crystalline solid routinely contaminated with approximately 10% (w/w) of triphenylphosphine oxide Yield: 68% MS-ESI: 252 [M+H]+

In two separate batches: To a stirred solution of 26 (380 g; 1.51 mol) in THF (3 l) at 0° C. was added solid pellets of lithium aluminium hydride (229.4 g; 6.04 mol) over a period of 2 hours under a blanket of nitrogen. The resulting grey suspension was allowed to warm to room temperature and stirred for 4 days after which HPLC showed no remaining starting material. The reaction mixture was diluted with THF (1 l), cooled to 0° C. and solid sodium sulfate decahydrate was added over a period of 2 hours with rapid agitation. When the effervescence had subr sided, the resulting suspension was filtered and the filtrate acidified with gaseous HCl affording a thick white precipitate which was collected by filtration, washed with THF (2×500 ml) and dried to a constant weight to afford 108 (batch 1: 86.8 g; 43%) (batch 2: 97.3 g; 49%) as a white solid. The filter cakes obtained from the first filtration were suspended in 6N NaOH (400 ml) and filtered. The filtrate was extracted with diethyl ether (4 l). The organic layer was acidified with gaseous HCl affording a thick white precipitate which was collected by filtration, washed with diethyl ether (2×500 ml) and dried to a constant weight in a vacuum oven at 40° C. to afford 27.HCl (105.9 g) as a white solid.

Yield: 72% $^1$H NMR (DMSO-d$_6$) 1.57 (m, 4H); 1.86 (m, 4H); 4.12 (s, 2H); 8.80–9.05 (br s, 1H).

Examples 5.1–5.3

Following a procedure similar to that described in Example 5, the compounds of table 5 were prepared.

TABLE 5

| Example | | MS-ESI |
|---|---|---|
| 5.1 | 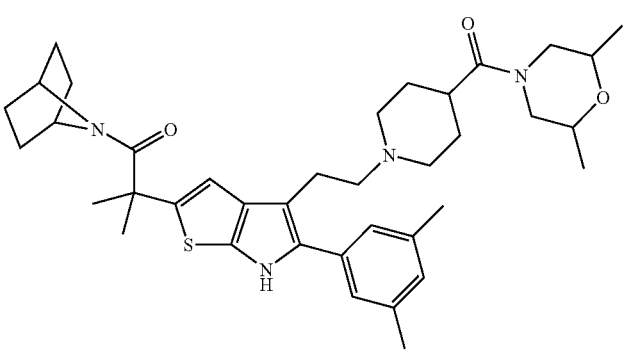 | 645 [M + H]$^+$ |
| 5.2 | 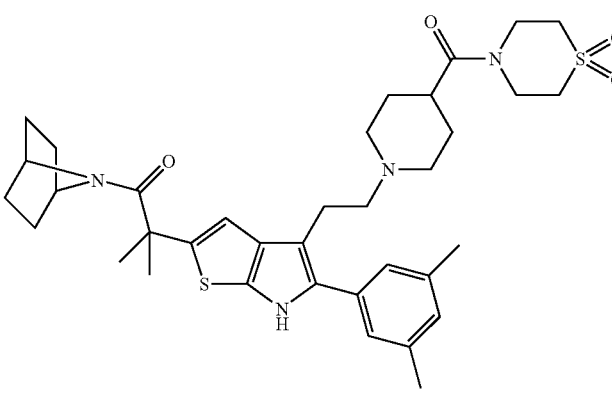 | 665 [M + H]$^+$ |
| 5.3 | 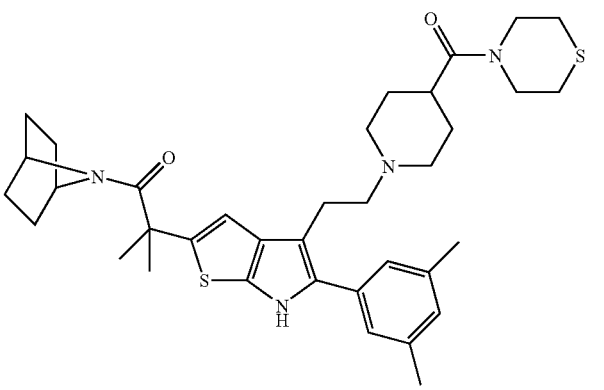 | 633 [M + H]$^+$ |

Example 6

2-[1,1-Dimethyl-2-oxo-2-azabicyclo[2.2.1]heptan-7-ylethyl]-4-[1-oxo-2-{4-(1,1-dioxidotetrahydrothien-3-yl)piperazin-1-yl}ethyl]-5-(3,5-dimethylphenyl)-6H-thieno[2,3-b]pyrrole

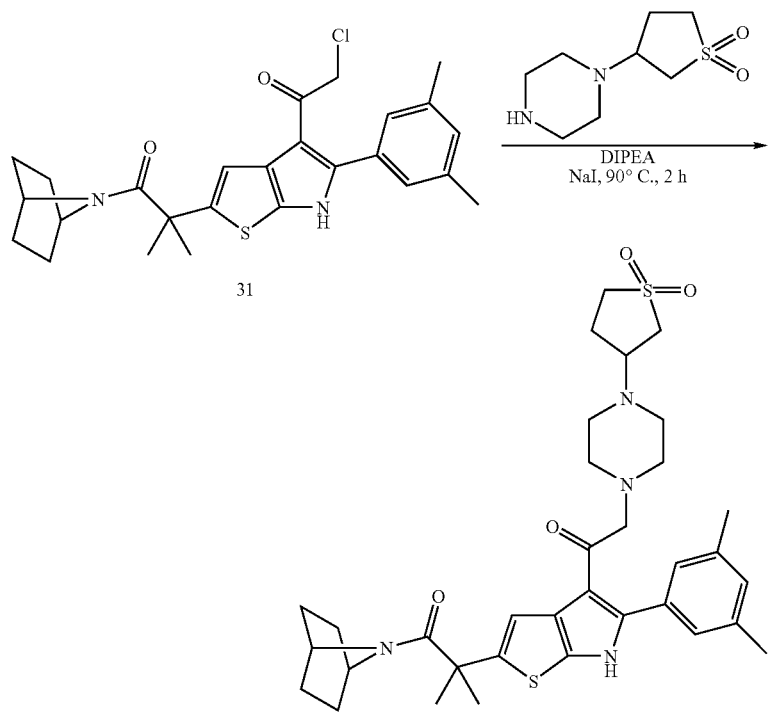

1-(tetrahydro-1,1-dioxido-3-thienyl)-piperazine (0.044 g, 0.22 mmol) was added to a stirred solution of 31 (0.050 g, 0.11 mmol), catalytic NaI and diisopropylethyl amine (93 µl, 0.55 mmol) in DMF (3 ml). After stirring for 2 h at 90° C. under nitrogen the reaction mixture was evaporated to dryness under reduced pressure. The residue was partitioned between DCM and water, the organics were washed with brine, dried and evaporated to dryness. The crude product was purified by chromatography on silica, eluting with 0–10% MeOH/DCM to give example 6 as a yellow foam (0.054 g). Yield: 79% MS-ESI: 637 (M$^+$+H). $^1$H NMR (DMSOd$_6$) 1.20–1.40 (m, 4H), 1.47–1.80 (m, 10H), 2.00–2.19 (m, 1H), 2.37 (s, 6H), 2.44–2.65 (m, 9H), 2.90–3.10 (m, 2H), 3.15–3.29 (m, 3H), 3.42 (s, 2H), 4.00–5.00 (m, 2H), 7.06 (s, 1H), 7.14 (m, 3H), 8.86 (s, 1H)

Synthesis of 31

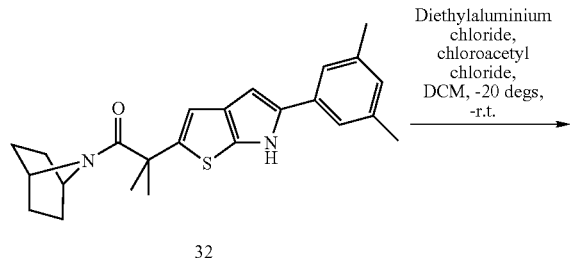

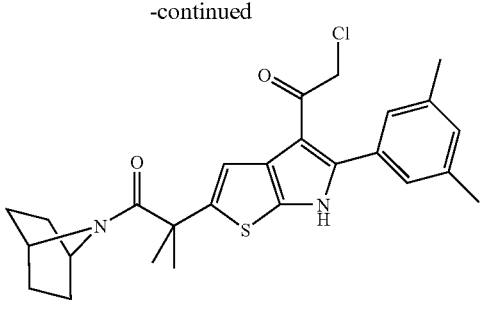

The starting material 31 was prepared as follows:

A 1.0 M solution of diethylaluminium chloride in hexanes (25 ml; 25 mmol) was added dropwise to a cooled solution of 32 (2.0 g; 5.1 mmol) in DCM(150 ml) stirred under a nitrogen atmosphere at –20° C. The reaction was allowed to warm to 0° C. and kept at this temperature for 30 mins. It was then cooled back down to –20° C. and chloroacetyl chloride (3.4 g; 30 mmol) was added and the reaction was then warmed to ambient temperature and stirred for a further two hours. It was cooled back to –20° C. and water (20 ml) was added carefully so that the temperature did not rise above –10° C. It was then warmed to ambient temperature and the organics were separated, dried and evaporated to dryness under reduced pressure. The residue was purified on a silica flash column which was eluted with 10–20% EtOAc/DCM and then EtOAc to give 31 (1.35 g) as a pale yellow solid.

MS-ESI: 469.13, 471.12 (M$^+$+H). $^1$H NMR (DMSOd$_6$) 1.54–1.64 (m, 8H), 1.70 (s, 6H), 2.46 (s, 6H), 4.34–4.56 (m, 2H), 4.70 (m, 2H), 7.23 (s, 2H), 7.33 (s, 2H), 12.45 (br s, 1H).

Compound 32 was prepared as follows:

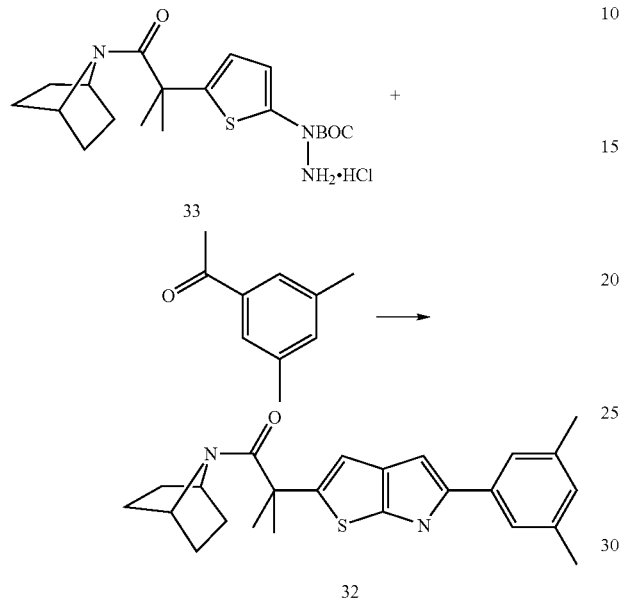

To a stirred solution of 33 (20.75 g, 50 mmol), 3,5-dimethylacetophenone (7.5 g, 50 mmol) and anisole (25 ml) in 2-butanol (25 ml) was slowly added a solution of HCl 4M in dioxane (15 ml). The mixture was warmed up to reflux for 30 minutes. After evaporation of the solvents, the crude product was precipitated in AcOEt, filtered and washed with EtOAc. This crude product was purified by flash chromatography eluting first with a gradient 25/75 to 50/50 AcOEt/methylene chloride then a gradient 10/40/50 MeOH/AcOEt/methylene chloride to give after trituration in methylene chloride 32 as a pale brown solid.

Yield: 19% MS-ESI: 393 [M$^+$+H]$^+$ 33 was prepared following a procedure similar to that described for the preparation of intermediate 9 (see Example 1). $^1$H NMR (CDCl$_3$): 1.32 (m, 4H); 1.52 (s, 9H); 1.56 (s, 6H); 1.50–1.61 (m, 4H) 4.00–5.00 (br m, 1H+1H); 6.60 (s, 1H); 6.94 (s, 1H).

Examples 6.1–6.31

Following a procedure similar to that described in example 6, the compounds of table 6 were prepared.

| Example | Structure | $^1$H NMR(CDCl$_3$) | MS-ESI: (M$^+$ + H) |
|---|---|---|---|
| 6.1 | 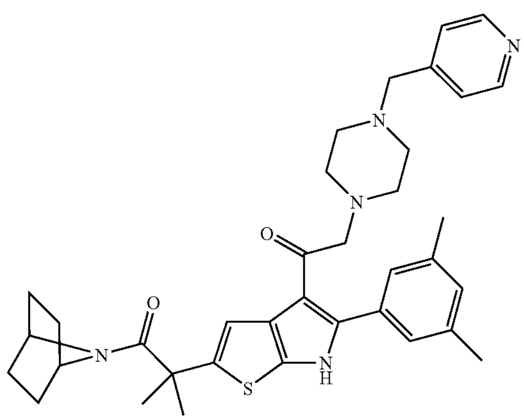 | 1.19–1.38(m, 4H), 1.46–1.73(m, 10H), 2.34(s, 6H), 2.35–2.58(m, 8H), 3.42(d, 4H), 4.00–4.90(m, 2H), 7.03(s, 1H), 7.16(m, 3H), 7.23(d, 2H), 8.47(d, 2H), 10.20(s, 1H) | 610 |

| Example | Structure | ¹H NMR(CDCl₃) | MS-ESI: (M⁺ + H) |
|---|---|---|---|
| 6.2 | 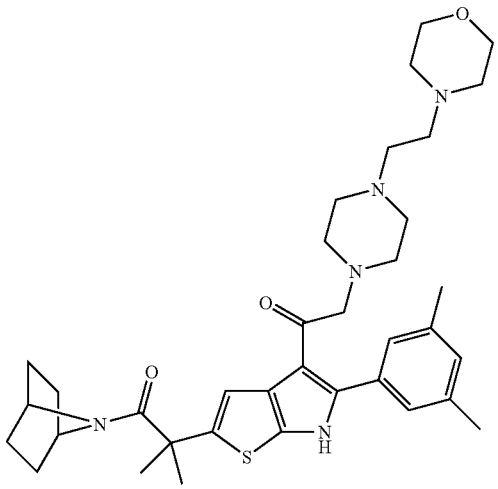 | 1.18–1.40(m, 4H), 1.45–1.80(m, 10H), 2.34(s, 6H), 2.35–2.70(m, 12H), 3.38(s, 2H), 3.60–3.76(m, 8H), 3.90–5.00(m, 2H), 7.06(s, 1H), 7.15(m, 3H), 9.48(s, 1H) | 632 |
| 6.3 | 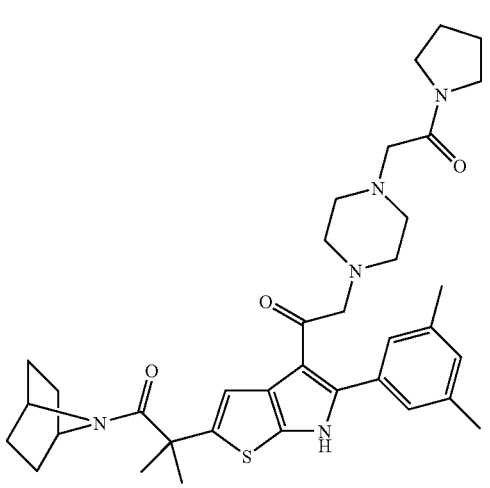 | 1.15–1.40(m, 8H), 1.42–1.83(m, 10H), 2.33(s, 6H), 2.40–2.65(m, 6H), 3.07(s, 2H), 3.38(s, 2H), 3.38–3.50(m, 6H), 3.90–5.00(m, 2H), 7.03(s, 1H), 7.14(m, 3H), 9.40(s, 1H) | 630 |
| 6.4 | 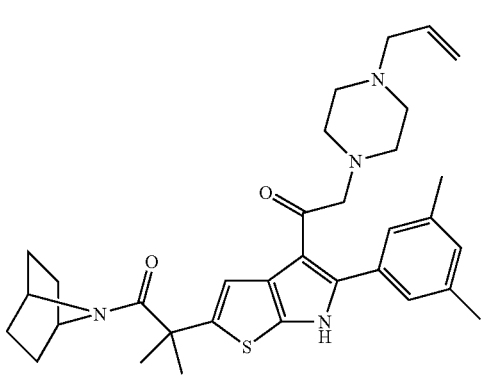 | 1.15–1.36(m, 4H), 1.45–1.75(m, 10H), 2.35(s, 6H), 2.35–2.65(m, 4H), 2.90–3.00(m ,4H), 3.37(s, 2H), 3.80–5.00(m, 2H), 5.05–5.20(m, 3H), 5.73–5.90(m, 2H), 7.04(s, 1H), 7.14(s, 3H), 9.70(s, 1H) | 559 |

-continued

| Example | Structure | ¹H NMR(CDCl₃) | MS-ESI: (M⁺ + H) |
|---|---|---|---|
| 6.5 | 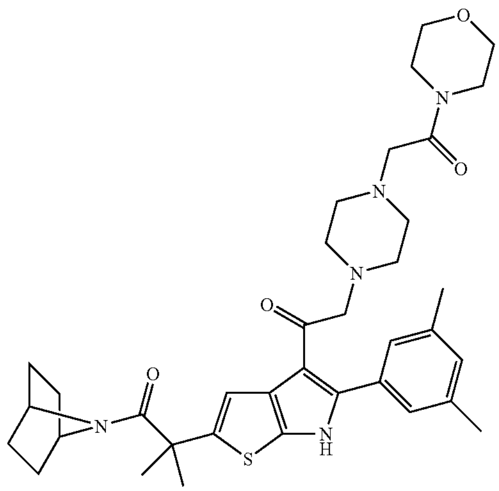 | 1.20–1.40(m, 4H), 1.50–1.75(m, 10H), 2.35(s, 6H), 2.38–2.57(m, 8H), 3.10(s, 2H), 3.39(s, 2H), 3.50–3.70(m, 8H), 4.00–5.00(m, 2H), 7.04(s, 1H), 7.15(m, 3H), 9.60(s, 1H) | 646 |
| 6.6 | 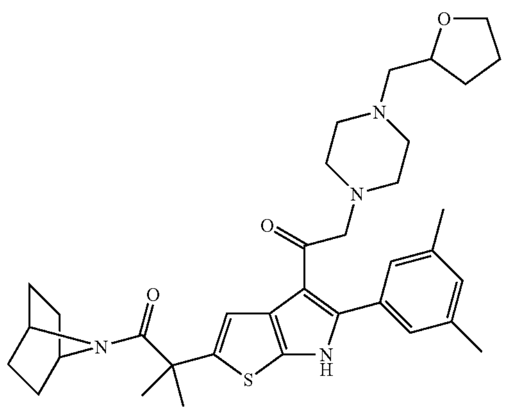 | 1.20–1.37(m, 4H), 1.38–1.74(m, 11H), 1.78–1.89(m, 2H), 1.90–2.00(m, 1H), 2.32(s, 6H), 2.35–2.65(m, 10H), 3.35(s, 2H), 3.63–3.75(m, 1H), 3.77–3.90(m, 1H), 3.91–4.03(m, 1H), 4.20–5.00(m, 2H), 7.00(s, 1H), 7.14(s, 3H), 10.00(s, 1H) | 603 |
| 6.7 | 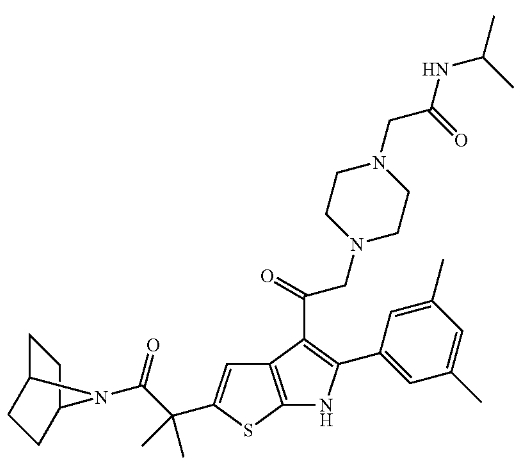 | 1.12(d, 6H), 1.20–1.40(m, 4H), 1.45–1.80(m, 10H), 2.36(s, 6H), 2.38–2.60(m, 8H), 2.89(s, 2H), 3.44(s, 2H), 3.98–4.14(m, 1H), 4.15–5.00(m, 2H), 6.90(d, 1H), 7.04(s, 1H), 7.10–7.20(m, 3H), 9.60(s, 1H) | 618 |

| Example | Structure | ¹H NMR(CDCl₃) | MS-ESI: (M⁺ + H) |
|---|---|---|---|
| 6.8 | 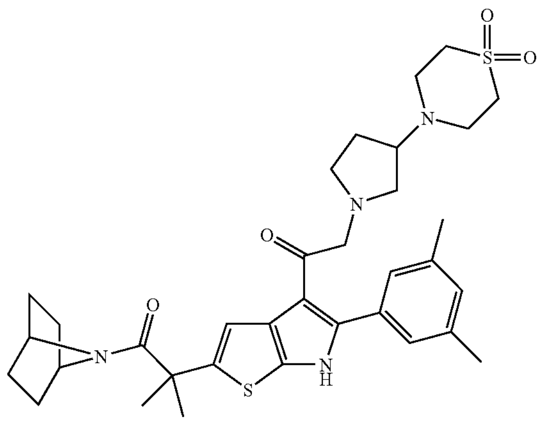 | 1.15–1.40(m, 4H), 1.45–1.73(m, 10H), 1.86–1.98(m, 1H), 2.34(s, 6H), 2.50–2.75(m, 5H), 2.80–3.05(m, 8H), 3.10–3.22(m, 1H), 3.43(d, 1H), 3.62(d, 1H), 4.00–5.00(m, 2H), 7.04(s, 1H), 7.10(s, 1H), 7.18(s, 2H), 9.62(s, 1H) | 637 |
| 6.9 | 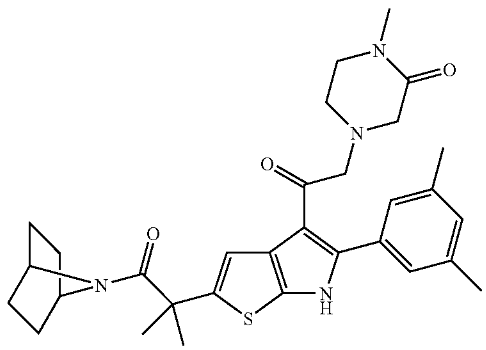 | 1.15–1.40(m, 4H), 1.45–1.73(m, 10H), 1.86–1.98(m, 1H), 2.34(s, 6H), 2.50–2.75(m, 5H), 2.80–3.05(m, 8H), 3.10–3.22(m, 1H), 3.43(d, 1H), 3.62(d, 1H), 4.00–5.00(m, 2H), 7.04(s, 1H), 7.10(s, 1H), 7.18(s, 2H), 9.62(s, 1H) | 547 |
| 6.10 | 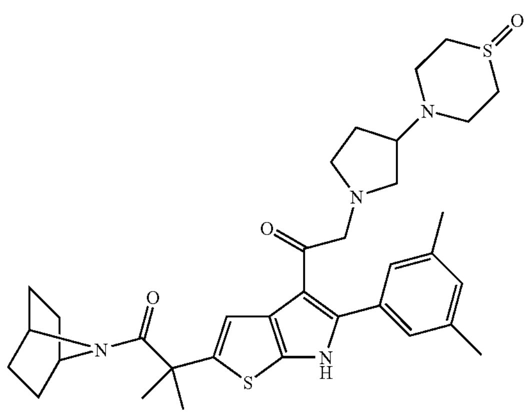 | 1.16–1.40(m, 4H), 1.45–1.80(m, 10H), 1.88–2.00(m, 1H), 2.35(s, 6H), 2.46–2.65(m, 3H), 2.66–2.90(m, 8H), 2.93–3.13(m, 3H), 3.47(d, 1H), 3.61(d, 1H), 4.00–5.00(m, 2H), 7.06(s, 1H), 7.12(s, 1H), 7.18(s, 2H), 9.63(s, 1H) | 621 |
| 6.11 | 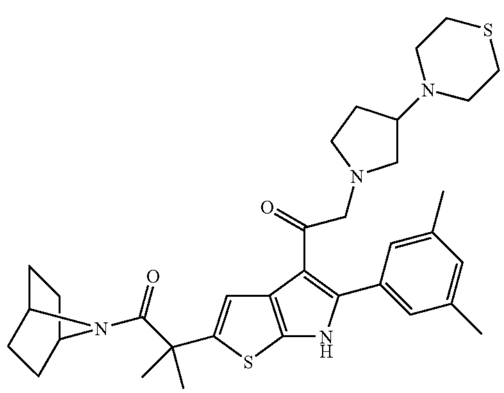 | 1.20–1.38(m, 4H), 1.45–1.75(m, 10H), 1.84–1.96(m, 1H), 2.25–2.53(m, 9H), 2.55–2.80(m, 10H), 2.83–3.05(m, 1H), 3.45(d, 1H), 3.58(d, 1H), 4.00–5.00(m, 2H), 7.06(s, 1H), 7.12(s, 1H), 7.18(s, 2H), 9.42(s, 1H) | 605 |

-continued
| Example | Structure | ¹H NMR(CDCl₃) | MS-ESI: (M⁺ + H) |
|---|---|---|---|
| 6.12 | 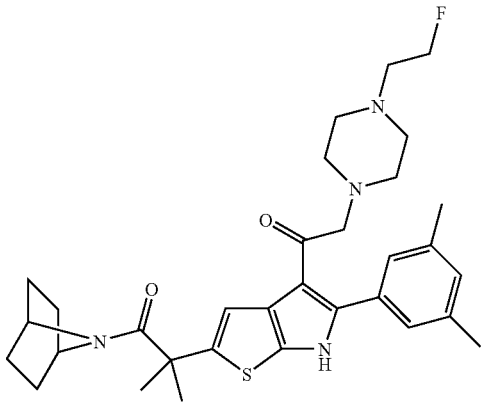 | 1.10–1.30(m, 4H), 1.40–1.70(m, 10H), 2.28(s, 6H), 2.30–2.64(m, 10H), 3.30(s, 2H), 4.00–5.00(m, 4H), 6.97(s, 1H), 7.08(m, 3H), 9.51(s, 1H) | 565 |
| 6.13 | 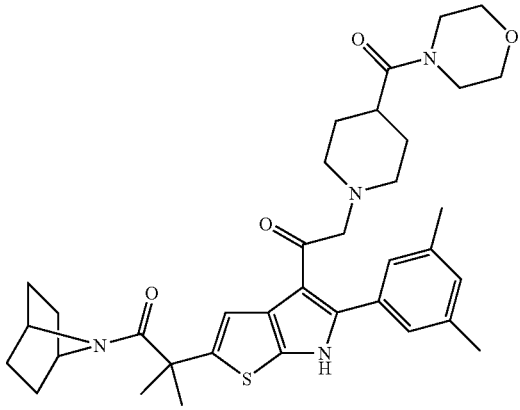 | 1.18–1.40(m, 4H), 1.42–1.87(m, 14H), 2.10–2.22(t, 2H), 2.24–2.44(m, 7H), 2.74(d, 2H), 3.30–3.70(m, 12H), 4.00–5.00(m, 2H), 7.00(s, 1H), 7.16(s, 3H), 9.90(s, 1H) | 631 |
| 6.14 | 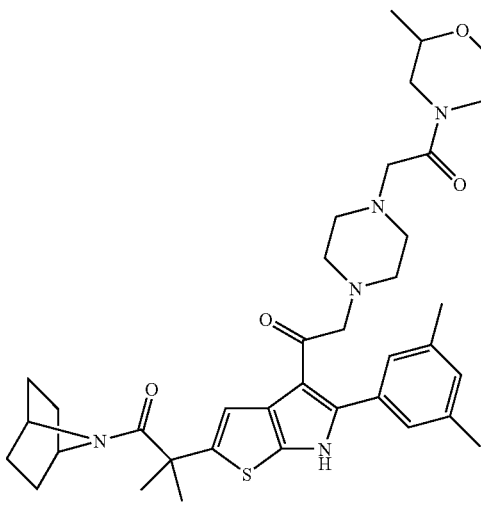 | 1.10–1.40(m, 10H), 1.45–1.85(m, 10H), 2.35(s, 6H), 2.36–2.60(m, 8H), 2.70(t, 1H), 3.00–3.70(m, 7H), 3.93–5.00(m, 4H), 7.06(s, 1H), 7.10–7.20(m, 3H), 8.80(s, 1H) | 674 |

-continued
| Example | Structure | ¹H NMR(CDCl₃) | MS-ESI: (M⁺ + H) |
|---|---|---|---|
| 6.15 | 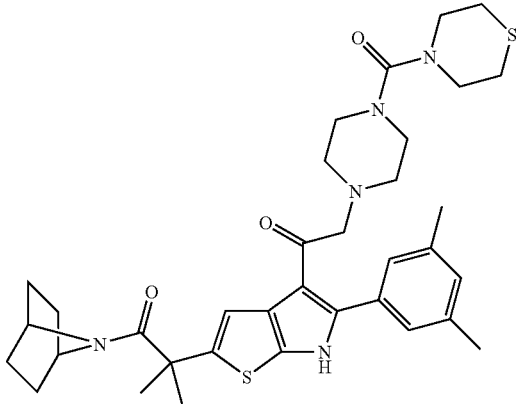 | 1.20–1.40(m, 4H), 1.45–1.80(m, 12H), 2.10–2.42(m, 11H), 2.48–2.67(m, 4H), 2.70–2.83(d, 2H), 3.42(s, 2H), 3.62–3.92(m, 4H), 4.00–5.00(m, 2H), 7.04(s, 1H), 7.15(s, 3H), 9.48(s, 1H) | 647 |
| 6.16 | 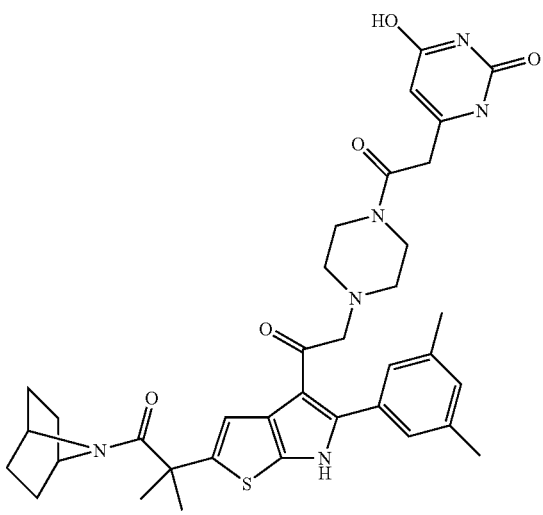 | 1.20–1.70(m, 14H), 2.20–3.60(m, 18H), 3.90–4.70(m, 2H), 5.30(s, 1H), 7.03(s, 1H), 7.09(s, 1H), 7.20(s, 2H), 10.70(s, 1H), 10.90(s, 1H), 12.15(s, 1H) | 671 |
| 6.17 | 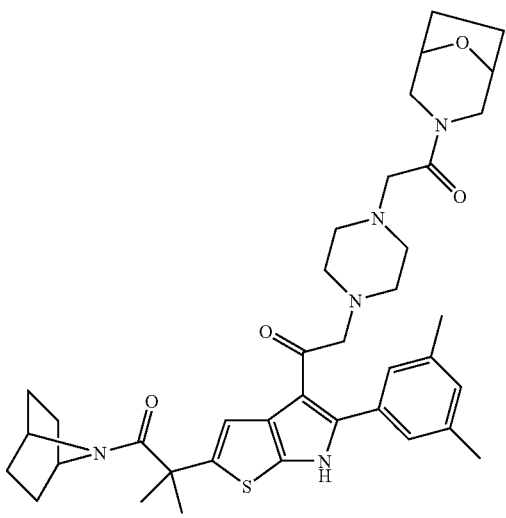 | 1.18–1.40(m, 4H), 1.45–1.73(m, 10H), 1.78–1.98(m, 4H), 2.32(s, 6H), 2.35–2.60(m, 8H), 2.80(d, 2H), 3.17(d, 1H), 3.30(d, 1H), 3.40(s, 2H), 3.79(d, 1H), 4.05(d, 1H), 4.34(d, 2H), 4.40–5.00(m, 2H), 7.04(s, 1H), 7.10–7.20(m, 3H), 9.75(s, 1H) | 672 |

-continued

| Example | Structure | ¹H NMR(CDCl₃) | MS-ESI: (M⁺ + H) |
|---|---|---|---|
| 6.18 | 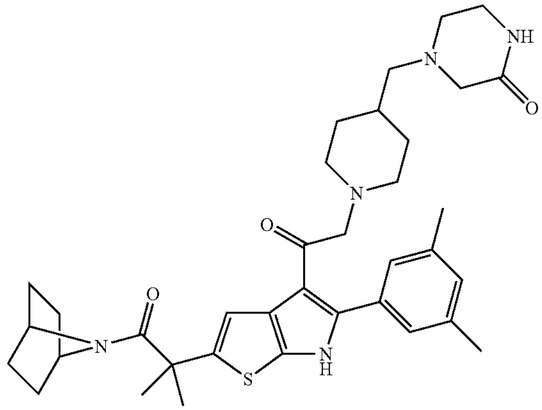 | 1.15–1.85(m, 19H), 1.95–2.15(m, 2H), 2.17–2.26(d, 2H), 2.36(s, 6H), 2.60(m, 2H), 2.75–2.94(m, 2H), 3.08(s, 2H), 3.34(s, 2H), 3.45(s, 2H), 4.00–5.00(m, 2H), 5.79(s, 1H), 7.07(s, 1H), 7.16(m, 3H), 8.94(s, 1H) | 630 |
| 6.19 | 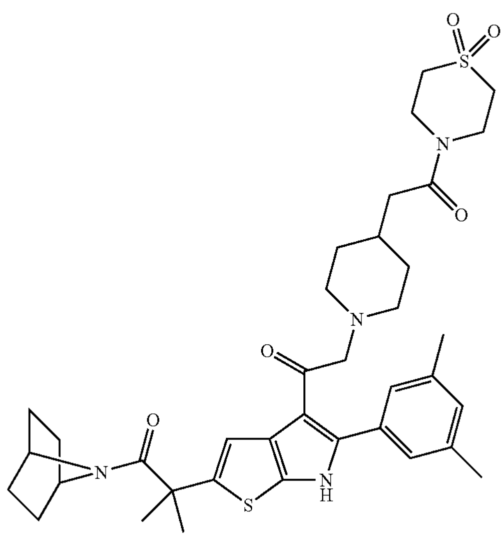 | 1.15–1.40(m, 8H), 1.45–1.72(m, 10H), 1.75–1.90(m, 1H), 2.00–2.18(m, 2H), 2.27(d, 2H), 2.34(s, 6H), 2.80–3.08(m, 6H), 3.36–3.52(m, 2H), 3.95(s, 2H), 4.08(s, 2H), 4.09–4.80(m, 2H), 7.05(s, 1H), 7.15(m, 3H), 9.60(s, 1H) | 693 |
| 6.20 | 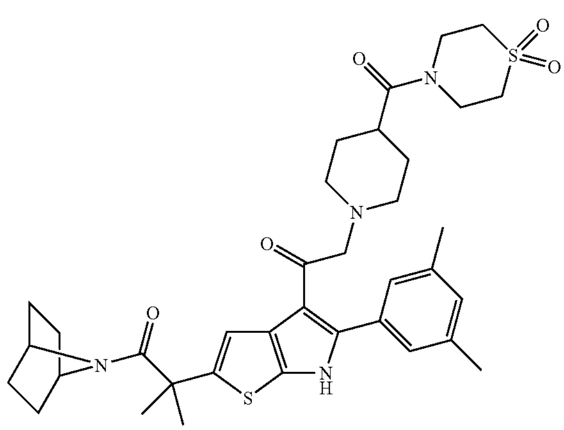 | 1.20–1.40(m, 4H), 1.45–1.70(m, 12H), 1.71–1.80(m, 2H), 2.25(t, 2H), 2.35(s, 6H), 2.37–2.49(m, 1H), 2.80(d, 2H), 2.95–3.08(m, 4H), 3.44(s, 2H), 3.85–4.13(m, 4H), 4.14–5.00(m, 2H), 7.05(s, 1H), 7.15(m, 3H), 9.42(s, 1H) | 679 |

-continued

| Example | Structure | ¹H NMR(CDCl₃) | MS-ESI: (M⁺ + H) |
|---|---|---|---|
| 6.21 | 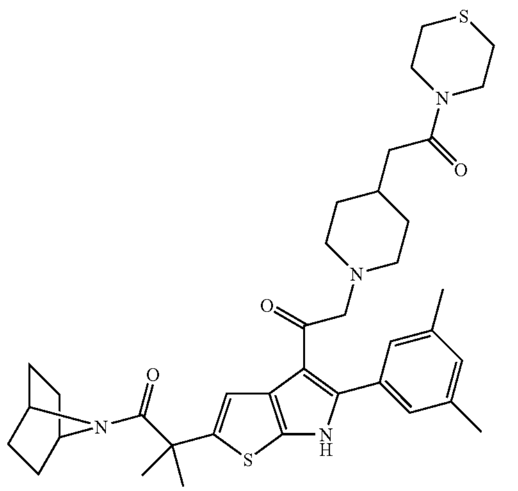 | 1.18–1.39(m, 7H), 1.45–1.86(m, 12H), 1.93–2.10(m, 2H), 2.16(d, 2H), 2.34(s, 6H), 2.50–2.64(m, 4H), 2.83(d, 2H), 3.40(s, 2H), 3.72(m, 2H), 3.85(m, 2H), 4.00–5.00(m, 2H), 7.04(s, 1H), 7.14(m, 3H), 9.74(s, 1H) | 661 |
| 6.22 | 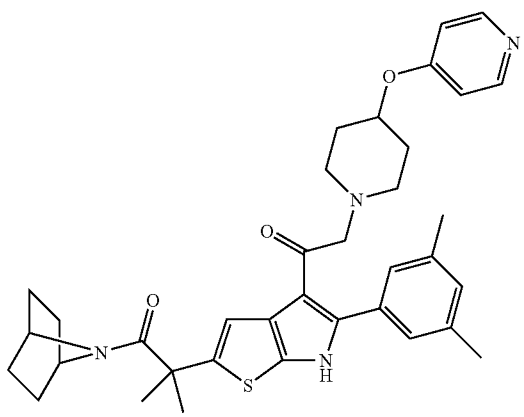 | 1.18–1.40(m, 4H), 1.45–1.70(m, 10H), 1.71–1.86(m, 2H), 1.90–2.00(m, 2H), 2.34(s, 6H), 2.37–2.50(m, 2H), 2.60–2.73(m, 2H), 3.47(s, 2H), 4.00–5.00(m, 3H), 6.75(d, 2H), 7.05(s, 1H), 7.17(m, 3H), 8.35(d, 2H), 9.87(s, 1H) | 611 |
| 6.23 | 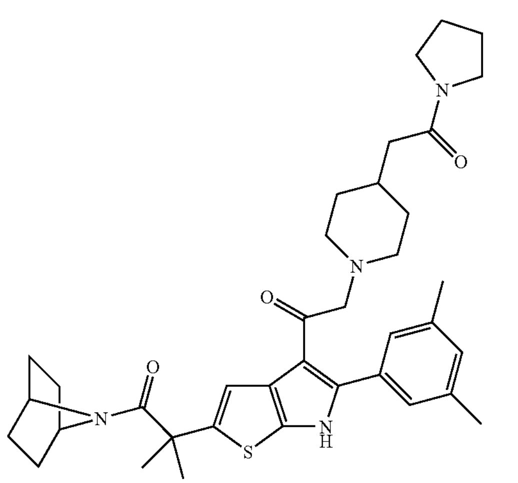 | 1.17–1.38(m, 6H), 1.40–1.73(m, 12H), 1.74–2.07(m, 7H), 2.12(d, 2H), 2.32(s, 6H), 2.81(d, 2H), 3.28–3.47(m, 6H), 4.00–5.00(m, 2H), 7.02(s, 1H), 7.14(m, 3H), 9.92(s, 1H) | 629 |

-continued

| Example | Structure | ¹H NMR(CDCl₃) | MS-ESI: (M⁺ + H) |
|---|---|---|---|
| 6.24 | 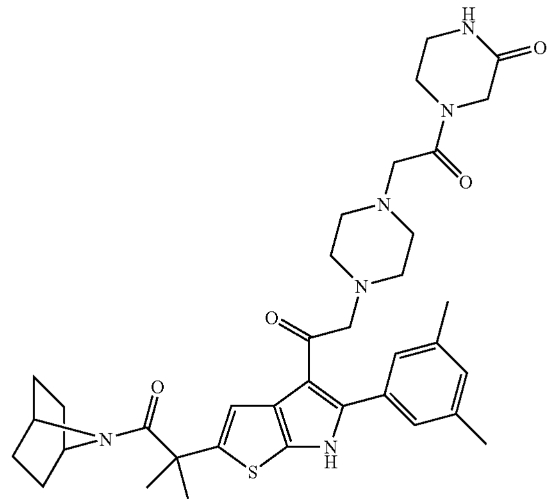 | 1.17–1.40(m, 4H), 1.45–1.80(m, 10H), 2.36(s, 6H), 2.40–2.65(s, 7H), 3.18(d, 2H), 3.30–3.50(m, 4H), 3.75–3.87(m, 2H), 4.00–5.00(m, 4H), 6.20(d, 1H), 7.06(s, 1H), 7.15(m, 3H), 8.94(d, 1H) | 659 |
| 6.25 | 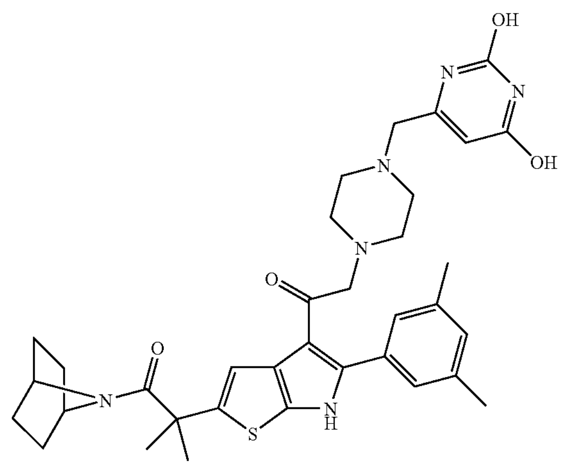 | 1.18–1.70(m, 14H), 2.15–2.50(m, 14H), 3.05–3.50(m, 4H), 4.00–4.60(m, 2H), 5.43(s, 1H), 6.95–7.13(m, 2H), 7.14–7.30(s, 2H), 10.60(s, 1H), 10.90(s, 1H), 12.15(s, 1H) | 643 |
| 6.26 | 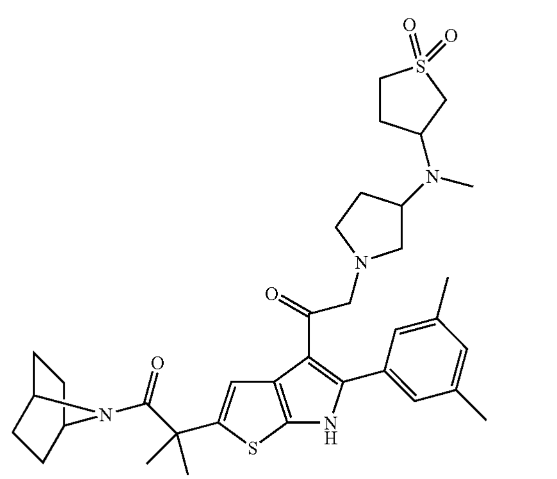 | 1.20–1.40(m, 4H), 1.44–1.80(m, 11H), 1.88–2.00(m, 1H), 2.05–2.19(m, 1H), 2.23(d, 3H), 2.24–2.44(m, 7H), 2.50–3.75(m, 12H), 4.00–5.00(m, 2H), 7.07(s, 1H), 7.13(s, 1H), 7.18(s, 2H), 9.22(s, 1H) | 651 |

-continued
| Example | Structure | ¹H NMR(CDCl₃) | MS-ESI: (M⁺ + H) |
|---|---|---|---|
| 6.27 | 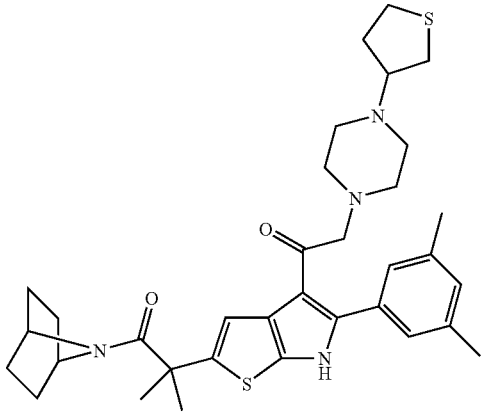 | 1.18–1.38(m, 4H), 1.45–1.83(m, 11H), 2.17–2.27(m, 1H), 2.35(s, 6H), 2.38–2.60(m, 8H), 2.66(t, 1H), 2.75–2.92(m, 4H), 3.38(s, 2H), 4.00–5.00(m, 2H), 7.04(s, 1H), 7.15(m, 3H), 9.76(s, 1H) | 605 |
| 6.28 | 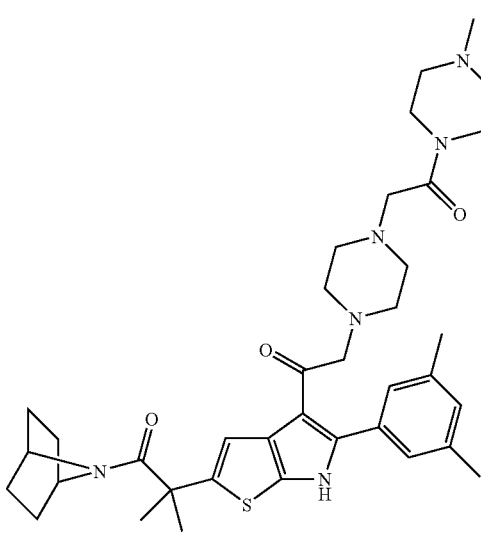 | 1.20–1.40(m, 4H), 1.50–1.80(m, 10H), 2.35(s, 6H), 2.38–2.60(m, 8H), 3.00(s, 3H), 3.10–3.20(m, 2H), 3.29–3.47(m, 4H), 3.77–3.90(m, 2H), 4.13–4.22(m, 1H), 4.30–5.00(m, 2H), 7.06(s, 1H), 7.10–7.20(m, 3H), 9.10–9.23(m, 1H) | 673 |
| 6.29 | 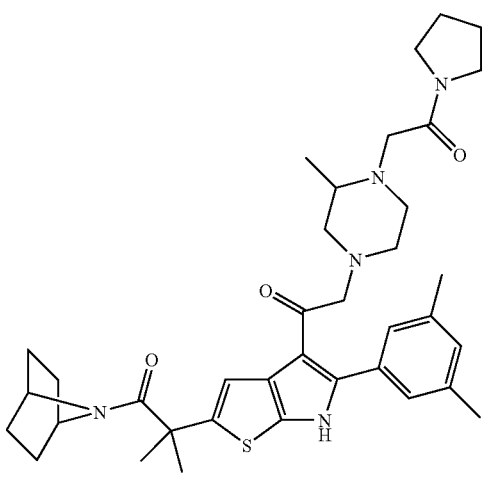 | 0.95(d, 3H), 1.20–1.38(m, 4H), 1.45–1.70(m, 10H), 1.75–2.05(m, 8H), 2.10–2.85(m, 10H), 3.30–3.70(m, 7H), 4.00–5.00(m, 2H), 7.02(s, 1H), 7.15(m, 3H), 9.57(s, 1H) | 644 |

-continued
| Example | Structure | $^1$H NMR(CDCl$_3$) | MS-ESI: (M$^+$ + H) |
|---|---|---|---|
| 6.30 | 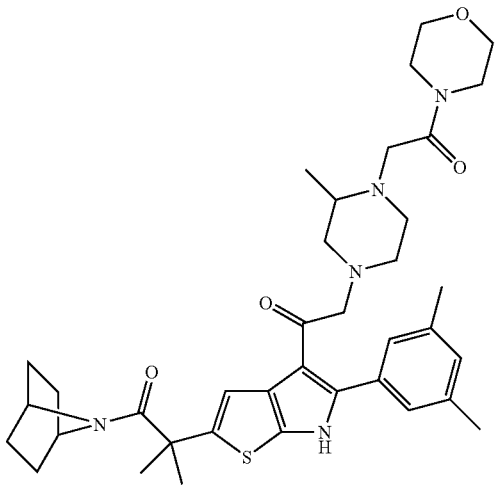 | 0.95(d, 3H), 1.20–1.36(m, 4H), 1.45–1.70(m, 10H), 1.90–2.45(m, 9H), 2.55–2.89(m, 4H), 3.30–3.88(m, 12H), 4.00–5.00(m, 2H), 7.02(s, 1H), 7.15(m, 3H), 9.68(s, 1H) | 660 |
| 6.31 | 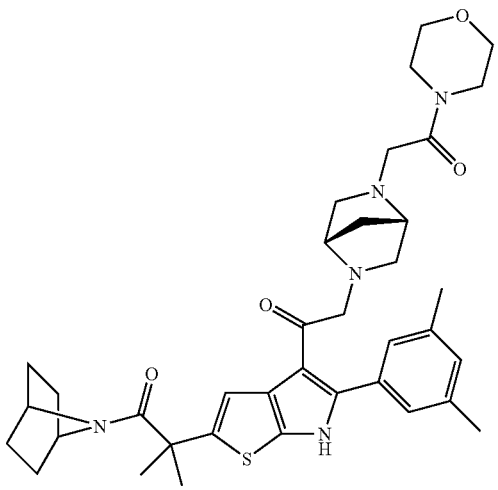 | 1.20–1.40(m, 4H), 1.45–1.85(m, 10H), 2.35(s, 6H), 2.65–2.95(m, 4H), 3.25–3.77(m, 16H), 4.00–5.00(m, 2H), 7.06(s, 1H), 7.10–7.20(m, 3H), 9.28(s, 1H) | 658 |
Novel intermediates used in the coupling syntheses were prepared as follows:
37 for Example 6.8
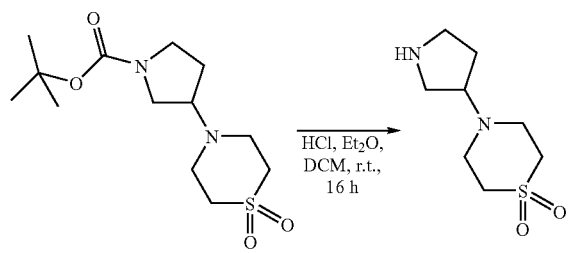

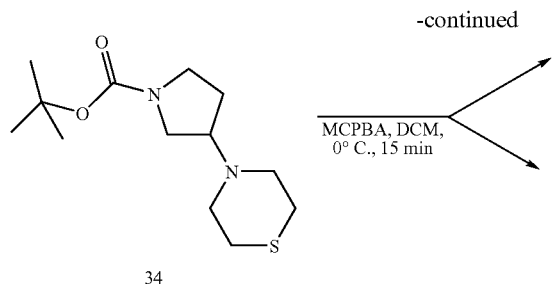

MCPBA (2.44 g, 9.88 mmol) was added to a stirred solution of 34 (1.075 g, 3.95 mmol) [see intermediate for Example 6.11] in DCM (15 ml) at 0° C. under nitrogen. After stirring for 15 min at 0° C. the reaction was quenched by the addition of aq. saturated sodium metabisulfite (20 ml). The phases were separated and the organics were washed with sat.sodium bicarbonate solution (20 ml), sat.brine (20 ml), dried and evaporated to dryness under reduced pressure. The residue was purified by chromatography on silica, eluting with 20% DCM/EtOAc followed by 0–5% MeOH/DCM to give 36 as a yellow solid (0.070 g) and 35 as a cream coloured solid (0.65 g).

35

MS-ESI: 289 (M$^+$+H). $^1$H NMR (CDCl$_3$) 1.48 (s, 9H), 1.70–1.90 (m, 1H), 2.00–2.18 (m, 1H), 2.69 (d, 1H), 2.73–3.30 (m, 10H), 3.45–3.80 (m, 2H).

36

MS-ESI: 305 (M$^+$+H). $^1$H NMR (CDCl$_3$) 1.40–2.15 (m, 11H), 2.93–3.20 (m, 6H), 3.21–3.78 (m, 7).

1.0M HCl in Et$_2$O (5 ml, 5.0 mmol) was added to a solution of 36 (0.122 g, 0.40 mmol) in DCM (2 ml). After stirring at ambient temperature for 16 h the solvent were evaporated away under reduced pressure to give 37 as a yellow solid (0.097 g). MS-ESI: 205 (M$^+$+H).

38 for Example 6.10

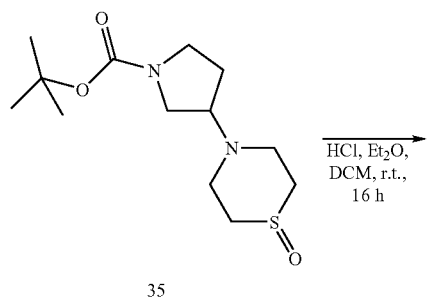

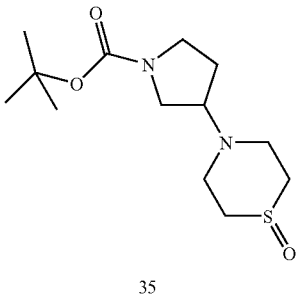

1.0M HCl in Et$_2$O (5 ml, 5.0 mmol) was added to a solution of 35 [see intermediate for Example 6.8] (0.1 g, 0.35 mmol) in DCM (1 ml). After stirring at ambient temperature for 16 h the solvents were evaporated under reduced pressure to give 38 as a pale yellow solid (0.078 g).
MS-ESI: 189 (M$^+$+H).

39 for Example 6.11

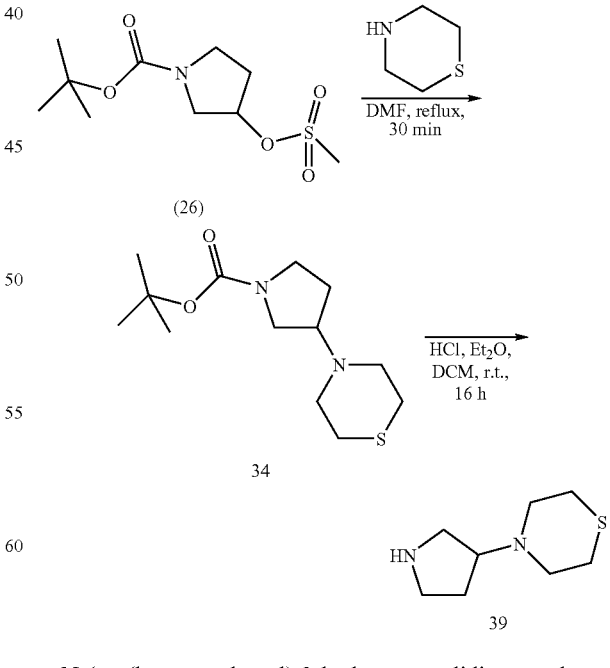

N-(tert(butoxycarbonyl)-3-hydroxypyrrolidine methanesulphonate (2.0 g, 7.55 mmol) was added to a solution of thiomorpholine (4 ml, 39.8 mmol) in DMF (4 ml). After stirring at reflux (153° C.) under nitrogen for 30 min the reaction mixture was allowed to cool and evaporated to dryness under reduced pressure. The residue was purified by column chromatography on silica, eluting with 0–10% MeOH/DCM to give 34 as a brown solid (2.1 g).

MS-ESI: 274 (M$^+$+H). $^1$H NMR (CDCl$_3$) 1.47 (s, 9H), 1.65–1.85 (m, 1H), 1.86–2.12 (m, 2H), 2.54–3.00 (m, 4H), 3.02–3.16 (m, 1H), 3.19–3.32 (m, 1H), 3.40–3.73 (m, 4H), 3.78–3.88 (m, 2H).

1.0M HCl in Et2O (8 ml, 8.0 mmol) was added to a solution of (27)(0.695 g, 2.55 mmol) in DCM (2 ml). After stirring at ambient temperature for 16 h the solvents were evaporated away under reduced pressure to give (28) as a pale brown solid (0.53 g).

MS-ESI: 173 (M$^+$+H). $^1$H NMR (CDCl$_3$) 2.20–4.15 (m, 15H), 9.30–10.20 (m, 1H).

pressure. The residue was purified by chromatography on silica, eluting with 0–10% MeOH/DCM to give 40 as a white solid (1.31 g).

MS-ESI: 342 (M$^+$+H). $^1$H NMR (CDCl$_3$) 1.20 (d, 6H), 1.46 (s, 9H), 2.34 (dd, 1H), 2.40–2.55 (m, 4H) 2.75 (dd, 1H), 3.10 (d, 1H), 3.27 (d, 1H), 3.35–3.60 (m, 6H), 3.94 (d, 1H), 4.40 (d, 1H).

1.0M HCl in Et$_2$O (10 ml, 10.0 mmol) was added to a solution of 40 (0.58 g, 1.70 mmol) in DCM (2 ml). After stirring at ambient temperature for 16 h conc. HCl (1 ml) was added. After stirring for 2 h the solvents were removed under reduced pressure to give 41 as a yellow solid (0.46 g).

MS-ESI: 242 (M$^+$+H).

NMR (CDCl3, δ values) 1.13 (d, 6H), 2.35 (t, 1H), 2.70 (t, 1H), 3.25–3.80 (m, 11H), 4.20 (d, 1H), 4.30–4.48 (m, 1H), 4.50–4.70 (m, 1H), 10.17 (s, 1H).

43 for Example 6.15

41 for Example 6.14

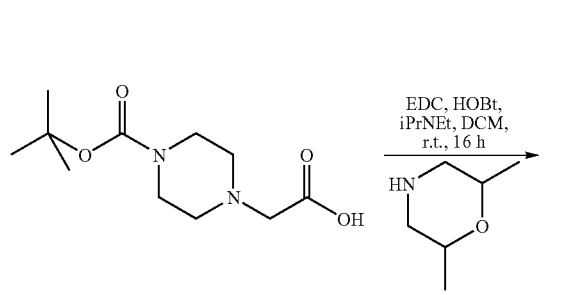

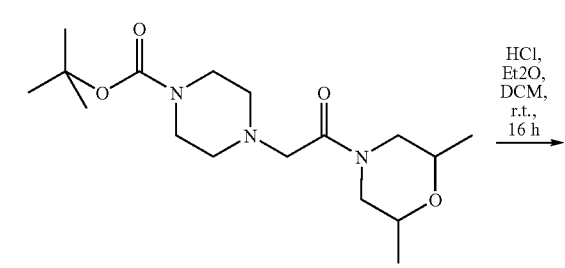

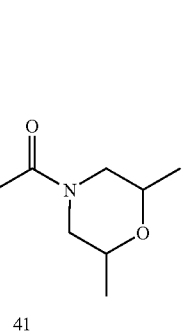

41

EDC (1.18 g, 6.15 mmol) was added to a stirred solution of N-Boc-piperazine acetic acid (1.00 g, 4.10 mmol), 2,6-dimethylmorpholine (605 μl, 4.92 mmol), 3-hydroxybenzotriazole (0.836 g, 6.15 mmol), and diisopropylethylamine (2.14 ml, 12.31 mmol) in DCM (30 ml) at ambient temperature under nitrogen. After stirring for 16 h the reaction was quenched by the addition of water (20 ml). The phases were separated and the organics were washed with sat.brine (20 ml), dried and evaporated to dryness under reduced

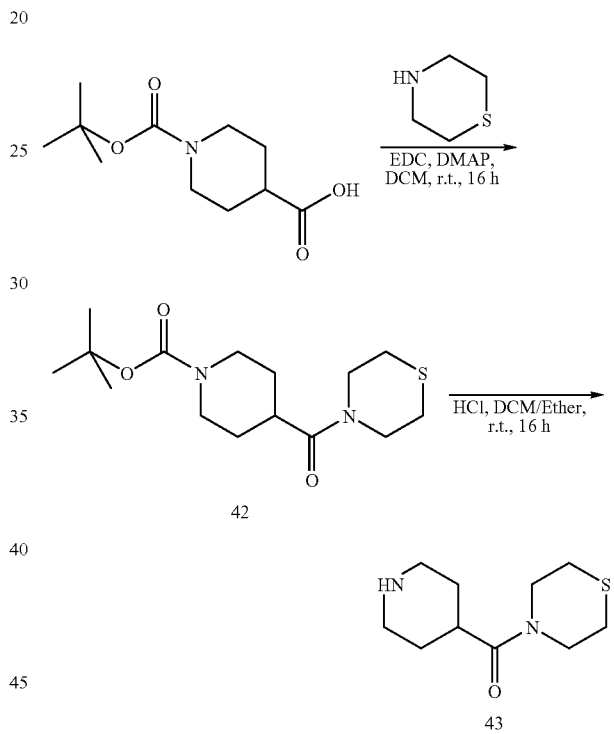

A mixture of N-Boc-4-piperidinecarboxylic acid (2.0 g, 8.72 mmol), thiomorpholine (1.2 g, 11.63 mmol), DMAP (4.3 g, 35.2 mmol) and EDC (2.2 g, 11.48 mmol) in dichloromethane (75 ml) was stirred under a nitrogen atmosphere for 16 h. The reaction mixture was washed with a 1.0M aq. citric acid solution, sat.sodium bicarbonate solution, the organics separated, dried and evaporated to dryness under reduced pressure. The residue was triturated with Et$_2$O to give a white solid, 42 (2.25 g). $^1$H NMR (CDCl$_3$) 1.44 (s, 9H), 1.55–1.82 (m, 4H), 2.50–2.89 (m, 5H), 2.87 (t, 2H), 3.87–3.97 (m, 4H), 4.04–4.28 (m, 2H).

A 1.0M solution of HCl in Et$_2$O (5 ml, 5 mmol) was added to a solution of 42 (0.7 g, 2.2 mol) in DCM (50 ml) and the mixture stirred for 16 h under a nitrogen atmosphere. The white precipitate was filtered, washed with Et$_2$O and dried to give 43 (0.55 g).

MS-ESI: 215 (M$^+$+H). $^1$H NMR (DMSOd$_6$) 1.73 (m, 4H), 2.43–2.69 (m, 4H), 2.80–3.00 (m, 3H), 3.15–3.35 (m, 2H), 3.70 (m, 4H), 8.71 (br s, 1H), 9.09 (br s, 1H).

45 for Example 6.16

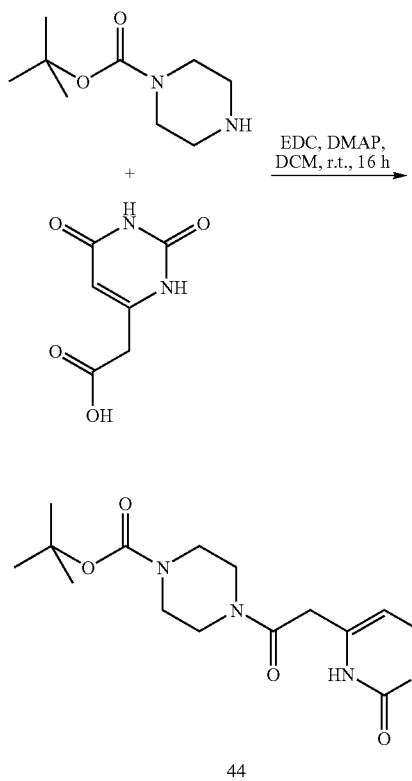

44

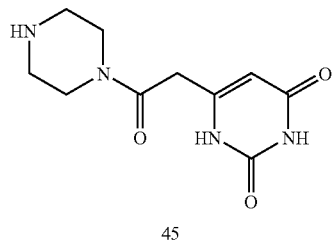

45

A mixture of N-Boc-piperazine (0.71 g, 3.82 mol), uracil-6-acetic acid (0.5 g, 2.94 mmol), DMAP (1.44 g, 11.79 mmol) and EDC (0.736 g, 3.84 mmol) in dichloromethane (40 ml) was stirred under a nitrogen atmosphere for 16 h. The reaction mixture was treated with 1.0M aq. citric acid solution (50 ml) to give a white precipitate which was filtered, washed with water, DCM and dried to give 44 (0.375 g). $^1$H NMR (DMSOd$_6$) 1.53 (s, 9H), 3.40–3.60 (m, 8H), 3.62 (s, 2H), 5.44 (s, 1H), 10.81 (br s, 1H), 11.04 (br s, 1H).

4.0M HCl in dioxane (10 ml, 40 mmol) was added to a solution of 44 (0.36 g, 1.06 mmol) in dioxane (30 ml) and the mixture stirred for 72 h under an atmosphere of nitrogen. The white precipitate was filtered, washed with more dioxane and then with Et$_2$O and dried to give 45 (0.26 g).

MS-ESI: 239 (M$^+$+H). $^1$H NMR (DMSOd$_6$) 3.08–3.33 (m, 4H), 3.65 (s, 1H), 3.80 (m, 4H), 5.45 (s, 1H), 9.60 (br s, 2H), 10.82 (br s, 1H), 11.05 (br s, 1H).

47 for Example 6.17

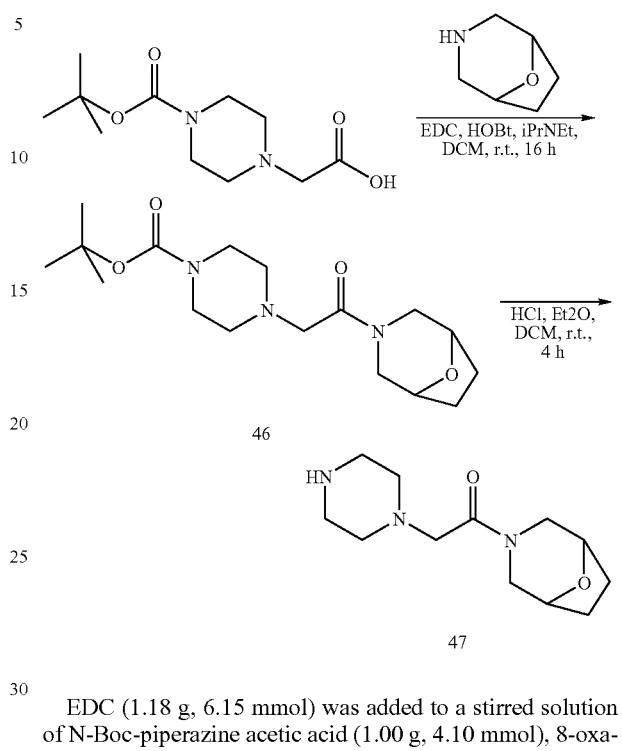

EDC (1.18 g, 6.15 mmol) was added to a stirred solution of N-Boc-piperazine acetic acid (1.00 g, 4.10 mmol), 8-oxa-3-aza-bicyclo [3.2.1.] octane (0.556 g, 4.92 mmol), 3-hydroxy benzotriazole (0.836 g, 6.15 mmol), and diisopropylethylamine (2.14 ml, 12.31 mmol) in DCM (20 ml) at ambient temperature under nitrogen. After stirring for 16 h the reaction was quenched by the addition of water (20 ml). The phases were separated and the organics were washed with sat.brine (20 ml), dried and evaporated to dryness under reduced pressure. The residue was purified by chromatography on silica, eluting with 0–10% MeOH/DCM to give 46 as a white solid (0.780 g).

MS-ESI: 340 (M$^+$+H). $^1$H NMR (CDCl$_3$) 1.45 (s, 9H), 1.80–2.00 (m, 4H), 2.30–2.58 (m, 4H), 2.85–3.04 (m, 2H), 3.25 (d, 1H), 3.30–3.57 (m, 3H), 3.78 (d, 1H), 4.12 (d, 1H), 4.36 (d, 3H).

1.0M HCl in Et$_2$O (10 ml, 10.0 mmol) and conc HCl (0.5 ml) were added to a solution of 46 (0.78 g, 2.30 mmol) in DCM (1.5 ml). After stirring at ambient temperature for 4 h the solvents were removed under reduced pressure to give 47 as a yellow solid foam (0.633 g).

49 for Example 6.18

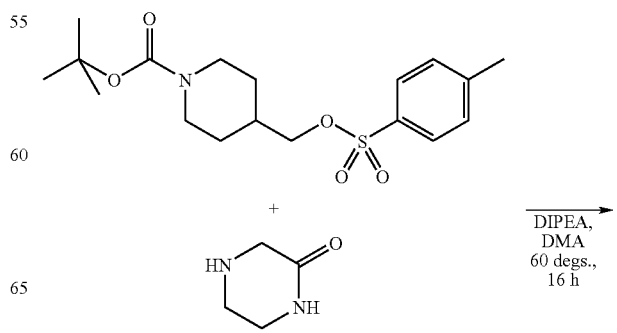

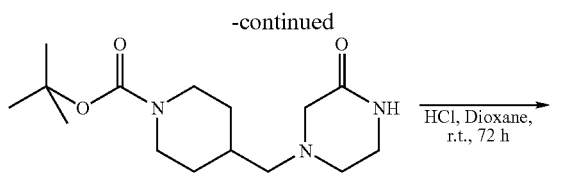

48

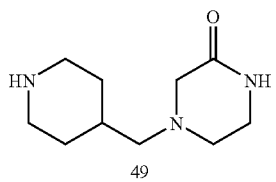

49

A mixture of N-(tert-butoxycarbonyl)-4-(tosyloxymethyl)-piperidine (0.5 g, 1.35 mmol), piperazin-2-one (0.298 g, 2.96 mmol), DIPEA (0.525 g, 4.06 mmol) in DMA (20 ml) was stirred at 60° C. for 16 h under a nitrogen atmosphere. The DMA was evaporated under reduced pressure and the residue portioned between 1.0M aq. citric acid and DCM. The organic layer was separated, dried and evaporated to dryness. It was purified on silica flash column chromatography eluting with EtOAc–20% MEOH/EtOAc to give 48 as a solid foam (0.25 g.).

MS-ESI: 298 (M$^+$+H). $^1$H NMR (DMSOd$_6$) 0.97–1.16 (m, 2H), 1.50 (s, 9H), 1.70–1.88 (m, 3H), 2.29 (d, 2H), 2.73–2.92 (m, 2H), 2.99 (s, 2H), 3.23 (m, 2H), 3.40 (s, 2H), 4.00 and 4.04 (2s, 2H), 7.80 (s, 1H).

4.0M HCl in dioxane (10 ml, 40 mmol) was added to a solution of 48 (0.2 g, 0.67 mmol) in dioxane (40 ml) and the mixture stirred for 72 h under an atmosphere of nitrogen. The dioxane was evaporated under reduced pressure to give a gummy solid. This was stirred with Et$_2$O for 3 h and the resultant white solid isolated by centrifugation and dried to give 49 (0.156 g).

MS-ESI: 198 (M$^+$+H). $^1$H NMR (DMSOd$_6$) 1.42–1.60 (m, 2H), 2.22–2.35 (m, 3H), 2.97 (t, 2H), 3.18 (d, 2H), 3.36 and 3.40 (2s, 2H), 3.38–4.00 (m, 6H).

52 for Example 6.19

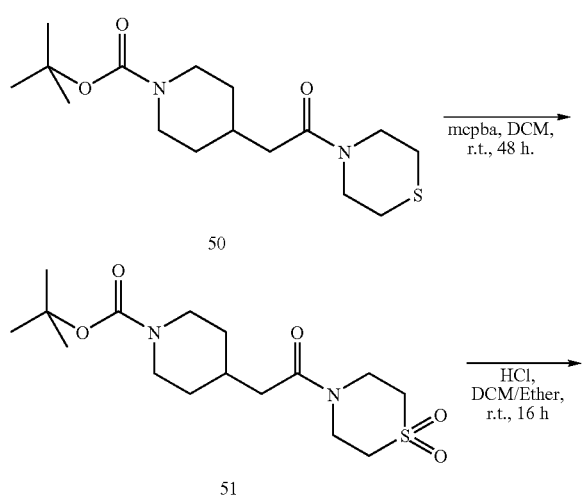

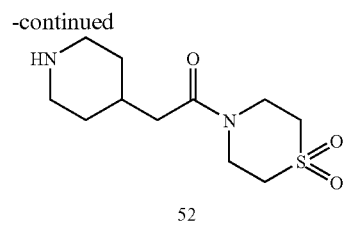

52

A mixture of 50 (1.5 g, 4.57 mmol) [see intermediate for Example 6.21] and MCPBA (70%) (2.25 g, 9.14 mmol) in DCM (50 ml) was stirred under a nitrogen atmosphere for 48 h. It was then washed with sat. sodium bicarbonate solution (2×50 ml), dried and evaporated to dryness under reduced pressure. The residue was washed with Et$_2$O and dried to give 51 (1.65 g) as a white solid.

MS-ESI: 361 (M$^+$+H). $^1$H NMR (DMSOd$_6$) 1.06–1.24 (m, 2H), 1.50 (s, 9H), 1.68–1.80 (m, 2H), 1.90–2.06 (m, 1H), 2.44 (d, 2H), 2.70–2.92 (m, 2H), 3.18 (m, 2H), 3.30 (m, 2H), 3.90–4.08 (m, 6H).

A 1.0M solution of HCl in Et$_2$O (19.4 ml, 19.4 mmol) was added to a solution of 51 (1.4 g, 3.9 mmol) in DCM (60 ml) and the mixture stirred for 16 h under a nitrogen atmosphere. The white precipitate was filtered, washed with Et$_2$O and dried to give 52 (0.96 g).

MS-ESI: 261 (M$^+$+H). $^1$H NMR (DMSOd$_6$) 1.40–1.60 (m, 2H), 1.86–2.00 (m, 2H), 2.00–2.20 (m, 1H), 2.50 (d, 2H), 2.88–3.05 (q, 2H), 3.20 (m, 2H), 3.24–3.40 (m, 2H), 3.56 (m, 2H), 3.97 (m, 4H), 8.95 (br s, 1H), 9.02 (br s, 1H).

54 for Example 6.20

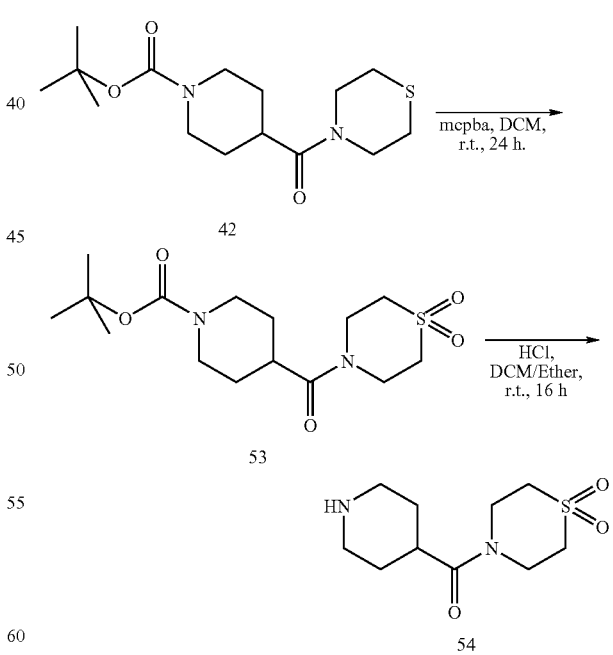

A mixture of 42 (1 g, 3.18 mmol) [see intermediate for Example 6.15] and mcpba (70%)(1.65 g, 6.7 mmol) in DCM (75 ml) was stirred under a nitrogen atmosphere for 72 h. It was then washed with sat. sodium bicarbonate solution(2× 50 ml), dried and evaporated to dryness under reduced pressure. The residue was washed with Et₂O and dried to give 53 (1 g) as a white solid.

MS-ESI: 369 (M⁺+Na). ¹H NMR (DMSOd₆) 1.29–1.52 (m, 2H), 1.45 (s, 9H), 1.55–1.72 (m, 2H), 2.64–2.96 (m, 3H), 3.00–3.28 (m, 4H), 3.72–4.00 (m, 6H).

A 1.0M solution of HCl in Et₂O (10 ml, 10 mmol) was added to a solution of 53 (1 g, 2.9 mmol) in DCM (80 ml) and the mixture stirred for 16 h under a nitrogen atmosphere. The white precipitate was filtered, washed with Et₂O and dried to give 54 (0.65 g).

MS-ESI: 247 (M⁺+H). ¹H NMR (DMSOd₆) 1.75–2.00 (m, 4H), 2.91–3.45 (m, 9H), 3.91 (m, 4H), 8.80 (br s, 1H), 9.10 (br s, 1H).

(55) for Example 6.21

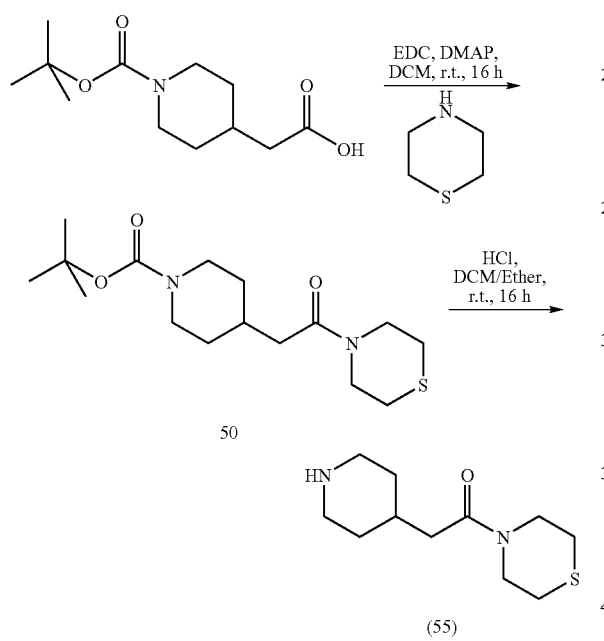

(55)

A mixture of N-Boc-4-piperidine-acetic acid (2.0 g, 8.2 mmol), thiomorpholine (1 g, 9.7 mmol), DMAP (4.0 g, 32.8 mmol) and EDC (2.0 g, 10.4 mmol) in dichloromethane (80 ml) was stirred under a nitrogen atmosphere for 16 h. The reaction mixture was washed with a 1.0M aq. citric acid solution (2×50 ml), sat.sodium bicarbonate solution, the organics separated, dried and evaporated to dryness under reduced pressure. The residue was purified by flash column chromatography on silica eluting with 50–80% EtOAc/isohexane to give 50 (2.1 g) as a white solid. ¹H NMR (CDCl₃) 1.03–1.22 (m, 2H), 1.46 (s, 9H), 1.67–1.80 (m, 2H), 1.90–2.05 (m, 1H), 2.22 (d, 2H), 2.58–2.64 (m, 4H), 2.74 (t, 2H), 3.75 (t, 2H), 3.90 (t, 2H), 4.00–4.20 (m, 2H).

A 1.0M solution of HCl in Et₂O (10 ml, 10 mmol) was added to a solution of 50 (0.5 g, 1.5 mmol) in DCM (30 ml) and the mixture stirred for 16 h under a nitrogen atmosphere. The white precipitate was filtered, washed with Et₂O and dried to give 55 (0.33 g).

MS-ESI: 229 (M⁺+H). ¹H NMR (DMSOd₆) 1.40–1.60 (m, 2H), 1.84–2.00 (m, 2H), 2.00–2.20 (m, 1H), 2.40 (d, 2H), 2.55–2.68 (m, 2H), 2.68–2.78 (m, 2H), 2.82–3.04 (q, 2H), 3.20–3.40 (m, 2H), 3.80 (m, 4H), 8.97 (br s, 1H), 9.15 (br s, 1H).

57 for Example 6.23

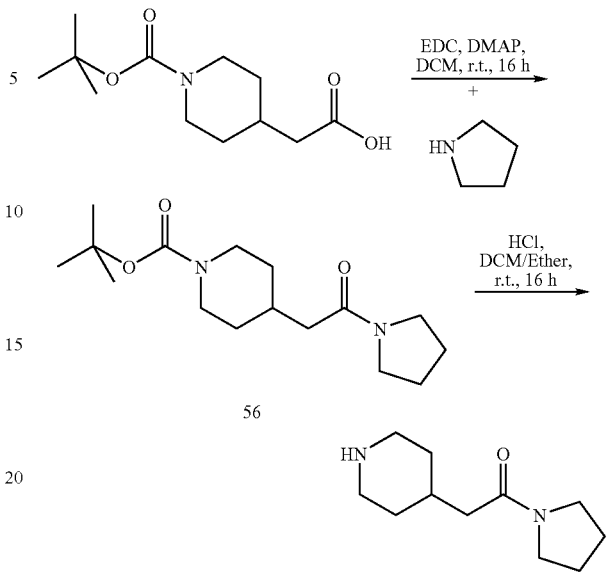

57

A mixture of N-Boc4-piperidine-acetic acid (1.0 g, 4.1 mmol), pyrrolidine (0.38 g, 5.3 mmol), DMAP (2.0 g, 16.4 mmol) and EDC (1.0 g, 5.2 mmol) in dichloromethane (60 ml) was stirred under a nitrogen atmosphere for 16 h. The reaction mixture was washed with a 1.0M aq. citric acid solution (2×50 ml), sat.sodium bicarbonate solution, the organics separated, dried and evaporated to dryness under reduced pressure. The residue was triturated and washed with Et₂O to give a white solid, 56 (1.15 g). ¹H NMR (CDCl₃) 1.04–1.21 (m, 2H), 1.45 (s, 9H), 1.68–1.79 (m, 2H), 1.80–2.13 (m, 5H), 2.18 (d, 2H), 2.72 (t, 2H), 3.40 (t, 2H), 3.46 (t, 2H), 3.98–4.20 (m, 2H).

A 1.0M solution of HCl in Et₂O (20 ml, 20 mmol) was added to a solution of 56 (1 g, 3.6 mmol) in DCM (50 ml) and the mixture stirred for 16 h under a nitrogen atmosphere. The solvent was decanted and the gummy solid washed with Et2O and then stirred with more Et₂O for 18 h. The precipitate was filtered and dried to give 57 (0.7 g) as a white solid.

MS-ESI: 197 (M⁺+H). ¹H NMR (DMSOd₆) 1.40–1.60 (m, 2H), 1.80–2.02 (m, 6H), 2.02–2.20 (m, 1H), 2.30 (d, 2H), 2.94 (q, 2H), 3.20–3.32 (m, 2H), 3.37 (t, 2H), 3.48 (t, 2H), 9.00 (br s, 1H), 9.20 (br s, 1H).

59 for Example 6.24

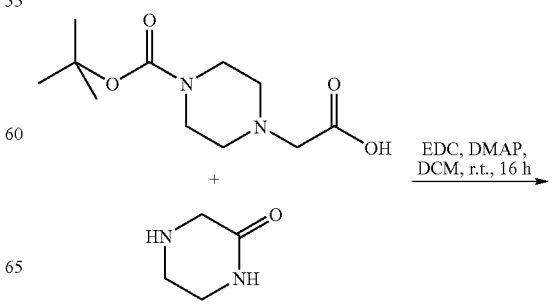

-continued

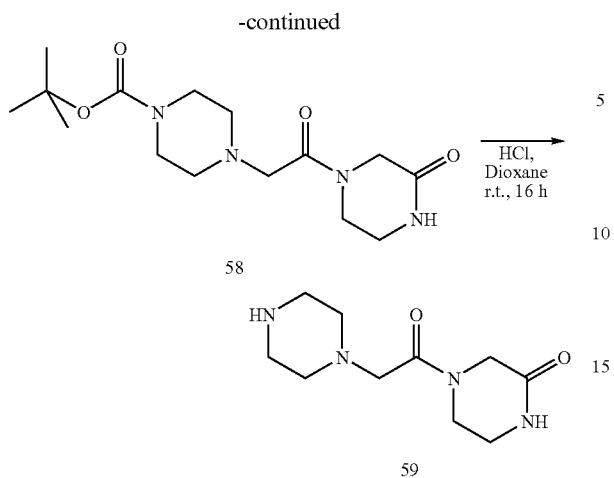

58

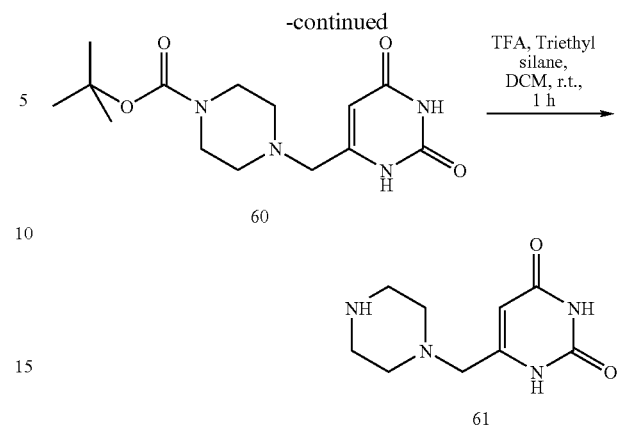

60

61

A mixture of N-Boc-piperazine acetic acid (0.5 g, 2.05 mmol), piperazin-2-one(0.3 g, 3.075 mmol), DMAP (1.25 g, 10.23 mmol) and EDC (0.51 g, 2.7 mmol) in dichloromethane (40 ml) was stirred under a nitrogen atmosphere for 16 h. The reaction mixture was washed with a 1.0M aq. citric acid solution and the organics separated, dried and evaporated to dryness under reduced pressure. The residue was purified by flash column chromatography on silica eluting with EtOAc—20% MeOH/EtoAc to give 58 as a solid foam (0.38 g).

MS-ESI: 327 (M$^+$+H). $^1$H NMR (DMSOd$_6$) 1.50 (s, 9H), 2.48 (t, 4H), 3.20–3.48 (m, 8H), 3.70 and 3.80 (2t, 2H), 4.02 and 4.25 (2s, 2H), 8.12 (s, 1H).

4.0M HCl in dioxane (10 ml, 40 mmol) was added to a solution of 58 (0.34 g, 0.094 mmol) in dioxane (50 ml) and the mixture stirred for 16 h under an atmosphere of nitrogen. The dioxane was evaporated under reduced pressure to give a gummy solid. This was stirred with Et$_2$O for 3 h and the resultant white solid isolated by centrifugation and dried to give 59 (0.224 g).

MS-ESI: 227 (M$^+$+H). $^1$H NMR (DMSOd$_6$) 3.26–3.80 (m, 12H), 4.10 (d, 2H), 4.57 (s, 1H), 4.64 (s, 1H), 8.30 (d, 1H), 10.22 (br s, 2H), 3.34–3.55.

61 for Example 6.25

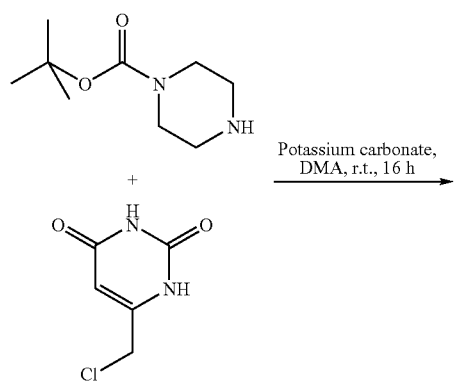

A mixture of 1-Boc-piperazine (1.0 g, 5.4 mmol), 6-chloromethyluracil(0.9 g, 5.6 mmol) and potassium carbonate (1.5 g, 10.9 mmol) in DMA (50 ml) was stirred at ambient temperature for 16 h under a nitrogen atmosphere. The DMA was evaporated away under reduced pressure and the residue was stirred with water (30 ml) and acidified with 1.0M aq. citric acid to pH 6–7. The resulting white solid precipitate was filtered and dried to give 60 (1.0 g).

MS-ESI: 311 (M$^+$+H). $^1$H NMR (DMSOd$_6$) 1.38 (s, 9H), 2.35 (t, 4H), 3.18 (s, 2H), 3.24–3.45 (m, 4H), 5.47 (s, 1H), 10.64 (br s, 1H), 10.91 (br s, 1H).

Triethylsilane (1.0 ml, 12 mmol) and then TFA (40 ml) was added to a stirred suspension of 60 (0.55 g, 1.8 mmol) in DCM(10 ml). under a nitrogen atmosphere. It was then stirred at ambient temperature for 1 h. The TEA and DCM were evaporated away under reduced pressure and the residue washed with Et$_2$O and dried to give 61 (0.5 g) as a cream solid.

MS-ESI: 211 (M$^+$+H). $^1$H NMR (DMSOd$_6$) 2.61 (t, 4H), 3.10 (m, 4H), 3.20 (s, 2H), 5.50 (s, 1H), 8.60 (br s, 2H), 10.65 (br s, 1H), 10.94 (br s, 1H).

63 for Example 6.26

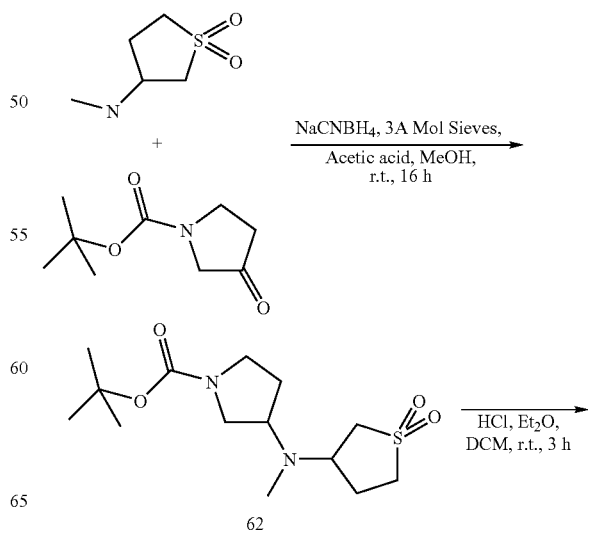

62

-continued

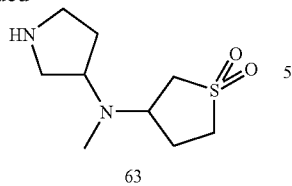

63

Glacial acetic acid (230 µl, 4.02 mmol) was added dropwise to a stirred solution of N-Boc-3-pyrrolidinone (0.3 g; 1.62 mmol), 3-methylamino-tetrahydrothiophene-1-dioxide hydrochloride (0.15 g, 0.81 mmol), sodium cyanoborohydride (0.102 g, 1.62 mmol), and 3A molecular sieves (0.3 g) in MeOH (3 ml) at ambient temperature under nitrogen. After stirring for 16 h the reaction mixture was filtered through a pad of celite and the filtrate evaporated to dryness under reduced pressure. The residue was partitioned between DCM (30 ml) and sat. NaHCO3 (20 ml), the organics were separated and further washed with sat.brine (20 ml), dried and evaporated to dryness. The residue was by chromatography on silica, eluting with 80% EtOAc/DCM then 2–5% MeOH/DCM to give 62 as a white solid (0.16 g).

MS-ESI: 319 ($M^+$+H). $^1$H NMR (CDCl$_3$) 1.47 (s, 9H), 1.70–1.90 (m, 1H), 1.95–2.10 (m, 1H), 2.12–2.40 (m, 5H), 2.90–3.35 (m, 7H), 3.40–3.73 (m, 3H).

1.0M HCl in Et$_2$O (2.5 ml, 2.5 mmol) and conc HCl (0.5 ml) were added to a solution of 62 (0.16 g, 0.50 mmol) in DCM (3 ml). After stirring at ambient temperature for 3 h the solvents were evaporated under reduced pressure to give 63 as a yellow solid (0.128 g).

MS-ESI: 219 ($M^+$+H). $^1$H NMR (CDCl$_3$) 2.10–2.40 (m, 17H), 9.73 (s, 1H).

-continued

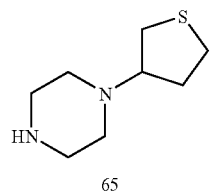

65

Glacial acetic acid (1.54 ml, 26.9 mmol) was added dropwise to a stirred solution of N-Boc-piperazine (1.0 g, 5.38 mmol), tetrahydro-thiophene-3-one (919 µl, 10.76 mmol), sodium cyanoborohydride (0.677 g, 10.75 mmol) and 3A molecular sieves (2.0 g) in MeOH (20 ml) at ambient temperature under nitrogen. After stirring for 16 h the reaction mixture was filtered through a pad of celite and the filtrate evaporated to dryness under reduced pressure. The residue was partitioned between DCM (50 ml) and sat. NaHCO3 (30 ml), the organics were separated and further washed with sat. brine (30 ml), dried and evaporated to dryness. The residue was purified by chromatography on silica, eluting with 10–40% EtOAc/DCM to give 64 as a white solid (0.74 g).

MS-ESI: 273 ($M^+$+H). $^1$H NMR (CDCl$_3$) 1.45 (s, 9H), 1.75–1.90 (m, 1H), 2.20–2.32 (m, 1H), 2.40–2.60 (m, 4H), 2.65–2.79 (m, 1H), 2.80–3.00 (m, 4H), 3.34–3.55 (m, 4H).

1.0M HCl in Et$_2$O (6.8 ml, 6.8 mmol) and conc HCl (0.5 ml) were added to a solution of 64 (0.37 g, 1.36 mmol) in DCM (2 ml). After stirring at ambient temperature for 3 h the solvents were evaporated away to give 65 as a yellow solid (0.283 g).

MS-ESI: 173 ($M^+$+H). $^1$H NMR (CDCl$_3$) 2.00–2.25 (m, 2H), 2.75–4.00 (m, 13H), 9.65 (br s, 1H).

67 for Example 6.28

65 for Example 6.27

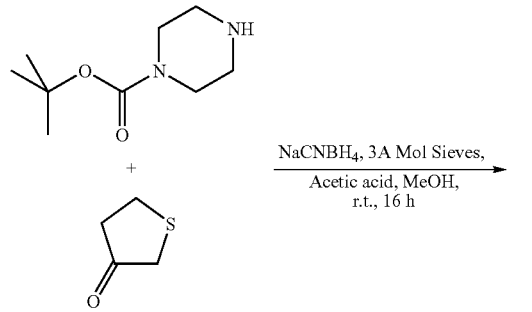

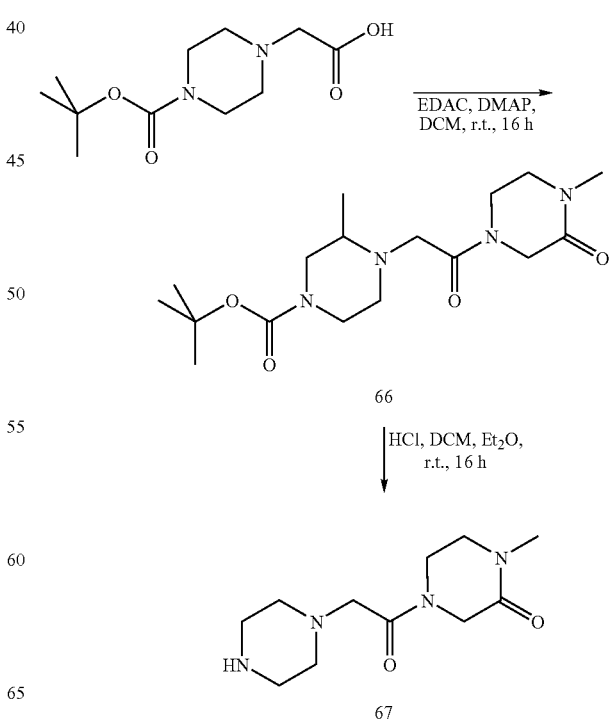

A mixture of N-Boc-4-piperazine-acetic acid hydrochloride dihydrate (0.4 g, 1.26 mmol), N-methyl-2-piperazinone (0.194 g, 1.7 mmol), DMAP (1.0 g, 8.2 mmol) and EDC (0.4 g, 2.1 mmol) in dichloromethane (60 ml) was stirred under a nitrogen atmosphere for 16 h. The reaction mixture was washed with a 1.0M aq. citric acid solution (2×50 ml), sat.sodium bicarbonate solution, the organics separated, dried and evaporated to dryness under reduced pressure. The residue was purified by chromatography on silica eluting with 10–20% MEOH/EtOAc to give 66 (0.3 g) as a solid foam.

MS-ESI: 341 (M$^+$+H). $^1$H NMR (DMSOd$_6$) 1.50 (s, 9H), 2.48 (m, 4H), 2.97 (s, 3H), 3.22–3.56 (m, 8H), 3.78 & 3.90 (2t, 2H), 4.09 & 4.29 (2s, 2H).

A 1.0M solution of HCl in Et$_2$O (7.6 ml, 7.6 mmol) was added to a solution of 66 (0.26 g, 0.76 mmol) in DCM (50 ml) and the mixture stirred for 16 h under a nitrogen atmosphere. The precipitate was filtered, washed with Et$_2$O and dried to give 67 (0.145 g) as a white solid.

MS-ESI: 241 (M$^+$+H). $^1$H NMR (DMSOd$_6$) 3.00 (s, 3H), 3.36–3.89 (m, 12H), 4.15 (s, 2H), 4.54 & 4.62 (2s, 2H), 10.08–10.25 (v.br s, 2H).

71 for Example 6.29 mmol), sodium iodide (0.1 g.) and N,N-diisopropylethylamine (3.48 ml, 20 mmol) in DCM (50 ml) at ambient temperature under nitrogen. After stirring for 16 h the reaction mixture was washed with water (30 ml), brine (30 ml), dried and evaporated to dryness under reduced pressure. The residue was purified by chromatography on silica, eluting with 0–8% MeOH/DCM to give 68 as a yellow oil (2.7 g).

MS-ESI: 273 (M$^+$+H). $^1$H NMR (CDCl$_3$) 1.05 (d, 3H), 1.47 (s, 9H), 2.50–2.85 (m, 4H), 3.03–3.13 (m, 1H), 3.34 (d, 1H), 3.44 (d, 1H), 3.70 (s, 3H), 3.71–3.82 (m, 2H).

2.0M NaOH (25 ml, 49.6 mmol) was added to a solution of 68 (2.7 g, 9.9 mmol) in THF (150 ml). After stirring at ambient temperature for 72 h the reaction mixture was adjusted to pH7 with 2N HCl and the solvents were evaporated. The residue was partitioned between water and EtOAc, the organics separated, dried and evaporated to dryness to give 69 as a yellow solid (2.56 g).

MS-ESI: 259 (M$^+$+H). $^1$H NMR (CDCl$_3$) 0.93 (d, 3H), 1.35 (s, 9H), 2.40–2.80 (m, 4H), 2.86–3.02 (m, 1H), 3.15 (d, 1H), 3.25 (d, 1H), 3.50–3.70 (m, 2H).

A mixture of 69 (1.28 g, 5.0 mmol), pyrrolidine (829 µl, 9.9 mmol), HOBt (1.0 g, 7.4 mmol) and EDC (1.7 g, 8.9 mmol) in DMF (30 ml) was stirred under a nitrogen atmo-

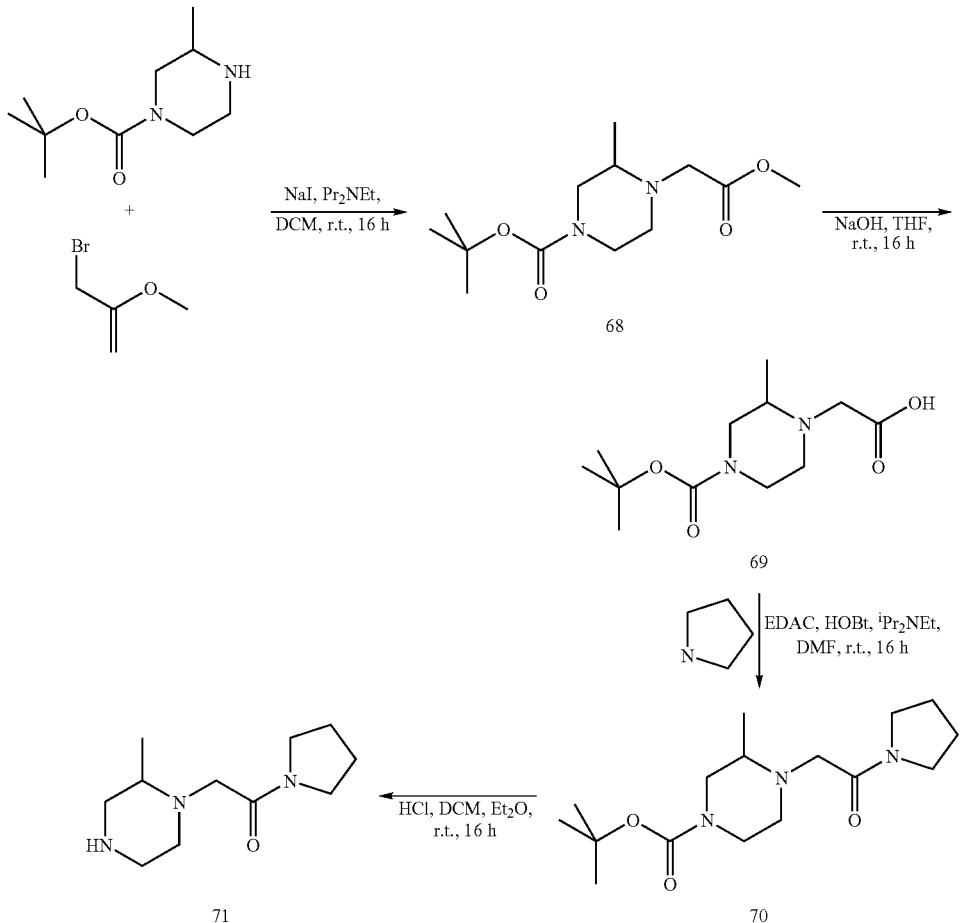

Methyl-bromoacetate (3.06 g, 20.0 mmol) was added to a stirred solution of 4-Boc-2-methyl-piperazine (2.0 g, 10.0 sphere for 16 h. The reaction mixture was evaporated under reduced pressure and the residue was partitioned between DCM (50 ml) and water (50 ml). The organic phase was washed with brine (20 ml), dried and evaporated to dryness. The residue was purified by chromatography on silica, eluting with 0–5% MeOH/DCM to give 70 as a yellow oil (0.904 g).

MS-ESI: 312 (M$^+$+H). $^1$H NMR (CDCl$_3$) 1.05 (d, 3H), 1.45 (s, 9H), 1.75–2.02 (m, 5H), 2.38–2.50 (m, 1H), 2.52–2.66 (m, 1H), 2.70–2.80 (m, 2), 3.02 (d, 1H), 3.09–3.20 (m, 1H), 3.37–3.60 (m, 5H), 3.62–3.80 (m, 1H).

10N HCl (0.9 ml, 29 mmol) was added to a solution of 70 (0.9 g, 2.9 mmol) in DCM (3 ml) and Et$_2$O (10 ml) and the mixture stirred for 16 h at ambient temperature. The solvents were evaporated and further azeotroped with toluene before triturating with MeOH/Et$_2$O to give 71 as a white solid (0.42 g).

MS-ESI: 212 (M$^+$+H). $^1$H NMR (DMSOd$_6$) 1.00–1.35 (m, 3H), 1.68–1.97(m, 4H), 2.80–3.80 (m, 13H).

73 for Example 6.30

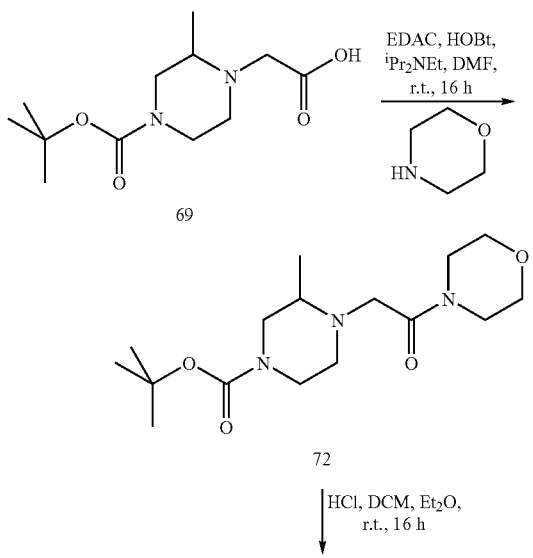

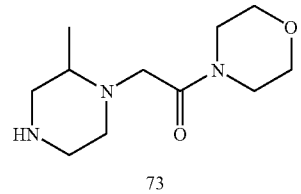

73

A mixture of 69 (1.28 g, 5.0 mmol), morpholine (872 µl, 9.9 mmol), DIPEA (2.58 g, 20 mmol), HOBt (1.0 g, 7.4 mmol) and EDC (1.7 g, 8.9 mmol) in DMF (30 ml) was stirred under a nitrogen atmosphere for 16 h. The reaction mixture was evaporated and the residue was partitioned between DCM (50 ml) and water (50 ml). The organic phase was washed with brine (20 ml), dried and evaporated to dryness under reduced pressure. The residue was purified by chromatography on silica, eluting with 0–5% MeOH/DCM to give 72 as a yellow oil (1.28 g).

MS-ESI: 328.2 (M$^+$+H). $^1$H NMR (CDCl$_3$) 1.05 (d, 3H), 1.48 (s, 9H), 2.30–2.40 (m, 1H), 2.41–2.55 (m, 1H), 2.70–2.80 (m, 1H), 2.95–3.07 (m, 1H), 3.10–3.20 (m, 1H), 3.40–3.83 (m, 12H).

10N HCl (0.6 ml, 20 mmol) was added to a solution of 72 (1.28 g, 3.9 mmol) in DCM (3 ml) and EtO2 (10 ml) and the mixture stirred for 16 h at ambient temperature. The solvents were evaporated and azeotroped with toluene before triturating with MeOH/Et$_2$Oto give 73 as a white solid (0.77 g).

MS-ESI: 228 (M$^+$+H). $^1$H NMR (DMSOd$_6$) 1.20–1.44 (m, 3H), 3.20–3.75 (m, 14H), 3.83–4.03 (m, 1H), 4.30–4.60 (m, 2H).

77 for Example 6.31

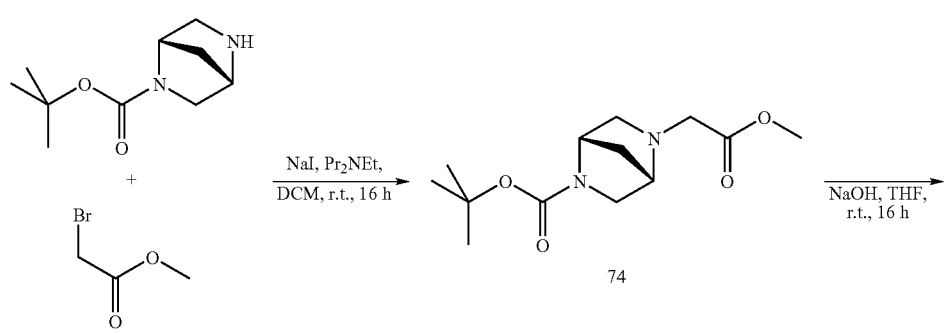

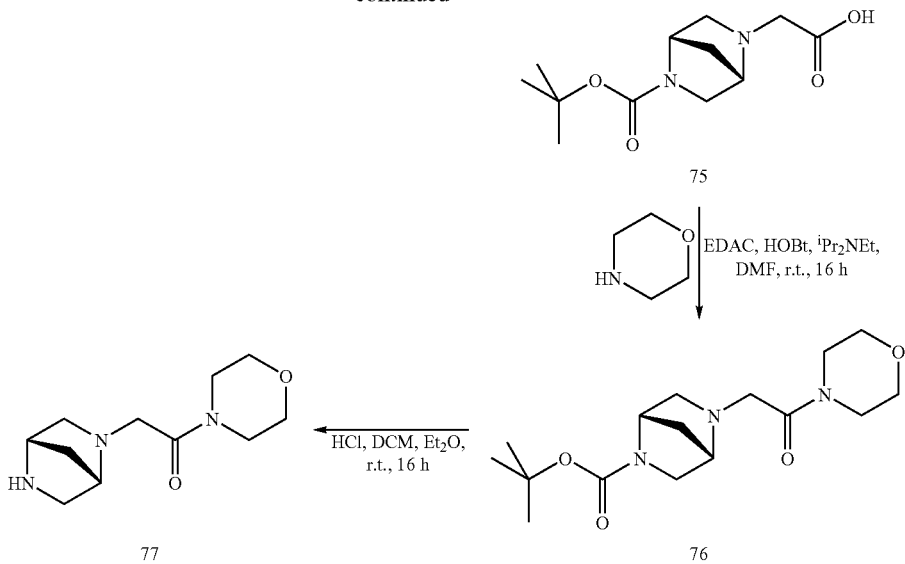

Methyl-bromo-acetate (771 mg, 5.0 mmol) was added to a stirred solution of tert-butyl (1S,4S)-(−)-2,5-diazabicyclo[2.2.1]-heptane-2-carboxylate (0.5 g, 2.5 mmol), sodium iodide (0.1 g.) and N,N-diisopropylethyl amine (1.32 ml, 7.6 mmol) in DCM (10 ml) at ambient temperature under nitrogen. After stirring for 16 h the reaction mixture was washed with water (30 ml), brine (30 ml), dried and evaporated to dryness. The residue was purified by chromatography on silica, eluting with 0–5% MeOH/DCM to give 74 as a yellow oil (0.25 g).

MS-ESI: 271 ($M^+$+H).

2.0M NaOH (2.3 ml, 4.6 mmol) was added to a solution of 74 (0.25 g, 0.9 mmol) in THF (3 ml). After stirring at ambient temperature for 24 h, the reaction mixture was adjusted to pH7 with 2N HCl and the solvents were evaporated off. The residue was partitioned between water and EtOAc, the organics separated, dried and evaporated to dryness to give 75 as a yellow solid (0.238 g).

MS-ESI: 257 ($M^+$+H).

A mixture of 75 (0.119 g, 0.5 mmol), morpholine (82 µl, 0.9 mmol), HOBt (0.095 g, 0.7 mmol), DIPEA (0.26 g, 2.0 mmol) and EDC (0.161 g, 0.8 mmol) in DMF (5 ml) was stirred under a nitrogen atmosphere for 16 h. The reaction mixture was evaporated and the residue was partitioned between DCM (20 ml) and water (10 ml). The organic phase was washed with brine (10 ml), dried and evaporated to dryness under reduced pressure. The residue was purified by chromatography on silica, eluting with 0–5% MeOH/DCM to give 76 as a yellow oil (0.03 g).

MS-ESI: 326 ($M^+$+H). $^1$H NMR (CDCl$_3$) 1.48 (s, 9H), 1.64–1.97 (m, 2H), 2.54–2.80 (m, 1H), 2.87–3.10 (m, 1H), 3.12–3.28 (m, 1H), 3.30–3.80 (m, 12H), 4.30 (d, 1H).

2N HCl in Et$_2$O (460 µl, 0.9 mmol) was added to a solution of 76 (0.03 g, 0.09 mmol) in DCM (0.5 ml) and stirred for 16 h at ambient temperature. The solvents were evaporated to give 77 as a yellow glass (0.024 g).

MS-ESI: 226 ($M^+$+H).

Example 7

2-[1,1-Dimethyl-2-oxo-2-azabicyclo[2.2.1]heptan-7-ylethyl]-4-[1-oxo-2-methyl-2-{4-(1,1-dioxidotetrahydro-3-thienyl)piperazin-1-yl}ethyl]-5-(3,5-dimethylphenyl)-6H-thieno[2,3-b]pyrrole

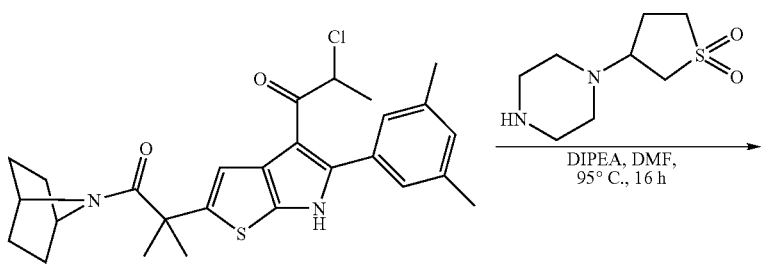

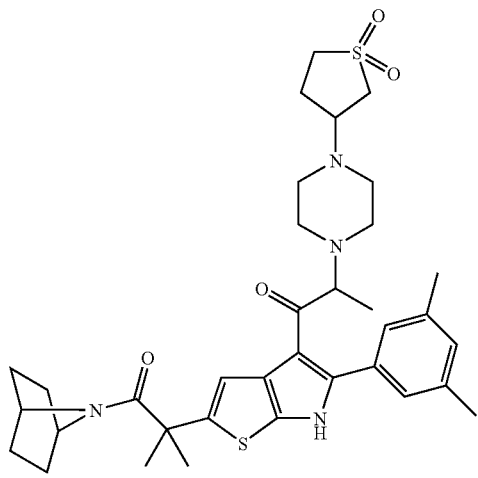

Example 7

1-(tetrahydro-1,1-dioxido-3-thienyl)-piperazine (0.084 g, 0.41 mmol) was added to a stirred solution of 78 (0.1 g, 0.21 mmol), catalytic NaI and diisopropyl ethyl amine (180 μl, 1.04 mmol) in DMF (3 ml). After stirring for 16 h at 90° C. under $N_2$ the reaction mixture was evaporated to dryness under reduced pressure. The residue was partitioned between DCM (10 ml) and water (5 ml), the organics separated, washed with brine (5 ml), dried and evaporated to dryness. The crude product was purified by chromatography on silica, eluting with 0–4% MeOH/DCM to give Example 7 as a yellow solid foam (0.068 g).

Yield: 51% MS-ESI: 651 (M$^+$+H). $^1$H NMR (DMSOd$_6$) 1.18 (d, 3H), 1.20–1.40 (m, 4H), 1.45–1.80 (m, 10H), 1.98–2.13 (m, 1H), 2.25–2.65 (m, 15H), 2.85–3.10 (m, 2H), 3.11–3.30 (m, 3H), 3.70–3.80 (m, 1H), 4.00–5.00 (m, 2H), 7.06 (s, 1H), 7.12 (s, 2H), 7.20 (s, 1H), 8.98 (s, 1H)

Synthesis of 78

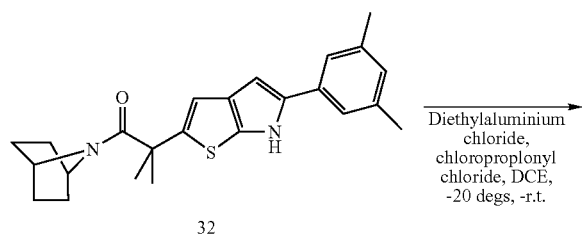

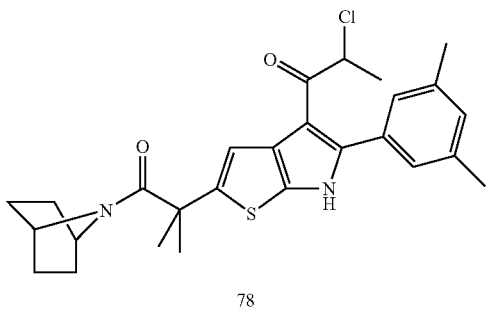

78

78 was prepared in a similar manner to the synthesis of 31 using 2-chloropropionyl chloride instead of chloroacetyl chloride and DCE instead of DCM (see Example 6).

MS-ESI: 482.95, 484.91 (M$^+$+H). $^1$H NMR (DMSOd$_6$) 1.2–1.6 (m, 8H), 1.50 and 1.52 (2s, 6H), 1.54 (d, 3H), 2.32 (s, 6H), 4.12–4.40 (m, 2H), 5.00 (q, 1H), 7.08 (s, 1H), 7.10 (s, 1H), 7.20 (s, 2H), 12.40 (br s, 1H).

Examples 7.1–7.2

Following a procedure similar to that described in Example 7, the compounds of table 7 were prepared.

TABLE 7

| Example | Structure | $^1$H NMR(CDCl$_3$) | MS-ESI: (M$^+$ + H) |
|---|---|---|---|
| 7.1 | 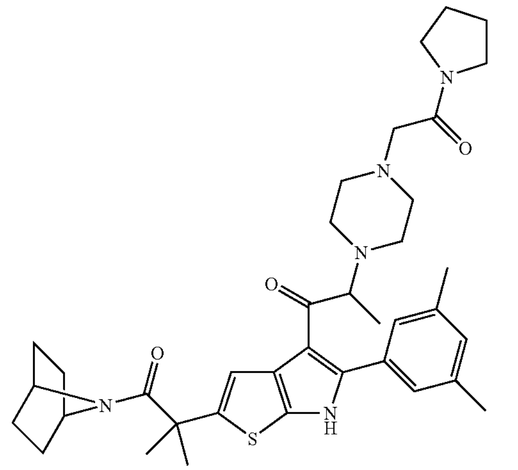 | 1.17(d, 3H), 1.20–1.38(m, 4H), 1.44–1.73(m, 10H), 1.75–2.04(m, 4H), 2.34(s, 6H), 2.38–2.65(m, 8H), 3.34–3.53(m, 4H), 3.54–3.66(m, 2H), 3.70–3.80(m, 1H), 4.00–5.00(m, 2H), 7.05(s, 1H), 7.14(s, 2H), 7.21(s, 1H), 9.64(s, 1H) | 644 |
| 7.2 | 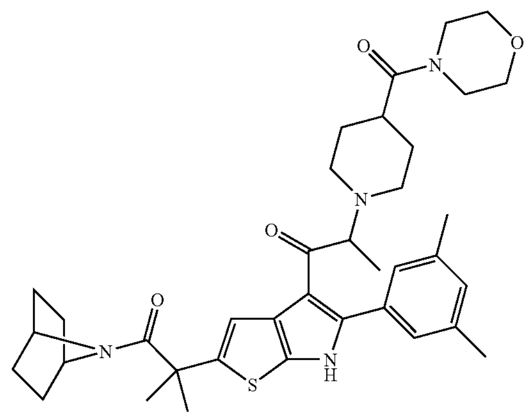 | 1.05–1.38(m, 8H), 1.40–1.80(m, 17H), 2.35(s, 6H), 3.35–3.75(m, 10H), 4.00–5.00(m, 2H), 7.05(s, 1H), 7.16(s, 2H), 7.24(s, 1H), 9.07(s, 1H) | 645 |

For the synthesis of the side-chain intermediates the reader is referred to Example 6.3 for Example 7.1 and Example 6.13 for Example 7.2.

Example 8

2-[1,1-Dimethyl-2-oxo-2-azabicyclo[2.2.1]heptan-7-ylethyl]-4-[1-oxo-3-{4-(1,1-dioxidotetrahydro-3-thienyl)piperazin-1-yl}propyl]-5-(3,5-dimethylphenyl)-6H-thieno[2,3-b]pyrrole

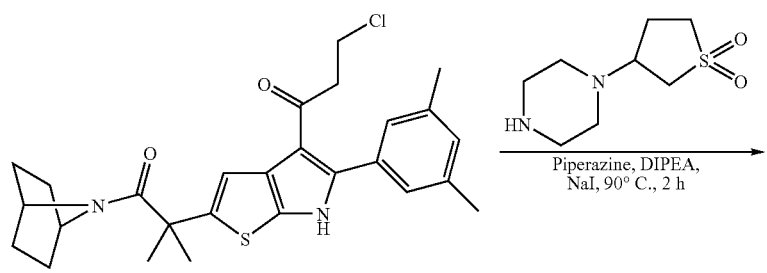

Piperazine, DIPEA, NaI, 90° C., 2 h

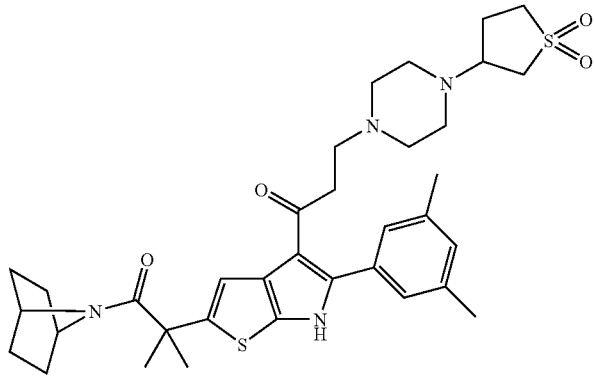

Example 8

Example 8 was prepared using the method in Example 6 and 79 instead of 31.

MS-ESI: 651 (M$^+$+H).

The starting material 79 was prepared from 32 using the procedure in the preparation of 31 and 3-chloropropionyl chloride instead of chloroacetyl chloride.

MS-ESI: 482.92, 484.90 (M$^+$+H). $^1$H NMR (DMSOd$_6$) 1.2–1.6 (m, 8H), 1.57 (s, 6H), 2.33 (s, 6H), 3.05 (t, 2H), 3.82 (t, 2H), 4.02–4.39 (m, 2H), 7.06 (s, 1H), 7.09 (s, 1H), 7.20 (s, 2H), 12.21 (br s, 1H).

Examples 8.1–8.5

Following a procedure similar to that described in Example 8, the compounds of table 8 were prepared.

TABLE 8

| Example | Structure | $^1$H NMR(DMSOd$_6$) | MS-ESI: (M$^+$ + H) |
|---|---|---|---|
| 8.1 | 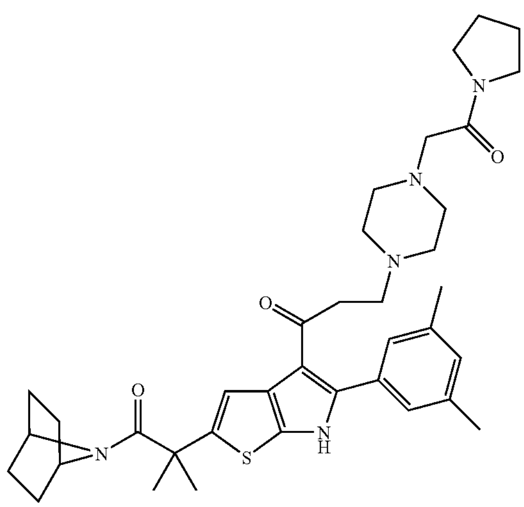 | 1.20–1.60(m, 8H), 1.53(s, 6H), 1.65–1.94(m, 4H), 2.20–2.80(m, 12H), 2.30(s, 6H), 3.00–3.48(m, 4H), 3.29(s, 2H), 4.10–4.40(m, 2H), 7.04(s, 1H), 7.08(s, 1H), 7.18(s, 2H) | 644 |

TABLE 8-continued
| Example | Structure | $^1$H NMR(DMSOd$_6$) | MS-ESI: (M$^+$ + H) |
|---|---|---|---|
| 8.2 | 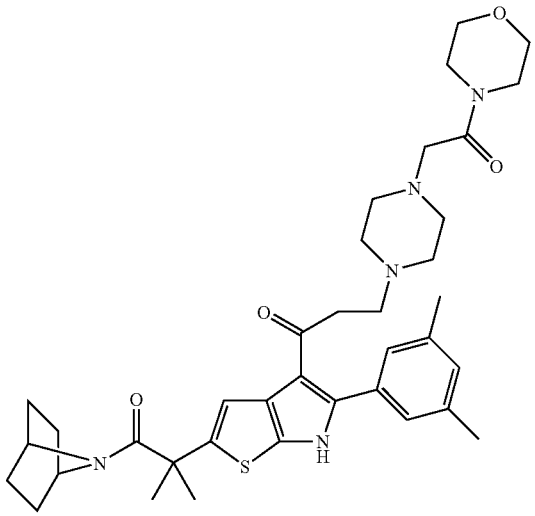 | 1.20–1.60(m, 8H), 1.53(s, 6H), 2.10–2.80(m, 10H), 2.32(s, 6H), 3.00–3.16(m, 2H), 3.21–3.60(m, 8H), 3.28(s, 2H), 4.10–4.40(m, 2H), 7.05(s, 1H), 7.08(s, 1H), 7.18(s, 2H), 12.15(br s, 1H) | 660 |
| 8.3 | 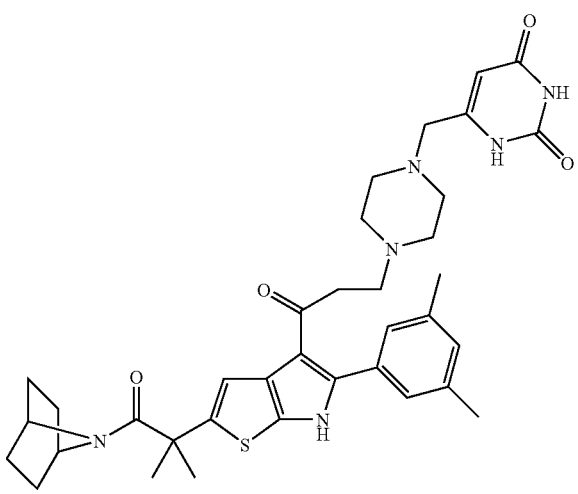 | 1.20–1.60(m, 8H), 1.53(s, 6H), 2.10–2.64(m, 8H), 2.32(s, 6H), 2.64–2.73(m, 2H), 3.04–3.20(m, 2H), 3.28(s, 2H), 4.10–4.50(m, 2H), 5.41(br s, 1H), 7.05(s, 1H), 7.08(s, 1H), 7.19(s, 2H) | 657 |
| 8.4 | 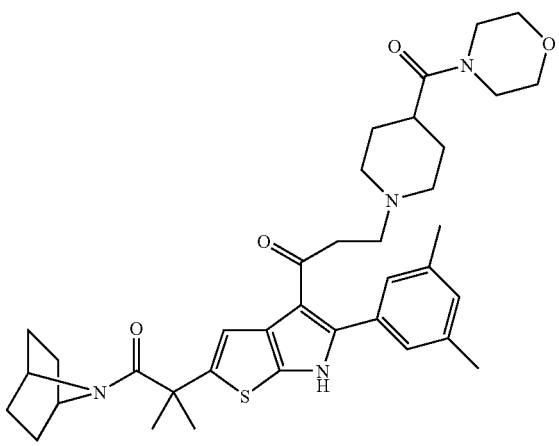 | 1.00–1.40(m, 8H), 1.40–1.63(m, 2H), 1.54(s, 6H), 1.63–1.89(m, 2H), 2.20–2.60(m, 8H), 2.32(s, 6H), 2.80–3.00(m, 1H), 3.00–3.70(m, 8H), 4.10–4.50(m, 2H), 7.06(s, 1H), 7.09(s, 1H), 7.22(s, 2H) | 645 |

TABLE 8-continued
| Example | Structure | $^1$H NMR(DMSOd$_6$) | MS-ESI: (M$^+$ + H) |
|---|---|---|---|
| 8.5 | 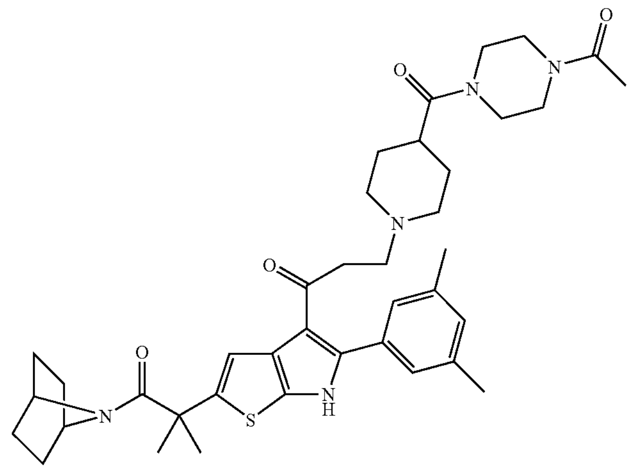 | 1.20–1.37(m, 4H), 1.37–1.60(m, 6H), 1.53(s, 6H), 1.79–1.94(m, 2H), 2.00(s, 3H), 2.25 & 2.43(2m, 1H), 2.31(s, 6H), 2.45–2.60(m, 4H), 2.60–2.80(m, 4H), 3.32–3.55(m, 8H), 4.10–4.50(m, 2H), 7.05(s, 1H), 7.09(s, 1H), 7.18(s, 2H), 12.15(br s, 1H) | 686 |
Example 9
2-[1,1-Dimethyl-2-oxo-2-azabicyclo[2.2.1]heptan-7-ylethyl]-4-[1-oxo-2,2-di-methyl-3-{4-(pyrrolidin-1-ylcarbonylmethyl)piperazin-1-yl}propyl]-5-(3,5-dimethylphenyl)-6H-thieno[2,3-b]pyrrole
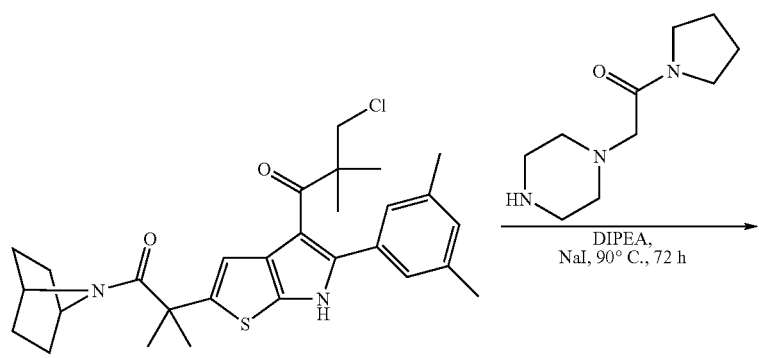
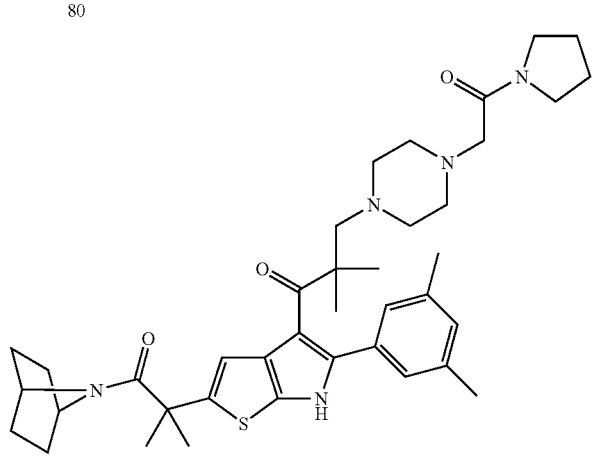
Example 9

Example 9 was prepared using the method in Example 6 and 80 instead of 31 and heating for 72 h.

MS-ESI: 672 (M++H). ¹H NMR (CDCl₃) 1.08–1.75 (m, 8H), 1.18 (s, 6H), 1.73 (s, 6H), 1.75–2.00 (m, 4H), 2.32 (s, 6H), 2.20–2.75 (m, 12H), 3.05 (s, 2H), 3.38–3.55 (m, 2H), 4.10–4.80 (m, 2H), 6.92 (s, 1H), 6.96 (s, 1H), 7.09 (s, 2H), 8.54 (s, 1H).

The starting material 80 was prepared from 32 using the procedure in the preparation of 31 with 3-chloropivaloyl chloride instead of chloroacetyl chloride.

MS-ESI: 511 (M++H). ¹H NMR (DMSOd₆) 1.20 (s, 6H), 1.20–1.60 (m, 8H), 1.52 (s, 6H), 2.27 (s, 6H), 3.80 (s, 2H), 4.04.4.40 (m, 2H), 6.96 (s, 1H), 7.04 (s, 2H), 7.26 (s, 1H), 12.10 (br s, 1H).

Example 9.1 was synthesised by the procedure used to prepare Example 9 and the appropriate starting material:

Example 9.1

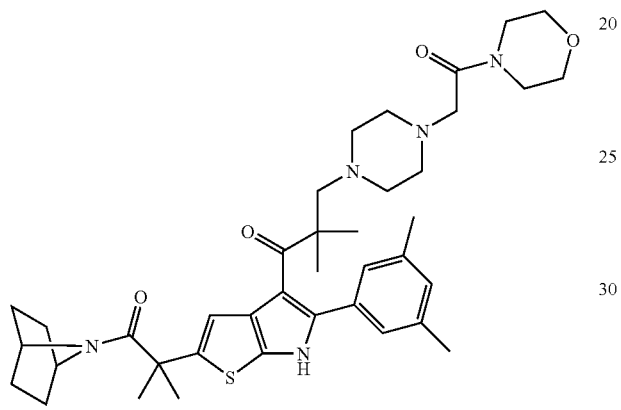

MS-ESI: 688 (M++H). ¹H NMR (DMSO d₆) 1.19–1.65 (m, 7H), 1.51 (s, 6H), 1.80–2.00 (m, 1H), 2.08–2.60 (m, 8H), 2.24 (s, 6H), 2.29 (s, 6H), 2.60–2.80 (m, 3H), 2.71 & 2.89 (2s, 2H), 2.80–2.95 (m, 1H), 2.95–3.40 (m, 6H), 4.09–4.45 (m, 2H), 7.04 (s, 1H), 7.08 (s, 1H), 7.17 (s, 2H), 12.13 (br s, 1H).

Example 10

2-[1,1-Dimethyl-2-oxo-2-azabicyclo[2.2.1]heptan-7-ylethyl]-4-[2-{4-pyrrolidin-1-ylcarbonylmethyl)piperazin-1-yl}ethyl]-5-(3,5-dimethylphenyl)-6H-thieno[2,3-b]pyrrole

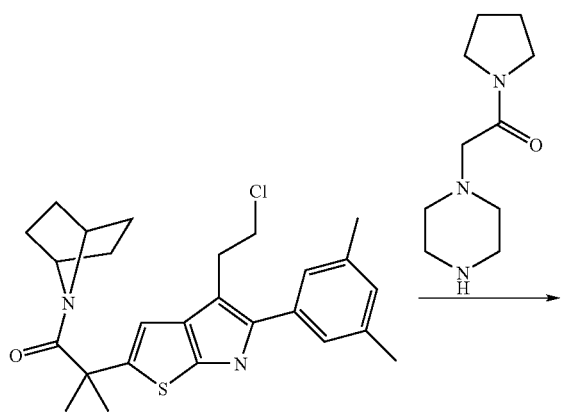

-continued

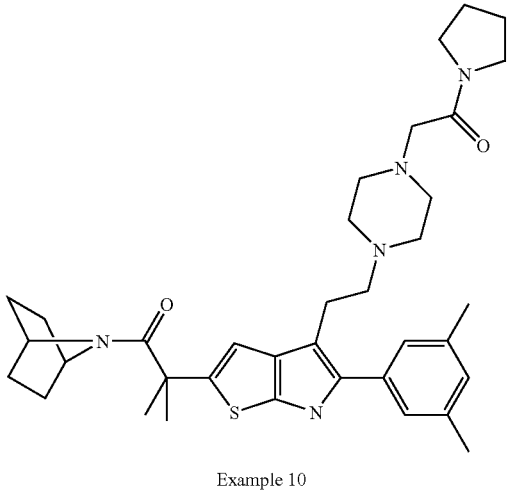

Example 10

A mixture of 29 (0.182 g; 0.4 mmol), N-(pyrrolidinocarbonylmethyl) piperazine (0.095 g, 0.48 mmol), NaI (0.072 g; 0.48 mmol) and K₂CO₃ (0.067 g; 0.48 mmol) in acetonitrile (4 ml) was heated at 80° C. under argon atmosphere for 8 hours. The crude mixture was evaporated and purified by flash chromatography eluting with a gradient 2–5% of 3.5 N NH₃ in MeOH/methylene chloride to give after trituration in ether/pentane Example 10 as a solid.

Yield: 42% ¹H NMR (CDCl₃): 1.15–1.4 (m, 6H); 1.45–1.75 (m, 6H); 1.59 (s, 6H); 1.8–2 (m, 4); 2.32 (s, 6H); 2.45–2.75 (m, 6H); 2.9–3 (m, 2H); 3.1 (s, 2H); 3.44–3.5 (m, 4H); 4–4.2 (m, br, 1H); 4.6–4.8 (m, br, 1H); 6.72 (s, 1H); 6.92 (s, 1H); 7.04 (s, 2H); 8.13 (s, 1H).

MS-ESI: 616 [M+H]⁺

Example 11

2-[1,1-Dimethyl-2-oxo-2-azabicyclo[2.2.1]heptan-7-ylethyl]-4-[2-{4-(2,4-dioxo-1,2,3,4-tetrahydropyrimidin-6-ylmethyl)piperazin-1-yl}ethyl]-5-(3,5-dimethylphenyl)-6H-thieno[2,3-b]pyrrole

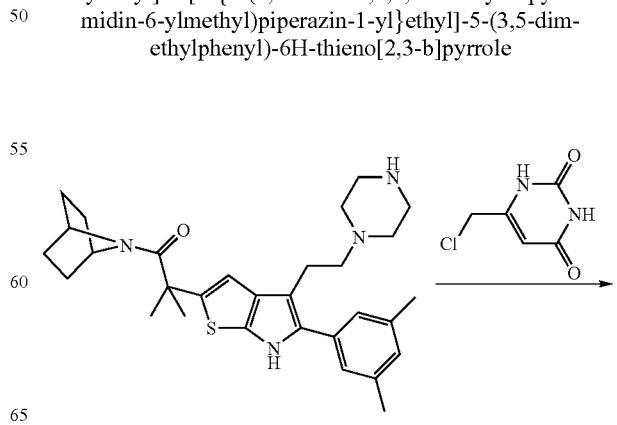

-continued

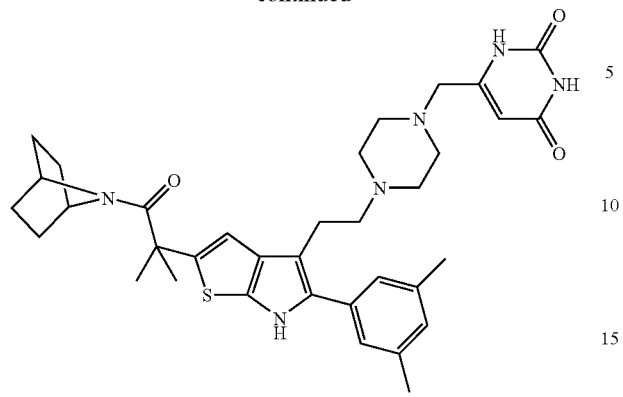

Example 11

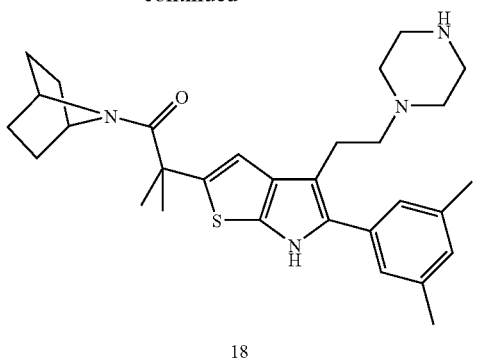

18

A mixture of 18 (0.252 g; 0.5 mmol), 6-chloromethyluracil (0.088 g; 0.55 mmol), K₂CO₃ (0.076 g; 0.55 mmol) and NaI (0.082 g; 0.55 mmol) in acetonitrile (5 ml) was heated at 85° C. under argon atmosphere for 4 hours. The mixture was purified by flash chromatography eluting with a gradient of 5–10% MeOH/CH₂Cl₂ to give Example 11 as a solid.

Yield: 63% $^1$H NMR (CDCl₃): 1.2–1.4 (m, 4H); 1.6 (s, 6H); 1.4–1.8 (m, 4H); 2.34 (s, 6H); 2.4–2.7 (m, 10H); 2.85–2.95 (m, 2H); 3.3 (s, 2H); 4–4.2 (m, br, 1H); 4.6–4.8 (m, br, 1H); 5.53 (s, 1H); 6.72 (s, 1H); 6.93 (s, 1H); 7.04 (s, 2H); 8.05–8.2 (m, 2H).

MS-ESI: 629 [M+H]$^+$

The starting material was prepared as follows:

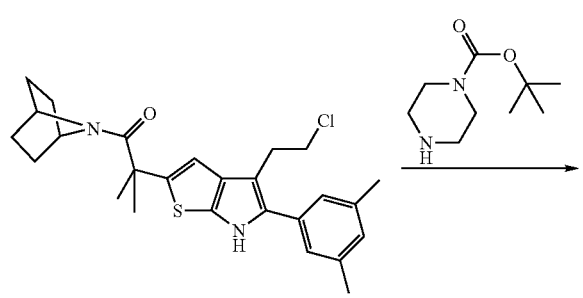

29

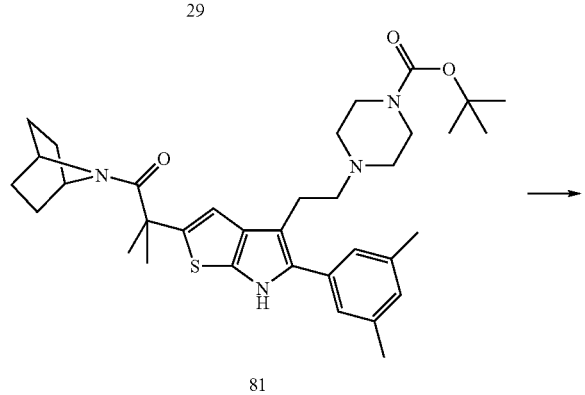

81

A mixture of 29 (12.4 g; 0.027 mol), N-(tert-butoxycarbonyl)piperazine (10.15 g; 0.054 mol), K₂CO₃ (7.52 g; 0.054 mol) in acetonitrile (120 ml) was heated at 85° C. under argon atmosphere for 3 hours. The mixture was evaporated and purified by flash chromatography, eluting with a 50–100 gradient of ethyl acetate/petroleum ether to give 81.

Yield: 94% $^1$H NMR (CDCl₃): 1.15–1.4 (m, 4H); 1.45–1.8 (m, 4H); 1.44 (s, 9H); 1.6 (s, 6H); 2.33 (s, 6H); 2.35–2.5 (m, 4H); 2.6–2.7 (m, 2H); 2.9–3 (m, 2H); 3.4–3.5 (m, 4H); 4.0–4.2 (m, br, 1H); 4.6–4.8 (m, br, 1H); 6.71 (s, 1H); 6.93 (s, 1H); 7.04 (s, 2H); 8.13 (s, 1H).

To a solution of 81 (15.32 g; 0.025 mol) in methylene chloride (250 ml) was added at 0° C. TFA (95 ml). After stirring at ambient temperature for 1 hour, the mixture was evaporated, treated with 3.5N NH₃ in MeOH (100 ml) and purified by flash chromatography eluting with a 5–8% gradient of 3.5N NH₃ in MeOH/CH₂Cl₂ to give after trituration with ether 18 as a solid.

Yield: 95% $^1$H NMR (CDCl₃): 1.15–1.4 (m, 4H); 1.45–1.75 (m, 4H); 1.6 (s, 6H); 2.33 (s, 6H); 2.5 (m, 4H); 2.6–2.7 (m, 2H); 2.85–3 (m, 6H); 4.0–4.2 (m, br, 1H); 4.6–4.8 (m, br, 1H); 6.72 (s, 1H); 6.92 (s, 1H); 7.05 (s, 2H); 8.15 (s, 1H).

Examples 11.1–11.7

Following a procedure similar to that described in Example 11, the compounds of table 11 were prepared.

TABLE 11
| Example | | MS-ESI |
|---|---|---|
| 11.1 | 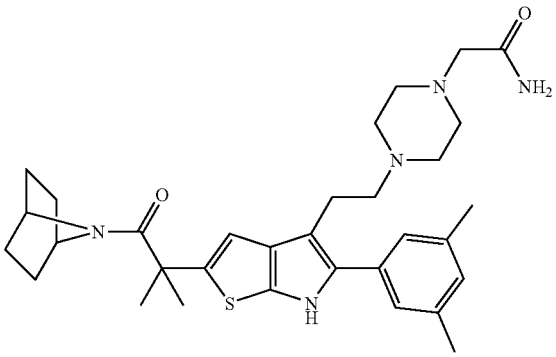 | 562 [M + H]+ |
| 11.2 | 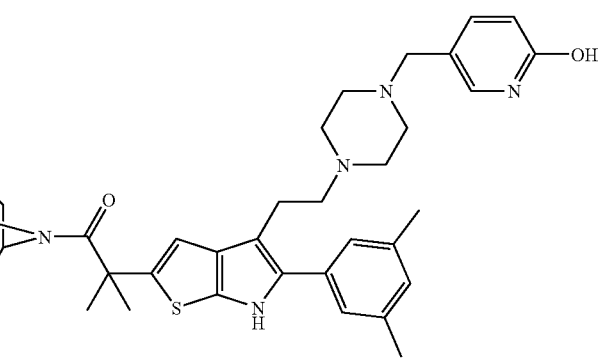 | 612 [M + H]+ |
| 11.3 | 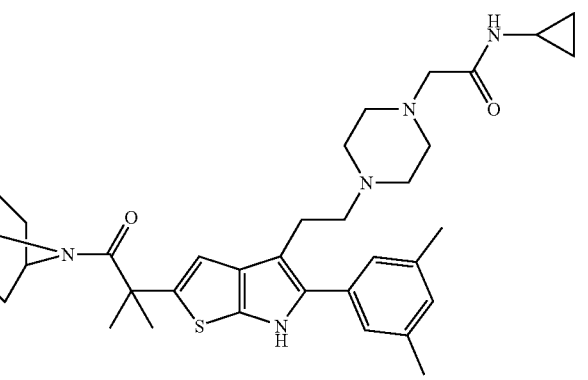 | 602 [M + H]+ |
| 11.4 | 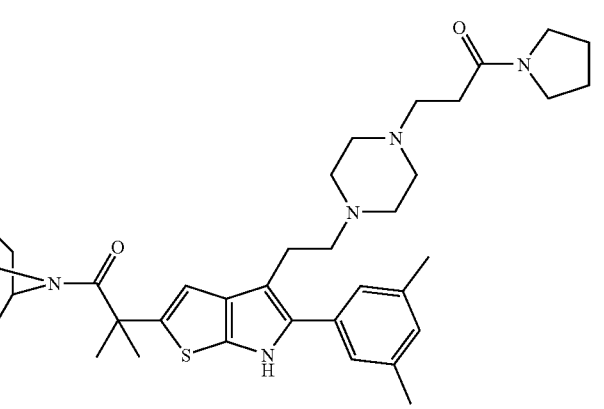 | 630 [M + H]+ |

TABLE 11-continued
| Example | | MS-ESI |
|---|---|---|
| 11.5 | 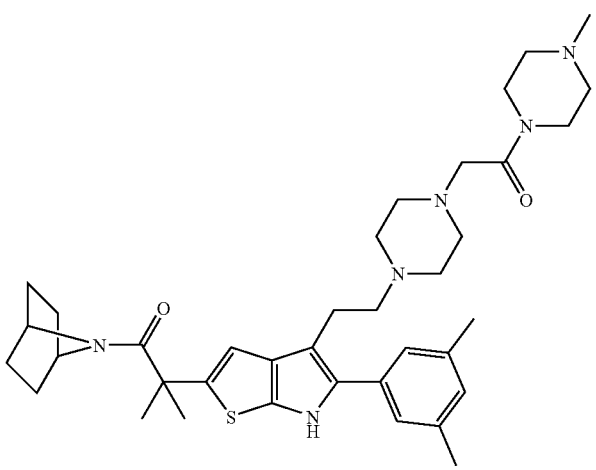 | 645 [M + H]+ |
| 11.6 | 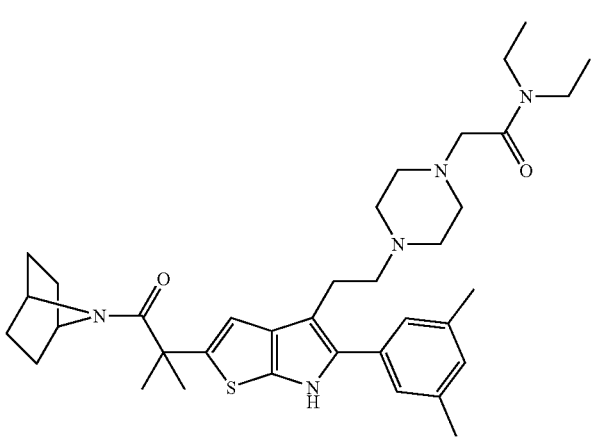 | 618 [M + H]+ |
| 11.7 | 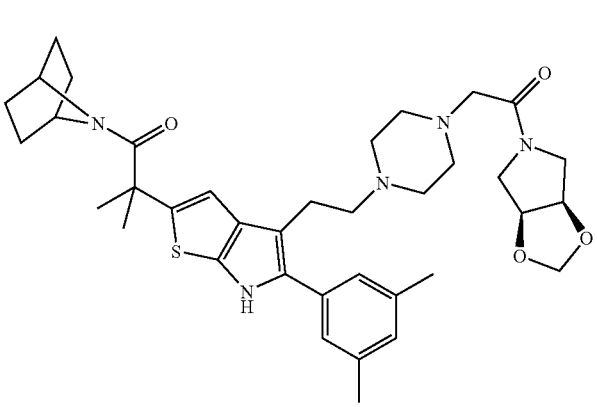 | 660 [M + H]+ |

Example 12

2-[1,1-Dimethyl-2-oxo-2-azabicyclo[2.2.1]heptan-7-ylethyl]-4-[2-{4-(morpholinocarbonyl)piperazin-1-yl}ethyl]-5-(3,5-dimethylphenyl)-6H-thieno[2,3-b]pyrrole

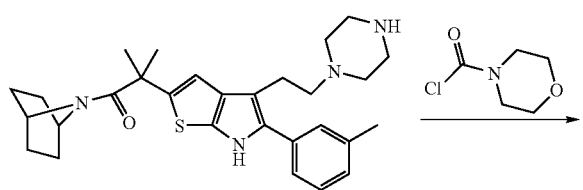

18

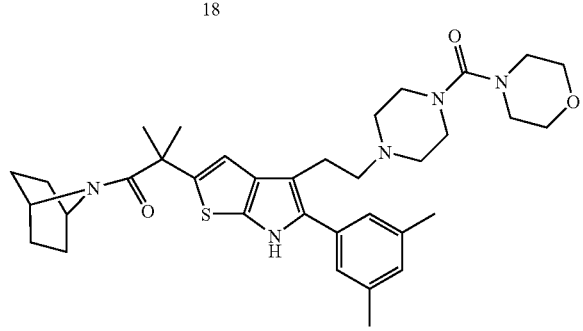

Example 12

4-morpholinecarbonyl chloride (0.058 g; 0.367 mmol) was added under argon atmosphere, at 0° C. to a suspension of 18 (0.185 g; 0.367 mmol) and triethylamine (0.054 ml; 0.385 mmol) in acetonitrile (4 ml). The mixture was stirred at ambient temperature for 3 hours. After evaporation to dryness, the residue was purified by flash chromatography, eluting with a gradient 5–7% of 3.5N $NH_3$ in MeOH/methylene chloride to give after trituration in ether Example 12 as a solid.

Yield: 60% $^1$H NMR (CDCl$_3$): 1.15–1.4 (m, 4H); 1.6 (s, 6H); 2.45–2.8 (m, 4H); 2.33 (s, 6H); 2.47–2.50 (m, 4H); 2.6–2.7 (m, 2H); 2.9–3 (m, 2H); 3.15–3.4 (m, 8H); 3.6–3.7 (m, 4); 4–4.2 (m, br, 1H); 4.6–4.8 (m, br, 1H); 6.7 (s, 1H); 6.93 (s, 1H); 7.03 (s, 2H); 8.13 (s, 1H).

MS-ESI: 618 [M+H]$^+$

Examples 12.1–12.7

Following a procedure similar to that described in Example 12, the compounds of table 12 were prepared.

TABLE 12

| | | |
|---|---|---|
| 12.1 | 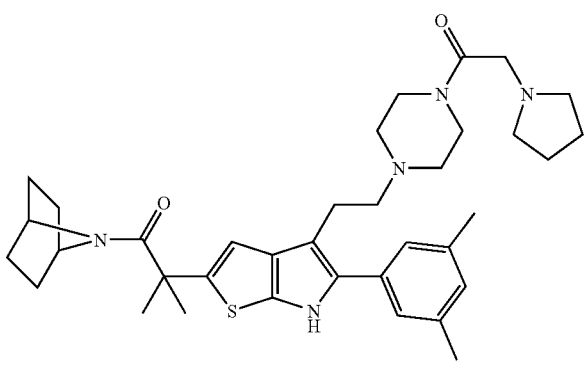 | 616 [M + H]$^+$ |
| 12.2 | 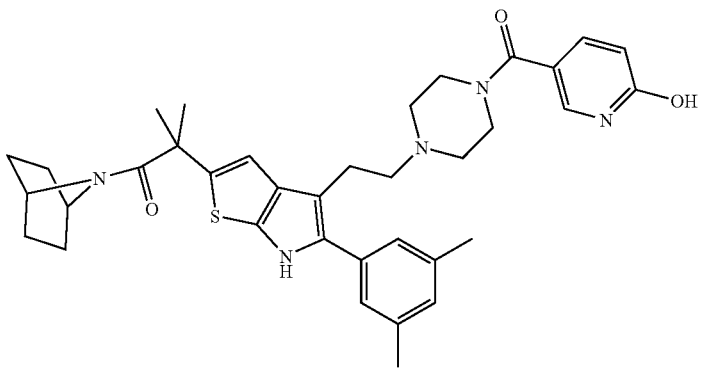 | 626 [M + H]$^+$ |

TABLE 12-continued
| 12.3 | 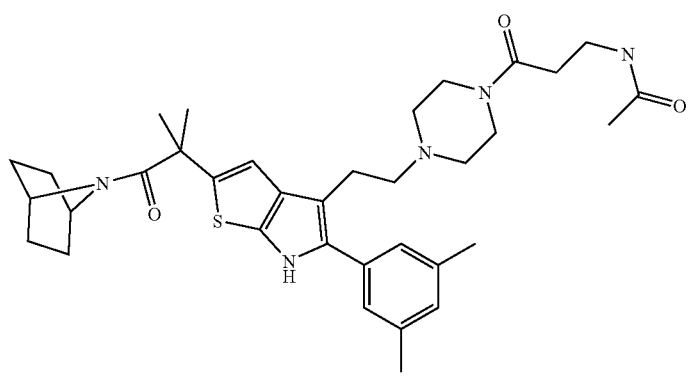 | 618 [M + H]+ |
| 12.4 | 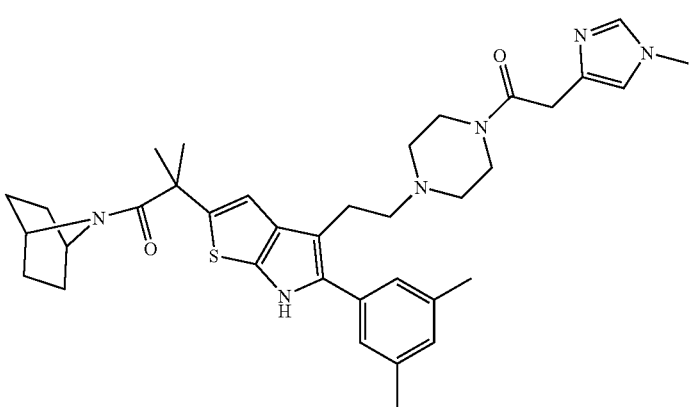 | 627 [M + H]+ |
| 12.5 | 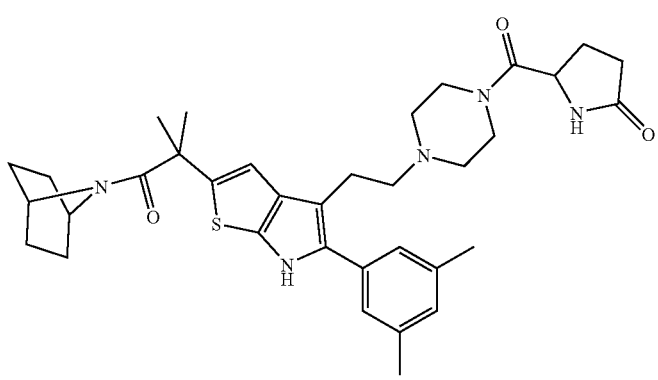 | 616 [M + H]+ |
| 12.6 | 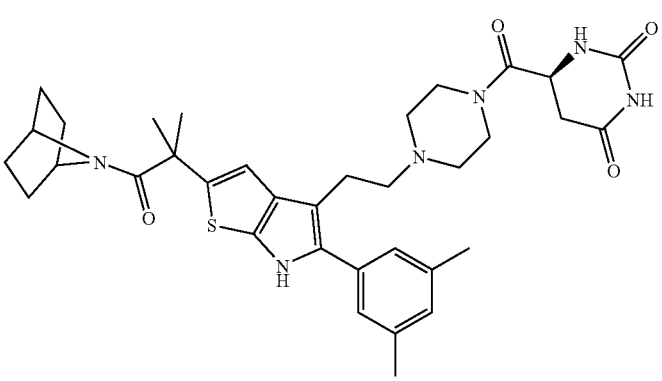 | 645 [M + H]+ |

TABLE 12-continued 12.7 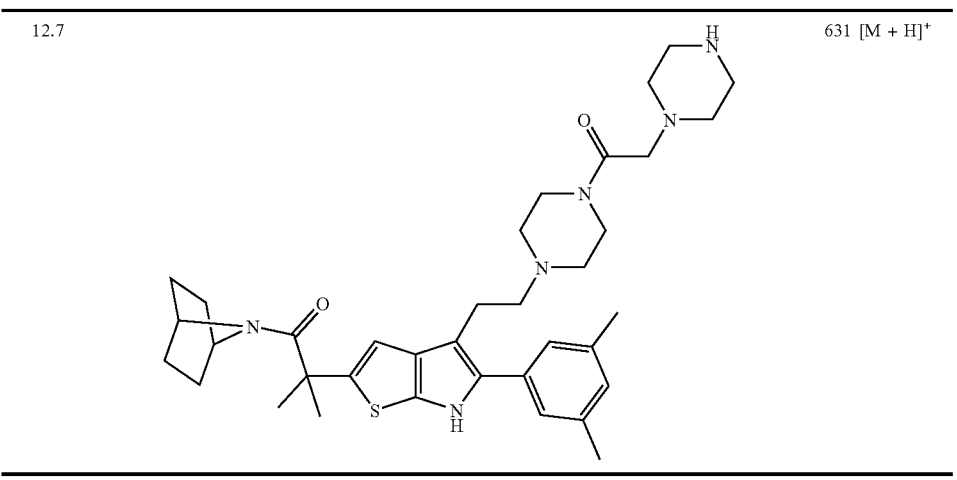 631 [M + H]⁺

Example 13

2-[1,1-Dimethyl-2-oxo-2-azabicyclo[2.2.]heptan-7-ylethyl]-4-[2-(4-{N,N-dimethylaminocarbonylmethyl}piperazin-1-yl)ethyl]-5-(3,5-dimethylphenyl)-6H-thieno[2,3-b]pyrrole Example 14

2-[1,1-Dimethyl-2-oxo-2-azabicyclo[2.2.1]heptan-7-ylethyl]-4-[2-{4-(N-isopropylaminocarbonylmethyl)piperazin-1-yl}ethyl]-5-(3,5-dimethylphenyl)-6H-thieno[2,3-b]pyrrole

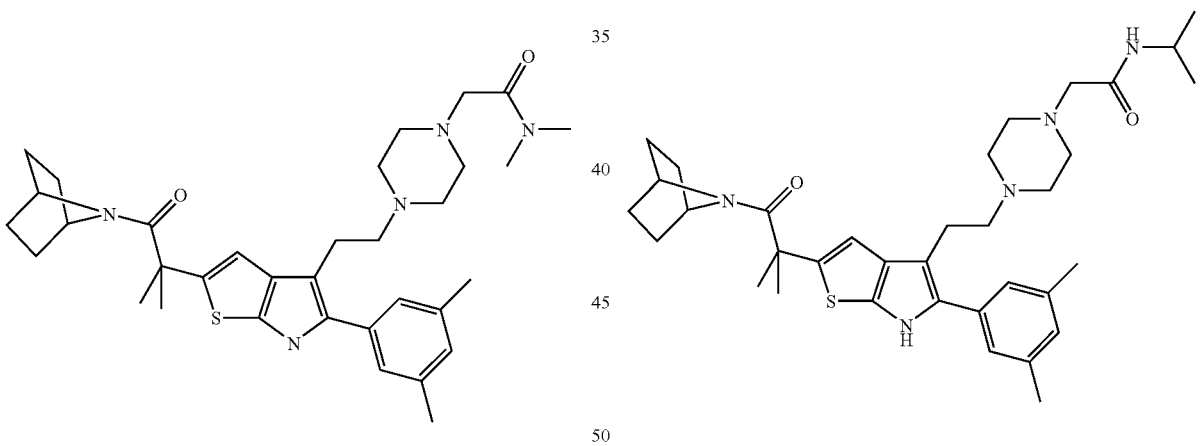

Example 13 was prepared following a procedure similar to that described in Example 11.

Yield: 89% ¹H NMR (CDCl₃): 1.2–1.4 (m, 4H); 1.63 (s, 6H); 1.5–1.8 (m, 4H); 2.36 (s, 6H); 2.63 (s, 6H); 2.5–2.7 (m, 10H); 2.9–3 (m, 2H); 3.18 (s, 2H); 4–4.2 (m, br, 1H); 4.65–4.85 (m, 1H); 6.75 (s, 1H); 6.95 (s, 1H); 7.08 (s, 2H); 8.52 (s, 1H). MS-ESI: 590[M+H]⁺

Example 14 was prepared following a procedure similar to that described in Example 10.

Yield: 68% ¹H NMR (CDCl₃): 1.15 (d, 6H); 1.2–1.4 (m, 4H); 1.6 (s, 6H); 1.5–1.8 (m, 4H); 2.3 (s, 6H); 2.45–2.7 (m, 10H); 2.85–3 (m, 2H); 2.95 (s, 2H); 4–4.20 (m, br, 2H); 4.6–4.8 (m, br, 1H); 6.71 (s, 1H); 6.93 (m, 2H); 7.04 (s, 2H); 8.12 (s, 1H).

MS-ESI: 604[M+H]⁺

Example 15

2-[1,1-Dimethyl-2-oxo-2-azabicyclo[2.2.1]heptan-7-ylethyl]-4-[2-(4-{tetrahydrofuran-2-ylcarbonyl}piperazin-1-yl)ethyl]-5-(3,5-dimethylphenyl)-6H-thieno[2,3-b]pyrrole

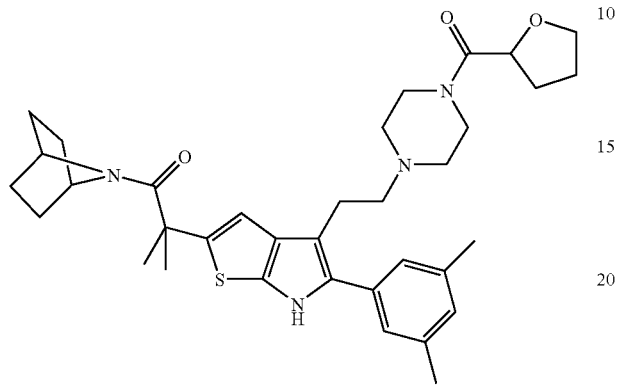

Example 15 was prepared following a procedure similar to that described in Example 10.

Yield: 73% $^1$H NMR (CDCl$_3$): 1.2–1.4 (m, 4H); 1.5–1.7 (m, 4H); 1.6 (s, 6H); 1.8–2.3 (m, 4H); 2.35 (s, 6H); 2.4–2.55 (m, 4H); 2.65–2.75 (m, 2H); 2.9–3 (m, 2H); 3.5–3.7 (m, 3.8–4(m, 2H); 4–4.2 (m, br, 1H); 4.6 (m, 1H); 4.6–4.8 (m, br, 1H); 6.73 (s, 1H); 6.95 (s, 1H); 7.06 (s, 2H); 8.16 (s, 1H).

MS-ESI: 603[M+H]$^+$

Example 16

2-[1,1-Dimethyl-2-oxo-2-azabicyclo[2.2.1]heptan-7-ylethyl]-4-[2-(4-{hydroxyethoxyethyl}piperazin-1-yl)ethyl]-5-(3,5-dimethylphenyl)-6H-thieno[2,3-b]pyrrole

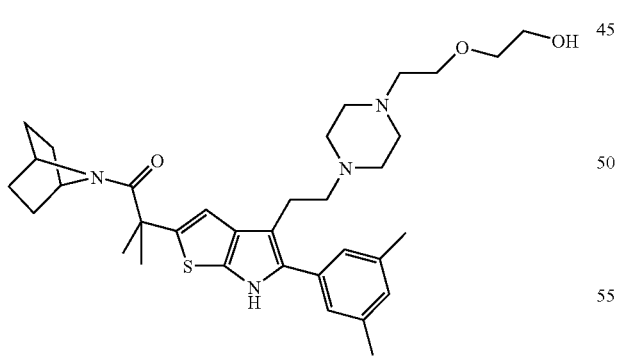

Example 16 was prepared following a procedure similar to that described in Example 10.

Yield: 34% $^1$H NMR (DMSOd$_6$): 1.2–1.4 (m, 4H); 1.5–1.65 (m, 4H); 1.55 (s, 6H); 2.34 (s, 6H); 2.4–2.7 (m, 12H); 2.9 (br s, 2H); 3.48 (t, 2H); 3.56 (t, 2H); 3.58 (br s, 2H); 4.1 (br s, 1H); 4.6 (br s, 1H); 6.73 (br s, 1H); 6.9 (s, 1H); 7.08 (s, 2H); 11–12 (br s, 1H).

MS-ESI: 593[M+H]$^+$

Example 17

2-[1,1-Dimethyl-2-oxo-2-azabicyclo[2.2.1]heptan-7-ylethyl]-4-[2-{4-(1,3-dimethyl-2,4-dioxo-1,2,3,4-tetrahydropyrimidin-6-ylmethyl)piperazin-1-yl}ethyl]-5-(3,5-dimethylphenyl)-6H-thieno[2,3-b]pyrrole

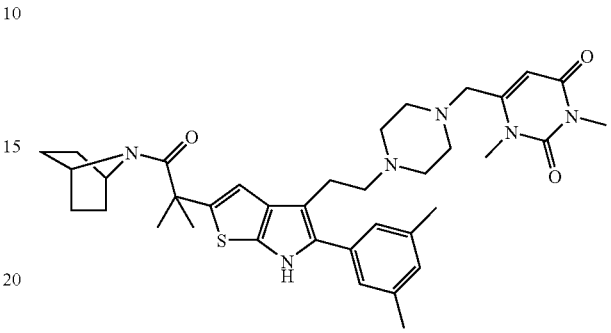

Example 17 was prepared following a procedure similar to that described in Example 11.

Yield: 54% $^1$H NMR (CDCl$_3$) (δ ppm) 1.22–1.44 (m, 4H); 1.52–1.79 (m, 10H); 2.34 (s, 6H); 2.44–2.73 (m, 8H); 2.93 (m, 2H); 3.26 (s, 2H); 3.34 (s, 3H); 3.42 (s, 3H); 4.10 (br s, 1H); 5.75 (br s, 1H); 5.73 (s, 1H); 6.73 (s, 1H); 6.94 (s, 1H); 7.03 (s, 2H); 8.12 (s, 1H).

MS-ESI: 657[M+H]$^+$

Example 18

2-[1,1-Dimethyl-2-oxo-2-azabicyclo[2.2.1]heptan-7-ylethyl]-4-[2-(4-{piperidin-1-ylcarbonylmethyl}piperazin-1-yl)ethyl]-5-(3,5-dimethylphenyl)-6H-thieno[2,3-b]pyrrole

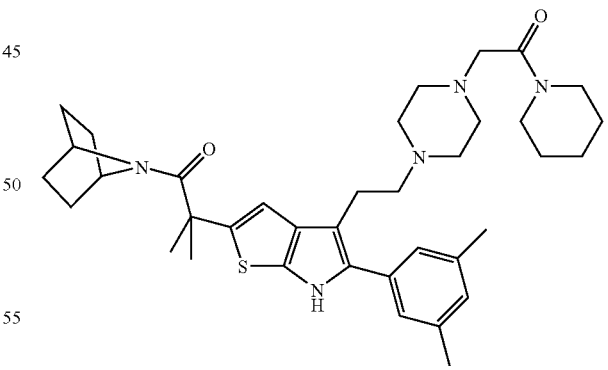

Example 18 was prepared following a procedure similar to that described in Example 11.

Yield: 50% $^1$H NMR (CDCl$_3$): 1.2–1.4 (m, 6H); 1.6 (s, 6H); 1.5–1.8 (m, 10H); 2.35 (s, 6H); 2.45–2.7 (m, 8H); 2.9–3 (m, 2H); 3.17 (s, 2H); 3.45–3.6 (m, 4H); 4.0–4.2 (m, br, 1H); 6.6–6.8 (m, br, 1H); 6.74 (s, 1H); 6.94 (s, 1H); 7.06 (s, 2H); 8.11 (s, 1H).

MS-ESI: 630[M+H]$^+$

Example 19

2-[1,1-Dimethyl-2-oxo-2-azabicyclo[2.2.1]heptan-7-ylethyl]-4-[2-(4-{azetidin-1-ylcarbonylmethyl}piperazin-1-yl)ethyl]-5-(3,5-dimethylphenyl)-6H-thieno[2,3-b]pyrrole

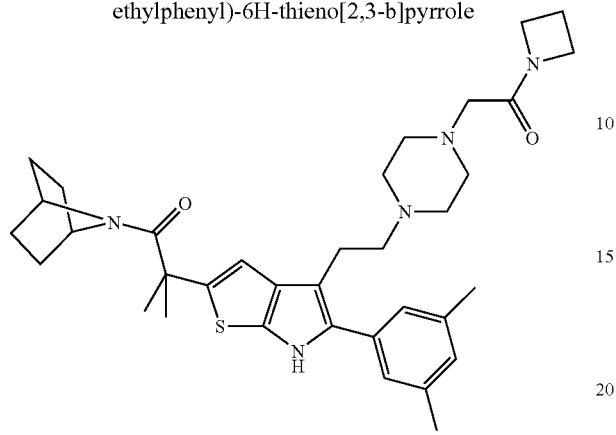

Example 19 was prepared following a procedure similar to that described in Example 11.

Yield: 50% $^1$H NMR (CDCl$_3$): 1.2–1.4 (m, 6H); 1.45–1.8 (m, 6H); 1.6 (s, 6H); 2.25–2.35 (m, 2H); 2.35 (s, 6H); 2.45–2.7 (m, 6H); 2.9–3 (m, 2H); 3.00 (s, 2H); 4.0–4.1 (m, 2H); 4.0–4.2 (m, br, 1H); 4.2–4.3 (m, 2H); 4.6–4.8 (m, br, 1H); 6.74 (s, 1H); 6.94 (s, 1H); 7.06 (s, 2H); 8.15 (1H).

MS-ESI: 602[M+H]$^+$

Example 20

2-[1,1-Dimethyl-2-oxo-2-azabicyclo[2.2.1]heptan-7-ylethyl]-4-[2-(4-pyrid-4-ylpiperidin-1-yl)ethyl]-5-(3,5-dimethylphenyl)-6H-thieno[2,3-b]pyrrole

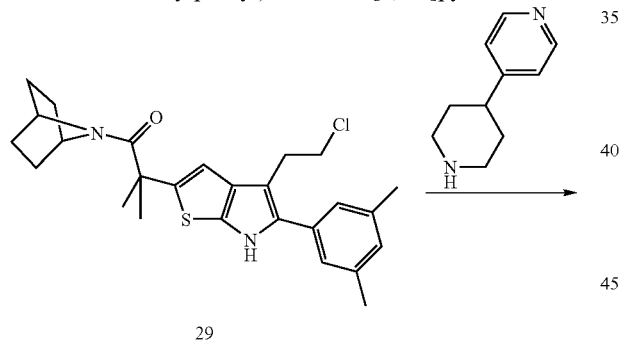

29

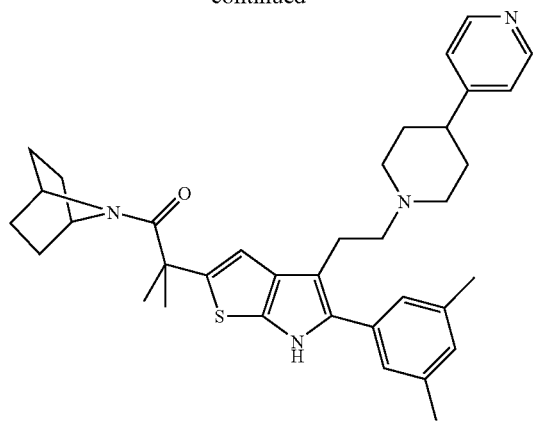

Example 20

A mixture of 29 (0.252 g; 0.555 mmol), 4-(4-piperidinyl)pyridine (0.090 g, 0.555 mmol), K$_2$CO$_3$ (0.092 g; 0.66 mmol) in acetonitrile (2 ml) was heated at 85° C. under argon atmosphere for 2 hours. The crude mixture was evaporated and purified by flash chromatography eluting with a gradient 5–7% of 3.5 N NH$_3$ in MeOH/methylene chloride to give after trituration in ether/pentane Example 20 as a solid.

Yield: 34% $^1$H NMR (CDCl$_3$): 1.2–1.45 (m, 4H); 1.65 (s, 6H); 1.5–1.8 (m, 4H); 1.8–1.95 (m, 4H); 2.18 (t, 2H); 2.38 (s, 6H); 2.5–2.6 (m, 1H); 2.7–2.8 (m, 2H); 2.95–3.05 (m, 2H); 3.15–3.25 (m, 2H); 4–4.2 (m, br, 1H); 4.65–4.85 (m, br, 1H); 6.78 (s, 1H); 6.98 (s, 1H); 7.10 (s, 2H); 7.18 (d, 2H); 8.22 (s, 1H); 8.53 (d, 2H).

MS-ESI: 581[M+H]$^+$

Examples 20.1–20.6

Following a procedure similar to that described in Example 20, the compounds of table 20 were prepared.

TABLE 20

| Example | | MS-ESI |
|---|---|---|
| 20.1 | ![structure] | 589 [M + H]$^+$ |

TABLE 20-continued
| Example | MS-ESI |
|---|---|
| 20.2 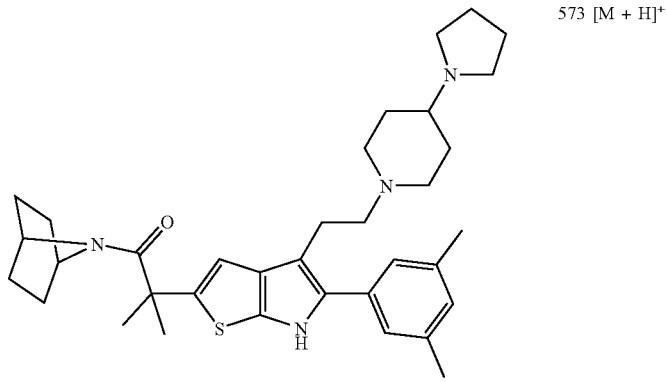 | 573 [M + H]+ |
| 20.3 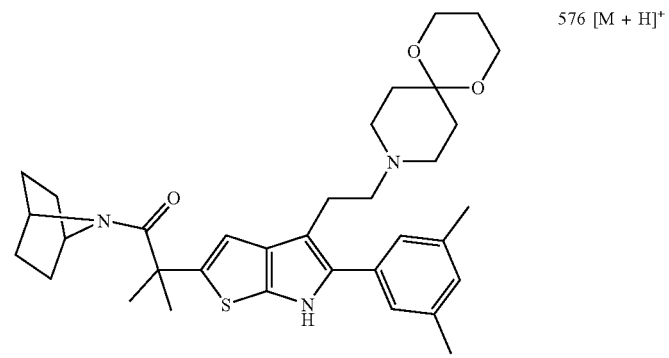 | 576 [M + H]+ |
| 20.4 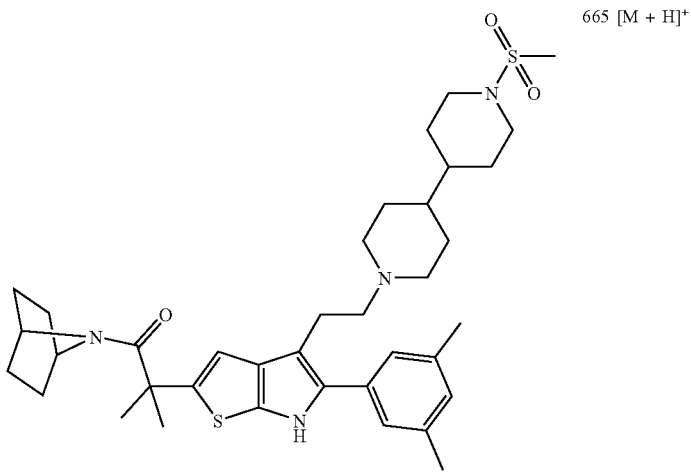 | 665 [M + H]+ |

TABLE 20-continued
| Example | | MS-ESI |
|---|---|---|
| 20.5 | 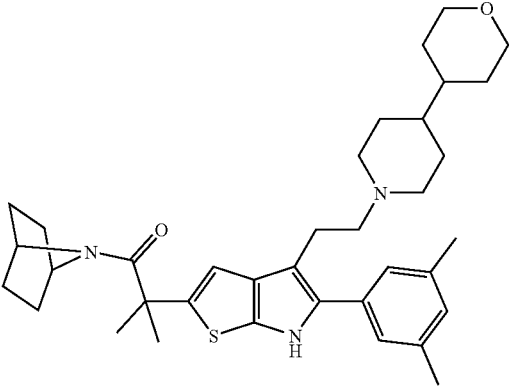 | 588 [M + H]⁺ |
| 20.6 | 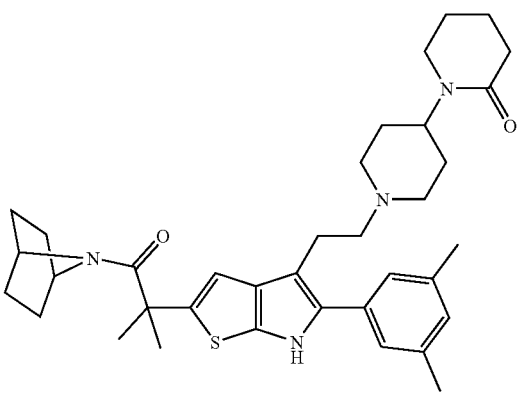 | 601 [M + H]⁺ |
Example 21
2-[1,1-Dimethyl-2-oxo-2-azabicyclo[2.2.1]heptan-7-ylethyl]-4-[2-{4-(1,1-dioxidotetrahydrothien-3-yl)piperazin-1-yl}ethyl]-5-(3,5-dimethylphenyl)-6H-thieno[2,3-b]pyrrole
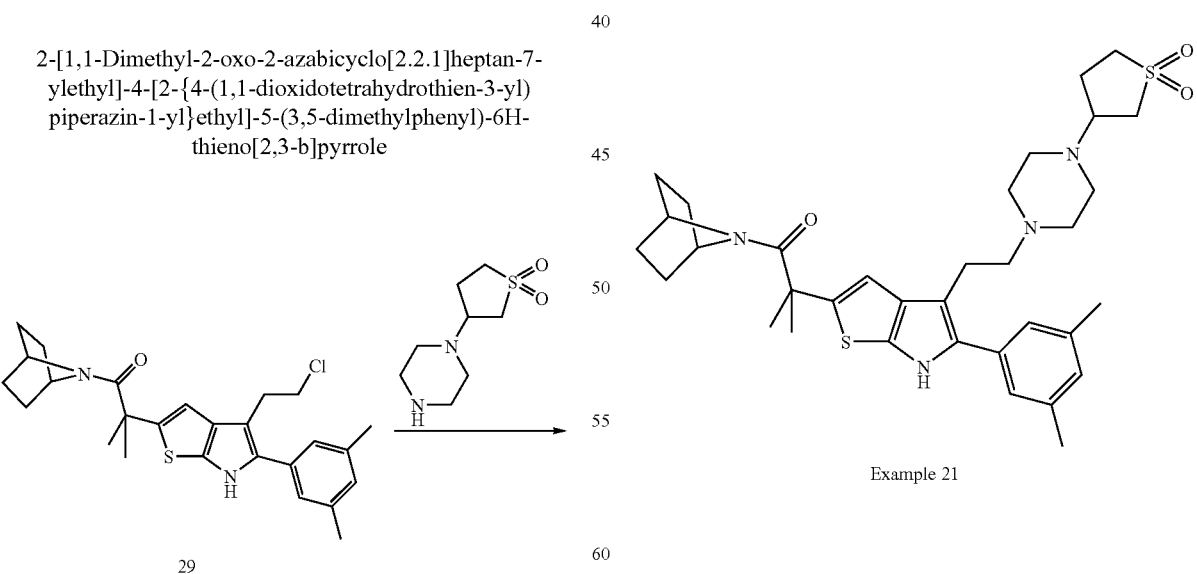
Example 21
A mixture of 29 (0.28 g; 0.5 mmol), 1-(1,1-dioxo-tetrahydro-1-gamma-(6)-thiophene-3-yl)-piperazine (0.24 g; 1.mmol), DIEA (0.435 ml; 2.5 mmol) and NaI (0.074 g;0.5 mmol) in DMF (4 ml) was heated at 110° C. under argon atmosphere for 24 hours. After extraction with ethyl acetate and evaporation, the mixture was purified by flash chromatography, eluting with methylene chloride/3.5 N NH₃ in MeOH to give Example 21.

Yield: 27% ¹H NMR (CDCl₃): 1.2–1.4 (m, 4H); 1.5–1.8 (m, 4H); 1.68 (s, 6H); 2.15 (m, 1H); 2.35 (s, 6H); 2.42 (m, 1H); 2.5–2.7 (m, 8H); 2.67 (m, 2H); 2.92 (m, 2H); 3–3.1 (m, 2H); 3.2–3.3 (m, 3H); 4.0–4.2 (m, br, 1H); 4.6–4.8 (m, br, 1H); 6.73 (s, 1H); 6.95 (s, 1H); 7.06 (s, 2H); 8.17 (s, 1H). MS-ESI: 623[M+H]⁺

Example 22

2-[1,1-Dimethyl-2-oxo-2-azabicyclo[2.2.1]heptan-7-ylethyl]-4-[2-{4-(4-methylpiperazin-1-ylcarbonyl)piperidin-1-yl}ethyl]-5-(3,5-dimethylphenyl)-6H-thieno[2,3-b]pyrrole

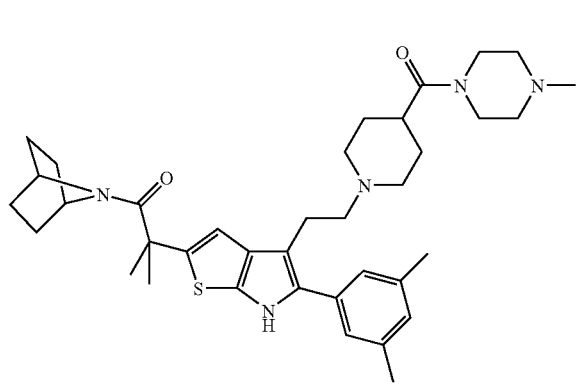

Example 22 was prepared following a procedure similar to that described in Example 5.

Yield: 71% ¹H NMR (CDCl₃): 1.2–1.4 (m, 6H); 1.45–1.75 (m, 6H); 1.6 (s, 6H); 1.85–2 (m, 2H); 2.0–2.1 (m, 2H); 2.25–2.5 (m, 3H); 2.31 (s, 3H); 2.37 (s, 6H); 2.6–2.7 (m, 2H); 2.9–3.15 (m, 4H); 3.45–3.7 (m, 4H); 4.0–4.2 (m, br, 1H); 4.6–4.8 (m, br, 1H); 6.74 (s, 1H); 6.94 (s, 1H); 6.94 (s, 1H); 7.07 (s, 2H); 8.13 (s, 1H). MS-ESI: 630 [M+H]⁺

Example 23

2-[1,1-Dimethyl-2-oxo-2-azabicyclo[2.2.1]heptan-7-ylethyl]-4-[2-{4-(4-acetylpiperazin-1-ylcarbonyl)piperidin-1-yl}ethyl]-5-(3,5-dimethylphenyl)-6H-thieno[2,3-b]pyrrole

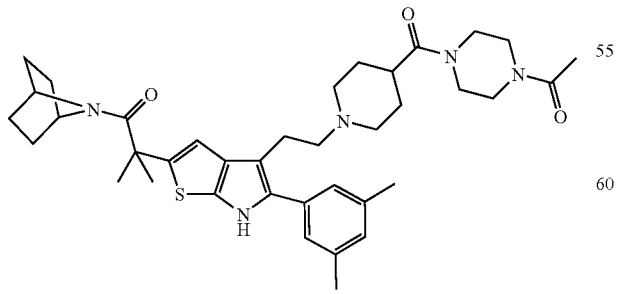

Example 23 was prepared following a procedure similar to that described in Example 5.

Yield: 26% ¹H NMR (CDCl₃): 1.2–1.4 (m, 4H); 1.5–1.8 (m, 6H); 1.62 (s, 6H); 1.85–2.14 (m, 4H); 2.13 (s, 3H); 2.35 (s, 6H); 2.4–2.5 (m, 1H); 2.6–2.75 (m, 2H); 2.9–3.15 (m, 4H); 3.4–3.7 (m, 8H); 4.0–4.2 (m, 1H); 4.6–4.8 (m, 1H); 6.74 (s, 1H); 6.95 (s, 1H); 7.07 (s, 2H); 8.15 (s, 1H). MS-ESI: 658 [M+H]⁺

Example 24

2-[1,1-Dimethyl-2-oxo-2-azabicyclo[2.2.1]heptan-7-ylethyl]-4-[2-{4-((3aR,6aS)-tetrahydro-3aH-[1,3]dioxolo[4,5-c]pyrrol-5-ylcarbonyl)piperidin-1-yl}ethyl]-5-(3,5-dimethylphenyl)-6H-thieno[2,3-b]pyrrole

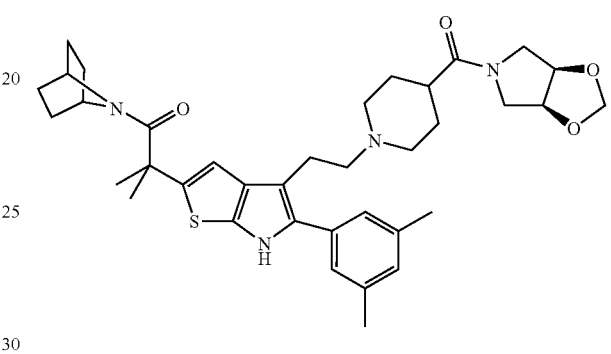

Example 24 was prepared following a procedure similar to that described in Example 5.

Yield: 26% ¹H NMR (CDCl₃): 1.2–1.4 (m, 4H); 1.5–2.1 (m, 10H); 1.64 (s, 6H); 2.3–2.4 (m, 1H); 2.35 (s,6H); 2.65–2.68 (m, 2H); 2.93–2.97 (m, 2H); 3.06–3.08 (m, 2H); 3.35–3.54 (m, 2H); 3.82–4.08 (m, 2H); 4.0–4.2 (m, br, 1H); 4.69–4.70 (m, 3H); 4.98 (d, 2H); 6.74 (s, 1H); 6.94 (s, 1H); 7.07 (s, 2H); 8.15 (s, 1H). MS-ESI: 645 [M+H]⁺

Example 25

2-[1,1-Dimethyl-2-oxo-2-azabicyclo[2.2.1]heptan-7-ylethyl]-4-[2-(3-pyrid-4-ylazetidin-1-yl)ethyl]-5-(3,5-dimethylphenyl)-6H-thieno[2,3-b]pyrrole

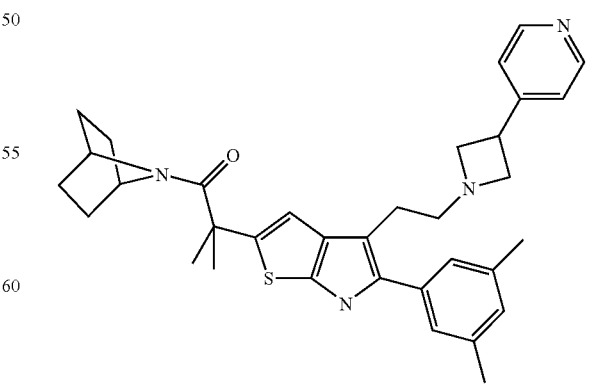

Example 25 was prepared following a procedure similar to that described in Example 4.

Yield: 26% ¹H NMR (CDCl₃): 1.1–1.3 (m, 4H); 1.35–1.7 (m, 4H); 1.52 (s, 6H); 2.24 (s, 6H); 2.74–2.8 (m, 4H); 3.05–3.2 (m, 2H); 3.5–3.7 (m, 3H); 3.95–4.15 (m, 1H); 4.5–4.7 (m, 1H); 6.67 (s, 1H); 6.84 (s, 1H); 7.01 (s, 2H); 7.09 (d, 2H); 8.42 (d, 2H); 8.75 (s, 1H). MS-ESI: [M+H]⁺

Example 26

2-[1,1-Dimethyl-2-oxo-2-azabicyclo[2.2.1]heptan-7-ylethyl]-4-[2-(4-{morpholinocarbonylmethyl}piperidin-1-yl)ethyl]-5-(3,5-dimethylphenyl)-6H-thieno[2,3-b]pyrrole

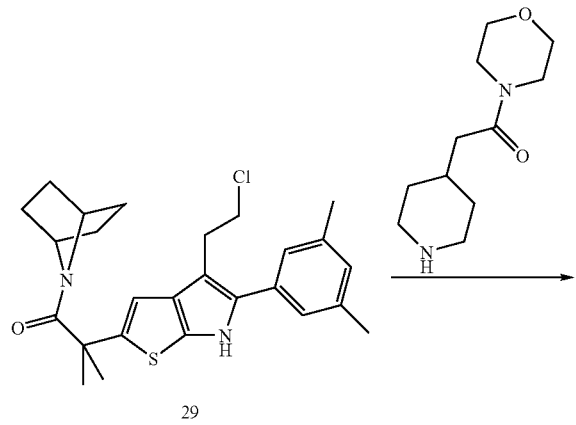

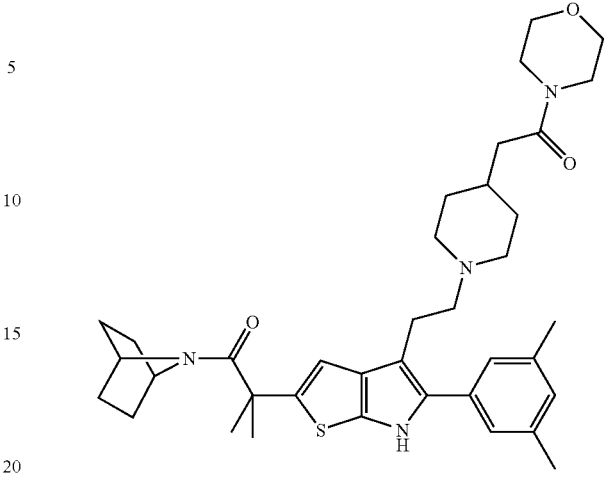

Example 26

A mixture of 29 (0.137 g; 0.3 mmol), 4-(4-piperidinylacetyl) morpholine (0.127 g, 0.51 mmol), K₂CO₃ (0.112 g; 0.81 mmol) in DMA (3 ml) was heated at 85° C. under argon atmosphere for 6 hours. The crude mixture was evaporated and purified by flash chromatography eluting with a gradient 5–7% of 3.5 N NH₃ in MeOH/methylene chloride to give after trituration in ether/pentane Example 26 as a solid.

Yield: 71% ¹H NMR (CDCl₃): 1.2–1.4 (m, 8H); 1.6 (s, 6H); 1.5–1.8 (m, 4H); 1.75–1.85 (m, 2H); 1.8–1.95 (m, br, 1H); 2–2.15 (m, 2H); 2.25–2.26 (m, 2H); 2.35 (s, 6H); 2.6–2.7 (m, 2H); 2.9–3.1 (m, 4H); 4.45–4.55 (m, 2H); 3.6–3.7 (m, 4H); 4–4.2 (m, br, 1H); 4.65–4.85 (m, br, 1H); 6.74 (s, 1H); 6.94 (s, 1H); 7.06 (s, 2H); 8.12 (s, 1H). MS-ESI: 631[M+H]⁺

Examples 26.1–26.5

Following a procedure similar to that described in Example 26, the compounds of table 26 were prepared.

TABLE 26

| Example | | MS-ESI |
|---|---|---|
| 26.1 | | 615 [M + H]⁺ |

TABLE 26-continued
| Example | | MS-ESI |
|---|---|---|
| 26.2 | 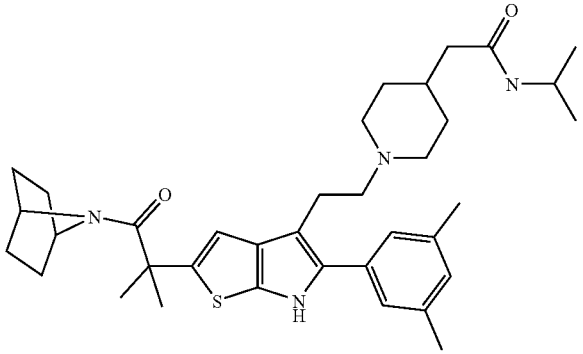 | 603 [M + H]+ |
| 26.3 | 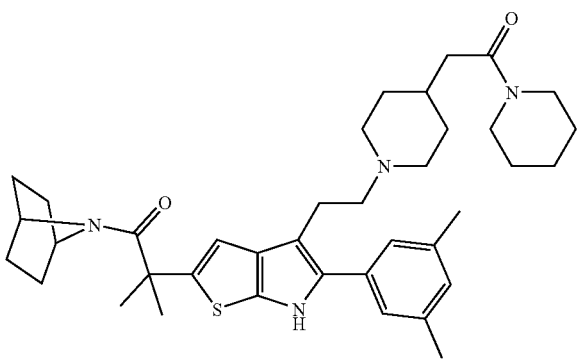 | 629 [M + H]+ |
| 26.4 | 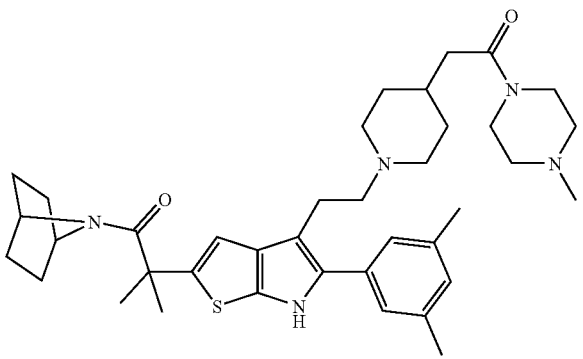 | 644 [M + H]+ |
| 26.5 | 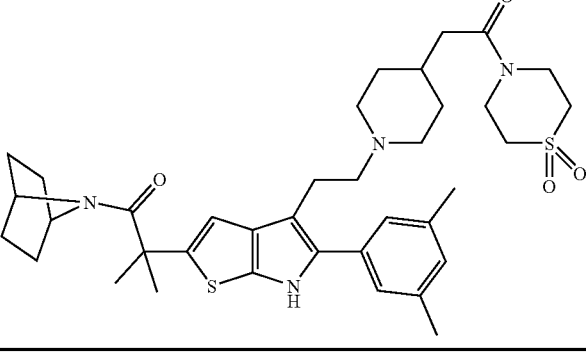 | 679 [M + H]+ |

Example 27

2-[1,1-Dimethyl-2-oxo-2-azabicyclo[2.2.1]heptan-7-ylethyl]-4-[2-(4-{tetrahydro-2H-pyran-4-ylcarbonylamino}piperidin-1-yl)ethyl]-5-(3,5-dimethylphenyl)-6H-thieno[2,3-b]pyrrole

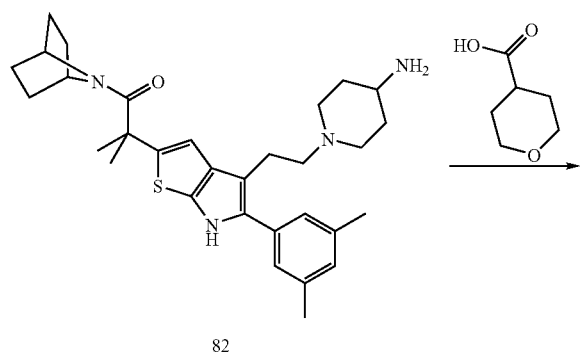

82

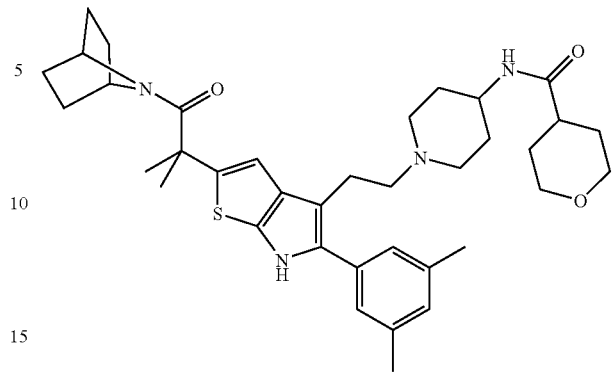

Example 27

EDC (0.091 g; 0.475 mmol) was added to a stirred solution of 82 (0.176 g; 0.317 mmol), HOBT (0.064 g; 0.475 mmol) and tetrahydropyran-4-yl-carboxylic acid (0.11 g; 0.634 mmol) in DMF (3 ml). After stirring for 1 hour, the mixture was evaporated and purified by flash chromatography, eluting with MeOH/methylene chloride 3/97 to give example 27 as a solid.

Yield: 50% $^1$H NMR (CDCl$_3$): 1.2–1.4 (m, 4H); 1.5–1.85 (m, 6H); 1.62 (s, 6H); 1.9–2(m, 2H); 2.1–2.4 (m, 7H); 2.35 (s, 6H); 2.65–2.75 (m, 2H); 2.9–3.05 (m, 4H); 3.35–3.45 (m, 2H); 3.73–3.9 (m, 1H); 4.0–4.1 (m, 2H); 4.0–4.2 (m, br, 1H); 4.65–4.85 (m, br, 1H); 5.5 (d, 1H); 1H); 7.05 (s, 2H); 8.14 (s, 1H). MS-ESI: 631[M+H]$^+$ The starting material was prepared as follows:

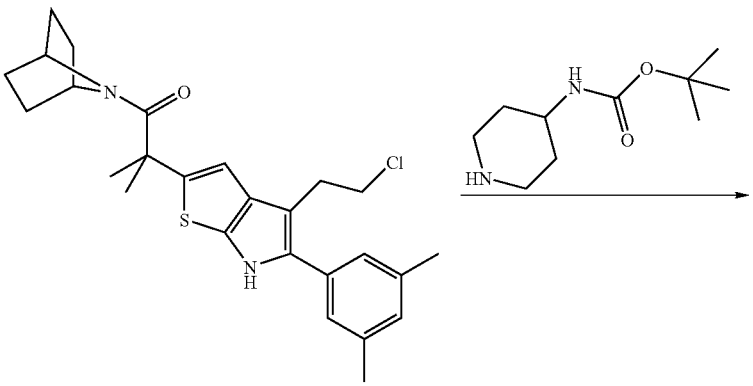

29

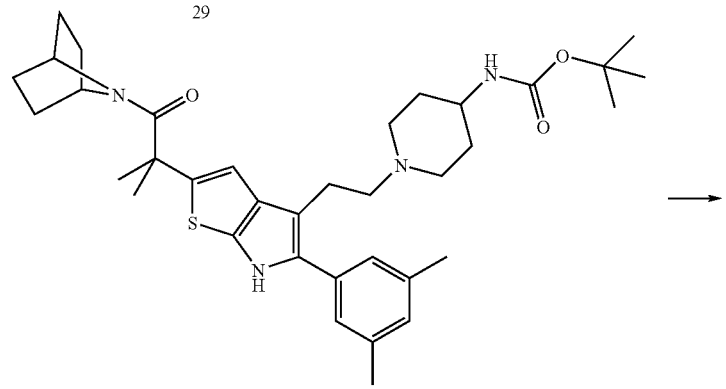

83

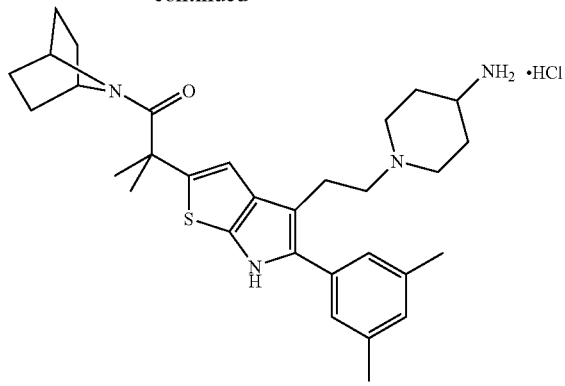

82

A mixture of 29 (0.1.7 g; 0.3.7 mmol), 4-N-(tert-butoxycarbonyl)-aminopiperidine (0.972 g, 4.85 mmol), NaI (0.554 g; 4.85 mmol) and $K_2CO_3$ (0.67 g; 4.85 mmol) in dimethylacetamide (17 ml) was heated at 85° C. under argon atmosphere for 3 hours. The crude mixture was evaporated and purified by flash chromatography eluting with a gradient 2–4% of 3.5 N $NH_3$ in MeOH/methylene chloride to give after trituration in pentane 83 as a solid.

Yield: 87% $^1$H NMR ($CDCl_3$): 1.2–1.4 (m, 4H); 1.44 (s, 9H); 1.5–1.8 (m, 4H); 1.63 (s, 6H); 1.9–2.1 (m, 2H); 2.10–2.40 (m, 2H); 2.36 (s, 6H); 2.6–2.9 (m, 2H); 2.9–3.2 (m, 2H); 3.48–3.62 (m, 1H); 4.0–4.2 (m, 1H); 4.5 (br s, 1H); 4.6–4.85 (br s, 1H); 6.81 (br s, 1H); 6.95 (s, 1H); 7.05 (s, 2H); 8.25 (br s, 1H).

A solution of 83 (2 g; 0.32 mmol) in dioxan (20 ml) was treated at 0° C. with 12N HCl (5 ml). After 1 hour, the mixture was stirred at ambient temperature for 3 hours; evaporated and triturated in ether/pentane to give 82 as a solid.

Yield: 100% $^1$H NMR ($DMSOd_6$): 12.–1.4 (m, 4H); 1.4–1.7 (m, 4H); 1.54 (s, 6H); 2.0 (m, 2H); 2.15 (m, 2H); 2.36 (s, 6H); 3.05–3.35 (m, 6H); 3.60–3.75 (m, 2H); 4.0–4.2 (m, 1H); 4.3–4.5 (m, 1H); 6.97 (s, 1H); 6.99 (s, 1H); 7.11 (s, 2H); 8.33 (br s, 2H); 10.8 (br s, 1H); 11.49 (s, 1H), MS-ESI: 519[M+M]$^+$ Examples 27.1–27.4

Following a procedure similar to that described in Example 27, the compounds of table 27 were prepared.

TABLE 27

| Example | | MS-ESI |
|---|---|---|
| 27.1 | | 657 [M + H]$^+$ |

TABLE 27-continued
| Example | | MS-ESI |
|---|---|---|
| 27.2 | 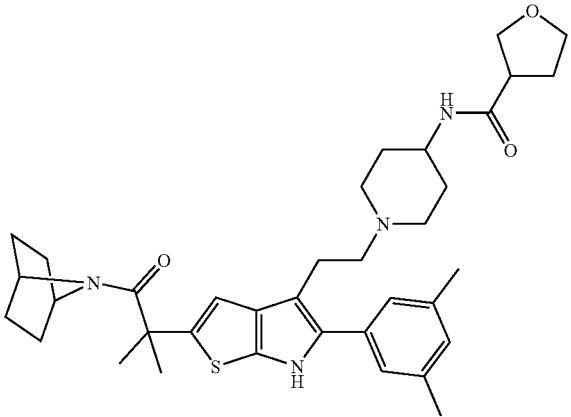 | 617 [M + H]+ |
| 27.3 | 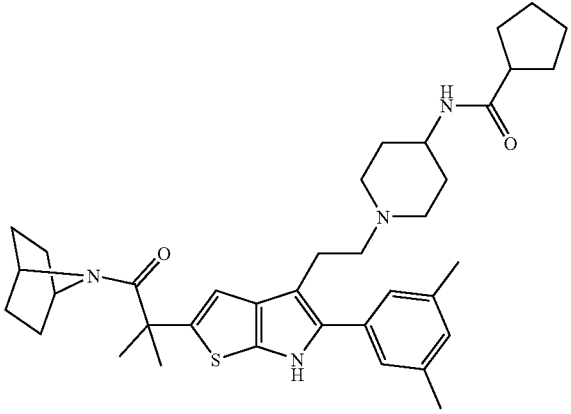 | 615 [M + H]+ |
| 27.4 | 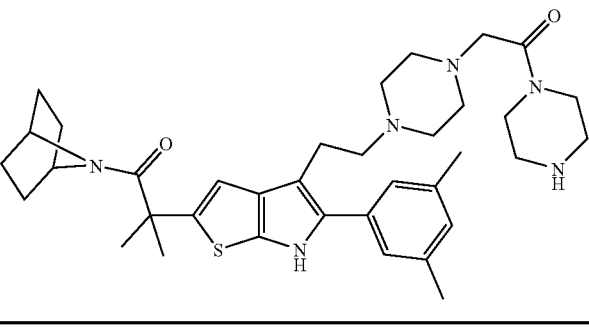 | 631 [M + H]+ |

Example 28

2-[1,1-Dimethyl-2-oxo-2-azabicyclo[2.2.1]heptan-7-ylethyl]-4-[2-(4-{morpholinocarbonylamino}piperidin-1-yl)ethyl]-5-(3,5-dimethylphenyl)-6H-thieno[2,3-b]pyrrole

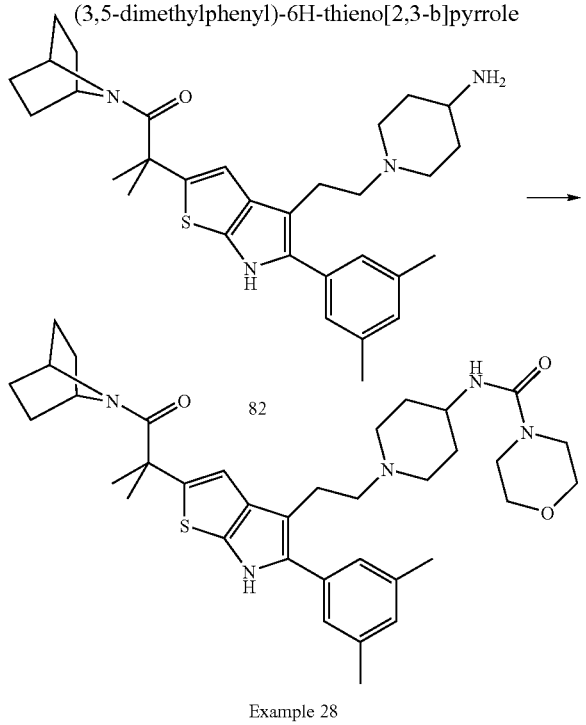

Example 28

4-nitrophenylchloroformate (0.111 g; 1.1 mmol) was added under argon atmosphere, at 0° C. to a solution of 82 (0.277 g; 0.5 mmol) and triethylamine; after stirring at ambient temperature for 1 hour, morpholine (0.052 ml; 0.6 mmol) was added. After 2 hours, the mixture was purified by flash chromatography eluting with a 2–8% gradient of 3.5N $NH_3$ in MeOH $CH_2Cl_2$/to give after trituration with pentane-ether example 28 as a solid.

Yield: 38% $^1$H NMR (CDCl$_3$): 1.2–1.8 (m, 10H); 1.61 (s, 6H); 1.95–2.05 (m, 2H); 2.1–2.25 (m, 2H); 2.34 (s, 6H); 2.6–2.7 (m, 2H); 2.9–3 (m, 4H); 3.3–3.4 (m, 4H); 3.65–3.8 (m, 5H); 4.0–4.2 (m, br, 1H); 4.4 (d, 1H); 4.6–4.8 (m, br, 1H); 6.8 (s, 1H); 6.94 (s, 1H); 7.05 (s, 2H); 8.17 (s, 1H). MS-ESI: 632 [M+H]$^+$

Examples 28.1–28.3

Following a procedure similar to that described in Example 28, the compounds of table 28 were prepared.

TABLE 28

| Example | | MS-ESI |
|---|---|---|
| 28.1 | | 630 [M + H]$^+$ |

TABLE 28-continued
| Example | | MS-ESI |
|---|---|---|
| 28.2 | 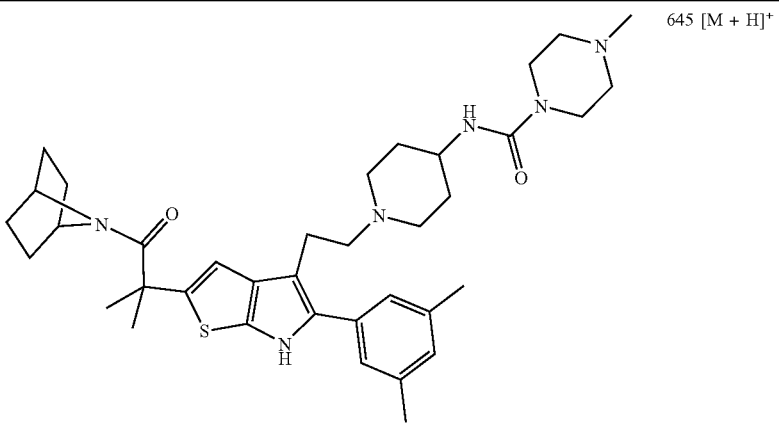 | 645 [M + H]⁺ |
| 28.3 | Chiral 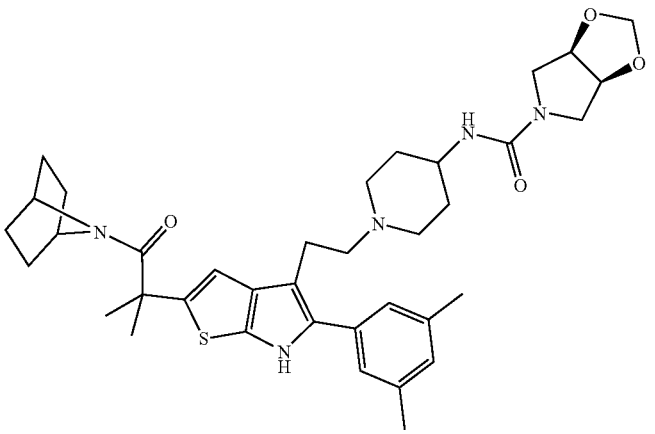 | 660 [M + H]⁺ |
Example 29
2-[1,1-Dimethyl-2-oxo-2-azabicyclo[2.2.1]heptan-7-ylethyl]-4-[2-(4-{N,N-dimethylaminosulphonylamino}piperidin-1-yl)ethyl]-5-(3,5-dimethylphenyl)-6H-thieno[2,3-b]pyrrole
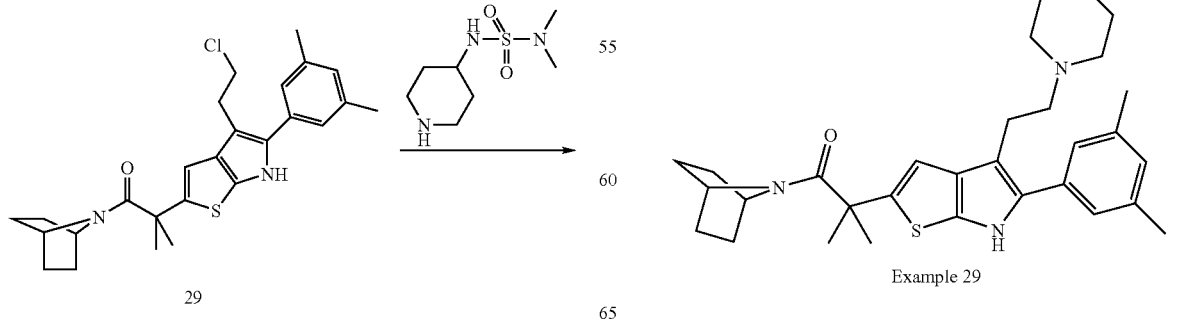

A mixture of 29 (0.225 g; 0.5 mmol), N,N-diethyl-N'-4-piperidinyl sulfamide (0.250 g, 0.6 mmol), and K$_2$CO$_3$ (0.083 g; 0.6 mmol) in dimethylacetamide (3 ml) was heated at 85° C. under argon atmosphere for 5 hours. The crude mixture was evaporated and purified by flash chromatography eluting with 3.5 N MeOH—NH$_3$/methylene chloride 95/5 to give after trituration in pentane Example 29 as a solid.

Yield: 50% $^1$H NMR (CDCl$_3$): 1.2–1.45 (m, 4H); 1.5–1.8 (m, 6H); 1.61 (s, 6H); 2.0–2.1 (m, 2H); 2.1–2.2 (m, 2H); 2.34 (s, 6H); 2.6–2.7 (m, 2H); 2.8 (s, 6H); 2.85–2.95 (m, 4H); 3.2–3.3 (m, 1H); 4.0–4.2 (m, br, 1H); 4.28 (d, 1H); 4.6–4.8 (m, br, 1H); 6.75 (s, 1H); 6.93 (s, 1H); 7.05 (s, 2H); 8.6 (s, 1H). MS-ESI: 626 [M+H]$^+$ Example 30

2-[1,1-Dimethyl-2-oxo-2-azabicyclo[2.2.1]heptan-7-ylethyl]-4-[2-(4-{3-oxo-3-morpholinoprop-1-yl}piperidin-1-yl)ethyl]-5-(3,5-dimethylphenyl)-6H-thieno[2,3-b]pyrrole A mixture of 29 (0.137 g; 0.3 mmol), 85 (0.158 g, 0.6 mmol), K$_2$CO$_3$ (1.24 g; 0.9 mmol) in acetonitrile (3 ml) and DMA (2 ml) was heated at 85° C. overnight under argon atmosphere. The crude mixture was evaporated and purified by flash chromatography eluting with a gradient 5–7% of 3.5 N NH$_3$ in MeOH/methylene chloride to give after trituration in ether/pentane Example 30 as a solid.

Yield: 61% $^1$H NMR (CDCl$_3$): 1.2–1.4 (m, 6H); 1.5–1.8 (m, 9H); 1.6 (s, 6H); 1.95–2.05 (m, br, 2H); 2.3–2.4 (m, 2H); 2.35 (s, 6H); 2.6–2.7 (m, 2H); 2.9–3.1 (m, 4H); 3.4–3.5 (m, 2H); 3.6–3.7 (m, 6H); 4.0–4.2 (m, br, 1H); 4.65–4.85 (m, br, 1H); 6.74 (s, 1H); 6.94 (s, 1H); 7.06 (s, 2H); 8.14 (s, 1H). MS-ESI: 646[M+H]$^+$ The starting material was prepared as follows:

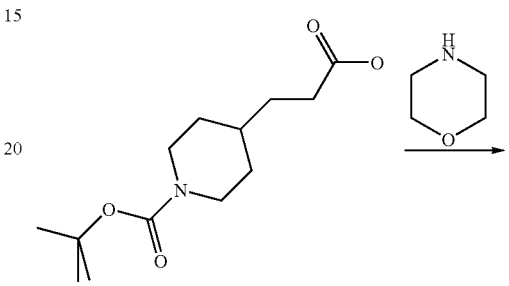

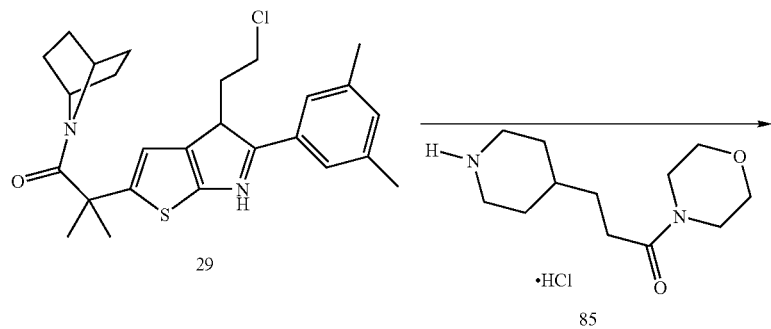

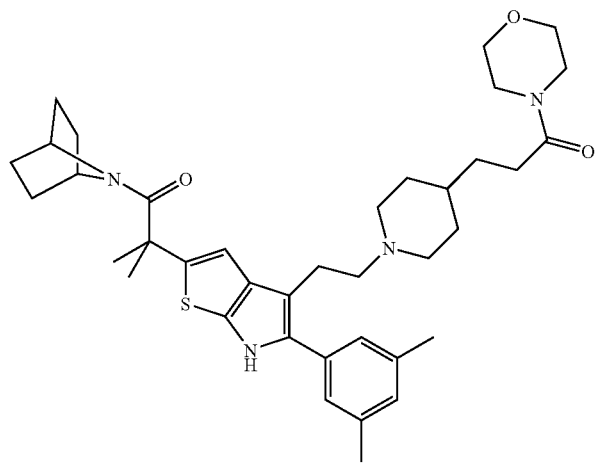

Example 30

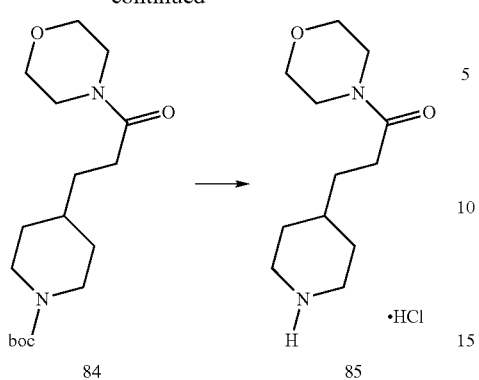

EDC (1.25 g; 6.5 mmol) was added to a stirred solution of 1-tert-butoxycarbonyl-4-piperidine propionic acid (1.29 g; 5 mmol), HOBT (0.878 g; 6.5 mmol) and morpholine (0.57 g; 6.5 mmol) in methylene chloride (15 ml). After stirring for 18 hours, the mixture was evaporated and purified by flash chromatography, eluting with MeOH/methylene chloride 3/97 to give 84 as a solid.

Yield: 100% $^1$H NMR (CDCl$_3$): 1.1–1.3 (m, 2H); 1.45 (s, 9H); 1.4–1.5 (m, 1H); 1.55–1.75 (m, 4H); 2.33 (t, 2H); 2.6–2.75 (m, 2H); 3.45 (m, 2H); 3.61 (m, 2H); 3.67 (m, 4H); 4.0–4.2 (m, 1H).

84 (1.54 g; 2.45 mmol) in solution in dioxan (15 ml) was treated with 12N HCl (4 ml) at 0° C.; After stirring at ambient temperature for 2 hours, the mixture was evaporated and triturated in ether to give 85 as a solid.

Yield: 100% $^1$H NMR (DMSO): 1.28–1.34 (m, 2H); 1.42–1.45 (m, 3H); 1.79 (d, 2H); 2.32 (t, 2H); 2.7–2.85 (m, 2H); 3.20 (d, 2H); 3.41 (m, 4H); 4.5–4.6 (m, 4H); 8.71 (m, br, NH).

Example 31

2-[1,1-Dimethyl-2-oxo-2-azabicyclo[2.2.1]heptan-7-ylethyl]-4-[4-(cyclobutylcarbonylaminomethyl)piperidin-1-ylmethyl]-5-(3,5-dimethylphenyl)-6H-thieno[2,3-b]pyrrole

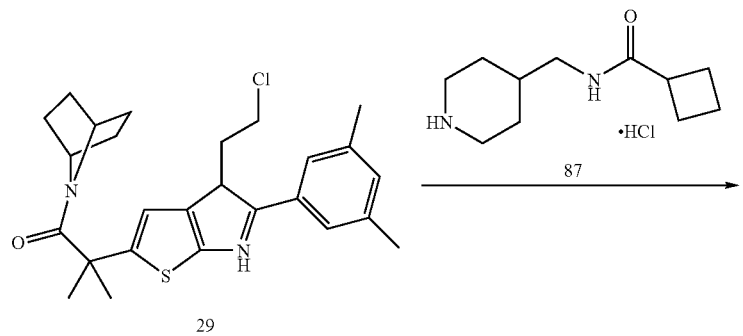

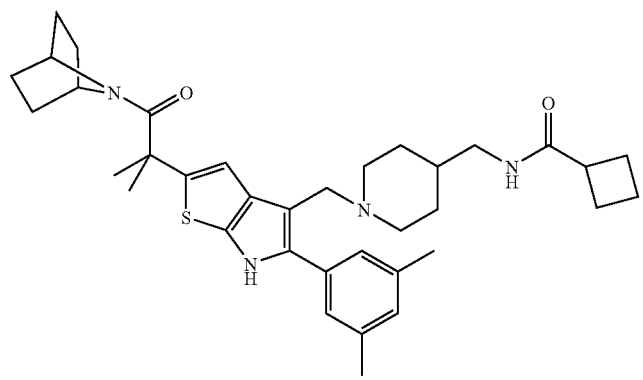

Example 31

A mixture of 29 (0.115 g; 0.25 mmol), 87 (0.116 g, 0.5 mmol), K₂CO₃ (0.07 g; 0.5 mmol) in acetonitrile (2 ml) and DMF (0.5 ml) was heated at 85° C. for 3 hours under argon atmosphere. The crude mixture was purified by flash chromatography eluting successively with AcOEt/methylene chloride 50/50, AcOEt and 3.5 N NH₃ in MeOH/AcOEt 10/90 to give after trituration in ether/pentane Example 31 as a solid.

Yield: 90% ¹H NMR (CDCl₃) (δ ppm) 1.26–1.32 (m, 6H); 1.45–1.75 (m, 8H); 1.61 (s, 6H); 1.8–2.3 (m, 8H); 2.34 (s, 6H); 2.6–2.75 (br s, 2H); 2.9–3.15 (m, 6H); 4.1 (br s, 1H) 4.75 (br s, 1H); 5.45 (br s, 1H); 6.72 (s, 1H); 6.944 (s, 1H); 7.058 (s, 2H); 8.19 1H). MS-ESI: 615 [M+H]⁺

The starting material was prepared as follows:

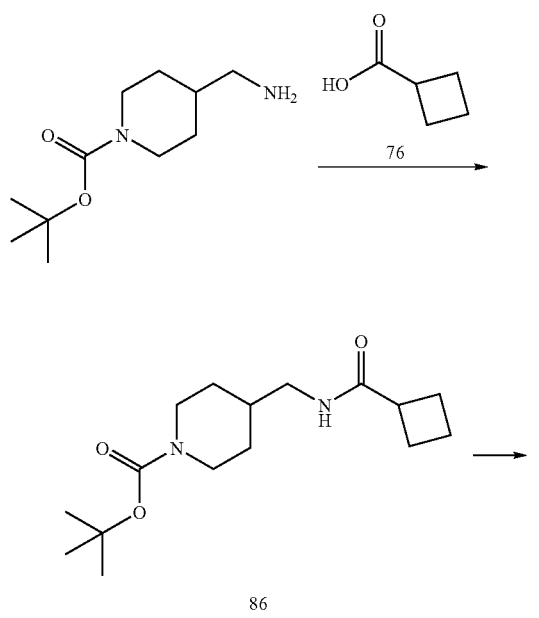

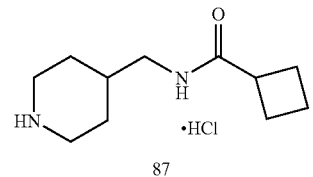

1-tert-butoxycarbonyl-4-aminomethyl piperidine (0.645 mg; 3 mmol) was added, under argon atmosphere to a stirred solution of cyclobutane carboxylic acid (0.3 g; 3 mmol), EDC (0.864 g; 4 mmol), DIEA (0.78 ml; 4.5 mmol) and DMAP (0.055 g; 0.45 mmol) in methylene chloride (30 ml). The mixture was stirred overnight, evaporated and purified by flash chromatography, eluting successively with methylene chloride, AcOEt and 3.5 N NH₃ in MeOH/AcOEt 10/90 to give 86 as a solid.

Yield: 56% ¹H NMR (CDCl₃) 1.23 (m, 2H); 1.44 (s, 9H); 1.61–1.65 (m, 3H); 1.80–2.30 (ms, 6H); 2.68 (br s, 2H); 2.98 (m, 1H); 3.12 (br s, 2H); 4.12 (br s, 2H); 5.42 (br s, 1H).

86 (0.44 g; 1.35 mmol) was dissolved in dioxan (3 ml) and treated with a solution made of 12N HCl/dioxan 5/25 (3 ml). The mixture was heated at 55° C. under argon atmosphere overnight. After evaporation to dryness, the residue was triturated in a mixture of MeOH, methylene chloride and ether to give 87 as solid.

Yield: 69% ¹H NMR (DMSO-d₆) 1.25 (m, 2H); 1.60–1.80 (m, 4H); 1.87 (m, 1H); 1.99 (m, 2H); 2.08 (m, 2H); 2.77 (m, 2H); 2.80–3.05 (m, 3H); 3.37 (m, 2H).

Examples 31.1–31.4

Following a procedure similar to that described in Example 31 the compounds of table 31 were prepared.

TABLE 31

| Example | | MS-ESI |
|---|---|---|
| 31.1 | | 629 [M + H]⁺ |

TABLE 31-continued
| Example | | MS-ESI |
|---|---|---|
| 31.2 | 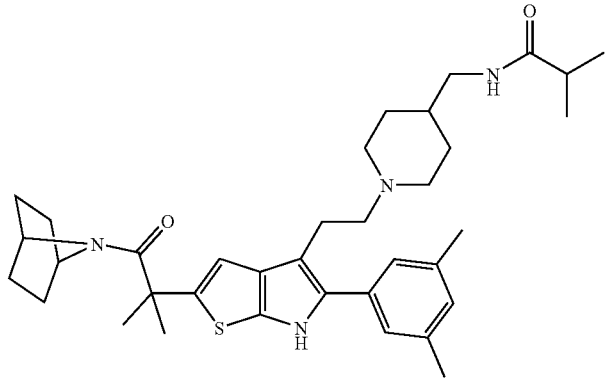 | 603 [M + H]+ |
| 31.3 | 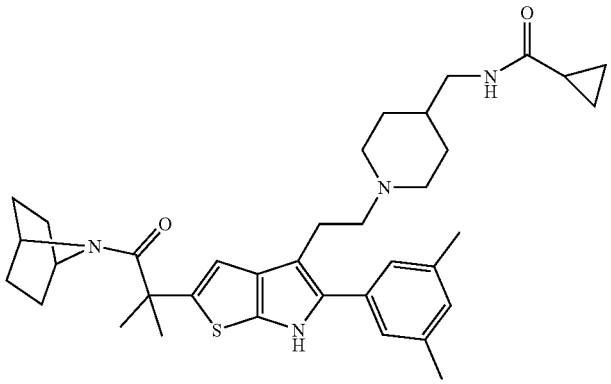 | 601 [M + H]+ |
| 31.4 | 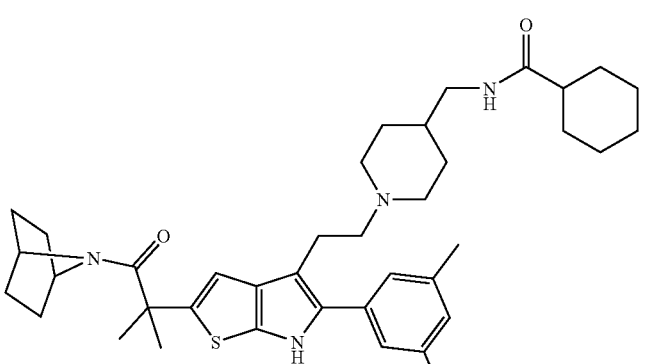 | 643 [M + H]+ |

Example 32
2-[1,1-Dimethyl-2-oxo-2-azabicyclo[2.2.1]heptan-7-ylethyl]-4-[2-(4-{isopropylsulphonylaminomethyl}piperidin-1-yl)ethyl]-5-(3,5-dimethylphenyl)-6H-thieno[2,3-b]pyrrole
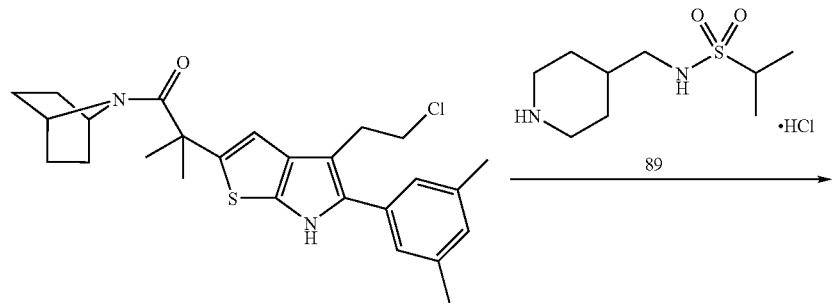
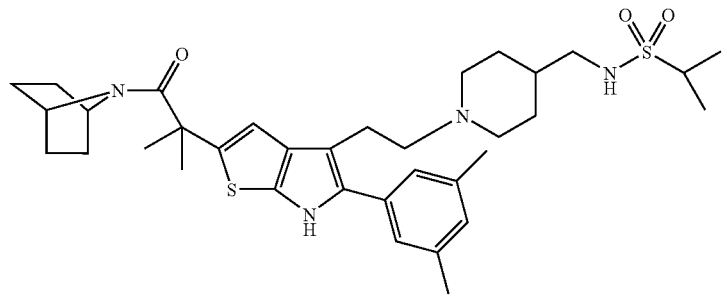
Example 32
Example 32 was prepared following a method described in Example 31.
Yield: 88% $^1$H NMR(CDCl$_3$): 1.25–1.40 (m, 4H); 1.38 (d, 6H); 1.45–1.80 (m, 7H); 1.62 (s, 6H); 1.90–2.10 (br s, 2H); 2.35 (s, 6H); 2.6–2.80 (br s, 2H); 2.90–3.15 (m, 8H); 3.15 (s, 1H); 4.10 (br s, 2H);
4.75 (br s, 1H); 6.75 (s, 1H); 6.95 (s, 1H); 7.05 (s, 2H); 8.16 (s, 1H). MS-ESI: 639[M+H]$^+$
The starting material was prepared as follows:
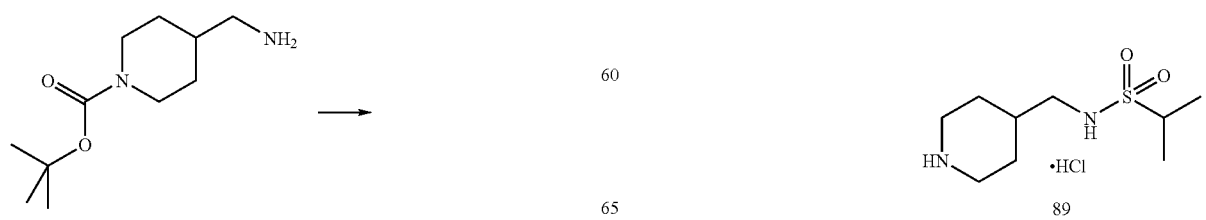

Isopropylsulfonyl chloride (0.230 ml; 2.05 mmol) was added under argon atmosphere at 0° C. to solution of 1-t-butoxycarbony-4-aminomethyl-piperidine (0.4 g; 1.87 mmol) and K₂CO₃ (0.285 ml; 2.05 mmol) in acetonitrile (15 ml). The mixture was stirred overnight at ambient temperature and purified by flash chromatography eluting successively with methylene chloride, AcOEt/methylene choride 80/20 to give 88 as a solid.

Yield: 41% ¹H NMR (CDCl₃) 1.13 (m, 2H); 1.38 (d, 6H); 1.45 (s, 9H); 1.60–1.80 (m, 3H); 2.68 (br s, 2H); 3.04 (m, 2H); 3.16 (m, 1H ); 4.06–4.20 (br s, 3H).

88 (0.340 g; 0.94 mmol) was dissolved in dioxan (3 ml)/methylene chloride (0.3 ml) and treated with a solution made of 12N HCl/dioxan 5/25 (2 ml). The mixture was stirred at ambient temperature under argon atmosphere overnight. After evaporation to dryness, the residue was triturated in a mixture of MeOH, methylene chloride and ether to give 89 as a solid.

Yield: 100% ¹H NMR (CDCl₃) 1.35 (d, 6H); 1.66 (m, 2H); 1.81 (br s, 1H); 1.92 (m, 2H); 3.08 (m, 2H); 3.17 (m, 1H); 3.51 (m, 2H).

Examples 32.1–32.2

Following a procedure similar to that described in Example 32, the compounds of table 32 were prepared.

| Example | | MS-ESI |
|---|---|---|
| 32.1 | 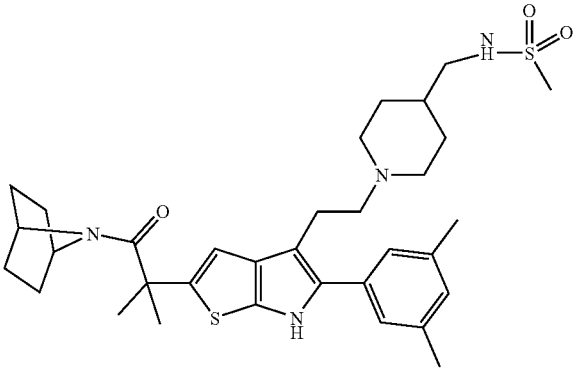 | 611 [M + H]⁺ |
| 32.2 | 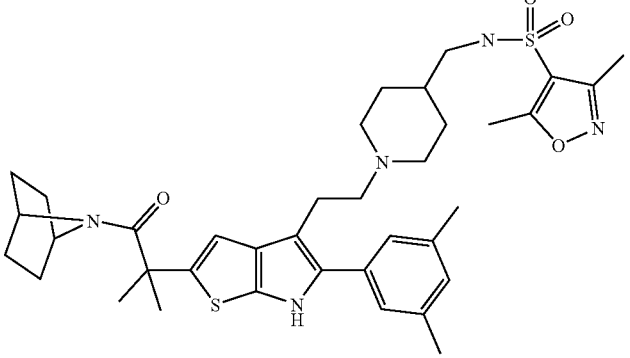 | 692 [M + H]⁺ |

Example 33

2-[1,1-Dimethyl-2-oxo-2-azabicyclo[2.2.1]heptan-7-ylethyl]-4-[2-(4-{isopropoxycarbonylaminomethyl}piperidin-1-yl)ethyl]-5-(3,5-dimethylphenyl)-6H-thieno[2,3-b]pyrrole

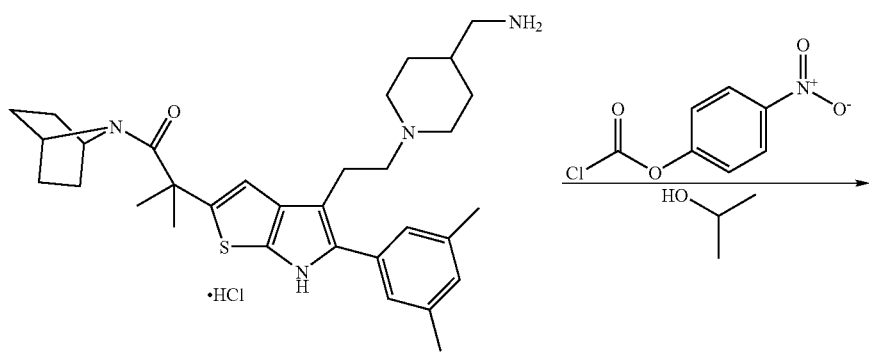

91

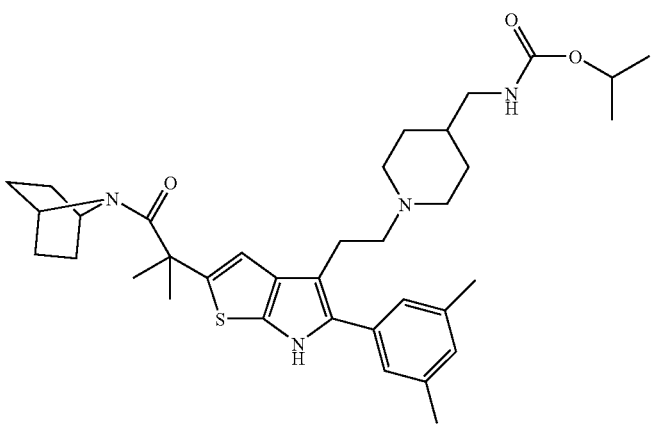

Example 33

4-nitrophenylchloroformate (0.110. g; 0.55 mmol) was added under argon atmosphere, at 0° C. to a solution of 91 (0.284 g; 0.5 mmol) and triethylamine (0.135 ml; 1.05 mmol) in methylene chloride (12 ml); after stirring at ambient temperature for 1 hour and evaporation, isopropanol (10 ml) was added. The mixture was refluxed for 7 hours, evaporate to dryness and purified on reverse phase chromatography eluting with a 10–80% gradient of MeOH/ $(NH_4)_2CO_3$—H2O 2 g/l to give after trituration with pentane-ether example 33 as a solid.

Yield: 52% $^1$H NMR (CDCl$_3$): 1.22 (d, 6H); 1.20–1.35 (m, 6H); 1.45–1.85 (m, 7H); 1.60 (s, 6H); 2.01 (br s, 2H); 2.35 (s, 6H); 2.66 (br s, 2H); 2.90–3.12 (m, 6H); 4.10 (br s, 1H); 4.67 (m, 2H); 4.89 m, 1H); 6.74 (s, 1H); 6.94 (s, 1H); 7.06 (s, 2H); 8.13 (s, 1H). MS-ESI: 619[M+H]$^+$ The starting material was prepared as follows:

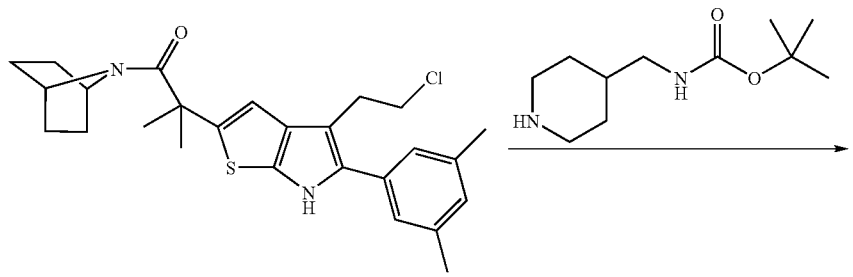

29

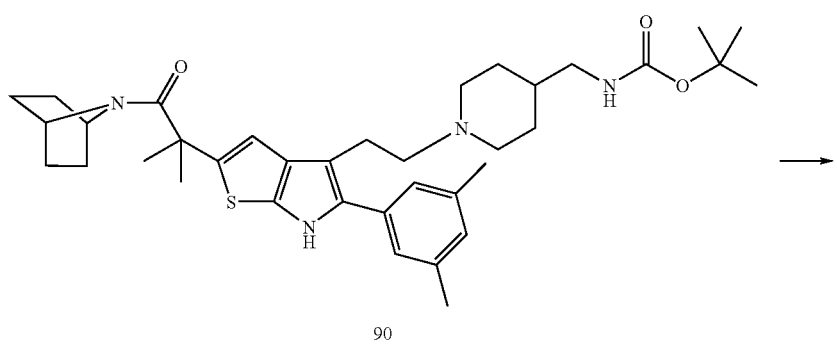

90

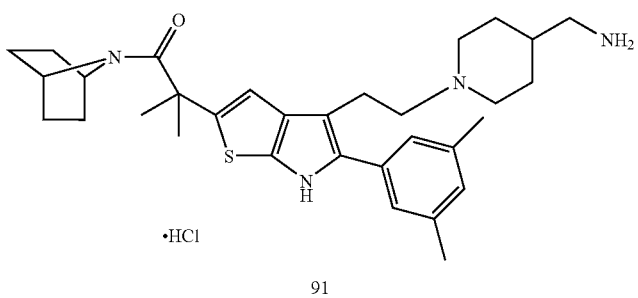

91

A mixture of 29 (3.27 g; 7.2 mmol), 4-tert-butoxycrbonylaminomethyl piperidine (03.08 g, 14.2 mmol), K₂CO₃ (1.95 g; 14.2 mmol) in acetonitrile (50 ml) and DMF (0.5 ml) was heated at 85° C. for 3 hours under argon atmosphere. The crude mixture was purified by flash chromatography eluting successively with AcOEt/methylene chloride 50/50, AcOEt and 3.5 N NH₃ in MeOH/AcOEt 20/80 to give 90 as a solid.

Yield: 80% ¹H NMR (CDCl₃) 1.26–1.40 (m, 6H); 1.44 (s, 9H); 1.45–1.75 (m, 7H); 1.59 (s, 6H); 2.00 (m, 2H); 2.35 (s, 6); 2.66 (m, 2H); 2.93–3.49 (ms, 6H); 4.10 (br s, 1H); 4.61 (br s, 1H); 4.75 (brs, 1H ); 6.74 (s, 1H); 6.94 (s, 1H); 7.06 (s, 2H); 8.13 (s, 1H).

90 (3.06 g; 4.84 mmol) was dissolved in dioxan (13 ml) and treated with a solution made of 12N HCl/dioxan 5/25 (9.7 ml). The mixture was stirred at ambient temperature under argon atmosphere overnight. After evaporation to dryness, the residue was triturated in a mixture of MeOH, methylene chloride and ether to give 91 as solid.

Yield: 100% ¹H NMR (DMSO-d₆)1.26–1.45 (m, 6H); 1.40–1.70 (m, 7H); 1.52 (s, 6H); 1.80–2.00 (m, 3H); 2.00 (m, 2H); 2.34 (s, 6H); 2.66 (m, 2H); 3.60 (m, 2H); 4.1 (br s, 1H); 4.55 (br s, 1H); 4.75 (br s, 1H); 6.95 (s, 1H); 6.98 (s, 1H); 7.10 (s, 2H); 8.07 (s, 1H).

Example 34

2-[1,1-Dimethyl-2-oxo-2-azabicyclo[2.2.1]heptan-7-ylethyl]-4-[2-(4-{tetrahydrofuran-2-ylcarbonylaminomethyl}piperidin-1-yl)ethyl]-5-(3,5-dimethylphenyl)-6H-thieno[2,3-b]pyrrole

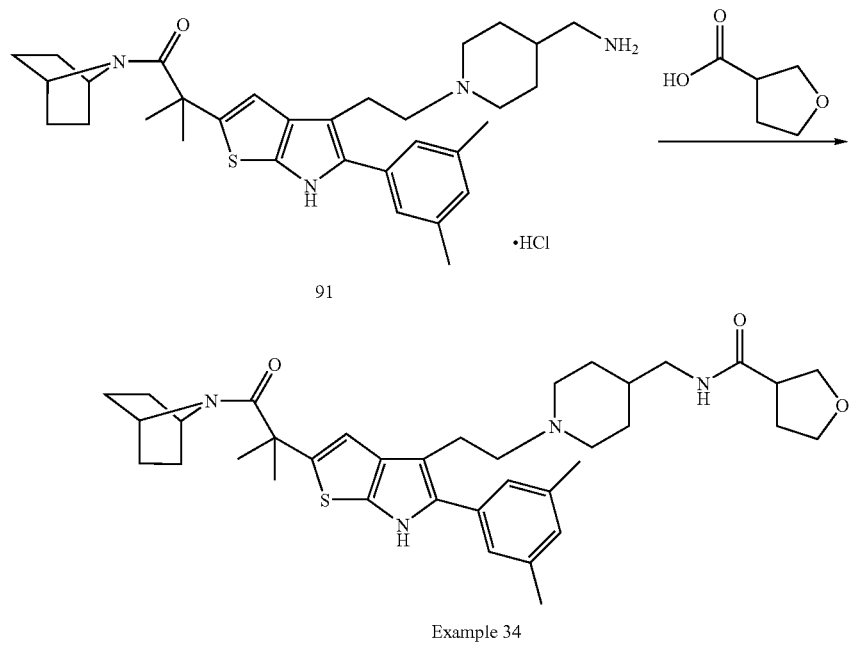

Example 34

To a suspension of tetrahydro-3-furoic acid (0.029 g; 0.25 mmol) in methylene chloride (2 ml), was added DIEA (0.190 ml; 1.09 mmol), HATU (0.104 g; 0.275 mmol) and 91 (0.146 g; 0.25 mmol). The mixture was stirred at ambient temperature overnight. The crude mixture was purified by flash chromatography eluting successively with AcOEt/methylene chloride 50/50 and 3.5 $NH_3$ in MeOH/AcOEt 5/95 to give Example 34 as a solid.

Yield: 83% $^1$H NMR (CDCl$_3$): 1.20–1.45 (m, 6H); 1.45–1.85 (m, 7H); 1.61 (s, 6H); 2.00 (m, 2H); 2.16 (m, 2H); 2.34 (s, 6H); 2.64 (m, 2H); 2.90 (m, 3H); 3.01 (m, 2H); 3.16 (t, 2H); 3.80 (m, 1H); 3.90 (m, 2H); 3.94 (m, 1H); 4.10 (br s, 2H); 4.75 (br s, 1H); 6.74 (s, 1H); 6.94 (s, 1H); 7.05 (s, 2 H); 8.15 (s, 1H). MS-ESI: 631[M+H]$^+$

Examples 34.1–34.6

Following a procedure similar to that described in Example 34, the compounds of table 34 were prepared.

TABLE 34

| Example | | MS-ESI |
|---|---|---|
| 34.1 | (structure) | 671 [M + H]$^+$ |

TABLE 34-continued
| Example | | MS-ESI |
|---|---|---|
| 34.2 | 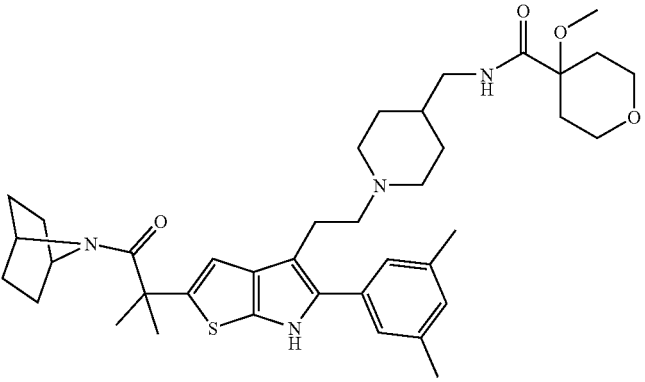 | 675 [M + H]+ |
| 34.3 | 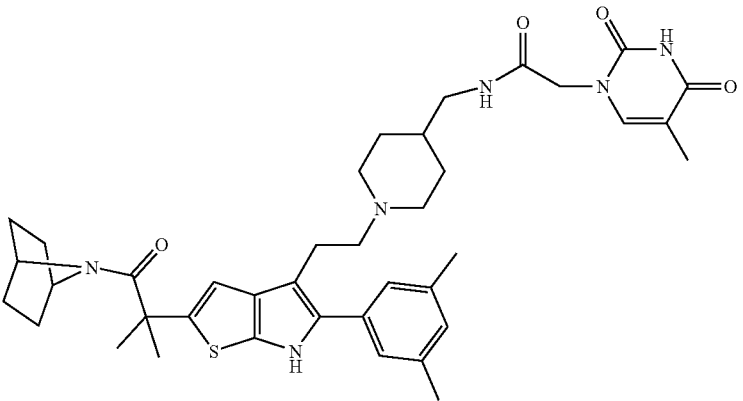 | 699 [M + H]+ |
| 34.4 | 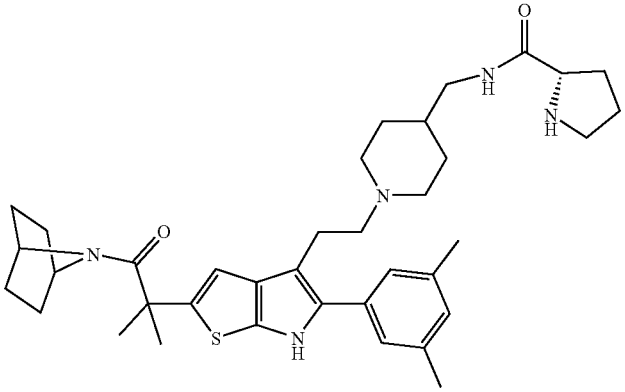 | 630 [M + H]+ |
| 34.5 | 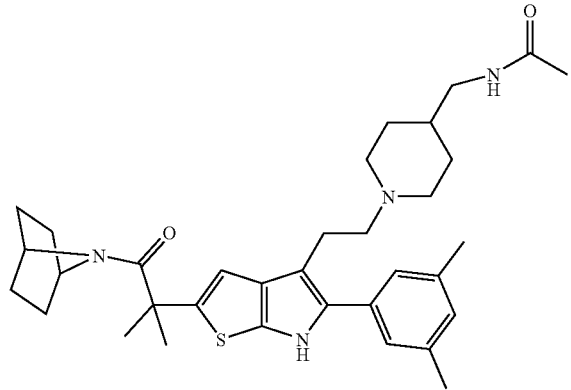 | 575 [M + H]+ |

| Example | | MS-ESI |
|---|---|---|
| 34.6 | 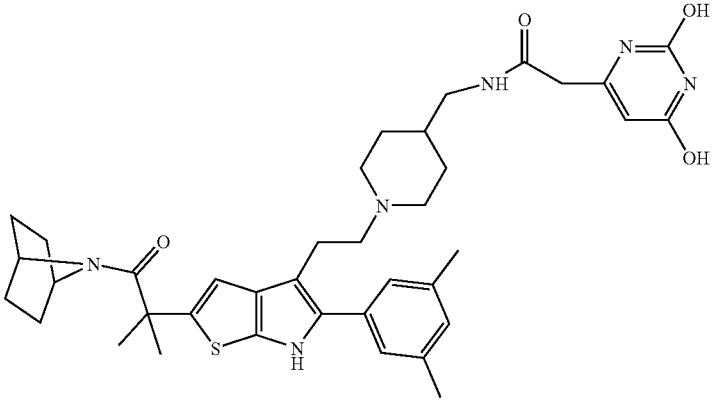 | 685 [M + H]⁺ |
Example 35
2-[1,1-Dimethyl-2-oxo-2-azabicyclo[2.2.1]heptan-7-ylethyl]-4-[2-(4-{pyrrolidin-1-ylcarbonylmethyl}piperidin-1-yl)ethyl]-5-(3,5-dimethylphenyl)-6H-thieno[2,3-b]pyrrole
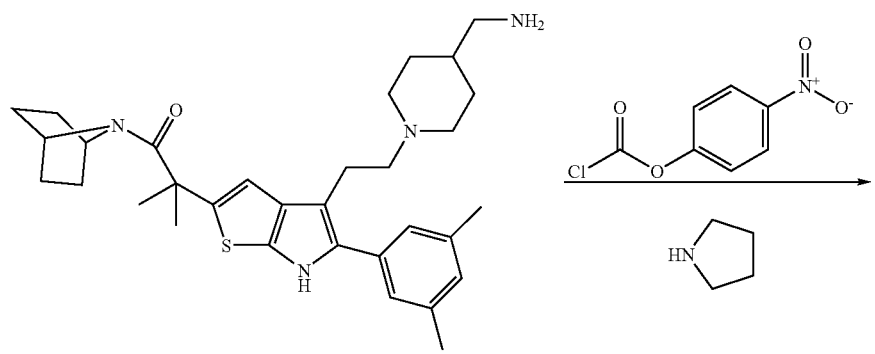
91
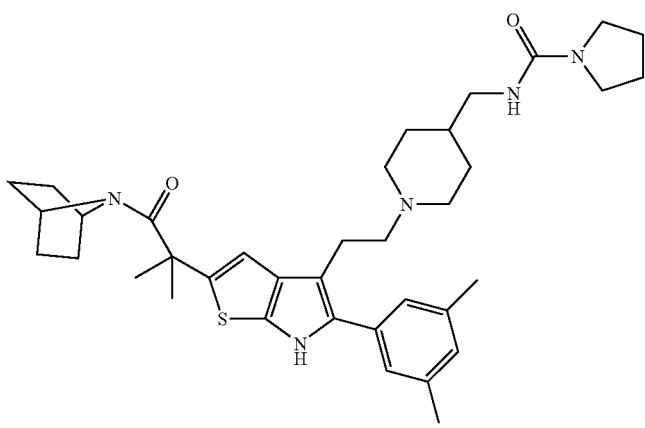
Example 35

4-nitrophenylchloroformate (0.056. g; 0.275 mmol) was added under argon atmosphere, at 0° C. to a solution of 91 (0.250 g; 0.25 mmol) and triethylamine (0.074 ml; 0.525 mmol) in methylene chloride (3 ml); after stirring at ambient temperature for 1 hour, pyrrolidine (0.023 ml) was added. The mixture was stirred at ambient temperature overnight, evaporated to dryness and purified by flash chromatography eluting with 3.5 N NH3 in MeOH/methylene chloride 6/94 to give example 35 as a solid.

Yield: 78% $^1$H NMR (CDCl$_3$): 1.20–1.35 (m, 4H); 1.45–1.75 (m, 4H); 1.64 (s, 6H); 1.45–1.95 (m, 10H); 2.03 (m, 2H); 2.36 (s, 6H); 2.60 (m, 2H); 3.12 (m, 2H); 3.18 (m, 6H); 3.54 (m, 2H); 4.18 (br s, 1H); 4.70 (br s, 1H); 6.90 (s, 1H); 6.93 (s, 1H); 7.03 (s, 2H); 8.55 (s, 1H).

Examples 35.1–35.4

Following a procedure similar to that described in Example 35, the compounds of table 35 were prepared.

| Example | | MS-ESI |
|---|---|---|
| 35.1 | 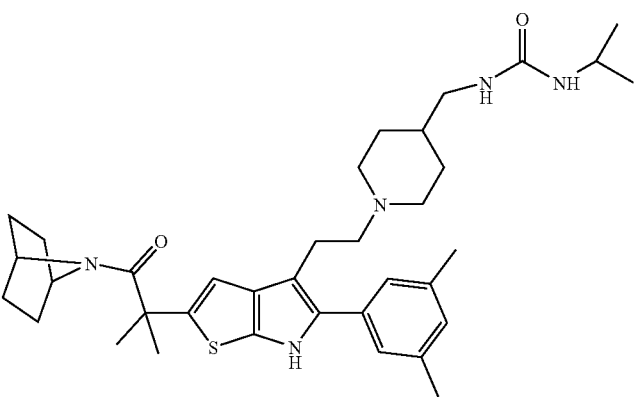 | 618 [M + H]$^+$ |
| 35.2 | 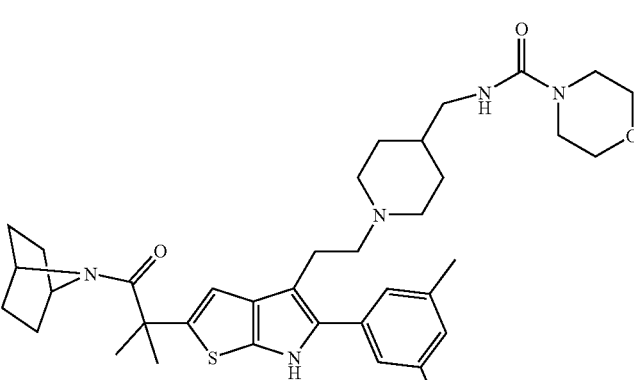 | 646 [M + H]$^+$ |
| 35.3 | 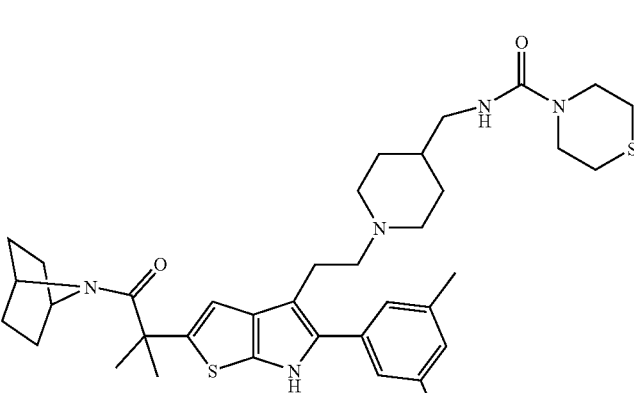 | 662 [M + H]$^+$ |

| Example | | MS-ESI |
|---|---|---|
| 35.4 | 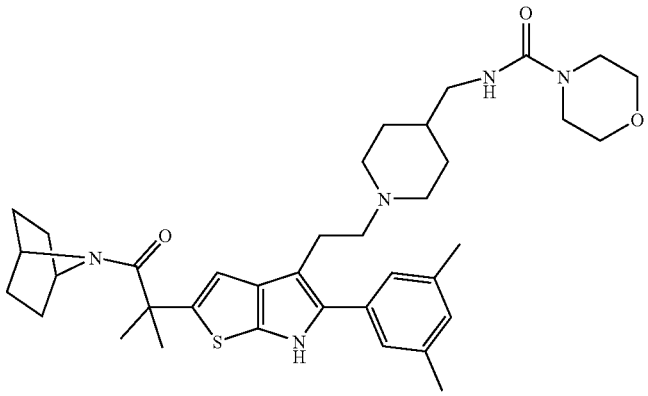 | 646 [M + H]+ |

Example 36

2-[1,1-Dimethyl-2-oxo-2-azabicyclo[2.2.1]heptan-7-ylethyl]-4-[2-(4-{N,N-dimethylaminocarbonyl}piperidin-1-yl)ethyl]-5-(3,5-diethylphenyl)-6H-thieno[2,3-b]pyrrole A mixture of 93 (0.137 g, 0.25 mmol), HATU (0.152 g; 0.4 mmol) and DIEA (0.09 ml; 0.5 mmol) in DMF (2 ml) was stirred at ambient temperature for 2 hours. The crude material was purified on reverse phase silica eluting with a gradient of 10–80% acetonitrile/1% acetic acid-H2O. The appropriate fractions were evaporated and triturated in ether to give Example 34 as a solid.

Yield: 54% ¹H NMR (DMSOd₆): 1.25–1.75 (m, 8H); 1.61 (s, 6H); 1.9–2.1 (m, 4H); 2.37 (6H); 2.9–3.24 (m, 13H); 3.45–3.5 (m, 2H); 4.0–4.2 (br m,1H); 4.6–4.8 (m, 1H); 6.77 (s, 1H); 6.98 (s, 1H); 7.05 (m, 2H). MS-ESI: 575 [M+H]+

The starting material was prepared as follows:

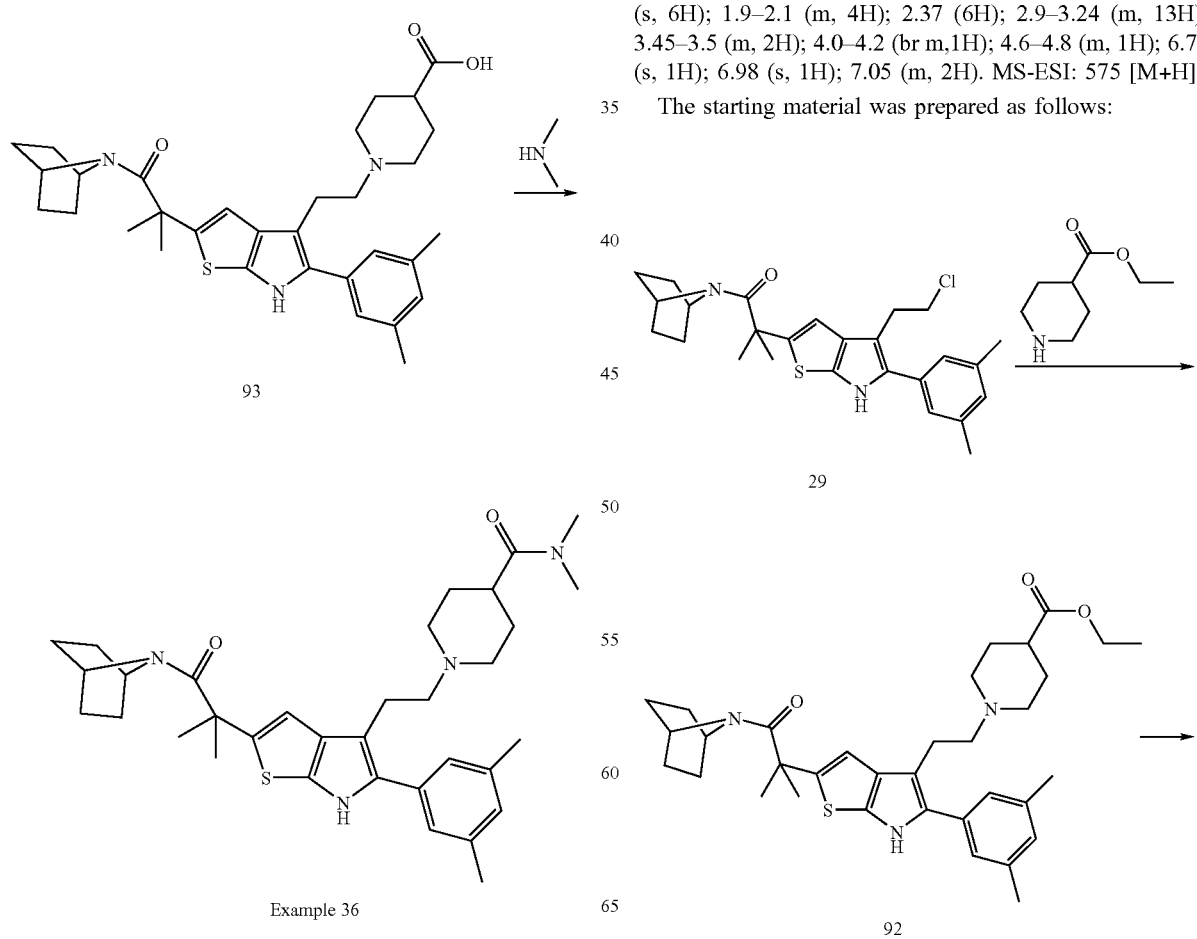

-continued

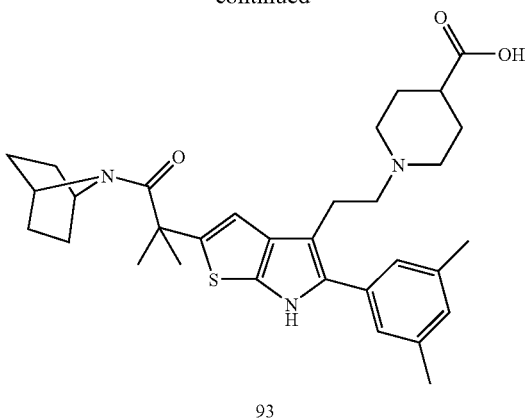

93

A mixture of 29 (4.55 g; 0.01 mol), 4-ethoxycarbonyl piperidine (2.36 g; 0.015 mol), triethylamine (1.53 ml; 0.011 mol) and NaI (1.5 g; 0.01 mol) in DMA (45 ml) was heated at 110° C. under argon atmosphere for 4 hours. After extraction with ethyl acetate and evaporation, the mixture was purified by flash chromatography, eluting with a gradient 80–100% ethyl acetate/petroleum ether to give 92.

Yield: 62% $^1$H NMR (CDCl$_3$): 1.25 (t, 3H); 1.2–1.45 (m, 4H); 1.5–1.8 (m, 4H); 1.62 (s, 6H); 1.7–2 (m, 4H); 2.05–2.15 (m, 2H); 2.25–2.35 (m, 1H); 2.35 (s, 6H); 2.64–2.67 (m, 2H); 2.93–2.98 (m, 4H); 4.13 (q, 2H); 4.0–4.2 (br m, 1H); 4.6–4.8 (br m, 1H); 6.74 (s, 1H); 6.94 (s, 1H); 7.07 (s, 2H); 8.13 (s, 1H).

A solution of 92 (3.61 g; 0.627 mmol) in 2N NaOH (5 ml) and EtOH (100 ml) was heated at 60)C for 2 hours. After extraction with methylene chloride/methanol (50/50) and evaporation, the residue was triturated in ether to give 93 as a solid.

Yield: 93% $^1$H NMR (DMSOd$_6$, AcOH): 1.30 (m, 4H); 1.40–1.70 (m, 4H); 1.53 (s, 6H); 1.80–2.00 (m, 4H); 2.05 (m, 2H); 2.34 (s, 6H); 2.65 (m, br, 1H); 3.14 (m, 2H); 3.27 (m, 2H); 3.30–3.60 (m, 2H); 4.10 (m, br, 1H); 4.50 (m, br, 1H); 6.96 (m, 2H); 7.09 (m, 2H).

Examples 36.1–36.8

Following a procedure similar to that described in Example 36 the compounds of table 36 were prepared.

TABLE 36

| Example | | MS-ESI |
|---|---|---|
| 36.1 | | 615 [M + H]$^+$ |
| 36.2 | | 587 [M + H]$^+$ |

TABLE 36-continued
| Example | | MS-ESI |
|---|---|---|
| 36.3 | 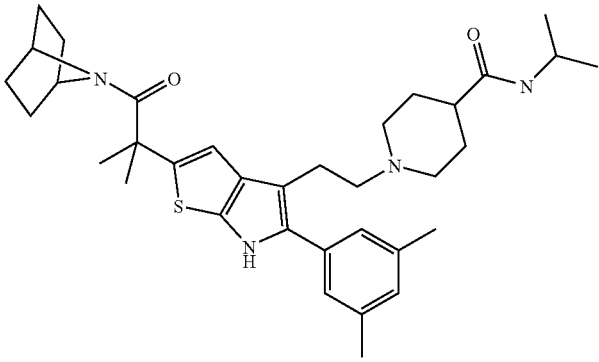 | 589 [M + H]+ |
| 36.4 | 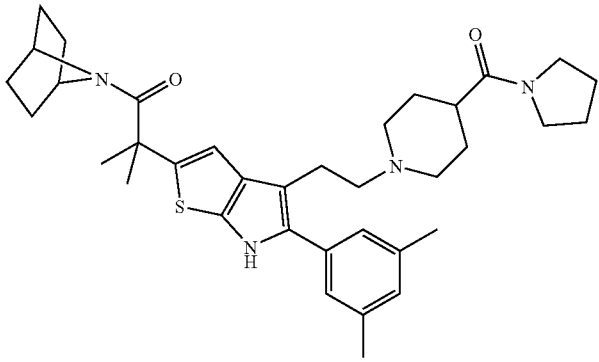 | 601 [M + H]+ |
| 36.5 | 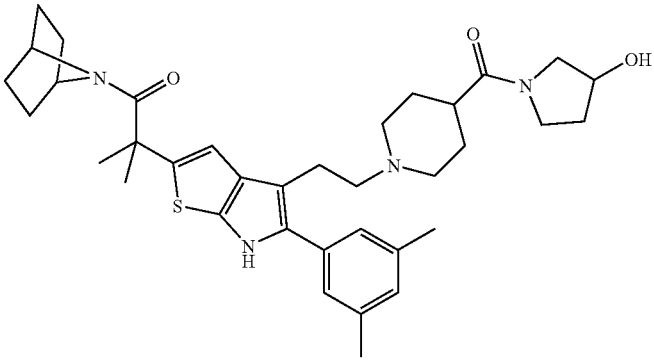 | 617 [M + H]+ |
| 36.6 | 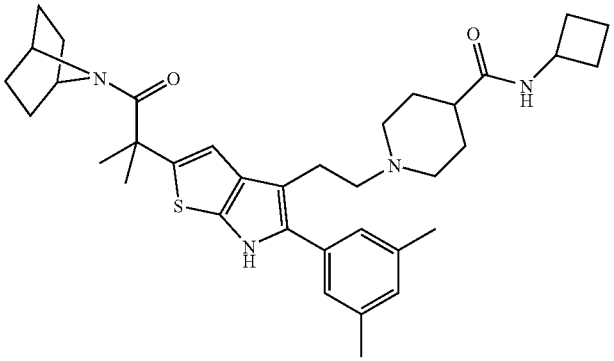 | 601 [M + H]+ |

TABLE 36-continued

| Example | | MS-ESI |
|---|---|---|
| 36.7 | 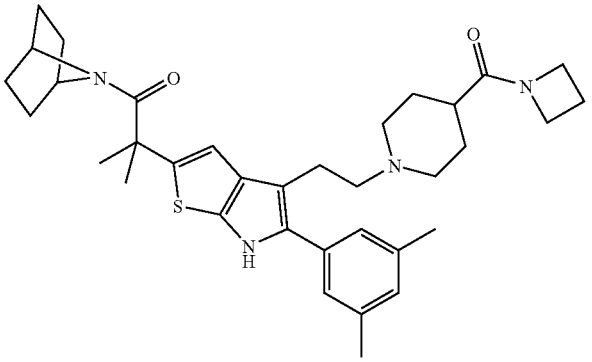 | 587 [M + H]+ |
| 36.8 | 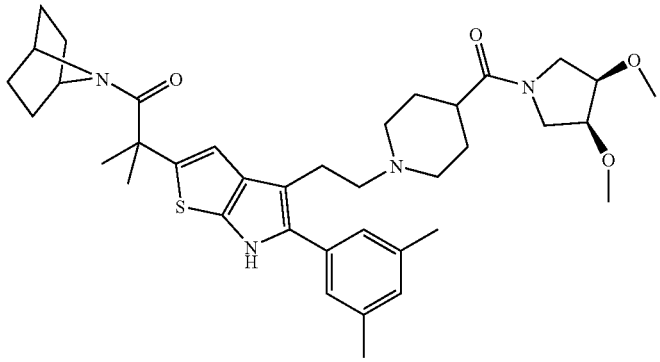 | 661 [M + H]+ |

Example 37

2-[N,N-Dibutylaminocarbonyl]-4-[2-(4-{pyrrolidin-1-ylcarbonylmethyl}piperazin-1-yl)ethyl]-5-(3,5-dimethylphenyl)-6H-thieno[2,3-b]pyrrole

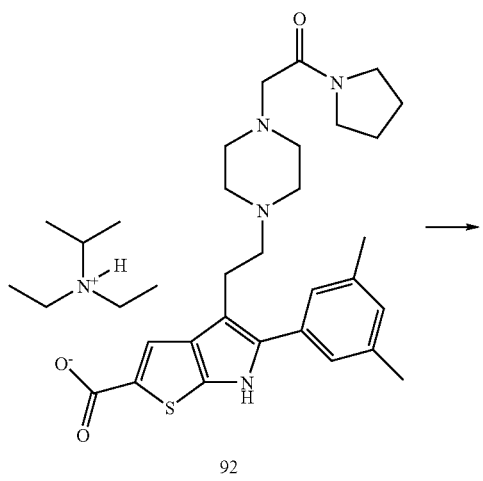

92

→

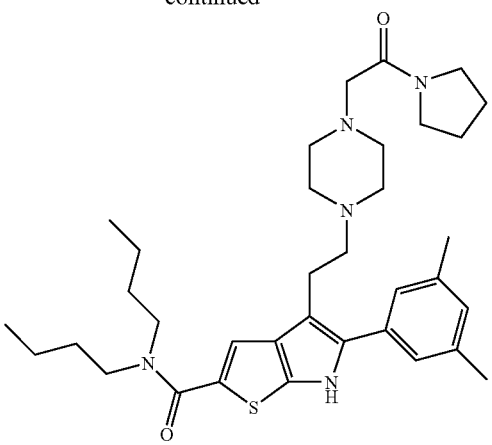

Example 37

To a solution of 94 (0.10 g; 0.161 mmol), dibutylamine (0.062 g ;0.483 mmol) and DIPEA (0.062 g; 0.483 mmol) in DMF (1 ml) at room temperature, was added solid HATU (0.183 g; 0.483 mmol) in one portion. The reaction mixture was allowed to stand for 1 hour after which HPLC showed no remaining starting material. The reaction mixture was purified by preparative LCMS (standard basic system) to afford example 37 (0.018 g) as a beige solid.
Yield: 18% MS-ESI: 606 [M+H]$^{+1}$H NMR (CDCl$_3$) 0.96 (t, 6H); 1.34–1.43 (m, 4H); 1.65–1.73 (m, 4H); 1.85 (m, 2H); 1.96 (m, 2H); 2.37 (s, 6H); 2.5–2.73 (m, 8H); 2.97 (m, 2H); 3.13 (s, 2H); 3.46–3.60 (m, 4H); 6.94 (s, 1H); 7.08 (s, 2H); 7.40 (s, 1H); 8.27 (s, 1H).
The intermediate 94 was prepared as follows:
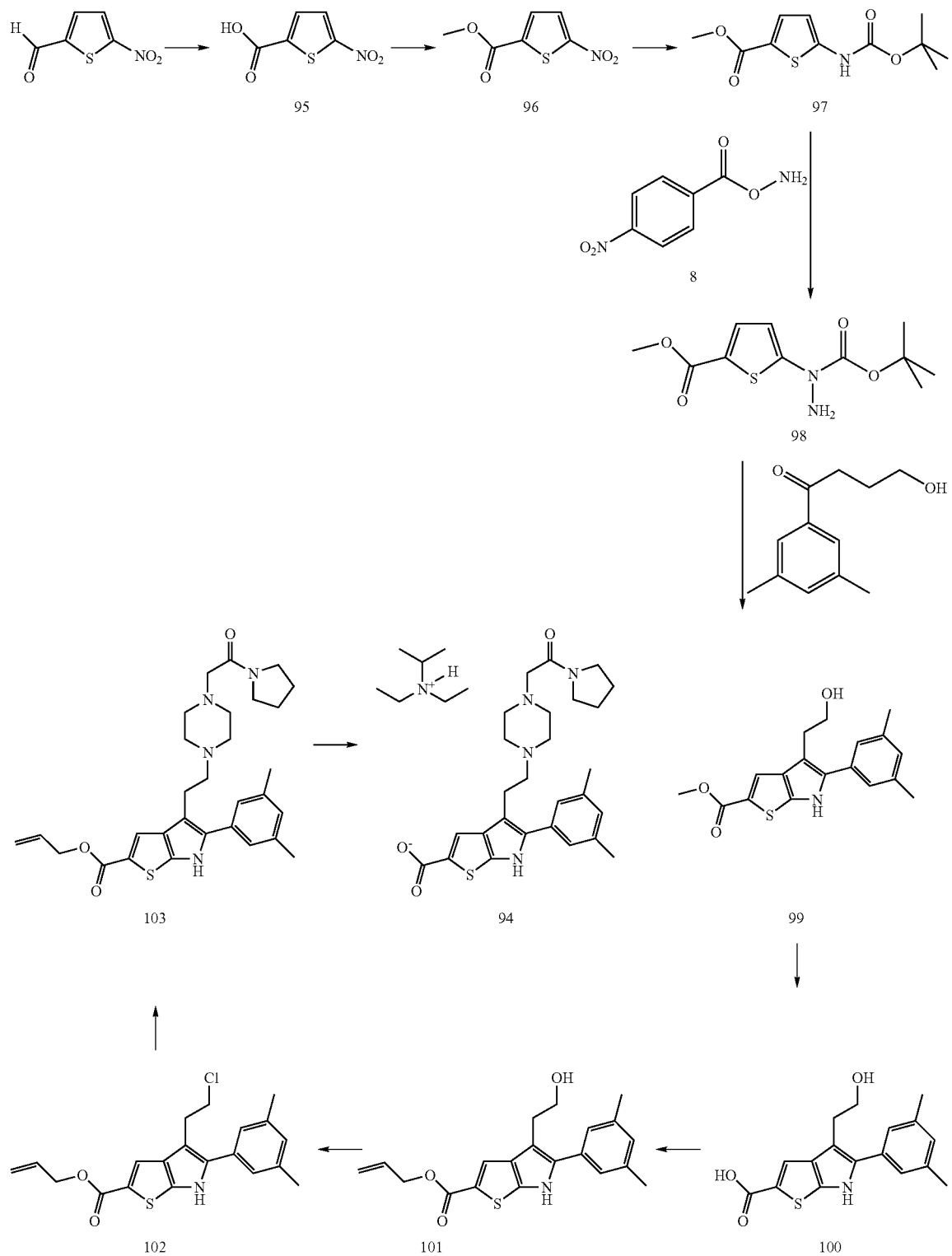

To a stirred solution of potassium dichromate (35.1 g; 143 mmol) in 5N $H_2SO_4$ (375 ml) at 0° C., was added solid 2-formyl-5-nitrothiophene (50.0 g; 318 mmol). The resulting suspension was heated to 100° C. for 1 hour after which HPLC showed no remaining starting material. The reaction mixture was cooled to room temperature, diluted with water (300 ml) and the resulting precipitate collected by filtration, washed with water (5×200 ml) and dried to a constant weight in a vacuum oven at 40° C. to afford 95 (39.5 g) as a light green solid.

Yield: 72% $^1$H NMR (DMSO-$d_6$) 7.70 (d, 1H); 8.09 (d, 1H).

To a stirred solution of 95 (40.0 g; 230 mmol) in DMF-acetone (1:5, 200 ml) at −10° C., were added potassium carbonate (95.8 g; 694 mmol) followed by dimethylsulfate (43.6 g; 346 mmol) dropwise over 10 minutes. The acetone was removed by evaporation and the resulting suspension was stirred at room temperature for 4 hours after which HPLC showed no remaining starting material. The reaction mixture was cooled to 5° C. and water (1 l) was added affording a thick precipitate, which was collected by filtration, washed with water (2×200 ml) and dried to a constant weight in a vacuum oven to afford 96 (38.3 g) as a beige solid.

Yield: 89% $^1$H NMR (DMSO-$d_6$) 3.85 (s, 3H); 7.74 (d, 1H); 8.21 (d, 1H).

To a stirred solution of 96 (35 g; 187 mmol) in MeOH (400 ml) was added a suspension of 10% palladium on carbon (30 g) in AcOH (100 ml)The resulting suspension was exposed to 1 atmosphere of hydrogen for 8 hours after which HPLC showed no remaining starting material. The catalyst was removed by filtration through a pad of Celite and the filtrate was evaporated to dryness and the residue purified by flash chromatography on silica gel eluting with DCM-MeOH (98:2) to afford the amine (11.4 g) as an off-white solid, which was used immediately in the next step. To a stirred solution of the amine (11.4 g; 72.9 mmol) in THF (20 ml) was added di-tert-butyldicarbonate ((Boc)$_2$O) (17.5 g; 80.2 mmol). The resulting solution was heated to reflux for 3 days after which HPLC showed no remaining starting material. The reaction mixture was evaporated to dryness and the residue obtained was triturated with diethyl ether (100 ml). The resulting precipitate was collected by filtration, washed with diethyl ether (2×50 ml) and dried to a constant weight to afford 97 (15.1 g) as an off-white crystalline solid.

Yield: 32% MS-ESI: 258 [M+H]$^{+1}$H NMR (DMSO-$d_6$) 1.53 (s, 9H), 3.74 (s, 3H); 6.55 (d, 1H); 7.57 (d, 1H).

To a stirred solution of 97 (13.2 g; 51.4 mmol) in DMF at −10° C. in an acetone-ice bath, was added a 60% (w/w) suspension of sodium hydride in mineral oil (2.26 g; 56.5 mmol). The resulting orange suspension was allowed to warm to room temperature and stirred for 1 hour. The reaction mixture was cooled again to −10° C., and a solution of 8 (10.3 g; 56.5 mmol) in DMF (50 ml) over a period of 10 minutes. During the addition of the last 10 ml the suspension thickened and diethyl ether (200 ml) was added to mobilise the suspension. The resulting suspension was stirred for a further 2 hours at room temperature after which HPLC showed no remaining starting material. The precipitate was collected by filtration, washed with diethyl ether (3×100 ml) and the filtrate was washed with water (3×100 ml), dried over magnesium sulfate and evaporated to afford an orange oil. The oil was dissolved in diethyl ether (300 ml), cooled to 0° C. and a 4.0M solution of HCl in 1,4-dioxane was added over a period of 10 minutes. The resulting thick white precipitate was collected by filtration, washed with diethyl ether (2×50 ml) and dried to a constant weight to afford 98 (9.63 g) as a white solid.

Yield: 61% MS-ESI: 273 [M+H]$^+$

To a stirred solution of 98 (10.0 g; 32.5 mmol) and 22 (7.85 g; 48.7 mmol) in 2-butanol at room temperature, was added zinc chloride (6.57 g; 48.7 mmol). The resulting suspension was heated at 110° C. for 3 hours. The reaction mixture was evaporated to dryness and the residue was purified by flash chromatography on silica gel eluting with DCM-acetonitrile (4:1) to afford 99 (7.1 g) as a beige solid.

Yield: 66% MS-ESI: 330 [M+H]$^+$

To a stirred solution of 99 (7.1 g; 21.5 mmol) in ethanol (50 ml) was added a solution of NaOH (4.3 g; 107 mmol) in water (22 ml). The resulting solution was heated at 70° C. for 1 hour after which HPLC showed no remaining starting material. The ethanol was removed on a rotary evaporator and to the remaining concentrate at 5° C. was added, with rapid agitation, concentrated HCl over period of 10 minutes. The resulting precipitate was collected by filtration, washed with water (3×100 ml) and dried to a constant weight in a vacuum oven at 40° C. to afford 100 (5.81 g).

Yield: 86% MS-ESI: 316 [M+H]$^+$

To a stirred suspension of 100 (5.81 g; 18.4 mmol) and potassium carbonate (3.31 g; 24.0 mmol) in DMF (100 ml) at 0° C., was added dropwise neat allyl bromide (2.45 g; 20.5 mmol) over a period of 10 minutes. The reaction mixture was stirred at room temperature for a further 4 hours after which HPLC showed no remaining starting material. The reaction mixture was triturated with water (300 ml) affording an oil. The liquid was removed by decantation and the oily residue dissolved in diethyl ether (300 ml), washed with water (3×100 ml), dried over magnesium sulfate and evaporated to afford 101 (5.84 g; 89.4%) as a beige foam which was used without further purification.

Yield: 89% MS-ESI: 355 [M+H]$^{-1}$H NMR (CDCl$_3$) 2.36 (s, 6H); 3.07 (t, 2H); 3.94 (t, 2H); 4.82 (d, 2H); 5.28 (dd, 1H); 5.42 (dd, 1H); 5.98–6.08 (m, 1H); 6.97 (s, 1H); 7.12 (s, 2H); 7.84 (s, 1H); 8.35 (s, 1H).

To a stirred solution of 101 (5.44 g; 15.4 mmol) in acetonitrile (50 ml) at 0° C., were added CCl$_4$ (5 ml) followed by triphenylphosphine (4.49 g; 16.9 mmol). The resulting orange solution was allowed to warm to room temperature and stirred for 4 hours after which HPLC showed no remaining starting material. The reaction mixture was evaporated to dryness to afford an orange residue, which was purified by flash chromatography on silica gel eluting with DCM to afford 102 (5.02 g) as an orange foam.

Yield: 88% MS-ESI: 371 [M+H]$^{-1}$NMR (CDCl$_3$) 2.39 (s, 6H); 3.25 (t, 211); 3.75 (t, 2H); 4.83 (d, 2H); 5.32 (dd, 1H); 5.44 (dd, 1H); 6.01–6.12 (m, 1H); 7.03 (s, 1H); 7.08 (s, 2H); 7.86 (s, 1H); 8.35 (s, 1H).

To a stirred solution of 102 (4.20 g; 11.3 mmol) in DMA (20 ml) were added sodium iodide (1.69 g; 11.3 mmol), potassium carbonate (2.35 g; 17.0 mmol) and 1-pyrrolidinocarbonylmethylpiperazine (3.35 g; 17.0 mmol). The resulting suspension was heated at 85° C. for 3 hours after which HPLC showed no remaining starting material. The reaction mixture was allowed to cool to room temperature and triturated with water (100 ml) affording a thick beige precipitate which was collected by filtration, washed with water (3 c 20 ml) and dried to a constant weight in a vacuum oven at 40° C. to afford 103 (6.03 g) which was used without further purification.

Yield: 100% MS-ESI: 535 [M+H]$^+$

To a stirred solution of 103 (6.93 g; 11.3 mmol) in THF (60 ml) at room temperature was added morpholine (0.984 g; 11.30 mmol) and Pd(PPh$_3$)$_4$(3.91 g; 3.89 mmol). The reaction mixture was stirred at room temperature for 3 hours after which HPLC showed no remaining starting material. The reaction mixture was evaporated to dryness and the residue was dissolved in MeOH (10 ml) and DIPEA (5 ml) was added. The resulting solution was evaporated to dryness to afford an orange oil. Toluene (10 ml) was added and the residue was evaporated to dryness again. The resulting orange oil was triturated with diethyl ether (100 ml) affording a grey precipitate, which was collected by filtration, washed with diethyl ether (2×10 ml) and dried to a constant weight to afford 94 (5.50 g) which was used without further purification.

Yield: 78% MS-ESI: 495 [M+H]$^+$

Example 38

2-[1,1-Dimethyl-2-oxo-2-azabicyclo[2.2.1]heptan7-ylethyl]-4-[1S-methyl-2-(4-{pyrrolidin-1-ylcarbonylmethyl}piperidin-1-yl)ethyl]-5-(3,5-dimethylphenyl)-6H-thieno[2,3-b]pyrrole

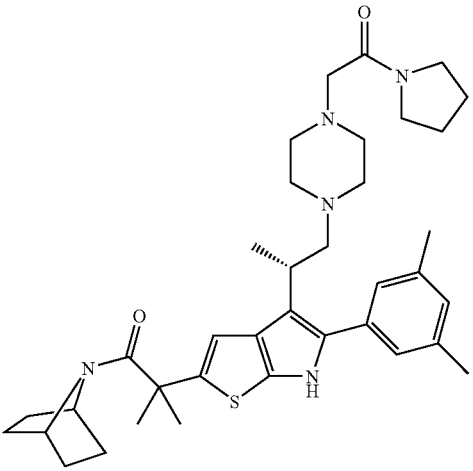

Example 38

To a stirred solution of 104 (0.27 g; 0.345 mmol) in MeOH (5 ml) at room temperature, was added solid magnesium powder (0.083 g; 3.45 mmol). The resulting suspension was stirred vigorously for 6 hours. The reaction mixture was cooled to 5° C. and a saturated solution of ammonium chloride (2 ml) was added. The resulting gel was mobilised with MeOH (20 ml) and filtered. The filtrate was evaporated to dryness and the residue dissolved in DMF (1 ml) and purified by preparative LCMS (standard basic system) to afford example 38 (0.132 g) as a beige solid.

Yield: 61% MS-ESI: 630 [M+H]$^{+1}$H NMR (CDCl$_3$) 1.21–1.42 (m, 7H); 1.45–1.75 (m, 12H); 1.85 (m, 2H); 1.93 (m, 2H); 2.36 (s, 6H); 2.40–2.69 (m, 8H); 3.05 (m, 2H); 3.26 (m, 1H); 3.48 (m, 4H); 4.08 (br, s 1H); 4.73 (br s, 1H); 6.75 (s, 1H); 6.94 (s, 1H); 7.07 (s, 2H); 8.08 (s, 1H).

Intermediate 104 was prepared as follows:

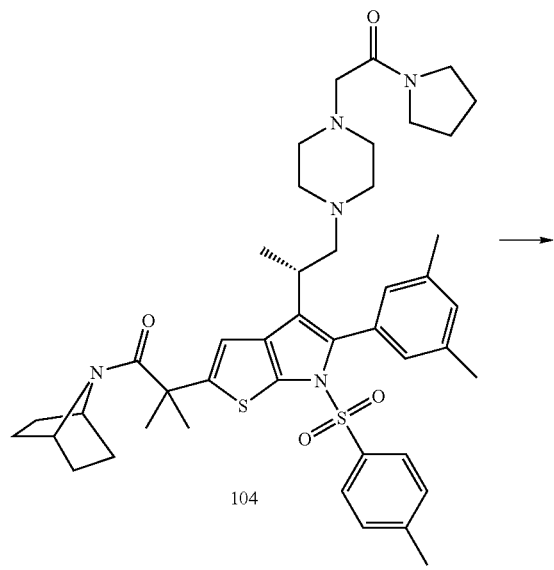

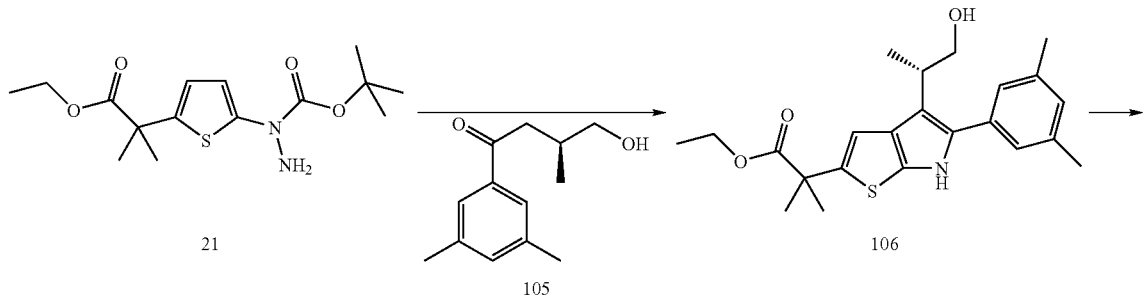

-continued

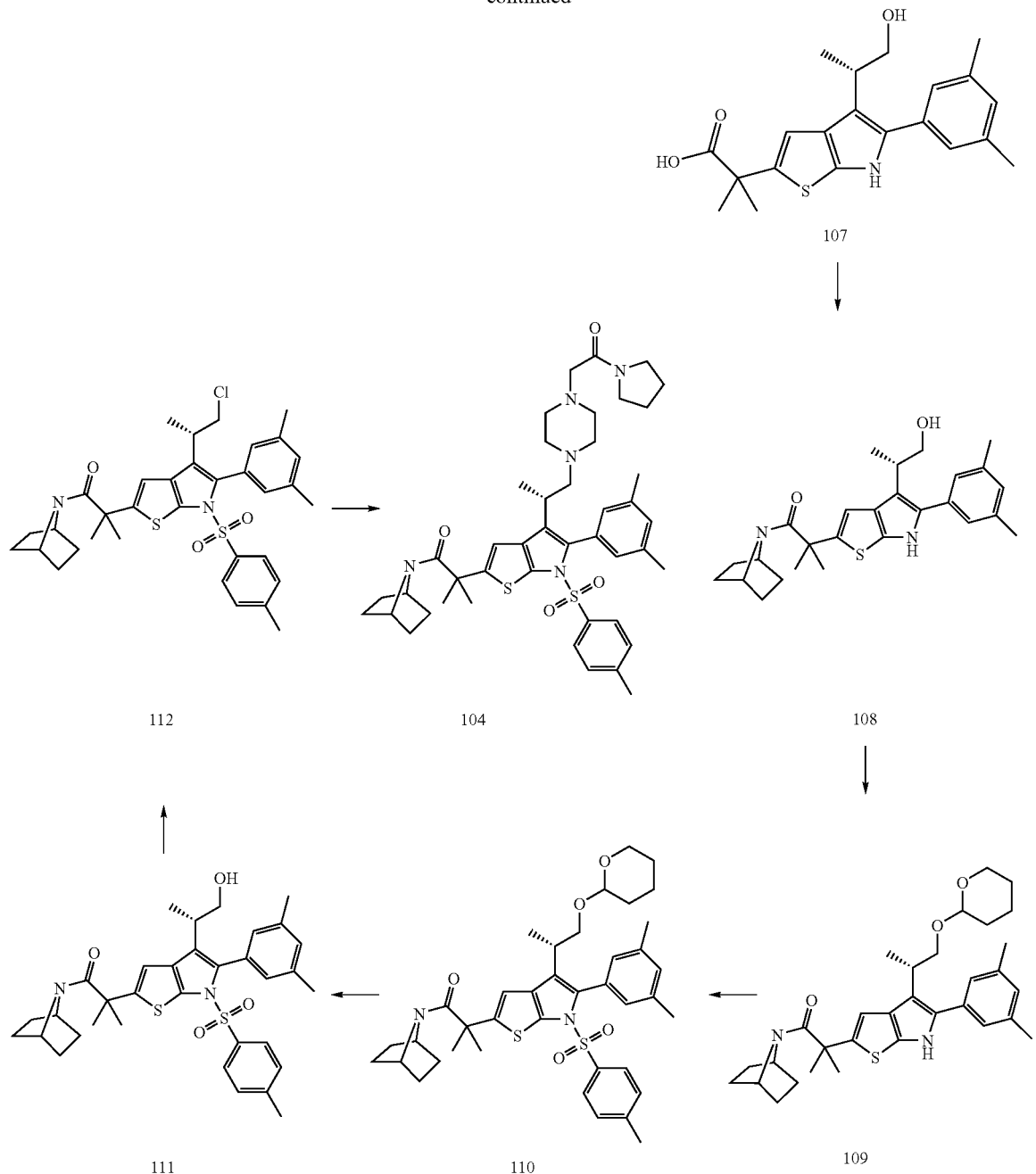

To a stirred solution of 105 (28.6 g; 139 mmol) in 2-butanol (250 ml) at 110° C. was added 21 (46.0 g; 126.4 mmol) over a period of 30 minutes. The reaction mixture was maintained at 110° C. for 2 hours. The reaction mixture was cooled to room temperature and zinc chloride (25.8 g; 190 mmol) was added. The resulting dark brown solution was heated at 110° C. for a further 3 hours after which HPLC showed no remaining starting material. The solvent was removed on a rotary evaporator and the dark brown residue purified by flash chromatography on silica gel eluting with DCM-ethyl acetate (9:1) to afford 106 (14.5 g) as a beige foam.

Yield: 29% MS-ESI: 400 [M+H]$^{+1}$H NMR (DMSO-d$_6$) 1.15 (t, 3H); 1.33 (d, 3H); 1.71 (s, 6H); 2.33 (s, 6H); 3.05 (m, 1H); 4.06 (m, 2H); 4.60 (t, 1H); 6.87 (s, 1H); 6.93 (s, 1H); 7.07 (s, 1H).

To a stirred solution of 106 (8.00 g; 20.1 mmol) in ethanol (200 ml) was added an aqueous solution of 1N NaOH (100 ml). The resulting solution was heated a 70° C. for 3 hours after which HPLC showed no remaining starting material. The ethanol was removed on a rotary evaporator and the remaining aqeous solution was cooled to 5° C. and acidified to pH 1 by the addition of concentrated HCl. The resulting precipitate was collected by filtration, washed to a neutral pH with water (5×50 ml) and dried to a constant weight to afford 107 (7.46 g) as a brown solid which was used without further purification.

Yield: 100% MS-ESI: 372 [M+H]⁺ ¹H NMR (CDCl₃) 1.32 (d, 3H); 1.73 (s, 6H); 2.33 (s, 6H); 3.26 (m, 1H); 3.80 (m, 3H); 6.94 (overlapping s, 2H); 7.08 (s, 2H); 8.12 (s, 1H).

To a stirred solution of the 107 (7.46 g; 20.0 mmol) in DCM (200 ml) at 0° C., were added DIPEA (10.4 g; 80.0 mmol) and 27.HCl (2.64 g; 20.0 mmol). Solid HATU (11.5 g; 30.2 mmol) was then added portionwise over a period of 5 minutes. The resulting solution was allowed to warm to room temperature and stirred for 1 hour after which HPLC showed no remaining starting material. The reaction mixture was diluted with DCM (100 ml), washed with 1N HCl (2×20 ml), water (2×20 ml), dried over magnesium sulfate and evaporated to dryness affording 108 (7.46 g) as a beige solid which was used without further purification.

Yield: 83% MS-ESI: 451 [M+H]⁺

To a stirred solution of 108 (7.6 g; 16.9 mmol) in THF (50 ml) at room temperature was added pyridinium p-toluenesulfonate (PPTS) (0.850 g; 3.4 mmol) and 3,4-dihydropyran (DHP) (4.62 g; 0.7 mmol). The resulting solution was heated to reflux for 3 hours after which HPLC showed no remaining starting material. The solvent was removed by evaporation and the residue purified by flash chromatography on silica gel eluting with DCM-ethyl acetate (4:1) to afford 109 (7.20 g).

Yield: 80% MS-ESI: 535 [M+H]⁺

To a stirred solution of 109 (7.0 g; 13.1 mmol) in THF (100 ml) at −10° C. was added a 60% (w/w) suspension of sodium hydride in mineral oil (0.682 g; 17.0 mmol) followed by solid p-toluenesulfonyl chloride (2.75 g; 14.4 mmol) over a period of 10 minutes. The reaction mixture was allowed to warm to room temperature and stirred for 3 hours after which HPLC indicated a complete conversion to 110. Concentrated HCl was added dropwise and the resulting solution was stirred for a further 2 hours at room temperature after which HPLC indicated a completed conversion of 110 to 111. The solvent was removed on a rotary evaporator and the residue was partitioned between water (100 ml) and DCM (300 ml). The organic layer was washed with a saturated aqueous solution of sodium bicarbonate (100 ml), brine (2×50 ml), dried over magnesium sulfate and evaporated to dryness to afford a white foam which. The foam was triturated with diethyl ether (30 ml) and the resulting mobile solid was collected by filtration, washed with diethyl ether (4×10 ml) and dried to a constant weight in a vacuum oven at 40° C. to afford 111 (2.12 g), which was used without any further purification.

Yield: 27% MS-ESI: 605 [M+H]⁺ ¹H NMR (DMSO-d₆) 1.06 (d, 3H); 1.20–1.50 (m, 8H); 1.57 (s, 6H); 2.26 (s, 6H); 2.50 (m, 1H); 3.05 (m, 2H); 3.26 (m, 1H); 3.48 (m, 4H); 4.00 (br s, 1H); 4.50 (br s, 1H); 6.65 (br s, 1H); 6.73 (br s, 1H); 6.85 (s, 1H); 7.06 (s, 1H); 7.22 (d, 2H); 7.34 (d, 2H).

To a stirred solution of 111 (1.0 g; 1.66 mmol) in acetonitrile (5 ml) at room temperature was added CCl₄ (0.5 ml) followed by triphenylphosphine (0.482 g; 1.82 mmol). The resulting suspension was stirred at room temperature for 3 hours after which HPLC indicated no remaining starting material. The solid was collected by filtration, washed with cold acetonitrile and dried to a constant weight to afford 112 (0.542 g) as a white solid.

Yield: 53% MS-ESI: 623 [M+H]⁺

To a stirred suspension of 112 (0.45 g; 0.721 mmol), potassium carbonate (0.50 g; 3.62 mmol) and sodium iodide (0.106 g; 0.721 mmol) in DMA (2 ml) at room temperature, was added 1-pyrrolidinocarbonylmethyl piperazine (0.712 g; 3.62 mmol). The resulting suspension was heated at 110° C. for 12 hours after which HPLC showed no remaining starting material. The reaction mixture was triturated with water (20 ml) and the resulting beige precipitate was collected by filtration, washed with water (2×10 ml) and dried to a constant weight. The resulting solid was dissolved in DCM (3 ml) and purified by flash chromatography eluting with DCM-MeOH (98:2) to afford 104 (0.270 g) as a beige solid.

Yield: 48% MS-ESI: 784 M+H]⁺

Example 39

2-[1,1-Dimethyl-2-oxo-2-azabicyclo[2.2.1]heptan-7-ylethyl]-4-[2-(3-oxo-4-{pyrrolidin-1-ylcarbonylmethyl}piperazin-1-yl)ethyl]-5-(3,5-dimethylphenyl)-6H-thieno[2,3-b]pyrrole

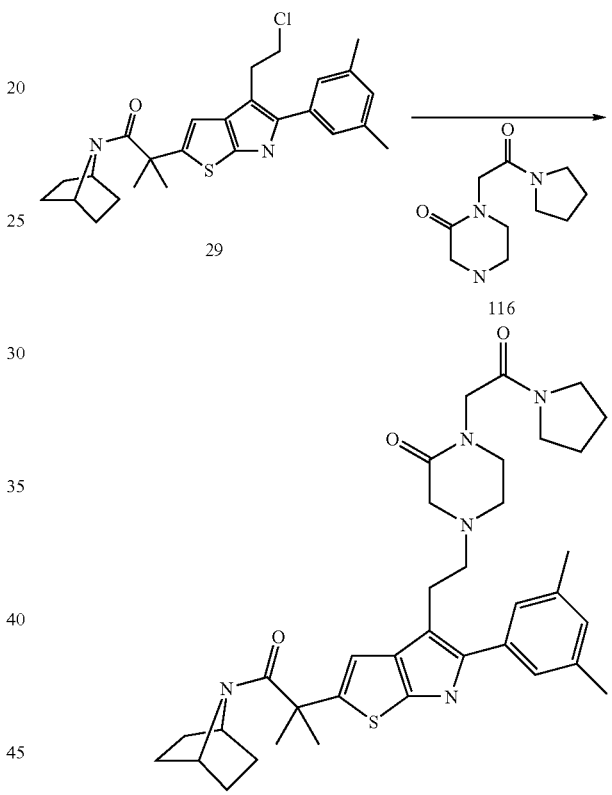

Example 39

To a stirred solution of 22 (0.30 g; 0.66 mmol) in DMA (3 ml) at room temperature were added potassium carbonate (0.27 g; 1.98 mmol) and 134 (0.42 g; 1.98 mmol). The resulting suspension was heated to 130° C. for 8 hours after which HPLC showed no remaining starting material. The reaction mixture was cooled to room temperature and triturated with water (10 ml). The resulting precipitate was collected by filtration, washed with water (2×5 ml) and dried. The resulting beige solid was dissolved in DCM (3 ml) and purified by flash chromatography on silica gel eluting with DCM-methanol (95:5) to afford Example 39 (0.12 g) as a white foam.

Yield: 25% MS-ESI: 630 [M+H]⁺ ¹H NMR (CDCl₃) 1.25–1.39 (m, 4H); 1.45–1.76 (m, 10H); 1.84 (m, 2H); 1.95 (m, 2H); 2.37 (s, 6H); 2.72 (m, 2H); 2.79 (m, 2H); 2.96 (m, 2H); 3.28 (s, 2H); 3.38 (m, 6H); 4.12 (2 overlapping s, 3H); 4.75 (br s, 1H); 6.73 (br s, 1H); 6.94 (s, 1H); 7.04 (s, 2H); 8.14 (s, 1H).

The intermediate 116 was prepared as follows:

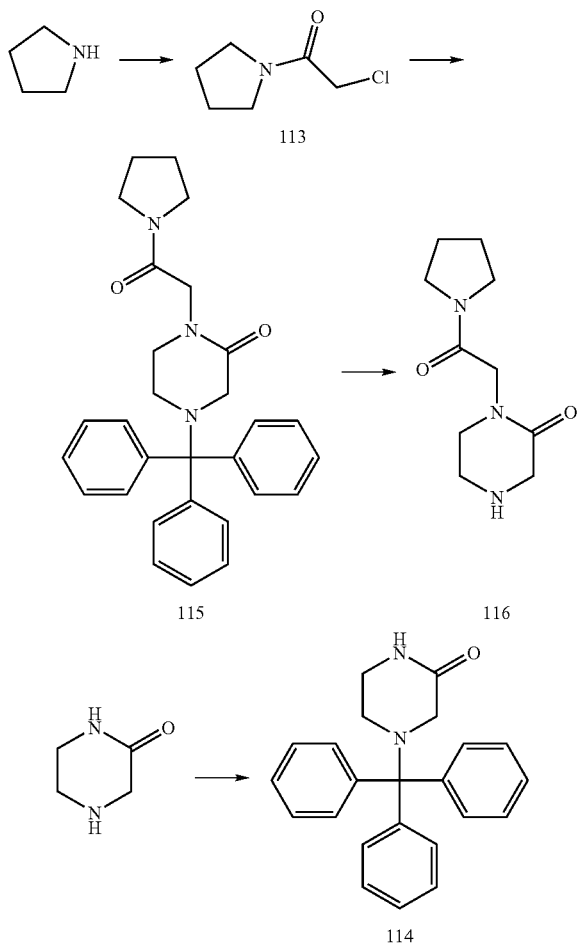

To a stirred solution of pyrrolidine (1.0 g; 14.1 mmol) and triethylamine (1.57 g; 15.5 mmol) in DCM (20 ml) at −10° C., was added chloroacetyl chloride (1.52 g; 13.4 mmol) over a period of 10 minutes. The reaction mxiture was diluted with DCM (20 ml) and washed with 2N HCl (2×10 ml), water (2×10 ml) and dried over magnesium sulfate. The organic layer was evaoprated to dryness to afford 113 (1.30 g).

Yield: 66%. $^1$H NMR (CDCl$_3$) 1.88 (m, 4H); 1.95 (m, 2H); 3.50 (m, 4H); 4.03 (s, 2H).

To a stirred solution of piperazin-2-one (2.0 g; 19.9 mmol) and triethylamine (2.42 g; 23.9 mmol) in THF (20 ml) at −10° C. in an acetone-ice bath, was added solid triphenyl-methylchloride (5.57 g; 19.9 mmol) over a period of 5 minutes. The reaction mixture was allowed to warm to room temperature and stirred over night after which HPLC showed no remaining starting material. The solvent was removed on a rotary evaporator and the the resulting white solid washed with diethyl ether (3×50 ml), water (4×50 ml) and dried to a constant weight in a vacuum oven to afford 114 (6.8 g) as a white solid.

Yield: 100%. $^1$H NMR (CDCl$_3$) (δ ppm) 2.50 (m, 2H); 3.11 (m, 2H); 3.46 (s, 2H); 5.93 (s,1H); 7.21 (m, 3H); 7.31 (m, 7H); 7.35 (m, 5H).

To a stirred solution of 114 (1.0 g; 5.84 mmol) in DMF (50 ml), was added a 60% (w/w) suspension of NaH in mineral oil (0.26 g; 6.43 mmol) at 0° C. The reaction mixture was allowed to stir for 1 hour at 0° C. before 113 (0.864 g; 5.84 mmol) was added portionwise over a period of 5 minutes. The resulting solution was allowed to warm to room temperature and stirred for an additional hour. The reaction mxiture was cooled to 0° C., triturated with water (100 ml) and the resulting precipitate was collected by filtration, washed with water (3×20 ml) and dried to a constant weight to afford 115 (2.20 g) as a white solid which was used without further purification.

Yield: 83%. $^1$H NMR (CDCl$_3$) 1.83 (m, 2H); 1.97 (m, 2H); 2.46 (m, 2H); 3.15 (m, 2H); 3.46 (m, 4H); 3.49 (m, 2H); 4.12 (s, 2H); 7.17 (m, 3H); 7.27 (m, 7H); 7.46 (m, 5H).

To a stirred solution of 115 (2.2 g; 4.80 mmol) in MeOH (20 ml) at room temperature, was added concentrated HCl (2 ml) in one portion. The reaction mxiture was stirred at room temperature for 1 hour after which TLC (SiO$_2$, DCM) showed no remainig starting material. The solvent was removed on a rotary evaporator to afford an oily orange residue. Toluene (50 ml) was added and the resulting suspension was evaporated to dryness to afford a thick orange oil which was dried under high vacuum to afford 116 (1.2 g; 100%) as an orange foam which was used without further purification.

Yield: 100%

Example 40

2-[1,1-Dimethyl-2-oxo-2-azabicyclo[2.2.1]heptan-7-ylethyl]-4-[2-(4-{4-oxo-4-pyrrolidin-1-ylbut-3-yl}piperazin-1-yl)ethyl]-5-(3,5-dimethylphenyl)-6H-thieno[2,3-b]pyrrole

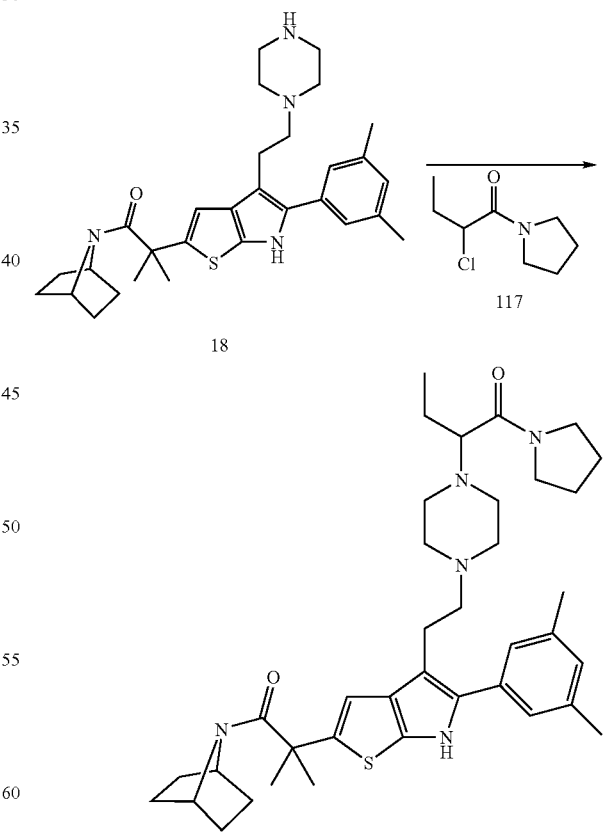

Example 40

To a stirred solution of 18 (0.30 g; 0.595 mmol) in DMF (1 ml) was added 117 (0.23 g; 1.19 mmol). The reaction mixture was heated at 130° C. for 8 hours after which HPLC showed no remaining starting material. The reaction mixture was purified by flahs chromatography on silica gel eluting with DCM-MeOH (96:4) to afford example 40 (0.09 g) as a beige solid.

Yield: 24% MS-ESI: 644 [M+H]$^{+1}$H NMR (CDCl$_3$) 0.83 (t, 3H); 1.17 (m, 2H); 1.25–1.39 (br m, 4H); 1.45–1.76 (m, 8H); 1.84 (m, 2H); 1.91 (m, 6H); 2.33 (s, 6H); 2.46–2.79 (m, 8H); 2.94 (m, 2H); 3.14 (m, 1H); 3.45 (m, 3H); 3.65 (m, 1H); 4.10 (br s,1H); 4.74 (br s, 1H); 6.73 (s, 1H); 6.92 (s, 1H); 7.04 (s, 2H); 8.16 (s, 1H).

The intermediate 117 was prepared as follows:

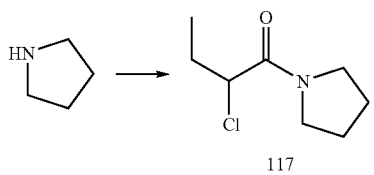

117

To a stirred suspension of pyrrolidine (1.0 g; 14.1 mmol) and triethylamine (1.57 g; 15.5 mmol) in DCM (20 ml) at −10° C., was added 2-chlorobutyryl chloride (1.80 g; 12.7 mmol) over a period of 10 minutes. The reaction mixture was allowed to warm to room temperature and stirred for an additional hour after. The reaction mixture was diluted with DCM (20 ml) and washed with 2N HCl (10 ml), water (2×10 ml), dried over magnesium sulfate and evaporated to dryness on a rotary evaporator to afford 117 (1.2 g).

Yield: 54% $^1$H NMR (CDCl$_3$) 1.03 (t, 3H); 1.61 (m, 2H); 1.84–2.01 (m, 4H); 2.10 (m, 1H); 3.45 (m, 2H); 3.66 (m, 1H); 4.21 (m,1H).

Example 41

2-[1,1-Dimethyl-2-oxo-2-azabicyclo[2.2.1]heptan-7-ylethyl]-4-[2-(4-{3-oxo-3-pyrrolidin-1-ylprop-2-yl}piperazin-1-yl)ethyl]-5-(3,5-dimethylphenyl)-6H-thieno[2,3-b]pyrrole

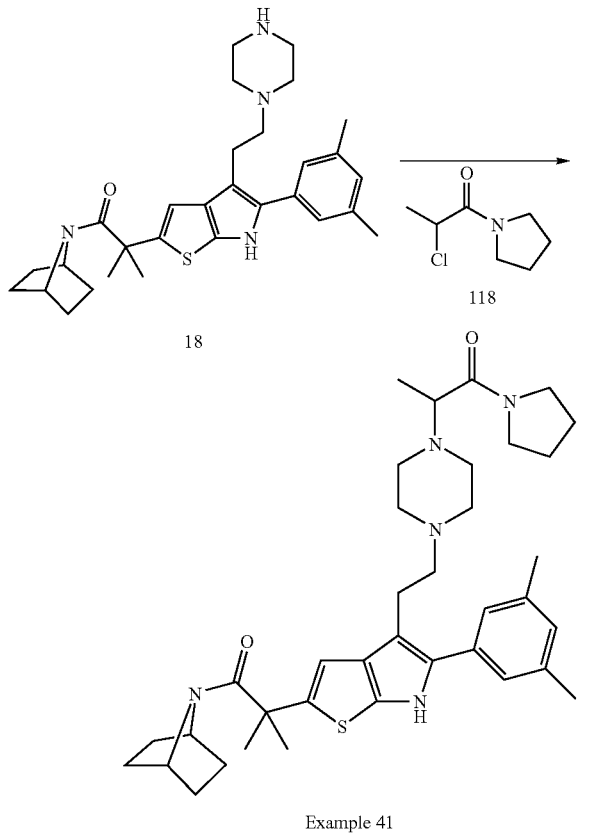

Example 41

Starting from 18 (0.40 g; 0.794 mmol) using a similar procedure described for the synthesis of example 40, example 41 (0.12 g) was obtained as an off-white solid.

Yield: 24% MS-ESI: 630 [M+H]$^{+1}$H NMR (CDCl$_3$) 1.19 (d, 3H); 1.20–1.40 (br m, 4H); 1.45–1.78 (m, 12H); 1.82 (m, 2H); 1.91 (m, 2H); 2.33 (s, 6H); 2.44–2.71 (m, 8H); 2.92 (m, 2H); 3.34 (m, 1H); 3.44 (m, 3H); 3.72 (m, 1H); 4.10 (br s,1H); 4.74 (br s, 1H); 6.72 (s, 1H); 6.93 (s, 1H); 7.03 (s, 2H); 8.21 (s, 1H).

Starting from pyrrolidine (1.0 g; 14.1 mmol) and the appropriate acid chloride using a similar procedure described for the synthesis of 117, 118 (1.47 g) was obtained as a yellow oil.

Yield: 57% $^1$H NMR (CDCl$_3$) 1.65 (d, 3H); 1.86 (m, 2H); 1.95 (m, 2H); 3.5 (m, 3H); 3.69 (m, 1H); 4.47 (m, 1H).

Example 42

2-[1,1-Dimethyl-2-oxo-2-azabicyclo[2.2.1]heptan-7-ylethyl]-4-[2-(4-{pyrrolidin-1-ylcarbonylmethyl}piperazin-1-yl)ethyl]-5-(3,5-dimethylphenyl)-6H-thieno[2,3-b]pyrrole

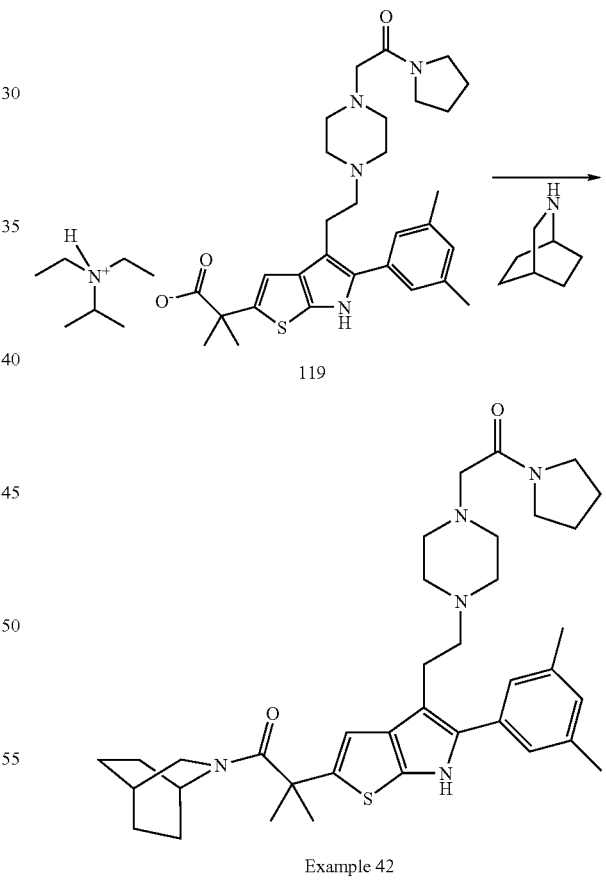

Example 42

To a solution of 119 (0.20 g; 0.30 mmol), 120.HCl (0.123 g; 0.901 mmol) and DIPEA (0.116 g; 0.901 mmol) in DMF (1 ml) at room temperature, was added solid HATU (0.343 g; 0.901 mmol) in one portion. The reaction mixture was allowed to stand for 1 hour after which HPLC showed no remaining starting material. The reaction mixture was puri fied by preparative LCMS (standard basic system) to afford example 42 (0.070 g) as a beige solid.

Yield: 37% MS-ESI: 630 [M+H]$^+$ $^1$H NMR (CDCl$_3$) 1.34–1.69 (m, 20H); 1.85 (m, 2H); 1.94 (m, 2H); 2.34 (s, 6H); 2.5–2.73 (m, 8H); 2.95 (m, 2H); 3.13 (s, 2H); 3.46–3.53 (m, 4H); 6.67 (s, 1H); 6.94 (s, 1H); 7.06 (s, 2H); 8.12 (s, 1H).

The intermediate 119 was prepared as follows:

To a stirred solution of 121 (4.89 g; 12.3 mmol) in acetonitrile (50 Ml) at 0° C., were added CCl$_4$ (5 ml) followed by triphenylphosphine (4.91 g; 18.5 mmol). The resulting orange solution was allowed to warm to room temperature and stirred for 2 hours after which HPLC showed no remaining starting material. The reaction mixture was evaporated to dryness to afford an orange residue, which

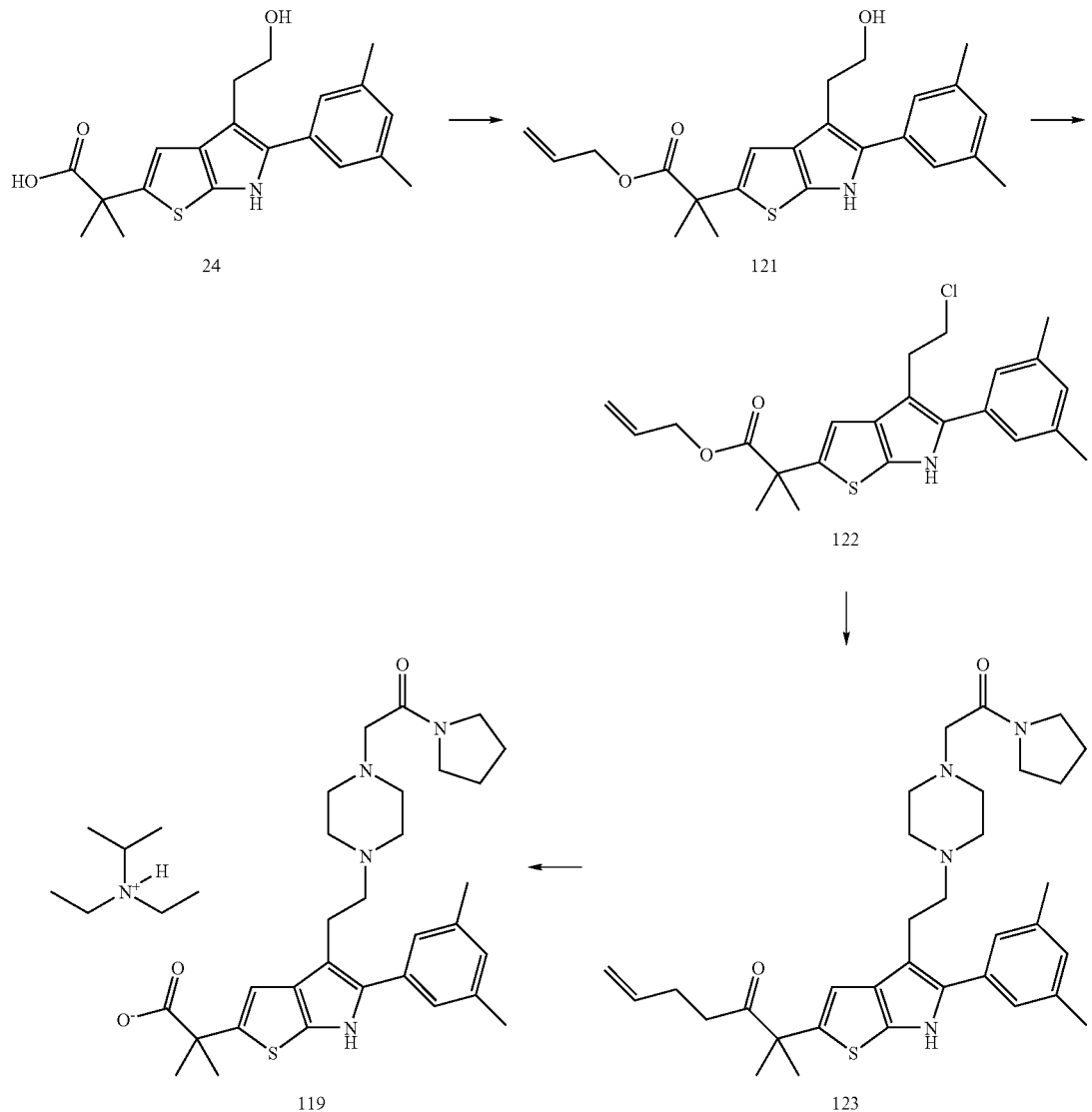

To a stirred suspension of 24 (5.0 g; 14.0 mmol) and potassium carbonate (2.48 g; 18.0 mmol) in DMF (50 ml) at 0° C., was added dropwise neat allyl bromide (1.86 g; 15.4 mmol) over a period of 10 minutes. The reaction mixture was stirred at room temperature for a further 4 hours after which HPLC showed no remaining starting material. The reaction mixture was partitioned between water (100 ml) and diethyl ether (300 ml). The organic layer was retained, washed with water (3×100 ml), dried over magnesium sulfate and evaporated to dryness to afford 121 (4.89 g) as a beige foam which was used without further purification.

Yield: 88% MS-ESI: 397 [M+H]$^+$ was purified by flash chromatography on silica gel eluting with DCM to afford 122 (2.5 g) as an orange foam.

Yield: 49% MS-ESI: 415 [M+H]$^+$

To a stirred solution of 122 (2.50 g; 6.04 mmol) in DMA (20 ml) were added sodium iodide (0.905 g; 6.04 mmol), potassium carbonate (1.24 g; 9.06 mmol) and 1-pyrrolidinocarbonylmethyl piperazine (1.79 g; 9.06 mmol). The resulting suspension was heated at 85° C. for 4 hours after which HPLC showed no remaining starting material. The reaction mixture was allowed to cool to room temperature and triturated with water (100 ml) affording an oil. The water was removed by decantation and the oil dissolved in DCM (100 ml), washed with water (3×10 ml), evaporated to dryness on a rotary evaporator and dried to a constant weight under high vacuum to afford 123 (2.87 g) which was used without further purification.

Yield: 82% MS-ESI: 577 [M+H]$^+$

To a stirred solution of 123 (2.87 g; 4.98 mmol) in THF (40 ml) at room temperature was added morpholine (0.409 g; 4.70 mmol) and Pd(PPh$_3$)$_4$ (1.63 g; 1.91 mmol). The reaction mixture was stirred at room temperature for 3 hours after which HPLC showed no remaining starting material. The reaction mixture was evaporated to dryness and the residue was dissolved in MeOH (10 ml) and DIPEA (5 ml) was added. The resulting solution was evaporated to dryness to afford an orange solid. Toluene (10 ml) was added and the residue was evaporated to dryness again. The resulting orange oil was triturated with diethyl ether (50 ml) affording a precipitate, which was collected by filtration, washed with diethyl ether (2×10 ml) and dried to a constant weight to afford 119 (2.74 g) as a beige solid which was used without further purification.

Yield: 83% MS-ESI: 537 [M+H]$^+$

Example 43

2-[1,1-Dimethyl-2-oxo-2-azabicyclo[2.2.1]heptan-7-ylethyl]-4-[2-(4-{1H-1,2,3-benzotriazol-5-ylaminocarbonylmethyl}piperazin-1-yl)ethyl]-5-(3,5-dimethylphenyl)-6H-thieno[2,3-b]pyrrole

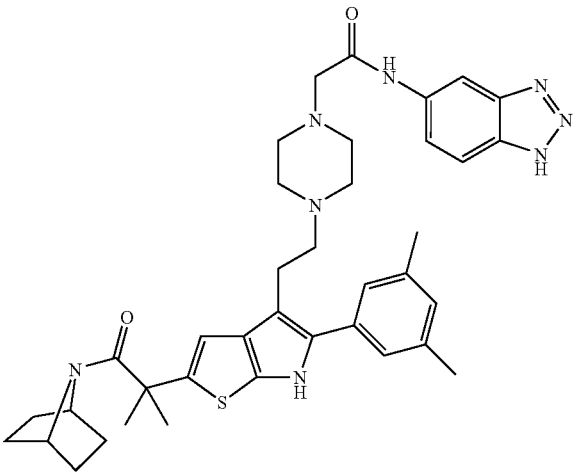

Example 43

To a solution of 125 (0.20 g; 0.334 mmol), 5-aminobenzotriazole (0.067 g; 0.501 mmol) and DIPEA (0.129 g; 1.0 mmol) in DMF (1 ml) at room temperature, was added solid HATU (0.191 g; 0.501 mmol) in one portion. The reaction mixture was allowed to stand for 16 hours after which HPLC showed no remaining starting material. The reaction mixture was purified by preparative LCMS (standard acidic system) to afford example 43 (0.028 g) as a brown solid.

Yield: 12% MS-ESI: 679 [M+H]$^+$ $^1$H NMR (DMSO-d$_6$) 1.24–1.33 (m, 4H); 1.35–1.56 (m, 10H); 1.88 (m, 4H); 2.35 (s, 6H); 2.5–2.73 (m, 2H); 2.84 (m, 2H); 3.15 (s, 2H); 3.46–3.53 (m, 4H); 4.10 (br s, 1H); 4.45 (br s, 1H); 6.81 (s, 1H); 6.92 (s, 1H); 7.09 (s, 2H); 7.43 (d, 1H); 7.86 (d, 1H); 8.32 (s, 1H); 9.94 (s, 1H); 11.26 (s, 1H).

The intermediate 125 was prepared as follows:

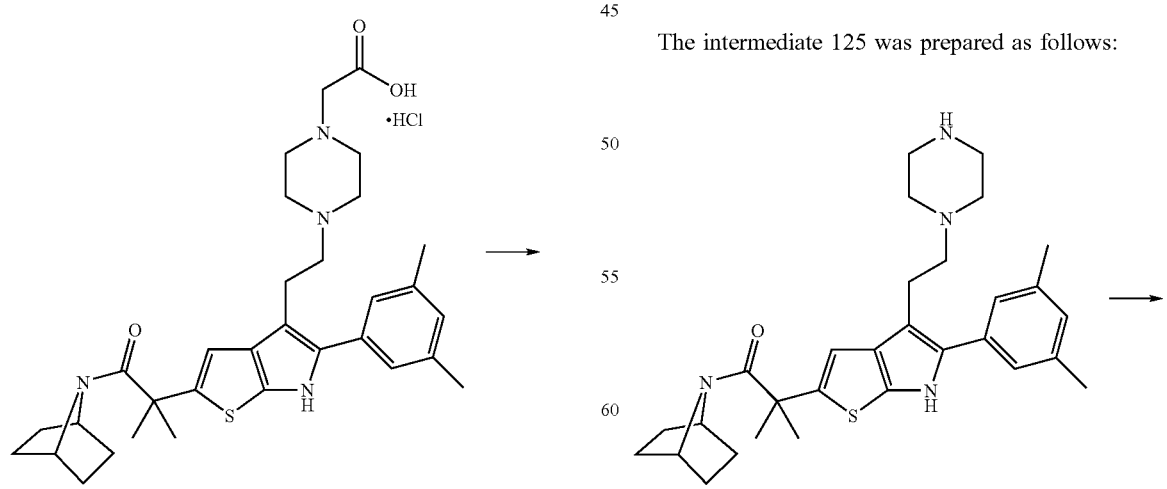

Example 44

2-[1,1-Dimethyl-2-oxo-2-azabicyclo[2.2.1]heptan-7-ylethyl]-4-[2-(4-hydroxy-4-{N,N-diethylaminomethyl}piperidin-1-yl)ethyl]-5-(3,5-dimethylphenyl)-6H-thieno[2,3-b]pyrrole

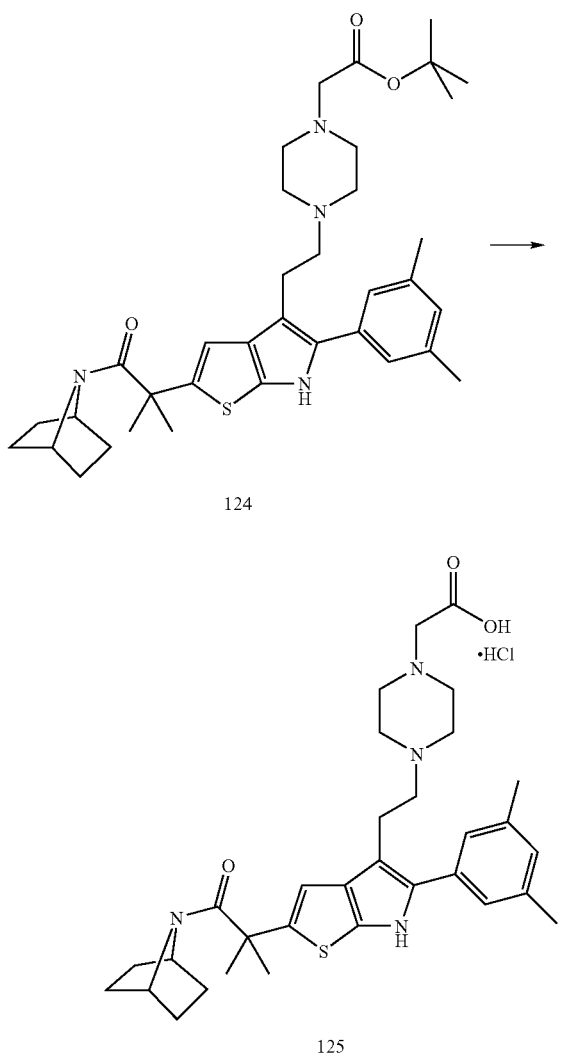

124

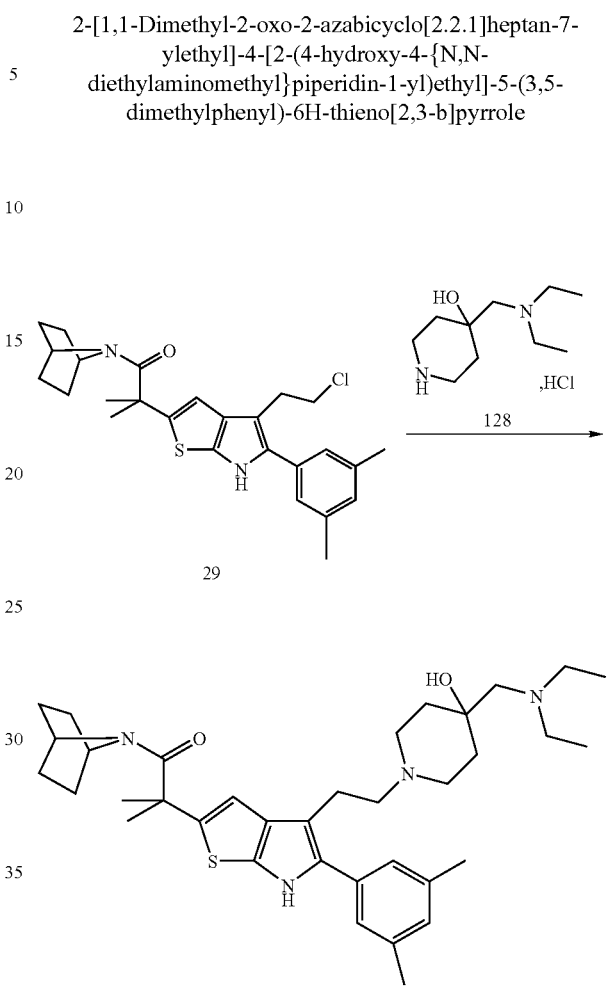

125

To a stirred suspension of 18 (6.82 g; 13.5 mmol) and potassium carbonate (2.43 g; 17.6 mmol) in DMF (20 ml) at room temperature, was added t-butyl bromoacetate (2.64 g; 13.5 mmol). The resulting orange suspension was heated at 50° C. for 2 hours after which HPLC showed no remaining starting material. The reaction mixture was cooled to 0–5° C. and water (300 ml) was added producing a thick precipitate, which was collected by filtration, washed with water (3×50 ml) and dried to a constant weight to afford 124 (7.0 g) as a beige solid.

Yield: 84% MS-ESI: 619[M+H]$^+$

To a stirred solution of 124 (7.0 g; 11.3 mmol) in DCM (50 ml) at room temperature, was added concentrated HCl (10 ml). The reaction mixture was heated at 40° C. for 2 hours after which HPLC showed no remaining starting material. The solvent was evaporated on a rotary evaporator to afford an orange residue. Toluene (50 ml) was added and the resulting oil suspension was evaporated to dryness and dried to a constant weight under high vacuum to afford 125 (6.77 g) as a beige foam which was used without further purification.

Yield: 100% MS-ESI: 563 [M+H]$^+$

A mixture of 29 (0.16 g; 0.35 mmol), 128 (0.153 g, 0.69 mmol), and $K_2CO_3$ (0.153 g; 1.04 mmol) in acetonitrile (3 ml) and DMF (2 ml) was heated at 90° C. under argon atmosphere for 3 hours. The crude mixture was purified by flash chromatography eluting with 3.5 N MeOH—$NH_3$/methylene chloride 95/5 to give after trituration in pentane Example 44 as a solid.

Yield: 51% MS-ESI: 605 [M+H]$^{+1}$H NMR (CDCl$_3$) 1.01 (t, 6H); 1.20–1.44 (m,4H); 1.50–1.70 (m, 8H ); 1.62 (s, 6H); 2.35 (s, 6H); 2.37 (m, 2H ); 2.45 (m, 2H); 2.59 (q, 4H); 2.69 (m, 2H); 2.72 (m, 2H); 2.97 (m, 2H); 4.1 (br s, 1H); 4.61 (br s, 1H); 4.75 (br s, 1H); 6.76 (s, 1H); 6.94 (s, 1H); 7.07 (s, 2H); 8.15 (s, 1H).

The starting material was prepared as follows:

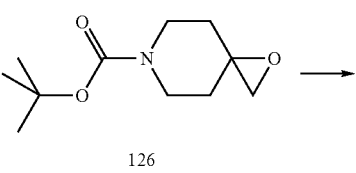

126

-continued

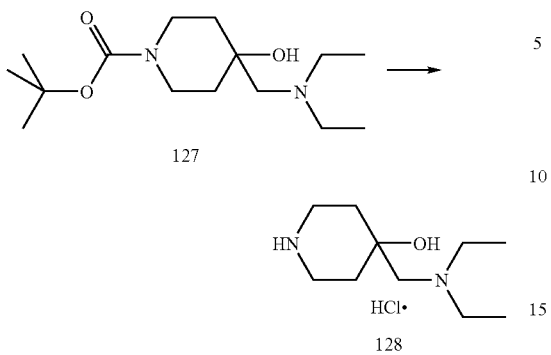

A solution of 126 (0.639 g; 3 mmol) and diethylamine (0.620 ml; 6 mmol) in ethanol (5 ml) was stirred overnight at ambient temperature under argon atmosphere. After evaporation to dryness, the residue was purified by flash chromatography eluting with 3.5 N MeOH—NH₃/methylene chloride 95/5 to give 127 as a solid.

Yield: 86% ¹H NMR (CDCl₃) 1.01 (t, 6H); 1.39 (m, 2H); 1.45 (s, 9H); 1.58 (m, 2H); 2.34 (s, 2H); 2.58 (q, 4); 3.15 (br s, 2H); 4.85 (br s, 2H).

127 (0.465 g; 1.62 mmol) was dissolved in methylene chloride (0.8 ml) and dioxan (6 ml) and treated with a solution made of 12N HCl/dioxan 5/25 (4.5 ml). The mixture was stirred at ambient temperature, under argon atmosphere overnight. After evaporation to dryness, the residue was triturated in a mixture of MeOH, methylene chloride and ether to give 128 as solid.

Yield: 100% ¹H NMR (DMSO-d₆) 1.25 (t, 6H); 1.81 (m, 2H); 1.96 (m, 2H); 2.51 (s, 2H); 3.02–3.30 (m, 6H); 3.37 (br s, 2H).

Example 45

2-[1,1-Dimethyl-2-oxo-2-azabicyclo[2.2.1]heptan-7-ylethyl]-4-[2-(4-methoxy-4-{N,N-diethylaminomethyl}piperidin-1-yl)ethyl]-5-(3,5-dimethylphenyl)-6H-thieno[2,3-b]pyrrole

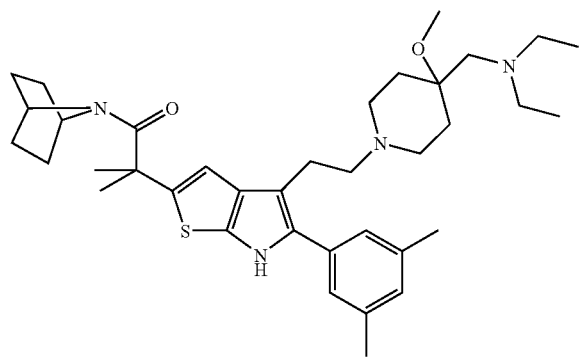

The compound was prepared using a method similar to that described in Example 44 with amine 131 instead of amine 128.

Yield: 72% MS-ESI: 619 [M+H]⁺ ¹H NMR (CDCl₃) 0.97 (t, 6H); 1.20–1.40 (m,4 H); 1.40–1.85 (m, 8H); 1.63 (s, 6H); 2.35 (s, 6H); 2.37–2.55 (m, 4H); 2.57 (q, 4H); 2.85 (m, 2H); 3.04 (m, 4H); 3.19 (s, 3H); 4.10 (br s, 1H); 4.70 (br s, 1H); 6.81 (s, 1H); 6.94 (s, 1H); 7.04 (s, 2H); 8.18 (s, 1H).

The starting material was prepared as follows:

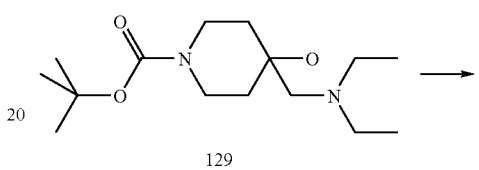

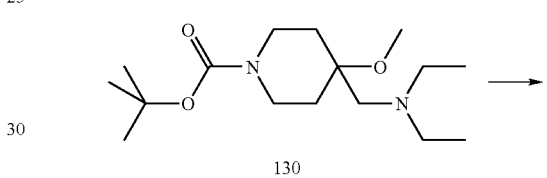

To a stirred solution of 129 (0.82 g; 2.6 mmol) in THF (18 ml), was added a 60% (w/w) suspension of sodium hydride in mineral oil (0.175 g). The resulting suspension was stirred at room temperature for 3 minutes. Methyl iodide (0.3 ml) and 15–5 crown ether were added and the reaction mixture was stirred further overnight. After evaporation to dryness, the residue was purified by flash chromatography eluting with 3.5 N MeOH—NH₃/methylene chloride 97/3 to give 130 as a solid.

Yield: 79% ¹H NMR (CDCl₃) 0.97 (t, 6H); 1.47 (s, 9H); 1.58 (m, 2H); 1.75 (m, 2H); 2.38 (s, 2H); 3.05 (br s, 2H); 3.21 (s, 3H); 3.85 (br s, 2H).

130 (0.680 g; 2.26 mmol) was dissolved in methylene chloride (1.2 ml) and dioxan (9 ml) and treated with a solution made of 12N HCl/dioxan 5/25 (5.5 ml). The mixture was stirred at ambient temperature, under argon atmosphere overnight. After evaporation to dryness, the residue was triturated in a mixture of MeOH, methylene chloride and ether to give 131 as solid.

Yield: 100% ¹H NMR (DMSO-d₆) 1.24 (t, 6H); 1.80 (m, 2H); 2.08 (m, 2H); 2.92 (m, 2H); 3.20 (s, 3H); 3.10–3.30 (m, 8H).

Example 46

2-[1,1-Dimethyl-2-oxo-2-azabicyclo[2.2.1]heptan-7-ylethyl]-4-[4-(pyrrolidin-1-ylcarbonylmethyl)piperazin-1-ylmethyl]-5-(3,5-dimethylphenyl)-6H-thieno[2,3-b]pyrrole

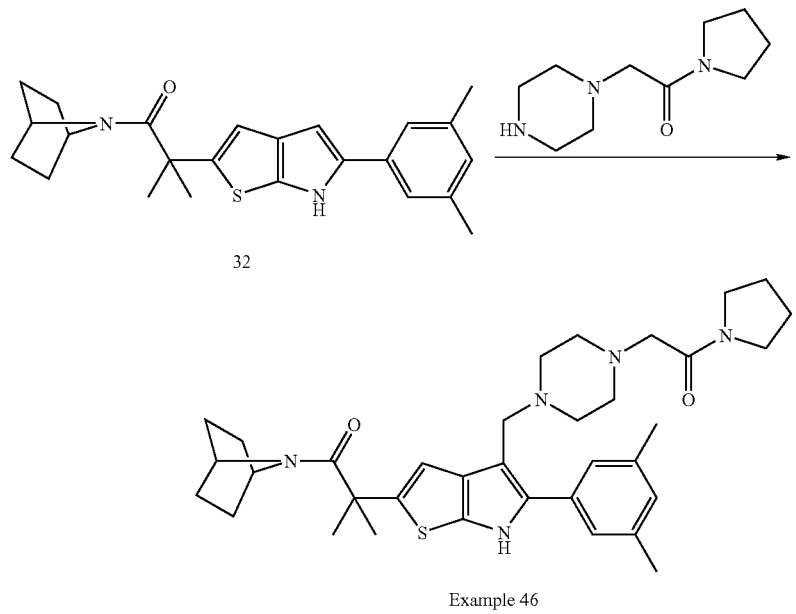

Example 46

To a mixture of 1-[2-Piperazin)-1-yl)acetyl]pyrrolidine (0.065 g; 0.33 mmol) and formaldehyde (0.013 g; 0.16 mmol) in acetic acid (5 ml) was added 32 (0.065 g; 0.17 mmol) in dioxane (8 ml) at room temperature. After 4 hours, the crude mixture was evaporated and purified by flash chromatography eluting with a gradient 2–10% of 3.5 N $NH_3$ in MeOH/methylene chloride to give after trituration in ether/pentane Example 46 as a solid.

Yield: 65% MS-ESI: 602 [M+H]$^+$ $^1$H NMR (CDCl$_3$): 1.20–1.40 (m, 4H); 1.45–1.80 (m, 4H); 1.62 (s, 6H); 1.84 (m, 2H); 1.94 (m, 2H); 2.35 (s, 6H); 2.54 (br m, 8H); 3.10 (s, 2H); 3.54–3.52 (m, 4); 3.54 (s, 2H); 4.14 (br m, 1H); 4.73 (br m, 1H); 6.81 (s, 1H); 6.94 (s, 1H); 7.26 (s, 2H); 8.25 (s, 1H).

Examples 46.1–46.5

Following a procedure similar to that described in Example 46, the compounds of table 46 were prepared.

TABLE 46

| Example | | MS-ESI |
|---|---|---|
| 46.1 | | 590 [M + H]$^+$ |

TABLE 46-continued

| Example | MS-ESI |
|---|---|
| 46.2 | 618 [M + H]+ |
| 46.3 | 576 [M + H]+ |
| 46.4 | 591 [M + H]+ |
| 46.5 | 527 [M + H]+ |

Example 47

2-[1,1-Dimethyl-2-oxo-2-azabicyclo[2.2.1]heptan-7-ylethyl]-4-[4-(2,4-dioxo-1,2,3,4-tetrahydropyrimidin-6-ylmethyl)piperazin-1-ylmethyl]-5-(3,5-dimethylphenyl)-6H-thieno[2,3-b]pyrrole

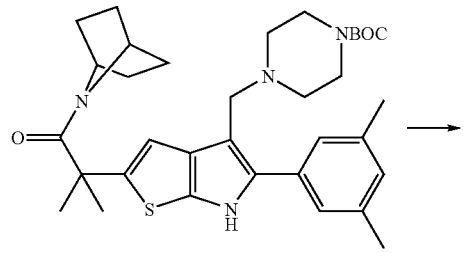
Example 48.4

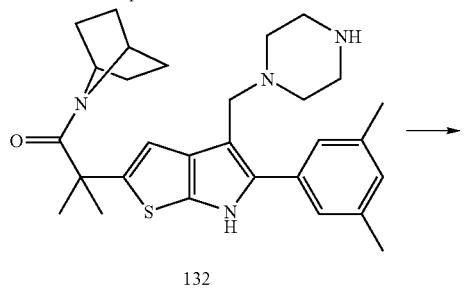
132

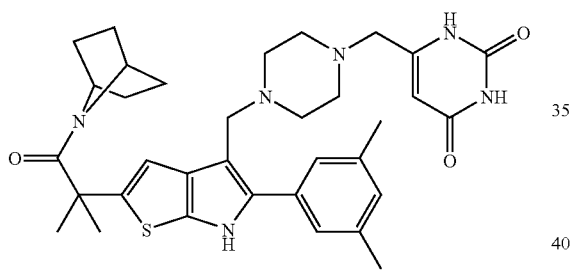
Example 47

A mixture of 132 (0.170 g; 0.35 mmol), chloromethyluracil (0.061 g; 0.38 mmol), NaI (0.057 g; 0.38 mmol) and $K_2CO_3$ (0.053 g; 0.38 mmol) in dimethylacetamide (8 ml) was heated at 80° C. under argon atmosphere for 17 hours. The crude mixture was evaporated and purified by flash chromatography eluting with a gradient 2–8% of 3.5 N $NH_3$ in MeOH/methylene chloride to give after trituration in ether/heptane Example 47 as a pale brown solid.

Yield: 41% MS-ESI: 615 [M+H]$^{+1}$H NMR (CDCl$_3$): 1.20–1.40 (br m, 4H); 1.56 (br m, 4H); 1.63 (s, 6H); 2.36 (s, 6H); 2.36 (s, 6H); 2.50 (br m, 8H); 3.29 (s, 2H); 3.58 (s, 2H); 4.15 (br m, 1H); 4.75 (br m, 1H); 5.53 (s, 1H); 6.80 (s, 1H); 6.96 (s, 1H); 7.21 (s, 2H); 7.97 (br s, 1H); 8.25 (s, 1H); 8.53 (br s, 1H).

Example 46.4 (0.878 g, 1.49 mmol) was deprotected with concentrated HCl (1.5 ml) in dioxane (15 ml) at room temperature for 4 hours. The crude mixture was evaporated, then 100 ml of 3.5 N $NH_3$ in MeOH was added, and evaporated again. The crude residue was purified by flash chromatography eluting with a gradient 0–10% of 3.5 N $NH_3$ in MeOH/methylene chloride to give 132.

Yield =100% MS-ESI: 491 [M+H]$^{+1}$H NMR (DMSO-d$_6$): 1.26 (br m, 4H); 1.45 (br m, 4H); 1.52 (s, 6H); 2.30 (s, 6H); 2.35 (m, 4H); 2.67 (m, 4H); 3.41 (m, 2H); 4.20–4.45 (br m, 2H); 6.79 (s, 1H); 6.90 (s, 1H); 7.31 (s, 2H); 11.34 (br s, 1H).

Example 48

2-[1,1-Dimethyl-2-oxo-2-azabicyclo[2.2.1]heptan-7-ylethyl[-4-]4-(morpholinocarbonyl)piperidin-1-ylmethyl]-5-(3,5-dimethylphenyl)-6H-thieno[2,3-b]pyrrole

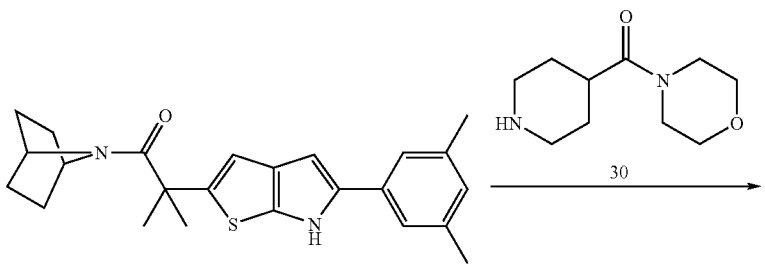
32

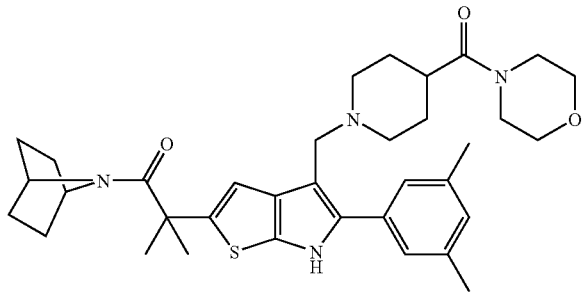

Example 48

To a mixture of 30 (0.058 g; 0.29 mmol) and formaldehyde (0.021 g; 0.26 mmol) in acetic acid (10 ml) was added 32 (0.104 g; 0.27 mmol) in dioxane (20 ml) at room temperature. After 4 hours, the crude mixture was evaporated and purified by flash chromatography eluting with a gradient 1–5% of 3.5 N $NH_3$ in MeOH/methylene chloride to give after trituration in ether/pentane Example 48 as a solid.

Yield: 98% MS-ESI: 603 [M+H]$^{+1}$H NMR (CDCl$_3$): 1.20–1.40 (m, 4H); 1.62 (s, 6H); 1.68 (m, 5H); 1.85 (m, 2H); 2.00 (m, 2H); 2.35 (s, 6H); 2.42 (m, 1H); 3.05 (m, 2H); 3.47 (m, 5H); 3.61 (m, 2H); 3.66 (m, 4H); 4.14 (br m, 1H); 4.73 (br m, 1H); 6.79 (s, 1H); 6.94 (s, 1H); 7.27 (s, 2H); 8.27 (s, 1H).

Example 49

2-[1,1-Dimethyl-2-oxo-2-azabicyclo[2.2.1]heptan-7-ylethyl]-4-[2-(3-(4-acetylpiperazin-1-yl)pyrrolidin-1-yl)ethyl]-5-(3,5-dimethylphenyl)-6H-thieno[2,3-b]pyrrole A mixture of 29 (0.133 g; 0.29 mmol), 135 (0.063 g, 0.32 mmol), NaI (0.048 g; 0.32 mmol) and K$_2$CO$_3$ (0.044 g; 0.32 mmol) in dimethylacetamide (3 ml) was heated at 85° C. under argon atmosphere for 4 hours. The crude mixture was evaporated and purified by flash chromatography eluting with a gradient 4–8% of 3.5 N $NH_3$ in MeOH/methylene chloride to give after trituration in ether/pentane Example 49 as a solid.

Yield: 52% MS-ESI: 616 [M+H]$^{+1}$H NMR (CDCl$_3$): 1.29 (m, 4H); 1.61 (s, 6H); 1.45–1.80 (m, 4H); 2.00 (m, 1H); 2.08 (s, 3H); 2.34 (s, 6H); 2.42 (m, 5H); 2.48 (m, 1H); 2.55 (m, 1H); 2.70 (m, 1H); 2.80 (m, 2H); 2.88 (m, 2H); 2.93 (m, 2H); 3.46 (m, 2H); 3.62 (m, 2H); 4.10 (br m, 1H); 4.75 (br m, 1H); 6.73 (s, 1H); 6.94 (s, 1H); 7.06 (s, 2H); 8.16 (s, 1H).

135 was prepared as follows:

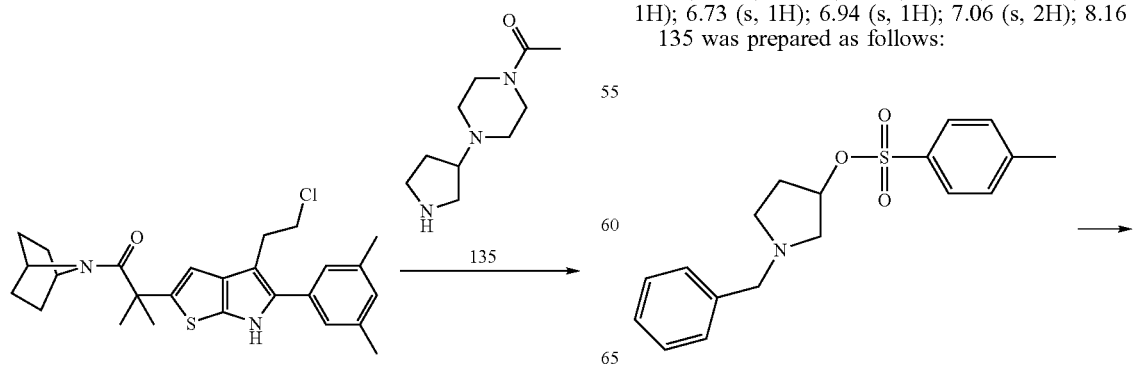

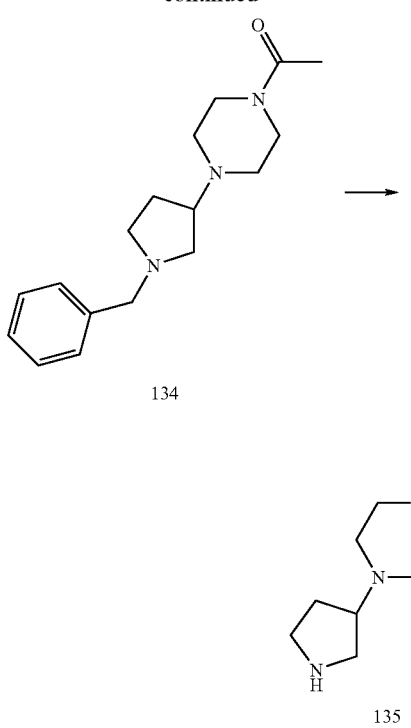

A mixture of 133 (0.461 g; 1.39 mmol) and acetyl piperazine (0.535 g; 4.17 mmol) in dimethylformamide (1 ml) was heated at reflux under argon atmosphere for 1 hour. The crude mixture was evaporated and purified by flash chromatography eluting with a gradient 0–3% of 3.5 N $NH_3$ in MeOH/methylene chloride to give 134 as an oil.

Yield: 80% MS-ESI: 288 $[M+H]^+$ $^1$H NMR ($CDCl_3$): 1.73 (m, 3H); 2.00 (m, 1H); 2.07 (s, 3H); 2.30–2.50 (m, 3H); 2.54 (m, 1H); 2.69 (m, 1H); 2.79 (m, 1H); 2.88 (m, 1H); 3.45 (m, 2H); 3.60 (m, 4H); 7.25 (m, 2H); 7.31 (m, 3H).

To a mixture of 134 (0.358 g; 1.25 mmol) in methanol (3 ml) were added ammonium formate (0.236 g; 3.74 mmol) and Pd/C (0.013 g, 0.125 mmol). The reaction was heated at reflux for one hour, then filtered through celite. The crude mixture was evaporated and purified by flash chromatography eluting with a gradient 10–20% of 3.5 N $NH_3$ in MeOH/methylene chloride to give 135 as an oil.

Yield: 66% MS-ESI: 198 $[M+H]^+$ $^1$H NMR ($CDCl_3$): 1.65 (m, 1H); 1.97 (m, 1H); 2.08 (s, 3H); 2.08 (br m, 2H); 2.41–2.50 (m, 3H); 2.76 (m, 2H); 2.97 (m, 1H); 3.07 (m, 1H); 3.12 (m, 1H); 3.47 (m, 2H); 3.62 (m, 2H).

Examples 49.1–49.3

Following a procedure similar to that described in Example 49, the compounds of table 49 were prepared.

TABLE 49

| Example | | MS-ESI |
|---|---|---|
| 49.1 | | 588 [M + H]$^+$ |
| 49.2 | | 575 [M + H]$^+$ |

TABLE 49-continued

| Example | MS-ESI |
|---|---|
| 49.3 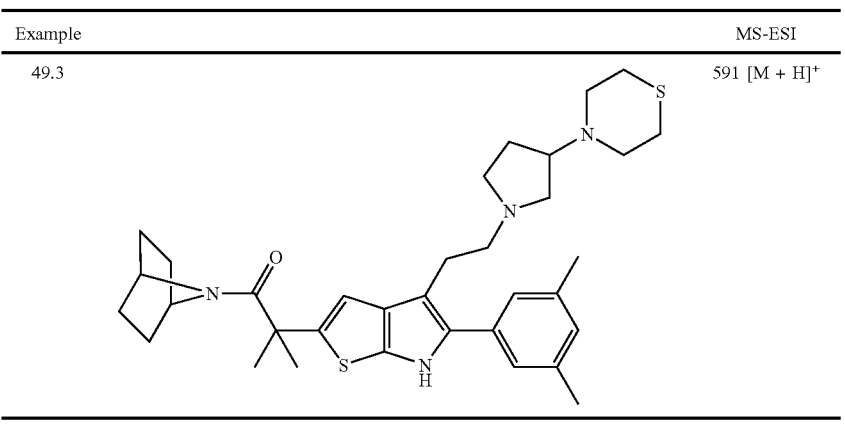 | 591 [M + H]+ |

Example 50

2-[1,1-Dimethyl-2-oxo-2-azabicyclo[2.2.1]heptan-7-ylethyl]-4-[2-(3-{morpholinocarbonyl}pyrrolidin-1-yl)ethyl]-5-(3,5-dimethylphenyl)-6H-thieno[2,3-b]pyrrole

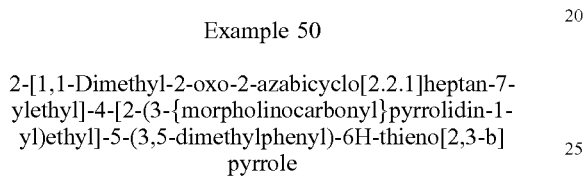

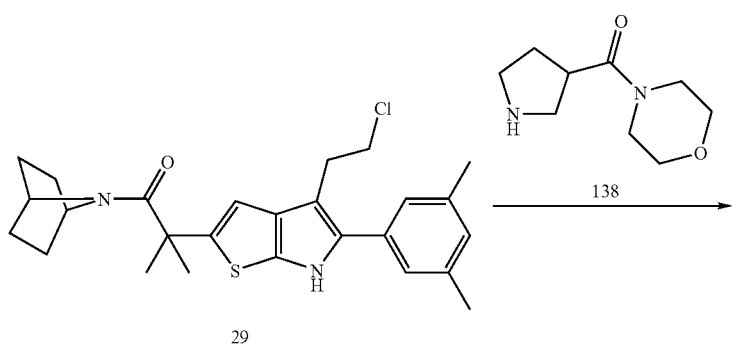

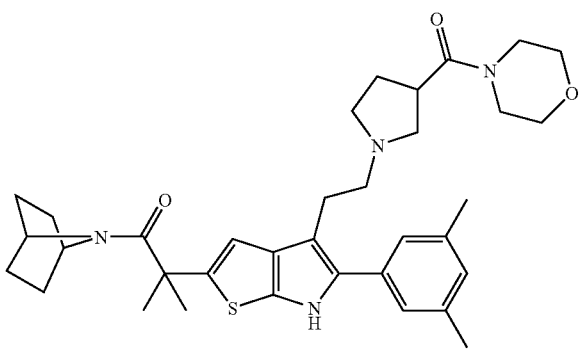

Example 50

A mixture of 29 (0.139 g; 0.31 mmol), 138 (0.062 g; 0.34 mmol), NaI (0.046 g; 0.31 mmol) and $K_2CO_3$ (0.051 g; 0.37 mmol) in dimethylacetamide (3 ml) was heated at 85° C. under argon atmosphere for 3 hours. The crude mixture was evaporated and purified by flash chromatography eluting with a gradient 1–3% of 3.5 N $NH_3$ in MeOH/methylene chloride to give after trituration in ether/pentane Example 50 as a white solid.

Yield: 62% MS-ESI: 603 [M+H]⁺ ¹H NMR (CDCl₃): 1.31 (m, 4H); 1.45–1.80 (m, 4H); 1.62 (s, 6H); 2.05–2.15 (m, 2H); 2.35 (s, 6H); 2.49 (m, 1H); 2.65 (m, 1H); 2.75 (m, 1H); 2.82 (m, 1H); 2.96 (m, 3H); 3.04 (m, 1H); 3.19 (m, 1H); 3.48 (m, 2H); 3.65 (m, 6H); 4.10 (br m, 1H); 4.75 (br m, 1H); 6.74 (s, 1H); 6.94 (s, 1H); 7.06 (s, 2H); 8.13 (s, 1H).

138 was prepared as follows:

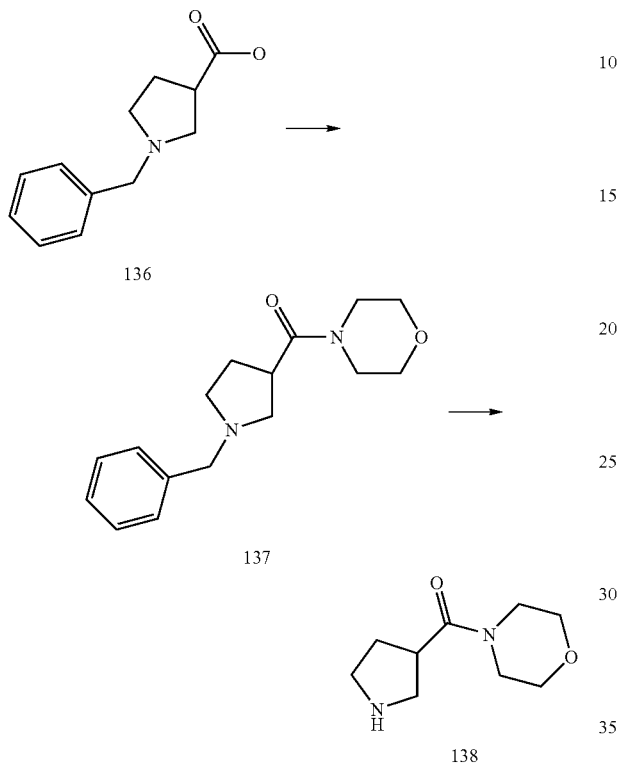

136

137

138

A mixture of 136 (0.127 g; 0.62 mmol), morpholine (0.081 ml; 0.93 mmol), EDCI (0.143 g; 0.74 mmol) and HOBT (0.084 g; 0.62 mmol) in methylene chloride (5 ml) was stirred at room temperature under argon atmosphere for 24 hours. The crude mixture was dissolved in ethyl acetate and washed with a 2 N NaOH solution. The organic layer was dried on magnesium sulphate, evaporated and purified by flash chromatography eluting with a gradient 5–10% of 3.5 N NH₃ in MeOH/methylene chloride to give 137 as an oil.

Yield: 75% MS-ESI: 275 [M+H]⁺ ¹H NMR (CDCl₃): 2.00–2.15 (m, 2H); 2.46 (q, J=9 Hz, 1H); 2.60 (t, J=8.5 Hz, 1H); 2.83 (m, 1H); 2.94 (t, J=9 Hz, 1H); 3.16 (m, 1H); 3.47 (m, 2H); 3.65 (m, 8H); 7.24 (m, 2H); 7.32 (m, 3H).

To a mixture of 137 (0.108 g; 0.30 mmol) in methanol (5 ml) were added ammonium formate (0.074 g; 1.18 mmol) and Pd/C (0.004 g; 0.04 mmol). The reaction was heated at reflux for 3 hours, then filtered through celite. The crude mixture was evaporated and purified by flash chromatography eluting with a gradient 20–22% of 3.5 N NH₃ in MeOH/methylene chloride to give 138 as an oil.

Yield: 88% MS-ESI: 185 [M+H]⁺ ¹H NMR (CDCl₃): 2.07 (m, 2H); 3.01 (m, 1H); 3.07 (m, 1H); 3.16 (m, 2H); 3.28 (m, 1H); 3.53 (m, 2H); 3.62 (m, 2H); 3.67 (m, 5H).

Examples 50.1–50.3

Following a procedure similar to that described in Example 50, the compounds of table 50 were prepared.

TABLE 50

| Example | | MS-ESI |
|---|---|---|
| 50.1 | | 651 [M + H]⁺ |

TABLE 50-continued
| Example | | MS-ESI |
|---|---|---|
| 50.2 | 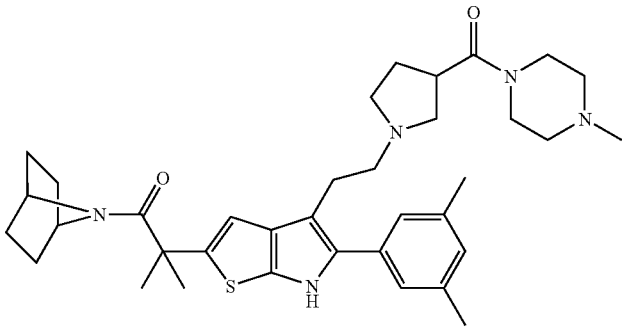 | 616 [M + H]+ |
Example 51
2-[1,1-Dimethyl-2-oxo-2-azabicyclo[2.2.1]heptan-7-ylethyl]-4-[2-(5-t-butoxycarbonyl-octahydropyrrolo[3,4-c]pyrrol-2-yl)ethyl]-5-(3,5-dimethylphenyl)-6H-thieno[2,3-b]pyrrole
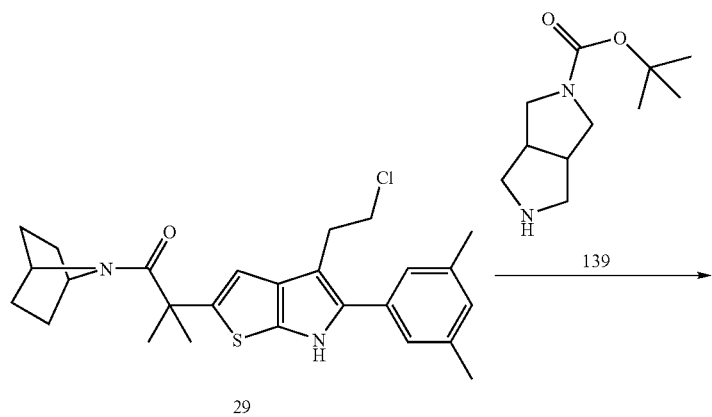
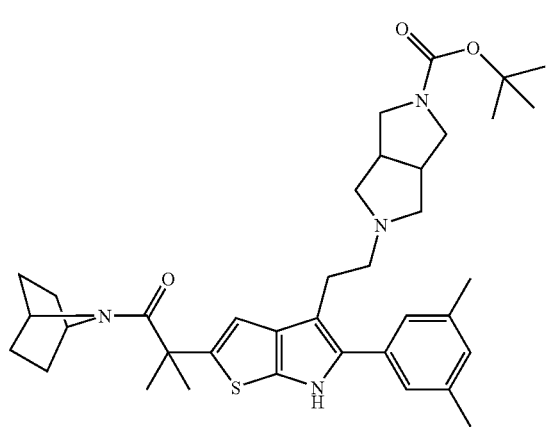
Example 51

A mixture of 29 (0.123 g; 0.27 mmol), 139 (0.063 g, 0.30 mmol), NaI (0.040 g; 0.27 mmol) and $K_2CO_3$ (0.045 g; 0.32 mmol) in dimethylacetamide (3 ml) was heated at 85° C. under argon atmosphere for 3 hours. The crude mixture was evaporated and purified by flash chromatography eluting with a gradient 1–3% of 3.5 N $NH_3$ in MeOH/methylene chloride to give after trituration in ether/pentane Example 51 as a white solid.

Yield: 78% MS-ESI: 631 $[M+H]^{+1}$H NMR ($CDCl_3$): 1.31 (m, 6H); 1.45 (s, 9H); 1.50–1.75 (m, 4H); 1.62 (s, 6H); 2.35 (s, 6H); 2.72 (m, 2H); 2.80 (m, 4H); 2.94 (m, 2H); 3.25 (br m, 2H); 3.55 (br m, 2H); 4.10–4.20 (br m, 1H); 4.70–4.80 (br m, 1H); 6.74 (s, 1H); 6.95 (s, 1H); 7.07 (s, 2H); 8.12 (s, 1H).

Examples 51.1

Example 51.1 was obtained by deprotection of Example 50 with HCl in dioxane.

TABLE 51

| Example | | MS-ESI |
|---|---|---|
| 51.1 | 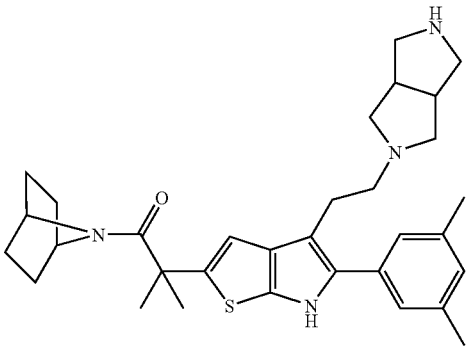 | 531 $[M + H]^+$ |

Example 52

2-[1,1-Dimethyl-2-oxo-2-azabicyclo[2.2.1]heptan-7-ylethyl]-4-[2-(3-{morpholinocarbonylamino}pyrrolidin-1-yl)ethyl]-5-(3,5-dimethylphenyl)-6H-thieno[2,3-b]pyrrole

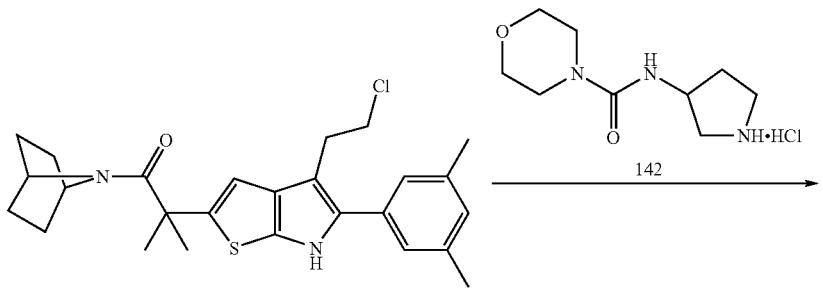

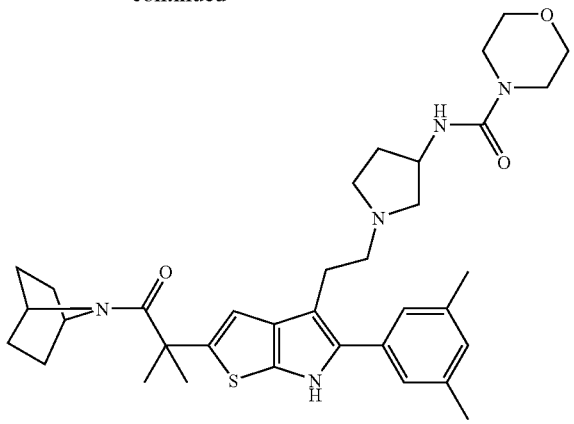

Example 52

A mixture of 29 (0.200 g; 0.44 mmol), 142 (0.178 g, 0.76 mmol), NaI (0.066g; 0.44 mmol) and K₂CO₃ (0.243 g; 1.76 mmol) in dimethylacetamide (4 ml) was heated at 85° C. under argon atmosphere for 4 hours. The crude mixture was evaporated and purified by flash chromatography eluting with a gradient 2–4% of 3.5 N NH₃ in MeOH/methylene chloride to give after trituration in ether/pentane Example 52 as a pale brown solid.

Yield: 42% MS-ESI: 618 [M+H]$^{+1}$H NMR (CDCl₃): 1.25–1.40 (m, 4H); 1.62 (s, 6H); 1.50–1.80 (m, 4H); 2.20–2.40 (m, 3H); 2.35 (s, 6H); 2.52 (m, 1H); 2.74 (m, 311); 2.95 (m, 3H); 3.32 (m, 4H); 3.67 (m, 4H); 4.10 (br m, 1H); 4.39 (br m, 1H); 4.71 (br m, 1H); 4.87 (br m, 1H); 6.74 (s, 1H); 6.95 (s, 1H); 7.06 (s, 2H); 8.16 (s, 1H).

142 was prepared as follows:

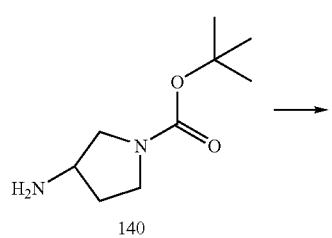

140

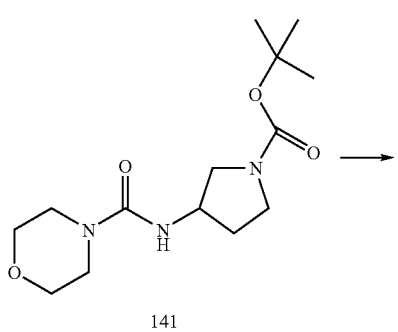

141

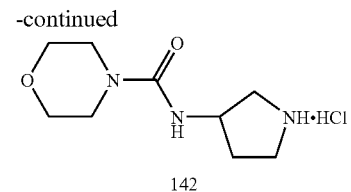

142

To a solution of 140 (0.500 g; 2.68 mmol) in methylene chloride (10 ml) were added at 0° C. triethylamine (0.410 ml; 2.95 mmol) then p-nitrochloroformate (0.594 g; 2.95 mmol). After 1 hour, morpholine (0.260 ml; 2.95 mmol) was added and the reaction mixture was stirred at room temperature under argon atmosphere for 24 hours. The crude mixture was washed with water. The organic layer was dried on magnesium sulphate, evaporated and purified by flash chromatography eluting with pure AcOEt first, then with 10% of 3.5 N NH₃ in MeOH/methylene chloride to give 141 as an white foam.

Yield: 86% MS-ESI: 300 [M+H]$^{+1}$H NMR (CDCl₃): 1.46 (s, 9H); 1.75–1.90 (m, 1H); 2.15 (m, 1H); 3.15 (m, 1H); 3.34 (m, 4H); 3.30–3.50 (m, 2H); 3.65 (m, 1H); 3.69 (m, 4H); 4.30–4.50 (m, 2H).

To a solution of 141 (0.680 g; 2.27 mmol) in dioxane (22 ml) was added concentrated HCl (0.60 ml). The reaction was stirred at room temperature for 7 hours, then evaporated to give after trituration in methylene chloride/ether/pentane 142 as a pale brown foam, which was used without further characterisation in Example 52.

Yield: 47%

Examples 52.1–52.3

Following a procedure similar to that described in Example 52, the compounds of table 52 were prepared.

TABLE 52
| Example | | MS-ESI |
|---|---|---|
| 52.1 | 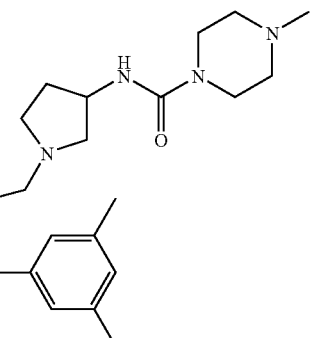 | 631 [M + H]+ |
| 52.2 | 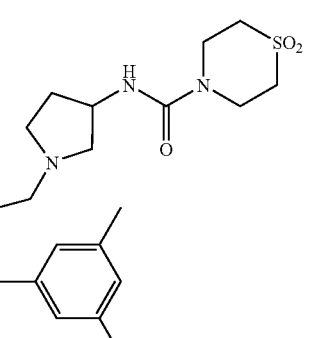 | 666 [M + H]+ |
| 52.3 | 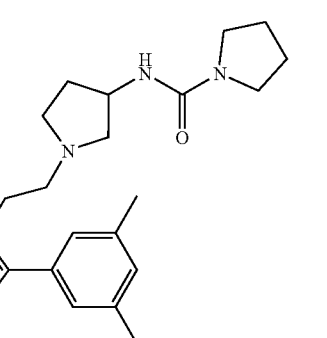 | 602 [M + H]+ |

Example 53

2-[1,1-Dimethyl-2-oxo-2-azabicyclo[2.2.1]heptan-7-ylethyl]-4-[2(3–1,1-dioxothiomorpholin-4-ylcarbonylmethyl}pyrrolidin-1-yl)ethyl]-5-(3,5-dimethylphenyl)-6H-thieno[2,3-b]pyrrole

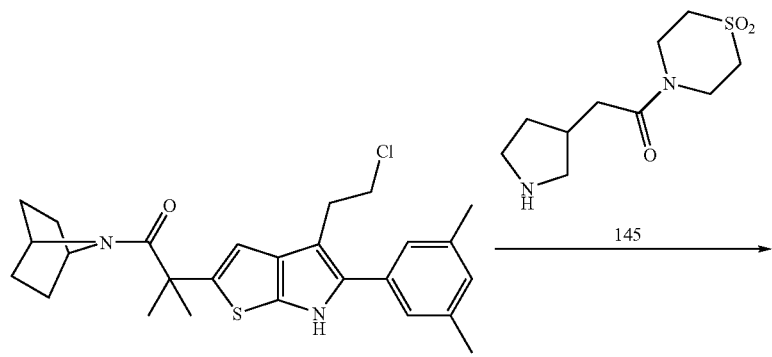

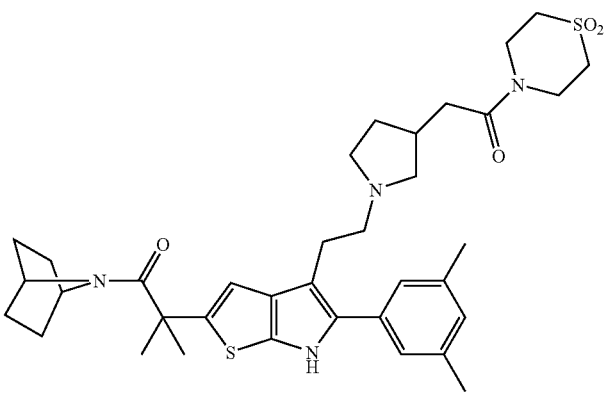

Example 53

A mixture of 29 (0.250 g; 0.55 mmol), 145 (0.203 g, 0.83 mmol), NaI (0.082 g; 0.55 mmol) and $K_2CO_3$ (0.228 g; 1.65 mmol) in dimethylacetamide (3 ml) was heated at 85° C. under argon atmosphere for 4 hours. The crude mixture was evaporated and purified by flash chromatography eluting with a gradient 2–6% of 3.5 N $NH_3$ in MeOH/methylene chloride to give after trituration in ether/pentane Example 53 as a solid.

Yield: 62% MS-ESI: 665 [M+H]$^{+1}$H NMR (CDCl$_3$): 1.32 (m, 4H); 1.62 (s, 6H); 1.40–1.78 (m, 8H); 2.16 (s, 1H); 2.35 (s, 6H); 2.52 (m, 3H); 2.65–2.78 (m, 4H); 2.95 (m, 2H); 3.02 (m, 3H); 3.95 (m, 2H); 4.10 (br m, 3H); 4.72 (br m, 1H); 6.73 (s, 1H); 6.95 (s, 1H); 7.07 (s, 2H); 8.16 (s, 1H).

145 was prepared as follows:

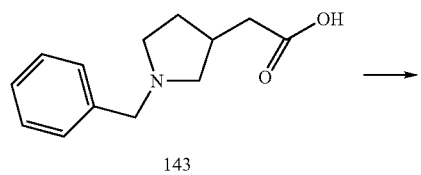

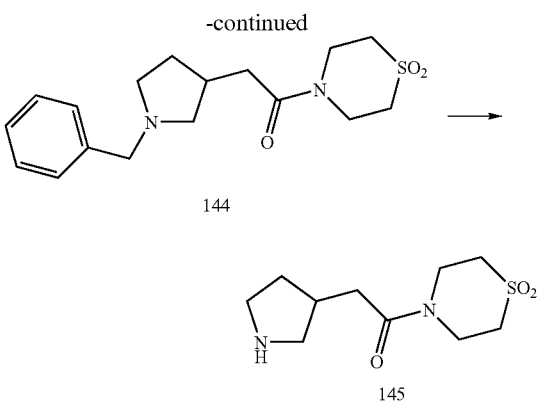

A mixture of 143 (0.558 g; 2.54 mmol), thiomorpholine-1,1-dioxide (0.516 g; 3.82 mmol), EDCI (0.585 g; 3.05 mmol) and HOBT (0.344 g; 2.54 mmol) in methylene chloride (10 ml) was stirred at room temperature under argon atmosphere for 24 hours. The crude mixture was dissolved in ethyl acetate and washed with a 2 N NaOH solution. The organic layer was dried on magnesium sulphate, evaporated and purified by flash chromatography eluting with a gradient 5–10% of 3.5 N NH₃ in MeOH/methylene chloride to give 144 as an oil.

Yield: 82% ¹H NMR (CDCl₃): 1.43 (m, 1H); 2.13 (m, 1H); 2.27 (m, 1H); 2.48 (m, 3H); 2.66 (m, 3H); 2,99 (m, 4H); 3.54 (d, J=13 Hz, 1H); 3.62 (d, J=13 Hz, 1H); 3.92 (m, 2H); 4.07 (m, 2H); 7.26 (m, 2H); 7.30 (m, 3H).

To a mixture of 144 (0.698 g; 2.08 mmol) in methanol (10 ml) were added ammonium formate (0.432 g; 6.85 mmol) and Pd/C (0.022 g; 0.21 mmol). The reaction was heated at reflux for 1.5 hours, then filtered through celite. The crude mixture was evaporated to give 145 as an oil used without further purification.

Yield: 95% ¹H NMR (CDCl₃): 1.73 (m, 1H); 2.25 (m, 2H); 2.55 (m, 1H); 2.70 (m, 1H); 2.85 (m, 1H); 3.03 (m, 4H); 3.19 (m, 2H); 3.38 (m, 2H); 3.87–4.07 (m, 3H); 4.24 (m, 1H).

Examples 53.1–53.3

Following a procedure similar to that described in Example 53, the compounds of table 53 were prepared.

TABLE 53

| Example | | MS-ESI |
|---|---|---|
| 53.1 | | 601 [M + H]⁺ |
| 53.2 | | 617 [M + H]⁺ |
| 53.3 | | 615 [M + H]⁺ |

Example 54

2(1,1-dimethyl-2-oxo-2-pyrrolidin-1-ylethyl)-5-(3,5-dimethylphenyl)-4-[(4-pyridin-4-ylpiperidin-1-yl)methyl]-6H-thieno[2,3-b]pyrrole

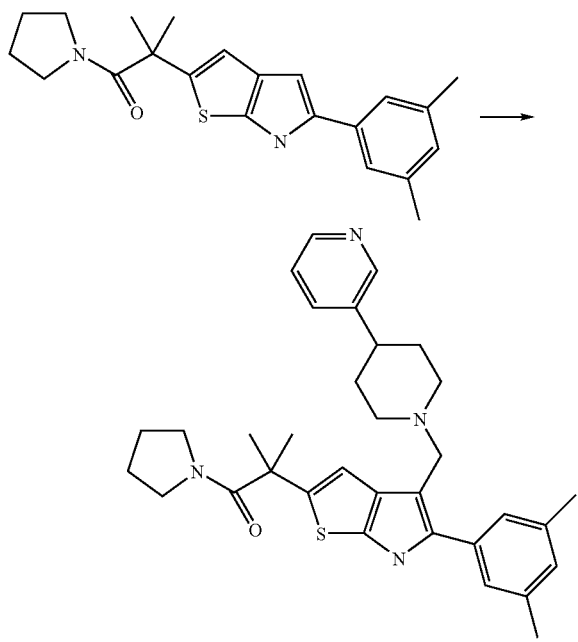

Example 54

4-piperidin-4-ylpyridine (see: Brown, George Robert; Newcombe, Nicholas John; Foubister, Alan John. 1-(Arylsulfonyl)-4-[[4-(4-pyridyl)piperidin-1-yl]carbonyl]piperazines and analogs useful as oxido-squalene cyclase inhibitors. PCT Int. Appl. (1998), WO 9835959 A1 19980820 CAN 129:189345 AN 1998:568822) (0.033 g, 0.20 mmol) was added to a solution of formaldehyde in acetic acid (2.8 ml made up from 0.61 ml of a 37% formaldehyde aqueous solution in 100 ml of acetic acid, 0.21 mmol) and the mixture was stirred at ambient temperature for five minutes. A solution of 2-(1,1-dimethyl-2-oxo-2-pyrrolidin-1-yl-ethyl)-5-(3,5-dimethylphenyl)-6H-thieno[2,3-b]pyrrole as a 1.1:1 mixture with triethyl phosphite (0.083 g, 0.16 mmol) in acetic acid (1 ml) was added dropwise and the mixture was then allowed to stir at ambient temperature for 30 minutes. The mixture was concentrated under vacuum and the residue partitioned between 2N hydrochloric acid and ethyl acetate. The aqueous layer was separated, made basic by the addition of 2N sodium hydroxide and extracted with ethyl acetate. The organic layer was separated, washed with a saturated brine solution, dried over magnesium sulfate and then evaporated to leave a yellow oil. Flash chromatography on silica eluting with 2–3% methanol (containing 7N ammonia) in dichloromethane gave the product as a pale yellow solid (0.043 g).

Yield: 50% $^1$H NMR (CDCl$_3$): 1.6–1.76 (m, 12H+H$_2$O), 1.78–1.86 (m, 2H), 2.10–2.18 (m, 2H); 2.36 (s, 6H), 2.46–2.55 (m, 1H), 3.08–3.20 (m, 4H), 3.50–3.58 (m, 2H), 3.60 (s, 2H); 6.84 (s, 1H); 6.95 (s, 1), 7.14 (d, 2H), 7.28 (s, 2H), 8.45 (s, 1H), 8.50 (d, 2H). MS-ESI: 541 [M+H]$^+$ Intermediate 146 was prepared according to the following scheme:

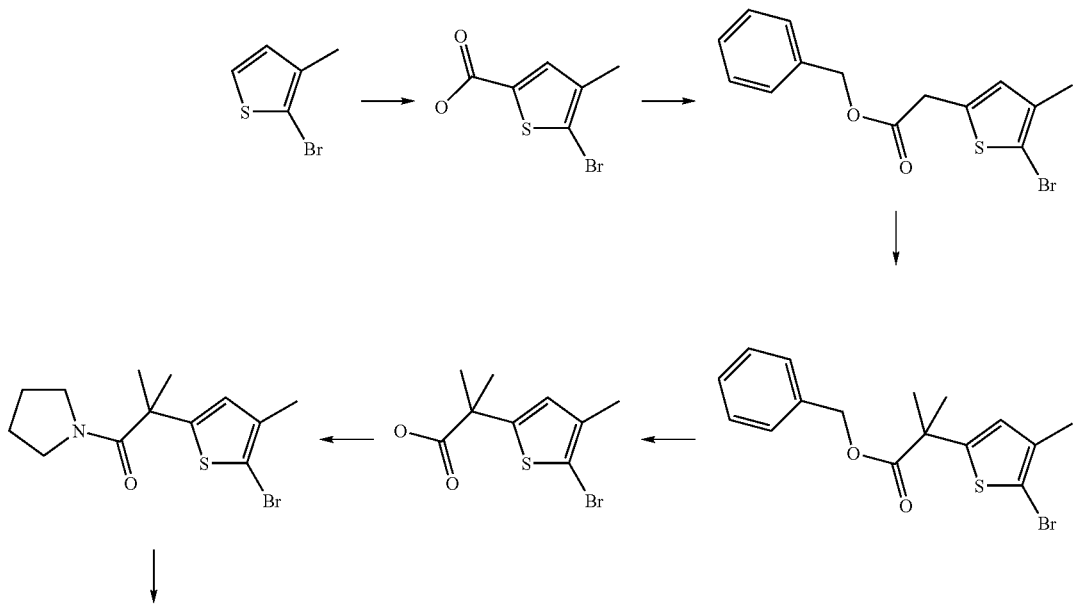

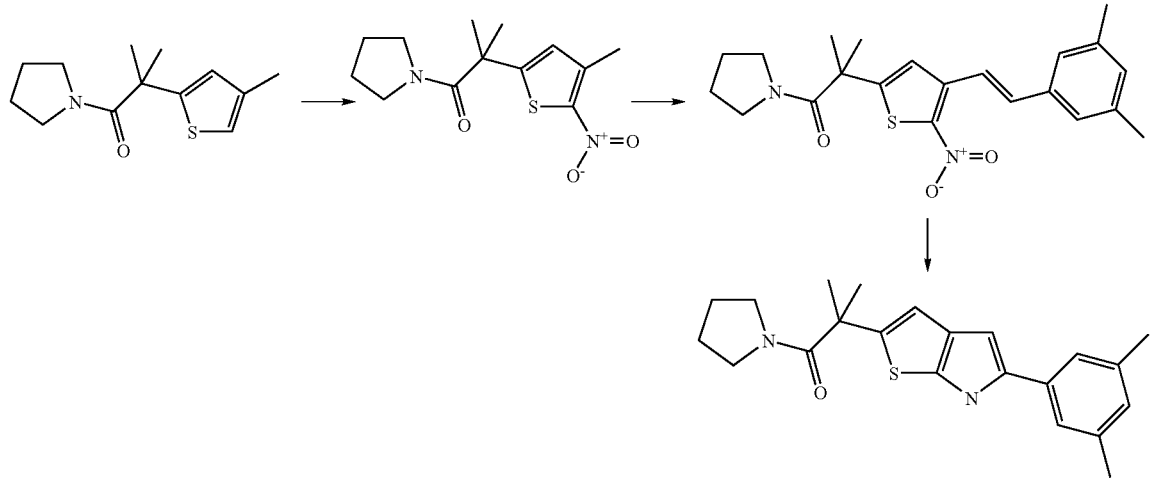

146

2-(1,1-dimethyl-2-oxo-2-pyrrolidin-1-ylethyl)-5-(3,5-dimethylphenyl)-6H-thieno[2,3-b]pyrrole was prepared as follows:

5-Bromo4-methylthiophene-2-carboxylic acid (Nemec, M.; Janda, Miroslav; Srogl, Jan; Stibor, I. Collection of Czechoslovak Chemical Communications (1974), 39(12), 3527–31.) (2.5 g, 11 mmol) was suspended in dichloromethane (25 ml) and dimethylformamide (0.1 ml). Oxalyl chloride (1.1 ml, 13 mmol) was added and the mixture was allowed to stir at ambient temperature for 2 hours. The solvent was evaporated and the crude acid chloride was dried under vacuum. The acid chloride was dissolved in a mixture of acetonitrile (20 ml), tetrahydrofuran (20 ml) and triethylamine (2.0 ml, 14 mmol) and the mixture was cooled in an ice-bath. A solution of (trimethylsilyl)diazomethane (8.5 ml) in hexane (2.0M, 17 mmol) was added dropwise and the mixture allowed to stir in an ice-bath for 20 hours. The solvent was evaporated and the residue partitioned between 1N hydrochloric acid and ethyl acetate. The organic layer was separated, dried over magnesium sulfate and then evaporated to leave a yellow solid. The crude alpha-diazoketone was dissolved in a mixture of benzyl alcohol (10 ml) and 2,4,6-trimethylpyridine (10 ml) and heated to 180 C for 2 hours. The mixture was allowed to cool and then purified directly by flash chromatography on silica eluting with a mixture of 10% ethyl acetate in iso-hexane to afford benzyl (5-bromo4-methyl-2-thienyl)acetate (0.982 g) as a dark yellow oil Yield: 27% $^1$H NMR (CDCl$_3$): 2.12 (s, 3H), 3.74 (s, 2H), 5.15 (s, 2H), 6.61 (s, 1H), 7.32–7.37 (m, 5H). MS-ESI: 325/327 [M+]$^+$ A solution of benzyl (5-bromo4-methyl-2-thienyl)acetate (0.982 g, 3.02 mmol) in tetrahydrofuran (3.5 ml) was added dropwise to a solution of lithium di-iso-propyl amide [made from di-iso-propyl amine (1.02 ml, 7.3 mmol) and a solution of n-butyl lithium (4.54 ml) in hexane (1.6M, 7.26 mmol) in tetrahydrofuran (5 ml)] cooled to –78 C. The mixture was stirred for 2 hours at –78 C and then methyl iodide (1.0 ml, 16 mmol) was added and the mixture was allowed to warm to ambient temperature over 4 hours. The mixture was poured into water and extracted with ethyl acetate. The organic layer was separated and then washed with a 1N solution of hydrochloric acid followed by a saturated solution of brine. The ethyl acetate solution was dried over magnesium sulfate and then evaporated to leave benzyl 2-(5-bromo-4-methyl-2-thienyl)-2-methylpropanoate as a yellow oil which was used in the next step without further purification. $^1$H NMR (CDCl$_3$): 1.61 (s, 6H), 2.11 (s, 3H), 5.12 (s, 2H), 6.59 (s, 1H); 72.5–7.37 (m, 5H).

A mixture of the benzyl 2-(5-bromo-4-methyl-2-thienyl)-2-methylpropanoate and sodium hydroxide (0.33 g, 8.3 mmol) in methanol (10 ml) and water (2.5 ml) was heated under reflux for 1 hour. The solvent was evaporated and the residue triturated with 1N hydrochloric acid and then extracted with ethyl acetate. The organic layer was separated, dried over magnesium sulfate and then evaporated to leave 2-(5-bromo-4-methyl-2-thienyl)-2-methylpropanoic acid as a yellow gum which was used in the next step without purification. $^1$H NMR (CDCl$_3$): 2.09 (s, 6H), 2.13 (s, 3H), 6.69 (s, 1H).

To a mixture of the 2-(5-bromomethyl-2-thienyl)-2-methylpropanoic acid in dichloromethane (10 ml) with a catalytic amount of dimethylformamide was added oxalyl chloride (0.30 ml, 0.34 mmol). The mixture was allowed to stir at ambient temperature for 2 hours. The solvent was evaporated and the crude acid chloride dried under vacuum. The crude acid chloride was dissolved in dichloromethane (10 ml) and cooled in an ice-bath. Pyrrolidine (1.2 ml, 14 mmol) was added and the mixture was allowed to stir for 30 minutes while being cooled in an ice-bath. The mixture was poured into ethyl acetate (25 ml) and then extracted with 1N hydrochloric acid. The organic layer was washed with a saturated brine solution, dried over magnesium sulfate and then evaporated to leave 1-[2-(5-bromo-4-methyl-2-thienyl)-2-methylpropanoyl]pyrrolidine as a red oil which was used in the next step without purification.

MS-ESI: 316/318 [M+H]$^+$

To a solution of the 1-[2-(5-bromo-4-methyl-2-thienyl)-2-methylpropanoyl]pyrrolidine in acetic acid (8 ml) and water (5 ml) was added zinc dust (1.1 g, 15 mmol). The mixture was heated under reflux for 24 hours. The solvent was evaporated and the residue was dissolved in ethyl acetate and then washed sequentially with 1N hydrochloric acid, 1N sodium hydroxide and a saturated brine solution. The ethyl acetate solution was dried over magnesium sulfate and then evaporated. The residue was purified by flash chromatography on silica eluting with a 20–75% mixture of ethyl acetate in iso-hexane to afford 1-[2-methyl-2-(4-methyl-2-thienyl)propanoyl]pyrrolidine (0.151 g) as a colourless solid.

Yield: 21% over 4 steps from benzyl (5-bromomethyl-2-thienyl)acetate. $^1$H NMR (CDCl$_3$): 1.46 (s, 6H), 1.56–1.65 (m, 4H), 2.14 (s, 3H), 2.90 (br, 2H), 3.30 (br, 2H), 6.67 (d, 1H), 6.92–6.95 (m, 1H). MS-ESI: 238 [M+H$^+$ Nitronium tetrafluoroborate (0.168 g, 1.26 mmol) was added to a solution of 1-[2-methyl-2-(4-methyl-2-thienyl) propanoyl]pyrrolidine (0.145 g, 0.61 mmol) in dimethoxy ethane (5 ml) cooled to –50 C. The mixture was allowed to warm to –30 C over 1 hour. The mixture was poured into water and extracted with ethyl acetate. The organic layer was separated and washed sequentially with a saturated solution of sodium bicarbonate and then with a saturated brine solution. The ethyl acetate solution was dried over magnesium sulfate and then evaporated to afford 1-[2-methyl-2-(4-methyl-5-nitro-2-thienyl)propanoyl]pyrrolidine as a yellow solid which was used in the next step without purification. $^1$H NMR (CDCl$_3$): 1.62 (s, 6H), 1.73–1.81 (m, 4H), 2.58 (s, 3H), 3.03 (br, 2H), 3.53 (br, 2H), 6.66 (3, 1H).

A mixture of the 1-[2-methyl-2-(4-methyl-5-nitro-2-thienyl)propanoyl]pyrrolidine and 3,5-dimethylbenzaldehyde (0.161 g, 1.2 mmol) in ethanol (5 ml) containing a catalytic amount of pyrrolidine was heated under reflux for 18 hours. The mixture was allowed to cool to ambient temperature and then the precipitate was filtered. The solid was washed with cold ethanol (2×5 ml) and then dried under vacuum to leave 1-(2-{4-[(E)-2-(3,5-dimethylphenyl)vinyl]-5-nitro-2-thienyl}-2-methylpropanoyl pyrrolidine (0.144 g) as a bright yellow fluffy solid which was used in the next step without further purification.

Yield: 59% over two steps from 1-[2-methyl-2-(4-methyl-2-thienyl)propanoyl]pyrrolidine. $^1$H NMR (d$_6$ DMSO): 1.57 (s, 6H), 1.64–1.70 (m, 4H), 2.30 (s, 6H), 3.04 (br, 2H); 3.37 (br, 2H), 7.02 (s, 1H), 7.25 (s, 2H), 7.61 (s, 1H), 7.63 (d, 1H), 7.88 (d, 1H).

A mixture 1-(2-{4-[(E)-2-(3,5-dimethylphenyl)vinyl]-5-nitro-2-thienyl )-2-methylpropanoyl pyrrolidine (0.140 g, 0.35 mmol) and triethyl phosphite (1.0 ml) was heated at 180 C for 1 hour. The mixture was concentrated and the residue purified directly by flash chromatography on silica eluting with a mixture of 20% ethyl acetate in iso-hexane to afford 2-(1,1-dimethyl-2-oxo-2-pyrrolidin-1-ylethyl)-5-(3,5-dimethylphenyl)-6H-thieno[2,3-b]pyrrole (0.107 g) as a red oil which was a 1.1:1 mixture with triethyl phosphite.

Yield: 59% (based on 1.1:1 mixture with triethyl phosphite) $^1$H NMR (CDCl$_3$): 1.65 (s, 6H), 1.70 (br, 4H), 2.34 (s, 6H), 3.13 (br, 2H), 3.54 (br, 2h), 6.57 (d, 1H), 6.74 (s, 1H), 6.87 (s, 1H), 7.19 (s, 2H), 9.25 (s, 1H). MS-ESI: 367 [M+H]$^+$ Therapeutic Uses Compounds of Formula (I) are provided as medicaments for antagonising gonadotropin releasing hormone (GnRH) activity in a patient, eg, in men and/or women. To this end, a compound of Formula (I) can be provided as part of a pharmaceutical formulation which also includes a pharmaceutically acceptable diluent or carrier (eg, water). The formulation may be in the form of tablets, capsules, granules, powders, syrups, emulsions (eg, lipid emulsions), suppositories, ointments, creams, drops, suspensions (eg, aqueous or oily suspensions) or solutions (eg, aqueous or oily solutions). If desired, the formulation may include one or more additional substances independently selected from stabilising agents, wetting agents, emulsifying agents, buffers, lactose, sialic acid, magnesium stearate, terra alba, sucrose, corn starch, talc, gelatin, agar, pectin, peanut oil, olive oil, cacao butter and ethylene glycol.

The compound is preferably orally administered to a patient, but other routes of administration are possible, such as parenteral or rectal administration. For intravenous, subcutaneous or intramuscular administration, the patient may receive a daily dose of 0.1 mgkg$^{-1}$ to 30 mgkg$^{-1}$ (preferably, 5 mgkg$^{-1}$ to 20 mgkg$^{-1}$) of the compound, the compound being administered 1 to 4 times per day. The intravenous, subcutaneous and intramuscular dose may be given by means of a bolus injection. Alternatively, the intravenous dose may be given by continuous infusion over a period of time. Alternatively, the patient may receive a daily oral dose which is approximately equivalent to the daily parenteral dose, the composition being administered 1 to 4 times per day. A suitable pharmaceutical formulation is one suitable for oral administration in unit dosage form, for example as a tablet or capsule, which contains between 10 mg and 1 g (preferably, 100 mg and 1 g) of the compound of the invention.

Buffers, pharmaceutically acceptable co-solvents (eg, polyethylene glycol, propylene glycol, glycerol or EtOH) or complexing agents such as hydroxy-propyl β cyclodextrin may be used to aid formulation.

One aspect of the invention relates to the use of compounds according to the invention for reducing the secretion of LH and/or FSH by the pituitary gland of a patient. In this respect, the reduction may be by way of a reduction in biosynthesis of the LH and FSH and/or a reduction in the release of LH and FSH by the pituitary gland. Thus, compounds according to the invention can be used for therapeutically treating and/or preventing a sex hormone related condition in the patient. By "preventing" we mean reducing the patient's risk of contracting the condition. By "treating" we mean eradicating the condition or reducing its severity in the patient. Examples of sex hormone related conditions are: a sex hormone dependent cancer, benign prostatic hypertrophy, myoma of the uterus, endometriosis, polycystic ovarian disease, uterine fibroids, prostatauxe, myoma uteri, hirsutism and precocious puberty. Examples of sex hormone dependent cancers are: prostatic cancer, uterine cancer, breast cancer and pituitary gonadotrophe adenoma.

The compounds of the invention may be used in combination with other drugs and therapies used to treat/prevent sex-hormone related conditions.

If formulated as a fixed dose such combination products employ the compounds of this invention within the dosage range described herein and the other pharmaceutically-active agent within its approved dosage range. Sequential use is contemplated when a combination formulation is inappropriate.

In the field of medical oncology examples of such combinations include combinations with the following categories of therapeutic agent:

i) anti-angiogenic agents (for example linomide, inhibitors of integrin αvβ3 function, angiostatin, endostatin, razoxin, thalidomide) and including vascular endothelial growth factor (VEGF) receptor tyrosine kinase inhibitors (RTKIs) (for example those described in international patent applications publication nos. WO-97/22596, WO-97/30035, WO-97/32856 and WO-98/13354, the entire disclosure of which documents is incorporated herein by reference);

ii) cytostatic agents such as anti-oestrogens (for example tamoxifen, toremifene, raloxifene, droloxifene, iodoxyfene), progestogens (for example megestrol acetate), aromatase inhibitors (for example anastrozole, letrozole, vorazole, exemestane), anti-progestogens, anti-androgens (for example flutamide, nilutamide, bicalutamide, cyproterone acetate), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example epidermal growth factor (EGF), platelet derived growth factor and hepatocyte growth factor such inhibitors include growth factor antibodies, growth factor receptor antibodies, tyrosine kinase inhibitors and serine/threonine kinase inhibitors);

iii) biological response modifiers (for example interferon);

iv) antibodies (for example edrecolomab); and v) anti-proliferative/anti-neoplastic drugs and combinations thereof, as used in medical oncology, such as anti-metabolites (for example anti-folates like methotrexate, fluoropyrimidines like 5-fluorouracil, purine and adenosine analogues, cytosine arabinoside); anti-tumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); anti-mitotic agents (for example vinca alkaloids like vincristine and taxoids like taxol, taxotere); enzymes (for example asparaginase); thymidylate synthase inhibitors (for example raltitrexed); topoisomerase inhibitors (for example epipodophyllotoxins like etoposide and teniposide, amsacrine, topotecan, irinotecan).

The compounds of the invention may also be used in combination with surgery or radiotherapy.

Assays

The ability of compounds according to the invention to act as antagonists of GnRH can be determined using the following in vitro assays.

Binding Assay Using Rat pituitary GnRH Receptor

The assay is performed as follows:

1. Incubate crude plasma membranes prepared from rat pituitary tissues in a Tris.HCl buffer (pH. 7.5, 50 mM) containing bovine serum albumin (0.1%), [I-125]D-t-Bu-Ser6-Pro9-ethyl amide-GnRH, and the test compound. Incubation is at 4° C. for 90 minutes to 2 hours.

2. Rapidly filter and repeatedly wash through a glass fibre filter.

3. Determine the radioactivity of membrane bound radio-ligands using a gamma counter.

From this data, the $IC_{50}$ of the test compound can be determined as the concentration of the compound required to inhibit radio-ligand binding to GnRH receptors by 50%. Compounds according to the present invention have activity at a concentration from 1 nM to 5 μM.

Binding Assay Using Human GnRH Receptor

Crude membranes prepared from CHO cells expressing human GnRH receptors are sources for the GnRH receptor. The binding activity of compounds according to the invention can be determined as an $IC_{50}$ which is the compound concentration required to inhibit the specific binding of [$^{125}$I]buserelin to GnRH receptors by 50%. [$^{125}$I]Buserelin (a peptide GnRH analogue) is used here as a radiolabelled ligand of the receptor.

Assay to Determine Inhibition of LH Release

The LH release assay can be used to demonstrate antagonist activity of compounds, as demonstrated by a reduction in GnRH-induced LH release.

Preparation of Pituitary Glands

Pituitary glands obtained from rats are prepared as follows. Suitable rats are Wistar male rats (150–200 g) which have been maintained at a constant temperature (eg, 25° C.) on a 12 hour light/12 hour dark cycle. The rats are sacrificed by decapitation before the pituitary glands are aseptically removed to tube containing Hank's Balanced Salt Solution (HBSS).

The glands are further processed by:

1. Centrifugation at 250×g for 5 minutes;
2. Aspiration of the HBSS solution;
3. Transfer of the glands to a petri dish before mincing with a scalpel;
4. Transfer of the minced tissue to a centrifuge tube by suspending the tissue three successive times in 10 ml aliquots of HBSS containing 0.2% collagenase and 0.2% hyaluronidase;
5. Cell dispersion by gentle stirring of the tissue suspension while the tube is kept in a water bath at 37° C.;
6. Aspiration 20 to 30 times using a pipette, undigested pituitary fragments being allowed to settle for 3 to 5 minutes;
7. Aspiration of the suspended cells followed by centrifugation at 1200×g for 5 minutes;
8. Re-suspension of the cells in culture medium of DMEM containing 0.37% $NaHCO_3$, 10% horse serum, 2.5% foetal bovine serum, 1% non essential amino acids, 1% glutamine and 0.1% gentamycin;
9. Treatment of the undigested pituitary fragments 3 times with 30 ml aliquots of the collagenase and hyaluronidase;
10. Pooling of the cell suspensions and dilution to a concentration of $3\times10^5$ cells/ml;
11. Placing of 1.0 ml of this suspension in each of a 24 well tray, with the cells being maintained in a humidified 5% $CO_2$/95% air atmosphere at 37° C. for 3 to 4 days Testing of Compounds The test compound is dissolved in DMSO to a final concentration of 0.5% in the incubation medium.

1.5 hours prior to the assay, the cells are washed three times with DMEM containing 0.37% $NaHCO_3$, 10% horse serum, 2.5% foetal bovine serum, 1% non essential amino acids (100×), 1% glutamine (100×), 1% penicillin/streptomycin (10,000 units of each per ml) and 25 mM HEPES at pH 7.4. Immediately prior to the assay, the cells are again washed twice in this medium.

Following this, 1 ml of fresh medium containing the test compound and 2 nM GnRH is added to two wells. For other test compounds (where it is desired to test more than one compound), these are added to other respective duplicate wells. Incubation is then carried out at 37° C. for three hours.

Following incubation, each well is analysed by removing the medium from the well and centrifuging the medium at 2000×g for 15 minutes to remove any cellular material. The supernatant is removed and assayed for LH content using a double antibody radio-immuno assay. Comparison with a suitable control (no test compound) is used to determine whether the test compound reduces LH release. Compounds according to the present invention have activity at a concentration from 1 nM to 5 μM.

What is claimed is:

1. A compound of Formula (I),

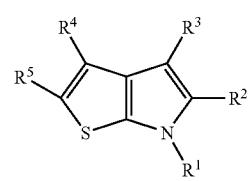

Formula (I)

wherein $R^1$ is selected from: hydrogen, optionally-substituted $C_{1-6}$alkyl, optionally substituted $C_{1-6}$alkanoyl, optionally substituted aryl or optionally-substituted aryl$C_{1-6}$alkyl;

$R^2$ is an optionally-substituted mono or bi-cyclic aromatic ring;

$R^3$ is a group of formula (IIb):

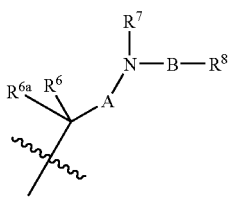

Formula (IIb)

$R^4$ is selected from: hydrogen, optionally substituted $C_{1-6}$alkyl, optionally substituted aryl, $C_{1-3}$perfluoroalkyl, cyano, nitro, halo, $R^9O(CH_2)_m$—, $R^9C(O)N(R^{10})$—, $R^9R^{10}NC(O)N(R^{10})(CH_2)_n$—, $R^9S(O_n)(CH_2)_m$— or $R^9R^{10}NC(O)$—$(CR^9R^{10})_t(CH_2)_m$—;

$R^5$ is a group of Formula (III):

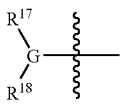

Formula (III)

$R^6$ and $R^{6a}$ are independently selected from hydrogen, fluoro, optionally substituted $C_{1-6}$alkyl, optionally-substituted aryl or optionally substituted aryl$C_{1-6}$alkyl, or $R^6$ and $R^{6a}$ taken together and the carbon atom to which they are attached form a carbocyclic ring of 3–7 atoms, or $R^6$ and $R^{6a}$ taken together and the carbon atom to which they are attached form a carbonyl group;

$R^7$ is selected from: hydrogen, optionally-substituted $C_{1-6}$alkyl, optionally-substituted aryl$C_{1-6}$alkyl, optionally-substituted aryl, optionally substituted heterocyclyl, optionally substituted heterocyclyl$C_{1-6}$alkyl, $R^9OC_{1-6}$alkyl-, $R^9R^{10}NC_{1-6}$alkyl-, $R^9R^{10}NC(O)C_{1-6}$alkyl, —$C(NR^9R^{10})$=NH;

$R^8$ is selected from:
(i) hydrogen, $C_{1-6}$alkyl, $C_{2-6}$alkenyl, $C_{2-6}$alkynyl, halo$C_{1-6}$alkyl, $C_{1-4}$alkoxy$C_{1-4}$alkyl, hydroxy, hydroxy$C_{1-6}$alkyl, cyano, N—$C_{1-4}$alkylamino, N,N-di-$C_{1-4}$alkylamino, $C_{1-6}$alkyl-$S(O_n)$—, —O—$R^b$, —$NR^bR^c$, —$C(O)$—$R^b$, —$C(O)O$—$R^b$, —$CONR^bR^c$, —NH—$C(O)$—$R^b$ or —$S(O_n)NR^bR^c$, where $R^b$ and $R^c$ are independently selected from hydrogen and $C_{1-4}$alkyl optionally substituted with hydroxy, amino, N—$C_{1-4}$alkylamino, N,N-di-$C_{1-4}$alkylamino, HO—$C_{2-4}$alkyl-NH— or HO—$C_{2-4}$alkyl-N($C_{1-4}$alkyl)-;
(ii) nitro when B is a group of Formula (IV) and X is CH and p is 0;
(iii) $C_{3-7}$cycloalkyl, aryl or aryl$C_{1-6}$alkyl each of which is optionally substituted by $R^{12}$, $R^{13}$ and $R^{14}$;
(iv) —(Q)-aryl, —(Q)-heterocyclyl, -aryl-(Q)-aryl, each of which is optionally substituted by $R^{12}$, $R^{13}$ and $R^{14}$ wherein—(Q)— is selected from E, F or a direct bond;
(v) heterocyclyl or heterocyclyl$C_{1-6}$alkyl each of which is optionally substituted by up to 4 substituents independently selected from $R^{12}$, $R^{13}$ and $R^{14}$;
(vi) a group selected from $R^{12}$, $R^{13}$ and $R^{14}$;

$R^9$ and $R^{10}$ are independently selected from: hydrogen, hydroxy, optionally substituted $C_{1-6}$alkyl, optionally substituted aryl, optionally substituted aryl$C_{1-6}$alkyl, an optionally substituted carbocyclic ring of 3–7 atoms, optionally substituted heterocyclyl, optionally substituted heterocyclyl$C_{1-6}$alkyl or $R^9$ and $R^{10}$ taken together can form an optionally substituted ring of 3–9 atoms or $R^9$ and $R^{10}$ taken together with the carbon atom to which they are attached form a carbonyl group;

$R^{11}$ is selected from: hydrogen, optionally substituted $C_{1-6}$alkyl, or $N(R^9R^{10})$;

$R^{12}$ is selected from: hydrogen, hydroxy, $R^{17}R^{18}N(CH_2)_{cc}$—, $R^{17}R^{18}NC(O)(CH_2)_{cc}$—, optionally substituted $C_{1-6}$alkyl-$C(O)N(R^9)(CH_2)_{cc}$—, optionally substituted $C_{1-6}$alkyl-$SO_2N(R^9)$—, optionally substituted aryl-$SO_2N(R^9)$—, $C_{1-3}$perfluoroalkyl-$SO_2N(R^9)$—; optionally substituted $C_{1-6}$alkyl-$N(R^9)SO_2$—, optionally substituted aryl-$N(R^9)SO_2$—, $C_{1-3}$perfluoroalkyl-$N(R^9)SO_2$— optionally substituted $C_{1-6}$alkanoyl-$N(R^9)SO_2$—; optionally substituted aryl-$C(O)N(R^9)SO_2$—, optionally substituted $C_{1-6}$alkyl-$S(O_n)$—, optionally substituted aryl-$S(O_n)$—, $C_{1-3}$perfluoroalkyl-, $C_{1-3}$perfluoroalkoxy, optionally substituted $C_{1-6}$alkoxy, carboxy, halo, nitro or cyano;

$R^{13}$ and $R^{14}$ are independently selected from: hydrogen, hydroxy, oxo, optionally substituted $C_{1-6}$alkyl, optionally substituted $C_{1-6}$alkanoyl, optionally substituted $C_{2-6}$alkenyl, cyano, nitro, $C_{1-3}$perfluoroalkyl-, $C_{1-3}$perfluoroalkoxy, optionally substituted aryl, optionally substituted aryl$C_{1-6}$alkyl, $R^9O(CH_2)_s$—, $R^9(O)O(CH_2)_s$—, $R^9OC(O)(CH_2)_s$—, $R^{16}S(O_n)(CH_2)_s$—, $R^9R^{10}NC(O)(CH_2)_s$— or halo;

$R^{15}$ is selected from: hydrogen, optionally substituted $C_{1-6}$alkyl, $R^{19}OC(O)$—, $R^9R^{10}NC(O)$—, $R^9C(O)$—, $R^9S(O_n)$—;

$R^{16}$ is selected from: hydrogen, $C_{1-6}$alkyl, $C_{1-3}$perfluoroalkyl or optionally-substituted aryl;

$R^{17}$ is independently selected from: hydrogen, hydroxy, cyano or optionally substituted $C_{1-6}$alkyl;

$R^{18}$ is a group of formula $R^{18a}$—$C(R^9R^{10})_{0-1}$— wherein $R^{18a}$ is selected from: $R^{19}OC(O)$—, $R^9R^{10}NC(O)$—, $R^9R^{10}N$—, $R^9C(O)$—, $R^9C(O)N(R^{10})$—, $R^9R^{10}NC(O)$—, $R^9R^{10}NC(O)N(R^{10})$—, $R^9SO_2N(R^{10})$—, $R^9R^{10}NSO_2N(R^{10})$—, $R^9C(O)O$—, $R^9OC(O)$—, $R^9R^{10}NC(O)O$—, $R^9O$—, $R^9S(O_n)$—, $R^9R^{10}NS(O_n)$—, hydrogen, optionally substituted $C_{1-6}$alkyl, optionally substituted heterocyclyl;
or $R^{17}$ and $R^{18}$ when taken together form an optionally substituted carbocyclic ring of 3–7 atoms or optionally substituted heterocyclyl;

$R^{19}$ is selected from: hydrogen, optionally substituted $C_{1-6}$alkyl, optionally substituted aryl, optionally substituted aryl$C_{1-6}$alkyl, optionally substituted $C_{3-7}$cycloalkyl, optionally substituted heterocyclyl or optionally substituted heterocyclyl$C_{1-6}$alkyl;

$R^{20}$ is selected from $R^{12}$ or $R^{13}$;

A is selected from:
(i) a direct bond;
(ii) optionally-substituted $C_{1-5}$alkylene wherein the optional substituents are independently selected from: optionally-substituted $C_{1-6}$alkyl optionally-substituted aryl, optionally substituted aryl$C_{1-6}$alkyl or substituted aryl$C_{1-6}$alkyl;

(iii) a carbocyclic ring of 3–7 atoms;
(iv) a carbonyl group or —C(O)—C(R$^d$R$^d$)—, wherein R$^d$ is independently selected from hydrogen and C$_{1-2}$alkyl;

B is selected from:
(i) a direct bond;
(ii) a group of Formula (IV)

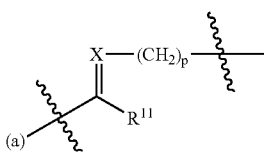

Formula (IV)

wherein:
X is selected from N, CH or a saturated heterocyclic ring,
wherein at position (a) Formula (IV) is attached to the nitrogen atom and the (CH$_2$)p group is attached to R$^8$; and
(iii) a group independently selected from: optionally substituted C$_{1-6}$alkylene, optionally substitute C$_{3-7}$cycloalkyl, optionally substituted C$_{3-6}$alkenylene, optionally substituted C$_{3-6}$alkynyl, C$_{1-6}$alkoxy, (C$_{1-5}$alkyl)$_{aa}$—S(O$_n$)—(C$_{1-5}$alkyl)$_{bb}$—, (C$_{1-5}$alkyl)$_{aa}$—O—(C$_{1-5}$alkyl)$_{bb}$— or (C$_{1-5}$alkyl)$_{aa}$—N(R$^{15}$)—(C$_{1-5}$alkyl)$_{bb}$, wherein R$^{15}$ and the (C$_{1-5}$alkyl)$_{aa}$ or (C$_{1-5}$alkyl)$_{bb}$ chain can be joined to form a ring;

or the group —B—R$^8$ represents a group of Formula (V)

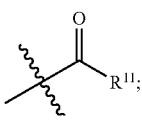

Formula (V)

or the group

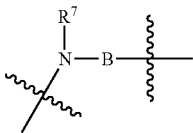

together forms an optionally substituted heterocyclic ring containing 4–7 carbons atoms;
or the group

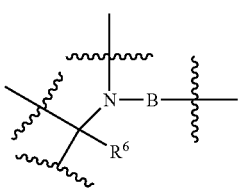

forms a heterocyclic ring containing 3–7 carbon atoms and one or more heteroatoms;

E is —O—, —S(O$_n$), —C(O)—, —NR$^{15}$— or —C(R$^9$R$^{10}$)$_q$;
F is —E(CH$_2$)$_r$— or —(CH$_2$)$_r$E—;
G is selected from: hydrogen, halo, CN, NO$_2$, N, O, S(O$_n$), C(O), C(R$^9$R$^{10}$)$_t$, optionally substituted C$_{2-6}$akenylene, optionally substituted C$_{2-6}$alkynylene, optionally substituted heterocyclyl or a direct bond to R$^{18}$,
m is an integer from 0 to 4;
n is an integer from 0 to 2;
p is an integer from 0 to 4;
q is an integer from 0 to 4;
r is an integer from 0 to 4;
s is an integer from 0 to 4;
t is an integer from 0 to 4;
aa and bb are independently selected from 0 or 1
cc is an integer between 0 to 2;
with the proviso that
(i) when G is hydrogen, halo, CN or NO$_2$ then R$^{17}$ and R$^{18}$ are both absent;
(ii) when G is O, S(O$_n$), C(O) or C(R$^{11}$R$^{12}$)$_t$ then G is substituted by a single group independently selected from the definition of R$^{17}$ or R$^{18}$ and when G is a direct bond to R$^{18}$ then G is substituted by a single group selected from R$^{18}$; and
(iii) when B is a group of Formula (IV), R$^8$ is selected from group (i) or (ii) above, R$^{11}$ is a group of the formula N(R$^{10}$R$^{11}$) and R$^1$, R$^2$ and R$^5$ are as defined above then R$^4$ cannot be hydrogen; or a salt, pro-drug or solvate thereof.

2. A compound according to claim 1 wherein R$^1$ is hydrogen.

3. A compound according to claim 1 wherein B is optionally substituted C$_{1-6}$alkylene or the group

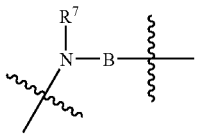

forms an optionally substituted C$_{5-7}$heterocyclic ring.

4. A compound according to claim 1 wherein R$^8$ is selected from
(i) hydrogen, C$_{1-6}$alkyl, C$_{2-6}$alkenyl, haloC$_{1-6}$alkyl, hydroxy, cyano, C$_{1-6}$alkylS(O$_n$)—, —O—R$^b$, C$_{1-4}$alkoxyC$_{1-4}$alkyl, —C(O)—R$^b$, C(O)O—R$^b$, —NH—C(O)—R$^b$, N,N-di-C$_{1-4}$alkylamino, —S(O$^r$)NR$^b$R$^c$ where R$^b$ and R$^c$ are independently selected from hydrogen and C$_{1-6}$alkyl, and n is 0, 1 or 2;
(ii) —(Q)-aryl;
(iii) C$_{4-7}$heterocyclyl, or
(iv) C$_{3-7}$carbocyclyl.

5. A compound according to claim 1 wherein R$^5$ is a group of Formula (III) wherein the group of Formula (III) is selected from one of III-a to III-l;

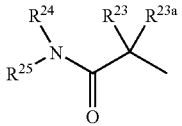

III-a

-continued

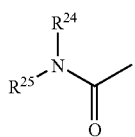
III-b

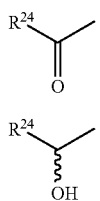
III-c

III-d

III-e

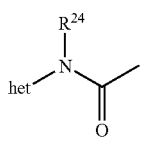

III-f

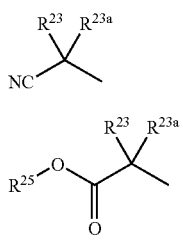

III-g

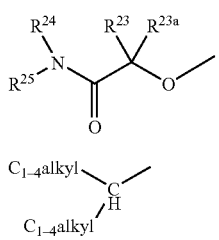

III-h

III-i

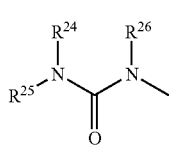

III-j

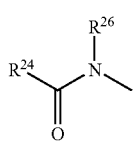

III-k

III-l wherein:
het represents an optionally substituted 3- to 8-membered heterocyclic ring containing from 1 to 4 heteroatoms independently selected from O, N and S;

$R^{23}$ and $R^{23a}$ are independently selected from hydrogen, fluoro or optionally substituted $C_{1-8}$alkyl; or $R^{23}$ and $R^{23a}$ together with the carbon to which they are attached form an optionally substituted 3 to 7-membered cycloalkyl ring;

$R^{24}$ is selected from hydrogen, optionally substituted $C_{1-8}$alkyl, optionally substituted aryl, —$R^d$—Ar, where $R^d$ represents $C_{1-8}$alkylene and Ar represents optionally substituted aryl, and optionally substituted 3- to 8-membered heterocyclic ring optionally containing from 1 to 3 further heteroatoms independently selected from O, N and S;

$R^{25}$ is selected from hydrogen; optionally substituted $C_{1-8}$alkyl and optionally substituted aryl;

or where the group of Formula (III) represents a group of Formula III-a, III-b or III-i, then the group $NR^{24}$(—$R^{25}$) represents an optionally substituted 3- to 8-membered heterocyclic ring optionally containing from 1 to 3 further heteroatoms independently selected from O, N and S;

or where the group of Formula (III) represents structure III-e, $R^{24}$ and $R^{25}$ together with the carbon to which they are attached represents an optionally substituted 3- to 8-membered heterocyclic ring optionally containing from 1 to 4 heteroatoms independently selected from O, N and S;

$R^{26}$ is selected from hydrogen or $C_{1-4}$alkyl.

6. A compound according to claim 1 wherein $R^2$ is selected from an optionally substituted monocyclic aromatic ring structure wherein the optional substituents are selected from cyano, $NR^eR^f$, optionally substituted $C_{1-8}$alkyl, optionally substituted $C_{1-8}$alkoxy or halo wherein $R^e$ and $R^f$ are independently selected from hydrogen, $C_{1-6}$alkyl or aryl.

7. A compound selected from:
{(2S)-2-[2-[2-(7-azabicyclo[2.2.1]hept-7-yl)-1,1-dimethyl-2-oxoethyl]-5-(3,5-dimethylphenyl)-6H-thieno[2,3-b]pyrrol-4-yl]propyl}(2-pyridin-4-ylethyl)amine;

2-[2-(7-azabicyclo[2.2.1]hept-7yl)-1.1-dimethyl-2-oxoethyl]-5-(3,5-dimethylphenyl)-4-[2-(3-pyridin-4-ylpyrrolidin-1-yl)ethyl]-6H-thieno[2,3-b]pyrrole;

2-[1,1-Dimethyl-2-oxo-2-azabicyclo[2.2.1]heptan-7-yl-ethyl]-4-[2-(4-pyrid-4-ylpiperidin-1-yl)ethyl]-5-(3,5-dimethylphenyl)-6H-thieno[2,3-b]pyrrole; and 2-[1,1-Dimethyl-2-oxo-2-azabicyclo[2.2.1]heptan-7-yl-ethyl]-4-[2-{4-(1,1-dioxidotetrahydrothien-3-yl)piperazin-1-yl}ethyl]-5-(3,5-dimethylphenyl)-6H-thieno[2,3-b]pyrrole or a salt, pro-drug or solyate thereof.

8. A pharmaceutical formulation comprising a compound, or salt, pro-drug or solvate thereof, according to claim 1 and a pharmaceutically acceptable diluent or carrier.

9. A method of treating a sex hormone related condition in a patient comprising administering according to claim 1, or salt, pro-drug or solvate thereof, to a patient selected form the group consisting of prostate cancer and pre-menopausal breast cancer.

10. A process of producing a compound, or salt, pro-drug or solvate thereof, according to claim 1, wherein the process comprises a reaction step selected from any one of (a) to (e):

(a) Reaction of a compound of formula XXXII with a compound of formula H—$R^{5'}$ to form a compound of Formula (I),

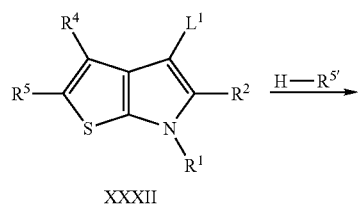

XXXII

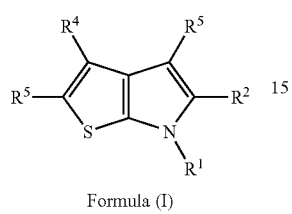

Formula (I)

wherein $L^1$ is selected from:

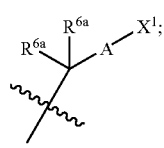

$X^1$ is a displaceable group; and
H—$R^{5\prime}$ is selected from:

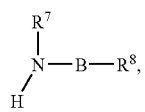

(b) Reaction of a compound of formula XXXIII with a compound of formula $L^2$—$R^{5\prime\prime}$ to form a compound of Formula (I),

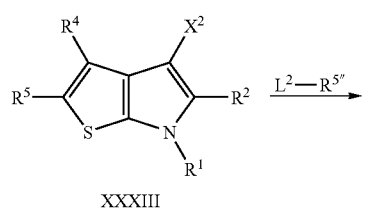

XXXIII

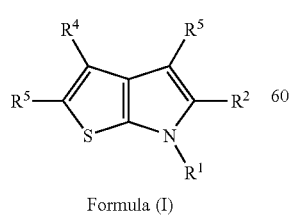

Formula (I)

wherein $X^2$ is selected from:

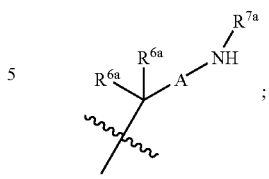

$R^{7a}$ is selected from the definition of $R^7$ above, and $L^2$—$R^{5\prime\prime\prime}$ is selected from:

(c) For compounds of Formula (I) wherein $R^7$ is other than part of a heterocyclic ring or hydrogen, reaction of a compound of Formula (I) wherein $R^7$ is hydrogen with a group of formula $L^3$—$R^{7a}$, wherein $R^{7a}$ is as defined above for $R^7$ with the exclusion of hydrogen and $L^3$ is a displaceable group;

(d) reaction of a compound of Formula XXXVI with an electrophillic compound of the formula $L^8$—$R^5$, wherein $L^8$ is a displaceable group

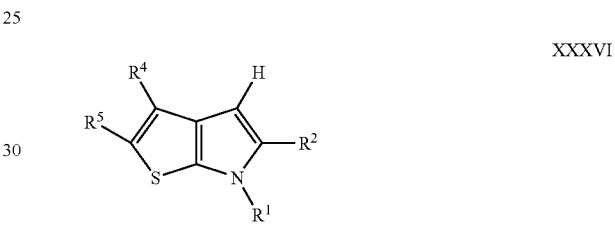

XXXVI (e) reaction of a compound of Formula XXXVII with a compound of the formula $L^8$—$R^5$, wherein $L^8$ is a displaceable group

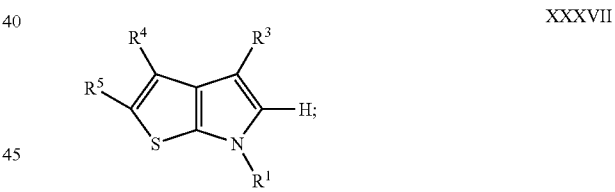

XXXVII and thereafter if necessary:
  i) converting a compound of the Formula (I) into another compound of the Formula (I);
  ii) removing any protecting groups;
  iii) forming a salt, pro-drug or solvate.

11. A compound according to claim 1 wherein $R^4$ is selected from hydrogen or $C_{1-4}$alkyl.

12. A compound according to claim 5 wherein $R^5$ is selected from one of the following groups:

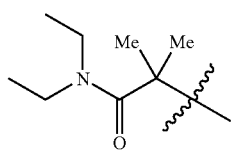 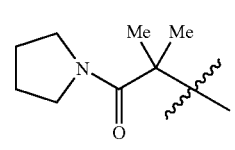

-continued

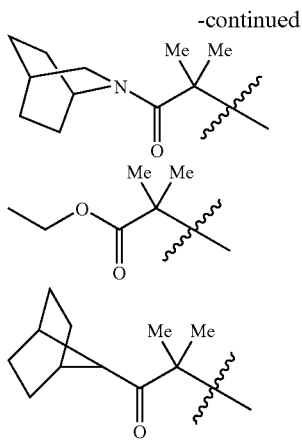

wherein Me represents methyl.

13. A compound according to claim 6 wherein $R^2$ is selected from an optionally substituted monocyclic aromatic ring structure wherein the optional substituents are selected from methyl, F or Cl.

14. A compound according to claim wherein A is selected from a direct bond, $C_{1-6}$alkylene optionally substituted with $C_{1-4}$alkyl, carbonyl or carbonylmethyl.

15. A compound according to claim 1 wherein B is unsubstituted $C_{1-6}$alkylene or the group

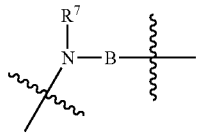

forms an optionally substituted saturated $C_{4-7}$heterocyclic ring selected from: azetidinyl, pyrrolidinyl, pyrazolinyl, pyrazolidinyl, imidazolinyl, imidazolidinyl, piperidiny, piperazinyl, hexahydropyrimidinyl, hexahydropyridazinyl, hexahydrotriazinyl, tetrahydrotriazinyl, dihydrotriazinyl, morpholinyl, thiomorpholinyl, thiazinanyl, thiazolidinyl, 1,5-dioxa-9-azaspiro[5.5]undecanyl or octahydropyrrolopyrrolyl, wherein the optional substituents are selected from, cyano, hydroxy, oxo, $C_{1-4}$alkyl, $C_{1-4}$alkoxy, $C_{1-4}$alkanoyl, $R^9OC(O)(CH_2)_w$—, $R^9R^{10}NC(O)(CH_2)_w$— or halo, wherein w is an integer between 0 and 4 and $R^9$ and $R^{10}$ are as defined in claim 1.

16. A compound according to claim 1 wherein $R^6$ and $R^{6a}$ are independently selected from hydrogen or unsubstituted $C_{1-4}$alkyl.

17. A compound according to claim 1 wherein $R^7$ is selected from hydrogen or $C_{1-4}$alkyl.

18. A compound according to claim 1 wherein $R^6$ is selected from
(i) hydrogen, $C_{1-6}$alkyl, $C_{2-6}$alkenyl, halo$C_{1-6}$alkyl, hydroxy, cyano, $C_{1-6}$alkylS(O$_n$)—, —O—$R^b$, $C_{1-4}$alkoxy$C_{1-4}$alkyl, —C(O)—$R^b$, C(O)O—$R^b$, —NH—C(O)—$R^b$, N,N-di-$C_{1-4}$alkylamino, —S(O$_n$)NR$^b$R$^c$ where R$^b$ and R$^c$ are independently selected from hydrogen and $C_{1-6}$alkyl, and n is 0,1 or 2;
(ii) —(Q)-aryl, wherein aryl is optionally substituted;
(iii) optionally substituted $C_{4-7}$heteracyclyl selected from: azirinyl, azetidinyl, pyrrolidinyl, pyrazolinyl, pyrazolidinyl, imidazolinyl, imidazolidinyl, piperidinyl, piperazinyl, hexahydrapyrimidinyl, hexahydropyridazinyl, hexahydrotriazinyl, tetraydrotriazinyl, dihydrotriazinyl, tetrahydrofuranyl, dioxolanyl, tetrahydropyranyl, dioxanyl, trioxanyl, tetrahydrothienyl, 1-oxotetrahydrothienyl, 1,1-dioxotetrahydrothienyl tetrahydrothiopyran, 1-oxotetrahydrothiopyran, 1,1-dioxotetrahydrothiopyran, dithianyl, trithianyl, morpholinyl, oxathiolanyl, oxathianyl, thiomorpholinyl, thiazinanyl, 1-oxo-thiomorpholinyl, 1,1-dioxo-thiomorpholinyl, thiazolidinyl, pyrrolyl, imidazolyl, triazolyl, pyridyl, pyrimidinyl, pyrazinyl, pyridazinyl, triazinyl, thiazolyl, thiadiazolyl, thiadiazinyl, oxazolyl, isoxazolyl, oxadiazolyl, furazanyl, octahydropyrrolopyrrolyl, octahydropyrrolopyrrolyl,benzotriazolyl, dihydrobenzotriazolyl, indolyl, indolinyl, benzimidazolyl, 2,3-dihydrobenzimidazoly, benzotriazolyl 2,3-dihydro benzotriazolyl quinolinyl, isoquinolinyl, cinnolinyl, phthalazinyl, quinazolinyl, quinozalinyl, naphthyridinyl, pteridinyl, benzodioxolyl, tetrahydrodioxolopyrrolyl, 1,5-dioxa-9-azaspiro[5.5]undecanyl and 8-oxa-3-azabicyclooctanyl; or
(iv) optionally substituted $C_{3-7}$carbocyclyl.

* * * * *